United States Patent
Pedersen et al.

(12) 
(10) Patent No.: US 6,277,611 B1
(45) Date of Patent: *Aug. 21, 2001

(54) LACCASE MUTANTS

(75) Inventors: Anders Hjelholt Pedersen, Lyngby; Allan Svendsen, Birkerød; Palle Schneider, Ballerup; Grethe Rasmussen, Farum; Joel Cherry, Hellerup, all of (DK)

(73) Assignee: Novozymeo A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 09/576,281

(22) Filed: May 23, 2000

Related U.S. Application Data

(60) Continuation of application No. 09/399,886, filed on Sep. 21, 1999, now Pat. No. 6,140,092, which is a division of application No. 08/993,318, filed on Dec. 18, 1997, now Pat. No. 5,998,353.
(60) Provisional application No. 60/035,413, filed on Jan. 23, 1997.

Foreign Application Priority Data

Dec. 19, 1996 (DK) .................................... 1449/96
Sep. 8, 1997 (DK) .................................... 1021/97

(51) Int. Cl.$^7$ ........................................ C12N 9/02
(52) U.S. Cl. .............................................. 435/189
(58) Field of Search ............................................ 435/189

(56) References Cited

U.S. PATENT DOCUMENTS

| | | |
|---|---|---|
| 5,480,801 | 1/1996 | Wahleithner et al. ............ 435/254.3 |
| 5,925,554 * | 7/1999 | Pedersen et al. ..................... 435/189 |

FOREIGN PATENT DOCUMENTS

| | | |
|---|---|---|
| WO 92/01046 | 1/1992 | (WO) . |
| WO 95/07988 | 3/1995 | (WO) . |
| WO 95/33836 | 12/1995 | (WO) . |
| WO 95/33837 | 12/1995 | (WO) . |
| WO 96/00290 | 1/1996 | (WO) . |
| WO 96/06930 | 3/1996 | (WO) . |
| WO 96/23874 | 8/1996 | (WO) . |

OTHER PUBLICATIONS

Kojima et al., J. Biol. Chem., 265, 25, Sep. 5, 1990, pp. 15224–15230.
Xu, F. et al. (1996) Biochimica et Biophysica Acta 1292:303–311.
Soon–ja, K. and Choi, H.T. (1995) FEMS Microbiology Letters 132;177–179.

* cited by examiner

Primary Examiner—Elizabeth Slobodyansky
(74) Attorney, Agent, or Firm—Elian J. Laubiris, Esq; Jason I. Garbell, Esq.

(57) ABSTRACT

The present invention relates to a method of designing laccase mutants with improved stability properties, which method is based on the hitherto unknown three-dimensional structure of *Coprinus cinereus* laccase.

9 Claims, No Drawings

LACCASE MUTANTS

CROSS-REFERENCE TO RELATED APPLICATIONS

This application is a continuation of U.S. application Ser. No. 09/399,886 filed Sep. 21, 1999, now U.S. Pat. No. 6,140,092, which is a divisional of U.S. application Ser. No. 08/993,318 filed Dec. 18, 1997 now U.S. Pat. No. 5,998,353 and claims priority under 35 U.S.C. 119 of Danish applications 1449/96 filed on Dec. 19, 1996 and 1021/97 filed Sept. 8, 1997, and of U.S. Provisional application No. 60/035,413 filed Jan. 23, 1997, the contents of which are fully incorporated herein by reference.

FIELD OF THE INVENTION

The present invention relates to a me-hod of designing laccase mutants with improved stability properties, which method is based on the hitherto unknown three-dimensional structure of laccases.

BACKGROUND OF THE INVENTION

Laccase is a polyphenol oxidase (EC 1.10.3.2) which catalyses the oxidation of a variety of inorganic and aromatic compounds, particularly phenols, with the concomitant reduction of molecular oxygen to water.

Laccase belongs to a family of blue copper-containing oxidases which includes ascorbate oxidase and the mammalian plasma protein ceruloplasmin. All these enzymes are multi-copper-containing proteins.

Because laccases are able to catalyze the oxidation of a variety of inorganic and aromatic compounds, laccases have been suggested in many potential industrial applications such as lignin modification, paper strengthening, dye transfer inhibition in detergents, phenol polymerization, hair colouring, and waste water treatment. A major problem with the use of laccases are their poor storage stability at temperatures above room temperature, especially at 40° C.

In Example 1 of the present application we have tested the stability of various laccases at 40° C., and it can be seen that after 2 weeks of storage the laccase activity is down to less than 50% of the initial value, and at low pH the laccase activity after 2 weeks is zero. For many purposes such a decrease is unacceptable, so it is the purpose of the present invention to create laccase variants with improved stability by using the information of a three-dimensional structure of a *Coprinus cinereus* laccase. No three-dimensional structural information has been available for a laccase before.

BRIEF DISCLOSURE OF THE INVENTION

The three-dimensional structure of a laccase has now been elucidated. On the basis of an analysis of said structure it is possible to identify structural parts or specific amino acid residues which from structural or functional considerations appear to be important for the stability of a laccase.

Furthermore, when comparing the three-dimensional structure of the Coprinus laccase structure with known amino acid sequences of various laccases, it has been found that some similarities exist between the sequences. The present invention is based on these findings.

Accordingly, in a first aspect the invention relates to a method of constructing a variant of a parent Corrinus laccase, which variant has laccase activity and improved stability as compared to said parent laccase, which method comprises i) analysing the three-dimensional structure of the parent Coprinus laccase to identify at least one amino acid residue or at least one structural part of the Coprinus laccase structure, which amino acid residue or structural part is believed to be of relevance for altering the stability of the parent Coprinus laccase (as evaluated on the basis of structural or functional considerations), ii) constructing a Coprinus laccase variant, which as compared to the parent Coprinus laccase, has been modified in the amino acid residue or structural part identified in i) so as to alter the stability, and, optionally, iii) testing the resulting Coprinus laccase variant with respect to stability In a second aspect the present invention relates to a method of constructing a variant of a parent Coprinus-like laccase, which variant has laccase activity and improved stability as compared to said parent laccase, which method comprises i) comparing the three-dimensional amino acid structure of the Coprinus laccase with an amino acid sequence of a Coprinus-like laccase, ii) identifying a part of the Coprinus-like laccase amino acid sequence which is different from the Coprinus laccase amino acid sequence and which from structural or functional considerations is contemplated to be responsible for differences in the stability of the Coprinus and Coprinus-like laccase, iii) modifying the part of the Coprinus-like laccase identified in ii) whereby a Coprinus-like laccase variant is obtained, which has an improved stability as compared to the parent Coprinus-like laccase, and optionally, iv) testing the resulting Coprinus-like laccase variant with respect to stability.

In still further aspects the invention relates to variants of a Coprinus laccase and of Coprinus-like laccases, DNA encoding such variants and methods of preparing the variants. Finally, the invention relates to the use of the variants for various industrial purposes.

DETAILED DISCLOSURE OF THE INVENTION

The Coprinus-like laccases

A number of laccases produced by different fungi are homologous on the amino acid level. For instance, when using the homology percent obtained from UWGCG program using the GAP program with the default parameters (penalties: gap weight=3.0, length weight=0.1; WISCONSIN PACKAGE Version 8.1-UNIX, August 1995, Genetics Computer Group, 575 Science Drive, Madison, Wis., USA 53711) the following homology was found:

*Coprinus cinereus* laccase comprising the amino acid sequence shown in SEQ ID No. 1: 100%;

*Polyporus pinsitus* (I) laccase comprising the amino acid sequence shown in SEQ ID No. 2: 74.4%;

*Polyporus pinsitus* (II) laccase comprising the amino acid sequence shown in SEQ ID No. 3: 73.8%;

*Phlebia radiata* laccase comprising the amino acid sequence shown in SEQ ID No. 4: 69.9%;

*Rhizoctonia solani* (I) laccase comprising the amino acid sequence shown in SEQ ID No. 5: 64.8%;

*Rhizoctonia solani* (II) laccase comprising the amino acid sequence shown in SEQ ID No. 6: 63.0%;

*Rhizoctonia solani* (III) laccase comprising the amino acid sequence shown in SEQ ID No. 7: 61.0%;

*Rhizoctonia solani* (IV) laccase comprising the amino acid sequence shown in SEQ ID No. 8: 59.7%;

*Scytalidiurn thermophilum* laccase comprising the amino acid sequence shown in SEQ ID No. 9: 57.4%;

*Myceliophthora thermophila* laccase comprising the amino acid sequence shown in SEQ ID No. 10: 56.5%.

Because of the homology found between the above mentioned laccases, they are considered to belong to the same class of laccases, namely the class of "Coprinus-like laccases".

Accordingly, in the present context, the term "Coprinus-like laccase" is intended to indicate a laccase which, on the amino acid level, displays a homology of at least 50% and less than 100% to the Coprinus cinereus laccase SEQ ID NO 1, or at least 55% and less than 100% to the Coprinus cinereus laccase SEQ ID NO 1, or at least 60% and less than 100% to the Coprinus cinereus laccase SEQ ID NO 1, or at least 65% and less than 100% to the Coprinus cinereus laccase SEQ ID NO 1, or at least 70% and less than 100% to the Coprinus cinereus laccase SEQ ID NO 1, or at least 75% and less than 100% to the Coprinus cinereus laccase SEQ ID NO 1, or at least 80% and less than 100% to the Coprinus cinereus laccase SEQ ID NO 1, or at least 85% and less than 100% to the Coprinus cinereus laccase SEQ ID NO 1, or at least 90% and less than 100% to the Coprinus cinereus laccase SEQ ID NO 1, or at least 95% and less than 100% to the Coprinus cinereus laccase SEQ ID NO 1.

In the present context, "derived from" is intended not only to indicate a laccase produced or producible by a strain of the organism in question, but also a la-case encoded by a DNA sequence isolated from such strain and produced in a host organism containing said DNA sequence. Finally, the term is intended to indicate a laccase which is encoded by a DNA sequence of synthetic and/or cDNA origin and which has the identifying characteristics of the laccase in question.

The three-dimensional Coprinus laccase structure

The Coprinus laccase which was used to elucidate the three-dimensional structure forming the basis for the present invention consists of the 539 amino acids derived from *Coprinus cinereus* laccase IFO 8371 as disclosed in sequence ID No. 1.

The obtained three-dimensional structure is believed to be representative for the structure of any Coprinus-like laccase.

The structure of the laccase was solved in accordance with the principle for X-ray crystallographic methods given in "X-Ray Structure Determination", Stout, G. K. and Jensen, L. H., John Wiley & Sons, inc. NY, 1989. The structural coordinates for the solved crystal structure of the laccase at 2.2 A resolution using the isomorphous replacement method are given in a standard PDB format (Brookhaven Protein Data Base) in Appendix 1. It is to be understood that Appendix 1 forms part of the present application.

In Appendix 1 the amino acid residues of the enzyme are identified by three-letter amino acid code (capitalized letters).

The laccase structure is made up of three plastocyanin-like domains. These three domains all have a similar beta-barrel fold.

3 copper atoms were observed in the three-dimensional structure:

The so-called type 1 copper ion is coordinated by two histidines and one cysteine.

The so-called type 2 copper of the trinuclear centre is missing in the structure disclosed in the present application.

The so-called type 3 copper consists of two type 3 copper atoms (pair of copper atoms) bound to a total of 6 histidine ligands.

When comparing the amino acid sequence of the crystallized three-dimensional structure with *Coprinus cinereus* amino acid sequence ID No. 1 the following four differences are observed:

18 amino acids are missing from the N—terminal of the crystallized protein;

17 amino acids are missing from the C-terminal of the crystallized protein;

Q19 in sequence ID No. 1 is an A1 in the crystallized protein; and

Q243 in sequence ID No. 1 is an E225 in the crystallized protein.

Generality of Structure

Because of the homology between the Coprinus laccase and the various Coprinus-like laccases, the solved structure defined by the coordinates of Appendix 1 is believed to be representative for the structure of all Coprinus-like laccases. A model structure of Coprinus-like laccases may be built on the basis of the coordinates given in Appendix 1 adapted to the laccase in question by use of an alignment between the respective amino acid sequences.

The above identified structurally characteristic parts of the Coprinus laccase structure may be identified in other Coprinus-like laccases on the basis of a model (or solved) structure of the relevant Coprinus-like laccase or simply on the basis of an alignment between the amino acid sequence of the Coprinus-like laccase in question with that of the Coprinus laccase used herein for identifying the amino acid residues of the respective structural elements.

Furthermore, in connection with Coprinus laccase variants of the invention, which are defined by modification of specific amino acid residues of the parent Coprinus laccase, it will be understood that variants of Coprinus-like laccases modified in an equivalent position (as determined from the best possible amino acid sequence alignment between the respective sequences) are intended to be covered as well.

Methods of the Invention for Design of Novel Laccase Variants

The analysis or comparison performed in step i) of the methods of the invention may be performed by use of any suitable computer programme capable of analysing and/or comparing amino acid sequences.

The structural part which is identified in step i) of the methods of the invent on may be composed o: one amino acid residue. However, normally the structural part comprises more than one amino acid residue, typically constituting one of the above mentioned parts of the Coprinus structure such as one of the copper centres.

According to the invention useful laccase variants may be modified in one or more amino acid residues present within 15 Å from any copper ion, preferably variants which are modified within 10 Å from any copper ion, in particular variants which are modified within 5 Å from any copper ion.

Determination of residues within 5 Å, 10 Å and 15 Å from the copper ions in the three-dimensional structure: The coordinates from the appendix are read into INSIGHT program provided by BIOSYM technologies. The spatial coordinates are presented showing the bonds between the atoms. The copper atoms are presented as well ds the water atoms. The program package contains a part which can be used for creating subsets. This part is used for creating a 5 Å, 10 Å and 15 Å subset around all Cu-ions present in the structure (the command ZONE is used). The found subsets contain all residues having an atom within 5, 10 and 15 Å from any of the Cu-ions present in the structure. All residues having an atom within this subset are compiled and written out by the LIST LMOLECULE command.

The amino acid residues found in this way within a distance of 15 Å from a copper ion in the *Coprinus cinereus* laccase are the following (SEQ ID No 1 numbering):

M27, V46, G51, P52, I54, L64, L76, T79, S80, I81, H82, W83, H84, G85, L86, F87, Q88, R89, T91, N92, W93, A94, D95, G96, A97, D98, G99, V100, N101, Q102, C103, P104,

Y113, F115, H120, G122, T123, F124, W125, Y126, H127, S128, H129, F130, G131, T132, Q133, Y134, C135, D136, G137, L138, R139, G140, P141, M142, V143, I144, I164, T165, L166, A167, D168, H170, G179, A180, A181, Q182, 2183, L217, I218, S219, L220, S221, C222, D223, P224, N225, W226, E239, V240, D241, G242, Q243, Q254, I255, F256, T257, G258, Q259, R260, Y261, N281, K282, F349, Q350, L351, G352, F353, S354, G356, R357, E358, T359, I360, N361, T363, A364, Y365, E366, S367, P368, Y371, T372, L373, P388, S391, Y392, L403, V404, V405, P406, A407, G408, V409, L410, G411, G412, P413, H414, P415, F416, H417, L418, H419, G420, H421, A422, F423, A429, K441, R442, D443, V444, V445, S446, L447, G448, V449, T450, D452, V454, I456, E458, N462, G464, P465, W466, F467, F468, H469, C470, H471, I472, E473, F474, H475, L476, M477, N478, G479, L480, A481, I482, V483, F484, A485, E486.

The amino acid residues found within a distance of 10 Å from a copper ion in the *Coprinus cinereus* laccase (SEQ ID No 1) are the following:

S80, I81, H82, W83, H84, G85, L86, D95, G96, A97, D98, V100, N101, F124, W125, Y126, H127, S128, H129, F130, G131, Y134, L138, R139, G140,, I218, S219, L220, S221, C222, D223, 2224, D241, F256, T257, G258, Q259, R260, K282, L351, G352, F353, F358, T359, V405, V409, L410, G411, G412, 2413, H414, 2415, F416, H417, L418, H419, G420, D443, V444, V445, S446, L447, G448, V454, I456, F458, W466, F467, F468, H469, C470, H471, I472, E473, F474, H.475, L476, M477, N478, G479, L480, A481, I482.

The amino acid residues found within a distance of 5 Å from a copper ion in the *Coprinus cinereus* laccase (SEQ ID No 1) are the following:
H82, H84, W125, H127, H129, G411, H414, P415, H417, H419, F467, H469, C470, H471, I472, H475, L480.

The 15 Å/10 Å/5 Å regions can be found in other laccases by comparison of the modelled structures or by taking the sequence homology numbers.

Modifications

The modification of an amino acid residue or structural part is typically accomplished by suitable modifications of a DNA sequence encoding the parent enzyme in question. The term "modified" as used in the methods according to the invention is intended to have the following meaning: When used in relation to an amino acid residue the term is intended to mean replacement of the amino acid residue in question with another amino acid residue. When used in relation to a structural part, the term is intended to mean: replacement of one or more amino acid residues of said structural part with other amino acid residues, or addition of one or more amino acid residues to said part, or deletion of one or more amino acid residues of said structural part.

The construction of the variant of interes is accomplished by cultivating a microorganism comprising a DNA sequence encoding the variant under conditions which are conducive for producing the variant, and optionally subsequently recovering the variant from the resulting culture broth. This is described in detail further below.

Variants with Altered Stability

It is contemplated that it is possible to improve the stability of a parent Coprinus laccase or a parent Coprinus-like laccase, wherein said variant is the result of a mutation, i.e. one or more amino acid residues having been deleted from, replaced or added to the parent laccase, the stability test performed as described below.

Preferred positions for mutations are the following:

| MtL: | StL: | CcL: | PpL1: | PpL2: | PrL: | RsL4: | RsL1: | RsL2: | RsL3: |
|------|------|------|-------|-------|------|-------|-------|-------|-------|
| M433 | M483 | — | — | — | — | — | — | — | — |
| W373 | W422 | — | — | — | — | W411 | W411 | W439 | — |
| W136 | W181 | W125 | W107 | W107 | W128 | W125 | W125 | W125 | W126 |
| Y145 | Y190 | Y134 | Y116 | Y116 | Y137 | Y134 | Y134 | Y134 | Y135 |
| M480 | M530 | — | — | — | — | — | — | — | — |
| Y137 | Y182 | Y126 | Y108 | Y108 | Y129 | Y126 | Y126 | Y126 | Y127 |
| Y176 | Y221 | Y170 | Y152 | Y152 | Y137 | Y170 | Y169 | Y170 | Y171 |
| M254 | M300 | — | — | — | — | — | — | — | — |
| — | — | M75 | M57 | M57 | M78 | M75 | M75 | M75 | M76 |
| — | — | M477 | — | | | | | | |
| | | | M328 | | | | | | |
| — | M313 | — | — | | | | | | |
| W507, | | | | | | | | | | wherein
CcL: *Coprinus cinereus* laccase comprising the amino acid sequence shown in SEQ ID No. 1;
PpL1: *Polyporus pinsitus* (I) laccase comprising the amino acid sequence shown in SEQ ID No. 2;
PpL2: *Polyporus pinsitus* (II) laccase comprising the amino acid sequence shown in SEQ ID No. 3;
PrL: *Phlebia radiata* laccase comprising the amino acid sequence shown in SEQ ID No. 4;
RsL3: *Rhizoctonia solani* (I) laccase comprising the amino acid sequence shown in SEQ ID No. 5;
RsL2: *Rhizoctonia solani* (II) laccase comprising the amino acid sequence shown in SEQ ID No. 6;
RsL4: *Rhizoctonia solani* (III) laccase comprising the amino acid sequence shown in SEQ ID No. 7;
RsL1: *Rhizoctonia solani* (IV) laccase comprising the amino acid sequence shown in SEQ ID No. 8;
StL: *Scytalidium thermophilum* laccase comprising the amino acid sequence shown in SEQ ID No. 9; and
MtL: *Myceliophthora thermophila* laccase comprising the amino acid sequence shown in SEQ ID No. 10.

The above shown rows have homologous positions. (–) or ( )=not present in this laccase.

The following variants are preferred:
A variant of a parent Coprinus laccase, which comprises one or more of the following substitutions in SEQ ID No. 1:
W125 A, V, L, I, P, F, M, G, S, T, C, Y, N, Q, D, E, K, R, H;
Y134 A, V, L, I, 2, F, W, G, S, T, C, M, N, Q, D, E, K, R, H;
Y126 A, V, L, I, P, F, W, G, S, T, C, M, N, Q, D, E, K, R, H;

Y170 A, V, L, I, P, F, W, G, S, T, C, M, N, Q, D, E, K, R, H;
MN5 A, V, L, I, P, F, W, G, S, T, C, Y, N, Q, D, E, K, R, H;
M477 A, V, L, I, P, F, W, G, S, T, C, Y, N, Q, D, E, K, R, H.

In particular a variant of a parent Coprinus laccase, which comprises one or more of the following substitutions in SEQ ID No. 1:
W125 F, H;
Y134 F;
Y126 F;
Y170 F;
M75 F, V, I, L, Q;
M477 F, V, I, L, Q.

A variant of a parent *Polyporus pinsitus* (I) laccase, which comprises a mutation in a position corresponding to at least one of the following positions in SEQ ID No. 2:
W107 A, V, L, I, P, F, M, G, S, T, C, Y, N, Q, D, E, K, R, H;
Y116 A, V, L, I, P, F, W, G, S, T, C, M, N, Q, D, E, K, R, H;
Y108 A, V, L, I, P, F, W, G, S, T, C, M, N, Q, D, E, K, R, H;
Y152 A, V, L, I, P, F, W, G, S, T, C, M, N, Q, D, E, K, R, H;
M57 A, V, L, I, P, F, W, G, S, T, C, Y, N, Q, D, E, K, R, H;
M328 A, V, L, I, P, F, W, G, S, T, C, Y, N, Q, D, E, K, R, H.

In particular a variant of a parent Polyporus pinsitus (I) laccase, which comprises a mutation in a position corresponding to at least one of the following positions in SEQ ID No. 2:
W107 F, H;
Y116 F;
Y108 F;
Y152 F;
M57 F, V, I, L, Q;
M328 F, V, I, L, Q.

A variant of a parent *Polyporus pinsitus* (II) laccase, which comprises a mutation in a position corresponding to at least one of the following positions in SEQ ID No. 3:
W107 A, V, L, I, P, F, M, G, S, T, C, Y, N, Q, D, E, K, R, H;
Y116 A, V, L, I, P, F, W, G, S, T, C, M, N, Q, D, E, K, R, H;
Y108 A, V, L, I, P, F, W, G, S, T, C, M, N, Q. D, E, K, R, H;
Y152 A, V, L, I, P, F, W, G, S, T, C, M, N, Q, D, E, K, R, H;
M57 A, V, L, I, P, F, W. G, S, T, C, Y, N, Q, D, E, K, R, H.

In particular a variant of a parent *Polyporus pinsitus* (II) laccase, which comprises a mutation in a position corresponding to at least one of the following positions in SEQ ID No. 3:
W107 F, H;
Y116 F;
Y108 F;
Y152 F;
M57 F, V, I, L, Q.

A variant of a parent *Phlebia radiata* laccase, which comprises a mutation in a position corresponding to at least one of the following positions in SEQ ID No. 4:
W128 A, V, L, I, P, F, M, G, S, T, C, Y, N, Q, D, E, K, R, H;
Y137 A, V, L, I, P, F, W, G, S, T, C, M, N, Q, D, E, K, R, H;
Y129 A, V, L, I, P, F, W, G, S, T, C, M, N, Q, D, E, K, R, H;
Y137 A, V, L, I, P, F, W, G, S, T, C, M, N, Q, D, E, K, R, H;
M78 A, V, L, I, P, F, W, G, S, T, C, Y, N, Q, D, E, K, R, H.

In particular a variant of a parent *Phlebia radiata* laccase, which comprises a mutation in a position corresponding to at least one of the following positions in SEQ ID No. 4:
W128 F, H;
Y137 F;
Y129 F;
Y137 F;
M78 F, V, I, L, Q.

A variant of a parent *Rhizoctonia solani* (I) laccase, which comprises a mutation in a position corresponding to at least one of the following positions in SEQ ID No. 5:
W126 A, V, L, I, P, F, M, G, S, T, C, Y, N, Q, D, E, K, R, H;
Y135 A, V, L, I, P, F, W, G, S, T, C, M, N, Q, D, E, K, R, H;
Y127 A, V, L, I, P, F, W, G, S, T, C, M, N, Q, D, E, K, R, H;
Y171 A, V, L, I, 2, F, W, G, S, T, C, M, N, Q, D, E, K, R, H;
M76 A, V, L, I, P, F, W, G, S, T, C, Y, N, Q, D, E, K, R, H.

In particular a variant of a parent *Rhizoctonia solani* (I) laccase, which comprises a mutation in a position corresponding to at least one of the following positions in SEQ ID No. 5:
W126 F, H;
Y135 F;
Y127 F;
Y171 F;
M76 F, V, I, L, Q.

A variant of a parent *Rhizoctonia solani* (II) laccase, which comprises a mutation in a position corresponding to at least one of the following positions in SEQ ID No. 6:
W439 A, V, L, I, P, F, M, G, S, T, C, Y, N, Q, D, E, K, R, H;
W125 A, V, L, I, P, F, M, G, S, T, C, Y, N, Q, D, E, K, R, H;
Y134 A, V, L, I, P, F, W, G, S, T, C, M, N, Q, D, E, K, R, H;
Y126 A, V, L, I, P, F, W, G, S, T, C, M, N, Q, D, E, K, R, H;
Y170 A, V, L, I, P, F, W, G, S, T, C, M, N, Q, D, E, K, R, H;
M75 A, V, L, I, P, F, W, G, S, T, C, Y, N, Q, D, E, K, R, H.

In particular a variant of a parent *Rhizoctonia solani* (II) laccase, which comprises a mutation in a position corresponding to at least one of the following positions in SEQ ID No. 6:
W439 F, H;
W125 F, H;
Y134 F;
Y126 F;
Y170 F;
M75 F, V, I, L, Q.

A variant of a parent *Rhizoctonia solani* (III) laccase, which comprises a mutation in a position corresponding to at least one of the following positions in SEQ ID No. 7:
W411 A, V, L, I, P, F, M, G, S, T, C, Y, N, Q, D, E, K, R, H;
W125 A, V, L, I, P, F, M, G, S, T, C, Y, N, Q, D, E, K, R, H;
Y134 A, V, L, I, P, F, W, G, S, T, C, M, N, Q, D, E, K, R, H;
Y126 A, V, L, I, 2, F, W, G, S, T, C, M, N, Q, D, E, K, P, H;

Y170 A, V, L, I, P, F, W, G, S, T, C, M, N, Q, D, E, K, R, H;
M75 A, V, L, I, P, F, W, G, S, T, C, Y, N, Q. D, E, K, R, H.

In particular a variant of a parent *Rhizoctonia solani* (III) laccase, which comprises a mutation in a position corresponding to at least one of the following positions in SEQ ID No. 7:
W411 F, H;
W125 F, H;
Y134 F;
Y126 F;
Y170 F;
M75 F, V, I, L, Q.

A variant of a parent *Rhizoctonia solani* (IV) laccase, which comprises a mutation in a position corresponding to at least one of the following positions in SEQ ID No. 8:
W411 A, V, L, I, P, F, M, G, S, T, C, Y, N, Q, D, E, K, R, H;
W125 A, V, L, I, P, F, M, G, S, T, C, Y, N, Q, D, E, K, R, H;
Y134 A, V, L, I, P, F, W, G, S, T, C, M, N, Q, D, E, K, R, H;
Y126 A, V, L, I, P, F, W, G, S, T, C, M, N, Q, D, E, K, R, H;
Y170 A, V, L, I, P, F, W, G, S, T, C, M, N, Q, D, E, K, R, H;
M75 A, V, L, I, P, F, W, G, S, T, C, Y, N, Q, D, E, K, R, H.

In particular a variant of a parent *Rhizoctonia solani* (IV) laccase, which comprises a mutation in a position corresponding to at least one of the following positions in SEQ ID No. 8:
W411 F, H;
W125 F, H;
Y134 F;
Y126 F;
Y170 F;
M75 F, V, I, L, Q.

A variant of a parent *Scytalidium thermophilum* laccase, which comprises a mutation in a position corresponding to at least one of the following positions in SEQ ID No. 9:
M483 A, V, L, I, P, F, W, G, S, T, C, Y, N, Q, D, E, K, R, H;
W422 A, V, L, I, P, F, M, G, S, T, C, Y, N, Q, D, E, K, R, H;
W181 A, V, L, I, P, F, M, G, S, T, C, Y, N, Q, D, E, K, R, H;
Y190 A, V, L, I, 2, F, W, G, S, T, C, M, N, Q, D, E, K, R, H;
M530 A, V, L, I, P, F, W, G, S, T, C, Y, N, Q. D, E, K, R, H;
Y182 A, V, L, I, P, F, W, G, S, T, C, M, N, Q, D, E, K, R, H;
Y221 A, V, L, I, P, F, W, G, S, T, C, M, N, Q, D, E, K, R, H;
M300 A, V, L, I, P, F, W, G, S, T, C, Y, N, Q, D, E, K, R, H;
M313 A, V, L, I, P, F, W, G, S, T, C, Y, N, Q, D, E, K, R, H.

In particular a variant of a parent *Scytalidium thermophilum* laccase, which comprises a mutation in a position corresponding to at least one of the following positions in SEQ ID No. 9:
M483 F, V, I, L, Q;
W422 F, H;
W181 F, H;
Y190 F;
M530 F, V, I, L, Q;
Y182 F;
Y221 F;
M300 F, V, I, L, Q;
M313 F, V, I, L, Q.

A variant of a parent *Myceliophthora thermophila* laccase, which comprises a mutation in a position corresponding to at least one of the following positions in SEQ ID No. 10:
M433 A, V, L, I, P, F, W, G, S, T, C, Y, N, Q, D, E, K, R, H;
W373 A, V, L, I, 2, F, M, G, S, T, C, Y, N, Q, D, E, K, R, H;
W136 A, V, L, I, P, F, M, G, S, T, C, Y, N, Q, D, E, K, R, H;
Y145 A, V, L, I, 2, F, W, G, S¢,T, C, M, N, Q, D, E, K, R, H;
M480 A, V, L, I, P, F, W, G, S, T, C, Y, N, Q. D, E, K, R, H;
Y137 A, V, L, I, P, F, W, G, S, T, C, M, N, .Q, D, E, K, R, H;
Y176 A, V, L, I, P, F, W, G, S, T, C, M, N, Q, D, E, K, R, H;
M254 A, V, L, I, P, F, W, G, S, T, C, Y, N, Q, D, E, K, R, H.

In particular a variant of a parent *Myceliophthora thermophila* laccase, which comprises a mutation in a position corresponding to at least one of the following positions in SEQ ID No. 10:
M433 F, V, I, L, Q;
W373 F, H;
W136 F, H;
Y145 F;
M480 F, V, I, L, Q;
Y137 F;
Y176 F;
M254 F, V, I, L, Q.

Methods of Preparing Laccase Variants

Several methods for introducing mutations into genes are known in the art. After a brief discussion of the cloning of laccase-encoding DNA sequences, methods for generating mutations at specific sites within the laccase-encoding sequence will be discussed.

Cloning a DNA Sequence Encoding a Laccase

The DNA sequence encoding a parent laccase may be isolated from any cell or microorganism producing the laccase in question, using various methods well known in the art. First, a genomic DNA and/or cDNA library should be constructed using chromosomal DNA or messenger RNA from the organism that produces the laccase to be studied. Then, if the amino acid sequence of the laccase is known, homologous, labelled oligonucleotide probes may be synthesized and used to identify laccase-encoding clones from a genomic library prepared from the organism in question. Alternatively, a labelled oligonucleotide probe containing sequences homologous to a known laccase gene could be used as a probe to identify laccase-encoding clones, using hybridization and washing conditions of lower stringency.

A method for identifying laccase-encoding clones involves inserting cDNA into an expression vector, such as a plasmid, transforming laccase-negative fungi with the resulting cDNA library, and then plating the transformed fungi onto agar containing a substrate for laccase, thereby allowing clones expressing the laccase to be identified.

Alternatively, the DNA sequence encoding the enzyme may be prepared synthetically by established standard methods, e.g. the phosphoroamidite method. In the phosphoroamidite method, oligonucleotides are synthesized, e.g.

in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers.

Site-directed Mutagenesis

Once a laccase-encoding DNA sequence has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the laccase-encoding sequence, is created in a vector carrying the laccase gene. Then the synthetic nucleotide, bearing the desired mutation, is annealed to a homologous portion of the single-stranded DNA. The remaining gap is then filled in with T7 DNA polymerase and the construct is ligated using T4 ligase. A specific example of this method is described in Morinaga et al. (1984). U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method of introducing mutations into laccase-encoding DNA sequences is described in Nelson and Long (1989). It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Random Mutagenesis

The random mutagenesis of a DNA sequence encoding a parent laccase may conveniently be performed by use of any method known in the art.

For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents.

The mutagenizing agent may, e.g., be one which induces transitions, transversions, inversions, scrambling, deletions, and/or insertions.

Examples of a physical or chemical mutagenizing agent suitable for the present purpose include ultraviolet (UV) irradiation, hydroxylamine, N-methyl-NI-nitro-N-nitrosoguanidine (MNNG), 0-methyl hydroxylamine, nitrous acid, ethyl methane sulphonate (EMS), sodium bisulphite, formic acid, and nucleotide analogues.

When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having -the desired properties.

When the mutagenesis is performed by the use of an oligonucleotide, the oligonucleotide may be doped or spiked with the three non-parent nucleotides during the synthesis of the oligonucleotide at the positions which are to be changed. The doping or spiking may be done so that codons for unwanted amino acids are avoided. The doped or spiked oligonucleotide can be incorporated into the DNA encoding the laccase enzyme by any published technique, using e.g. ICR, LCR or any DNA polymerase and ligase.

When PCR-generated mutagenesis is used, either a chemically treated or non-treated gene encoding a parent laccase enzyme is subjected to PCR under conditions that increase the mis-incorporation of nucleotides (Deshler 1992; Leung et al., Technique, Vol.1, 1989, pp. 11–15).

A mutator strain of *E. coli* (Fowler et al., Molec. Gen. Genet., 133, 1974, pp. 179–191), *S. cereviseae* or any other microbial organism may be used for the random mutagenesis of the DNA encoding the laccase enzyme by e.g. transforming a plasmid containing the parent enzyme into the mutator strain, growing the mutator strain with the plasmid and isolating the mutated plasmid from the mutator strain. The mutated plasmid may subsequently be transformed into the expression organism.

The DNA sequence to be mutagenized may conveniently be present in a genomic or CDNA library prepared from an organism expressing the parent laccase enzyme. Alternatively, the DNA sequence may be present on a suitable vector such as a plasmid or a bacteriophage, which as such may be incubated with or otherwise exposed to the mutagenizing agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to the expression step or the screening step being performed. Such amplification may be performed in accordance with methods known in the art, the presently preferred method being PCR-generated amplification using oligonucleotide primers prepared on the basis of the DNA or amino acid sequence of the parent enzyme.

Subsequent to the incubation with or exposure to the mutagenizing agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are fungal hosts such as *Aspergillus niger* or *Aspergillus oryzae*.

The mutated DNA sequence may further comprise a DNA sequence encoding functions permitting expression of the mutated DNA sequence.

Localized Random Mutagenesis

The random mutagenesis may advantageously be localized to a part of the parent laccase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized random mutagenesis is conveniently performed by use of PCR-generated mutagenesis techniques as described above or any other suitable technique known in the art.

Alternatively, the DNA sequence encoding the part of the DNA sequence to be modified may be isolated, e.g. by being inserted into a suitable vector, and said part may subsequently be subjected to mutagenesis by use of any of the mutagenesis methods discussed above.

With respect to the screening step in the above-mentioned method of the invention, this may conveniently be performed by use of aa filter assay based on the following principle:

A microorganism capable of expressing the mutated laccase enzyme of interest is incubated on a suitable medium and under suitable conditions for the enzyme to be secreted, the medium being provided with a double filter comprising a first protein-binding filter and on top of that a second filter exhibiting a low protein binding capability. The microorganism is located on the second filter. Subsequent to the incubation, the first filter comprising enzymes secreted from the microorganisms is separated from the second filter comprising the microorganisms. The first filter is subjected to screening for the desired enzymatic activity and the corresponding microbial colonies present on the second filter are identified.

The filter used for binding the enzymatic activity may be any protein binding filter e.g. nylon or nitrocellulose. The top filter carrying the colonies of the expression organism may be any filter that has no or low affinity for binding proteins e.g. cellulose acetate or Durapore™. The filter may be pretreated with any of the conditions to be used for screening or may be treated during the detection of enzymatic activity.

The enzymatic activity may be detected by a dye, fluorescence, precipitation, pH indicator, IR-absorbance or any other known technique for detection of enzymatic activity.

The detecting compound may be immobilized by any immobilizing agent, e.g., agarose, agar, gelatine, polyacrylamide, starch, filter paper, cloth; or any combination of immobilizing agents.

Testing of Variants of the Invention

The storage stability of Coprinus variants or Coprinus-like variants should be investigated at 40° C. for 2 weeks at pH 5, 8 and 9.3, respectively. The stability of the parent laccase and the variants may be tested both in a li-quid buffer formulation and in a lyophilized form.

According to the invention the residual activity of the variants following two weeks of incubation are then compared to the residual activity of the parent laccase, and variants with an improved stability at either pH 5, 8 or 9.3 are selected.

Laccase Activity

In the context of this invention, the laccase activity was measured using 10-(2-hydroxyethyl)-phenoxazine (HEPO) as substrate for the various laccases. HEPO was synthesized using the same procedure as described for 10-(2-hydroxyethyl)-phenothiazine, (G. Cauquil in Bulletin de la Society Chemique de France, 1960, p. 1049). In the presence of oxygen laccases (E.C. 1.10.3.2) oxidize HEPO to a HEPO radical that can be monitored photometrically at 528 nm.

The *Coprinus cinereus* laccase was measured using 0.4 mM HEPO in 50 mM sodium acetate, pH 5.0, 0.05% TWEEN-20 at 30° C. The absorbance at 528 nm was followed for 200 s and the rate calculated from the linear part of the progress curve.

The *Myceliophthora thermophila* laccase was measured using 0.4 mM HEPO in 25 mM Tris-HCl, pH 7.5, 0.05% Tween-20 at 30° C. The absorbance at 528 nm was followed for 200 s and the rate calculated from the linear part of the progress curve.

The *Polyporus pinsitus* laccase was measured using 0.4 mM HEPO in 50 mM MES-NaOH, pH 5.5. The absorbance at 528 nm was followed for 200 s and the rate calculated from the linear part of the progress curve.

Expression of Laccase Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

The recombinant expression vector carrying the DNA sequence encoding a laccase variant of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding a laccase variant of the invention, especially in a fungal host, are those derived from the gene encoding *A. oryzae* TAKA amylase, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

The expression vector of the invention may also comprise a suitable transcription terminator and, in eukaryotes, polyadenylation sequences operably connected to the DNA sequence encoding the laccase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene, the product of which complements a defect in the host cell, such as one which confers antibiotic resistance such as ampicillin, kanamycin, chloramphenicol or tetracyclin resistance. Furthermore, the vector may comprise Aspergillus selection markers such as amdS, argB, niaD and sC, a marker giving rise to hygromycin resistance, or the selection may be accomplished by co-transformation, e.g. as described in WO 91/17243.

The procedures used to ligate the DNA construct of the invention encoding a laccase variant, the promoter, terminator and other elements, respectively, and to insert them into suitable. vectors containing the information necessary for replication, are well known to persons skilled in the art (cf., for instance, Sambrook et al. (1989)).

The cell of the invention, either comprising a DNA construct or an expression vector of the invention as defined above, is advantageously used as a host cell in the recombinant production of a laccase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g. a fungal cell.

The filamentous fungus may advantageously belong to a species of Aspergillus, e.g. *Aspergillus oryzee* or *Aspergillus niger*. Fungal cells may be transformed by a process involving protoplast formation and transformation of the protoplasts followed by regeneration of the cell wall in a manner known per se. A suitable procedure for transformation of Aspergillus host cells is described in EP 238 023.

In a yet further aspect, the present invention relates to a method of producing a laccase variant of the invention, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the laccase variant of the invention. Suitable media are available from commercial suppliers or may be prepared according to published recipes (e.g. as described in catalogues of the American Type Culture Collection).

The laccase variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Industrial Applications

The laccase variants of this invention possesses valuable properties allowing for various industrial applications, in particular lignin modification, paper strengthening, dye transfer inhibition in detergents, phenol polymerization, hair dyeing, bleaching of textiles (in particular bleaching of denim as described in WO 96/12845 and WO 96/12846) and waste water treatment. Any detergent composition normally used for enzymes may be used, e.g., the detergent compositions disclosed in WO The invention is further illustrated in the following examples, which are not intended to be in any way limiting to the scope of the invention as claimed.

EXAMPLE 1

Storage Stability of the Wild Type *Myceliophthora thermophila* and the *Polyporus pinsitus* Laccases.

The storage stability of the *Myceliophthora thermophila* and the *Polyporus pinsitus* laccases was tested for 2 weeks at 40° C. at pH S, 8 and 9.3, respectively.

The laccase (1 mg/ml) was dialyzed against 0.1 M sodium acetate, pH 5, or 0.1 M Tris-maleate, pH 8, or 0.1 M Tris-maleate, pH 9.3. Following dialysis the different preparations were poured into two sets of glass vials with screw caps: one for the liquid formulation and the other one for the lyophilized form. After two weeks of incubation the enzyme activity was measured as described above and the residual activity of the enzymes was calculated in percentage using a preparation of *Myceliophthora thermophila* and *Polyporus pinsitus* kept at 4° C. as references. The results are given below in Table 1 and 2.

TABLE 1

Storage stability of *Myceliophthora thermophila*

| pH | Liquid formulation Residual activity (%) | Lyophilized form Residual activity (%) |
| --- | --- | --- |
| 5.0 | <5 | <5 |
| 8.0 | <5 | <5 |
| 9.3 | 35 | 30 |

TABLE 2

Storage stability of *Polyporus pinsitus*

| pH | Liquid formulation Residual activity (%) | Lyophilized form Residual activity (%) |
| --- | --- | --- |
| 5.0 | <5 | n.d. |
| 8.0 | 35 | n.d. |
| 9.3 | n.d* | n.d. |

*not determined

EXAMPLE 2

Homology Building of the *Polyporus pinsitus* 3D-structure

Using sequence homology of *Coprinus cinereus* (CcL) to other sequences, e.g., *Polyporus pinsitus*, Coprinus-like 3 D-structures can be found.

In comparison with the *Coprinus cinereus*, used for elucidating the structure, *Polyporus pinsitus* differs in a number of residues. The model may be built using the HOMOLOGY program from BIOSYM. The program substitutes the amino acids in the *Coprinus cinereus* with amino acids from *Polyporus pinsitus* in the homologous positions defined in the program as structurally conserved regions (SCR). The residues in between are built using the LOOP option with GENERATE. Using these steps a crude model may be obtained which gives information of spatial interactions.

The structure can be refined using the method described in the HOMOLOGY package.

EXAMPLE 3

Storage Stability of *Myceliophthora thermophila* Variants Laccase Activity:

In this Example the *Myceliophthora thermophila* laccase variants were measured using 0.4 mM HEPO in 0.1 M Tris-maleate, pH 7.5, 0.05% TWEEN-20 at 30° C. The absorbance at 528 nm was followed for 200 s and the rate calculated from the linear part of the progress curve.

The storage stability of the *Myceliophthora thermophila* variants were tested for 4 weeks at 40° C. at pH 5, 7, and 9.3, respectively. The laccase (1 mg/ml) was dialyzed against 0.1 M Tris-maleate, pH 5 or 0.1 M Tris-maleate, pH 7 or 0.1 M Tris-maleate, pH 9.3. Following dialysis the different preparations were poured into two set of glass vials with screw caps: one for the liquid formulation and the other set of glasses for lyophilization. Following two and four weeks of incubation the enzyme activity was measured as described above and the residual activity of the variants were calculated in percentage using a preparation kept at 4° C. as reference.

TABLE 3

Storage stability of *Myceliophthora thermophila* variants, lyophilized formulation

|  | Residual activity, pH 5 | | Residual activity, pH 7 | | Residual activity, pH 9.2 | |
|---|---|---|---|---|---|---|
|  | 2 weeks | 4 weeks | 2 weeks | 4 weeks | 2 weeks | 4 weeks |
| wt | 18 | 18 | 55 | 36 | 59 | 38 |
| W136F | <5 | <5 | 76 | 64 | 88 | 77 |
| Y137F | 12 | <5 | 58 | 41 | 64 | 49 |
| Y145F | <5 | <5 | 53 | 20 | 45 | 51 |
| W373F | 14 | 14 | 33 | 19 | 51 | 36 |
| M433I | 7 | <5 | 57 | 43 | 74 | 35 |
| M480L | 33 | 18 | 65 | 32 | 72 | 52 |
| W507F | 18 | <5 | 72 | 51 | 68 | 71 |

In lyophilized form none of the tested variants have improved stability at pH 5. At pH 7 and pH 9.2 both W136F and W507F have increased stability. At pH 9.2 M480L is also better than wt.

TABLE 4

Storage stability of *Myceliophthora thermophila* variants, liquid formulation

|  | Residual activity, pH 5, 2 weeks | Residual activity, ph 7, 2 weeks | Residual activity, pH 9.2, 2 weeks |
|---|---|---|---|
| wt | <5 | 5 | 20 |
| W136F | 5 | 28 | 55 |
| Y137F | <5 | <5 | <5 |
| Y145F | <5 | <5 | <5 |
| W373F | <5 | 40 | <5 |
| M433I | 8 | 40 | 65 |
| M480L | <5 | <5 | 15 |
| W507F | <5 | <5 | 22 |

Also in the liquid formulation none of the tested variants have improved stability at pH 5. At pH 7 and pH 9.2 both W136F and M433I has increased stability. At pH7 W373F has better stability than wt but the variant looses the stability completely at pH 9.2.

Of the tested variants only W136F has increased stability in both formulations.

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
        (A) LENGTH: 539 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 1:

```
Met Phe Lys Asn Leu Leu Ser Phe Ala Leu Leu Ala Ile Ser Val Ala
1               5                   10                  15

Asn Ala Gln Ile Val Asn Ser Val Asp Thr Met Thr Leu Thr Asn Ala
            20                  25                  30

Asn Val Ser Pro Asp Gly Phe Thr Arg Ala Gly Ile Leu Val Asn Gly
        35                  40                  45

Val His Gly Pro Leu Ile Arg Gly Gly Lys Asn Asp Asn Phe Glu Leu
    50                  55                  60

Asn Val Val Asn Asp Leu Asp Asn Pro Thr Met Leu Arg Pro Thr Ser
65                  70                  75                  80

Ile His Trp His Gly Leu Phe Gln Arg Gly Thr Asn Trp Ala Asp Gly
                85                  90                  95

Ala Asp Gly Val Asn Gln Cys Pro Ile Ser Pro Gly His Ala Phe Leu
            100                 105                 110

Tyr Lys Phe Thr Pro Ala Gly His Ala Gly Thr Phe Trp Tyr His Ser
        115                 120                 125
```

-continued

```
His Phe Gly Thr Gln Tyr Cys Asp Gly Leu Arg Gly Pro Met Val Ile
    130                 135                 140
Tyr Asp Asp Asn Asp Pro His Ala Ala Leu Tyr Asp Glu Asp Asp Glu
145                 150                 155                 160
Asn Thr Ile Ile Thr Leu Ala Asp Trp Tyr His Ile Pro Ala Pro Ser
                165                 170                 175
Ile Gln Gly Ala Ala Gln Pro Asp Ala Thr Leu Ile Asn Gly Lys Gly
                180                 185                 190
Arg Tyr Val Gly Gly Pro Ala Ala Glu Leu Ser Ile Val Asn Val Glu
            195                 200                 205
Gln Gly Lys Lys Tyr Arg Met Arg Leu Ile Ser Leu Ser Cys Asp Pro
    210                 215                 220
Asn Trp Gln Phe Ser Ile Asp Gly His Glu Leu Thr Ile Ile Glu Val
225                 230                 235                 240
Asp Gly Gln Leu Thr Glu Pro His Thr Val Asp Arg Leu Gln Ile Phe
                245                 250                 255
Thr Gly Gln Arg Tyr Ser Phe Val Leu Asp Ala Asn Gln Pro Val Asp
                260                 265                 270
Asn Tyr Trp Ile Arg Ala Gln Pro Asn Lys Gly Arg Asn Gly Leu Ala
            275                 280                 285
Gly Thr Phe Ala Asn Gly Val Asn Ser Ala Ile Leu Arg Tyr Ala Gly
    290                 295                 300
Ala Ala Asn Ala Asp Pro Thr Thr Ser Ala Asn Pro Asn Pro Ala Gln
305                 310                 315                 320
Leu Asn Glu Ala Asp Leu His Ala Leu Ile Asp Pro Ala Ala Pro Gly
                325                 330                 335
Ile Pro Thr Pro Gly Ala Ala Asp Val Asn Leu Arg Phe Gln Leu Gly
                340                 345                 350
Phe Ser Gly Gly Arg Phe Thr Ile Asn Gly Thr Ala Tyr Glu Ser Pro
            355                 360                 365
Ser Val Pro Thr Leu Leu Gln Ile Met Ser Gly Ala Gln Ser Ala Asn
    370                 375                 380
Asp Leu Leu Pro Ala Gly Ser Val Tyr Glu Leu Pro Arg Asn Gln Val
385                 390                 395                 400
Val Glu Leu Val Val Pro Ala Gly Val Leu Gly Gly Pro His Pro Phe
                405                 410                 415
His Leu His Gly His Ala Phe Ser Val Val Arg Ser Ala Gly Ser Ser
            420                 425                 430
Thr Tyr Asn Phe Val Asn Pro Val Lys Arg Asp Val Val Ser Leu Gly
    435                 440                 445
Val Thr Gly Asp Glu Val Thr Ile Arg Phe Val Thr Asp Asn Pro Gly
    450                 455                 460
Pro Trp Phe Phe His Cys His Ile Glu Phe His Leu Met Asn Gly Leu
465                 470                 475                 480
Ala Ile Val Phe Ala Glu Asp Met Ala Asn Thr Val Asp Ala Asn Asn
                485                 490                 495
Pro Pro Val Glu Trp Ala Gln Leu Cys Glu Ile Tyr Asp Asp Leu Pro
            500                 505                 510
Pro Glu Ala Thr Ser Ile Gln Thr Val Val Arg Arg Ala Glu Pro Thr
    515                 520                 525
Gly Phe Ser Ala Lys Phe Arg Arg Glu Gly Leu
    530                 535
```

(2) INFORMATION FOR SEQ ID NO: 2:

(i) SEQUENCE CHARACTERISTICS:
        (A) LENGTH: 499 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

```
Gly Ile Gly Pro Val Ala Asp Leu Thr Ile Thr Asn Ala Ala Val Ser
 1               5                  10                  15

Pro Asp Gly Phe Ser Arg Gln Ala Val Val Asn Gly Gly Thr Pro
            20                  25                  30

Gly Pro Leu Ile Thr Gly Asn Met Gly Asp Arg Phe Gln Leu Asn Val
            35                  40                  45

Ile Asp Asn Leu Thr Asn His Thr Met Leu Lys Ser Thr Ser Ile His
 50                  55                  60

Trp His Gly Phe Phe Gln Lys Gly Thr Asn Trp Ala Asp Gly Pro Ala
 65                  70                  75                  80

Phe Ile Asn Gln Cys Pro Ile Ser Ser Gly His Ser Phe Leu Tyr Asp
                 85                  90                  95

Phe Gln Val Pro Asp Gln Ala Gly Thr Phe Trp Tyr His Ser His Leu
                100                 105                 110

Ser Thr Gln Tyr Cys Asp Gly Leu Arg Gly Pro Phe Val Val Tyr Asp
            115                 120                 125

Pro Asn Asp Pro Ala Ala Asp Leu Tyr Asp Val Asp Asn Asp Asp Thr
130                 135                 140

Val Ile Thr Leu Val Asp Trp Tyr His Val Ala Ala Lys Leu Gly Pro
145                 150                 155                 160

Ala Phe Pro Leu Gly Ala Asp Ala Thr Leu Ile Asn Gly Lys Gly Arg
                165                 170                 175

Ser Pro Ser Thr Thr Thr Ala Asp Leu Ser Val Ile Ser Val Thr Pro
            180                 185                 190

Gly Lys Arg Tyr Arg Phe Arg Leu Val Ser Leu Ser Cys Asp Pro Asn
            195                 200                 205

Tyr Thr Phe Ser Ile Asp Gly His Asn Met Thr Ile Ile Glu Thr Asp
            210                 215                 220

Ser Ile Asn Thr Ala Pro Leu Val Val Asp Ser Ile Gln Ile Phe Ala
225                 230                 235                 240

Ala Gln Arg Tyr Ser Phe Val Leu Glu Ala Asn Gln Ala Val Asp Asn
                245                 250                 255

Tyr Trp Ile Arg Ala Asn Pro Asn Phe Gly Asn Val Gly Phe Thr Gly
            260                 265                 270

Gly Ile Asn Ser Ala Ile Leu Arg Tyr Asp Gly Ala Ala Ala Val Glu
            275                 280                 285

Pro Thr Thr Thr Gln Thr Thr Ser Thr Ala Pro Leu Asn Glu Val Asn
            290                 295                 300

Leu His Pro Leu Val Thr Thr Ala Val Pro Gly Ser Pro Val Ala Gly
305                 310                 315                 320

Gly Val Asp Leu Ala Ile Asn Met Ala Phe Asn Phe Asn Gly Thr Asn
                325                 330                 335

Phe Phe Ile Asn Gly Ala Ser Phe Thr Pro Pro Thr Val Pro Val Leu
                340                 345                 350
```

```
Leu Gln Ile Ile Ser Gly Ala Gln Asn Ala Gln Asp Leu Leu Pro Ser
        355                 360                 365

Gly Ser Val Tyr Ser Leu Pro Ser Asn Ala Asp Ile Glu Ile Ser Phe
    370                 375                 380

Pro Ala Thr Ala Ala Pro Gly Ala Pro His Pro Phe His Leu His
385                 390                 395                 400

Gly His Ala Phe Ala Val Val Arg Ser Ala Gly Ser Thr Val Tyr Asn
                405                 410                 415

Tyr Asp Asn Pro Ile Phe Arg Asp Val Val Ser Thr Gly Thr Pro Ala
            420                 425                 430

Ala Gly Asp Asn Val Thr Ile Arg Phe Arg Thr Asp Asn Pro Gly Pro
        435                 440                 445

Trp Phe Leu His Cys His Ile Asp Phe His Leu Glu Ala Gly Phe Ala
    450                 455                 460

Val Val Phe Ala Glu Asp Ile Pro Asp Val Ala Ser Ala Asn Pro Val
465                 470                 475                 480

Pro Gln Ala Trp Ser Asp Leu Cys Pro Thr Tyr Asp Ala Leu Asp Pro
                485                 490                 495

Ser Asp Gln (2) INFORMATION FOR SEQ ID NO: 3:

(i) SEQUENCE CHARACTERISTICS:
        (A) LENGTH: 499 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

Ala Ile Gly Pro Val Ala Ser Leu Val Val Ala Asn Ala Pro Val Ser
1               5                   10                  15

Pro Asp Gly Phe Leu Arg Asp Ala Ile Val Val Asn Gly Val Val Pro
                20                  25                  30

Ser Pro Leu Ile Thr Gly Lys Lys Gly Asp Arg Phe Gln Leu Asn Val
            35                  40                  45

Val Asp Thr Leu Thr Asn His Ser Met Leu Lys Ser Thr Ser Ile His
    50                  55                  60

Trp His Gly Phe Phe Gln Ala Gly Thr Asn Trp Ala Glu Gly Pro Ala
65                  70                  75                  80

Phe Val Asn Gln Cys Pro Ile Ala Ser Gly His Ser Phe Leu Tyr Asp
                85                  90                  95

Phe His Val Pro Asp Gln Ala Gly Thr Phe Trp Tyr His Ser His Leu
                100                 105                 110

Ser Thr Gln Tyr Cys Asp Gly Leu Arg Gly Pro Phe Val Val Tyr Asp
            115                 120                 125

Pro Lys Asp Pro His Ala Ser Arg Tyr Asp Val Asp Asn Glu Ser Thr
        130                 135                 140

Val Ile Thr Leu Thr Asp Trp Tyr His Thr Ala Ala Arg Leu Gly Pro
145                 150                 155                 160

Lys Phe Pro Leu Gly Ala Asp Ala Thr Leu Ile Asn Gly Leu Gly Arg
                165                 170                 175

Ser Ala Ser Thr Pro Thr Ala Ala Leu Ala Val Ile Asn Val Gln His
            180                 185                 190

Gly Lys Arg Tyr Arg Phe Arg Leu Val Ser Ile Ser Cys Asp Pro Asn
```

-continued

```
                195                 200                 205
Tyr Thr Phe Ser Ile Asp Gly His Asn Leu Thr Val Ile Glu Val Asp
        210                 215                 220
Gly Ile Asn Ser Gln Pro Leu Leu Val Asp Ser Ile Gln Ile Phe Ala
225                 230                 235                 240
Ala Gln Arg Tyr Ser Phe Val Leu Asn Ala Asn Gln Thr Val Gly Asn
                245                 250                 255
Tyr Trp Val Arg Ala Asn Pro Asn Phe Gly Thr Val Gly Phe Ala Gly
            260                 265                 270
Gly Ile Asn Ser Ala Ile Leu Arg Tyr Gln Gly Ala Pro Val Ala Glu
                275                 280                 285
Pro Thr Thr Thr Gln Thr Pro Ser Val Ile Pro Leu Ile Glu Thr Asn
        290                 295                 300
Leu His Pro Leu Ala Arg Met Pro Val Pro Gly Ser Pro Thr Pro Gly
305                 310                 315                 320
Gly Val Asp Lys Ala Leu Asn Leu Ala Phe Asn Phe Asn Gly Thr Asn
                325                 330                 335
Phe Phe Ile Asn Asn Ala Thr Phe Thr Pro Pro Thr Val Pro Val Leu
            340                 345                 350
Leu Gln Ile Leu Ser Gly Ala Gln Thr Ala Gln Asp Leu Leu Pro Ala
        355                 360                 365
Gly Ser Val Tyr Pro Leu Pro Ala His Ser Thr Ile Glu Ile Thr Leu
370                 375                 380
Pro Ala Thr Ala Leu Ala Pro Gly Ala Pro His Pro Phe His Leu His
385                 390                 395                 400
Gly His Ala Phe Ala Val Val Arg Ser Ala Gly Ser Thr Thr Tyr Asn
                405                 410                 415
Tyr Asn Asp Pro Ile Phe Arg Asp Val Val Ser Thr Gly Thr Pro Ala
            420                 425                 430
Ala Gly Asp Asn Val Thr Ile Arg Phe Gln Thr Asp Asn Pro Gly Pro
        435                 440                 445
Trp Phe Leu His Cys His Ile Asp Phe His Leu Asp Ala Gly Phe Ala
        450                 455                 460
Ile Val Phe Ala Glu Asp Val Ala Asp Val Lys Ala Ala Asn Pro Val
465                 470                 475                 480
Pro Lys Ala Trp Ser Asp Leu Cys Pro Ile Tyr Asp Gly Leu Ser Glu
                485                 490                 495
Ala Asn Gln
```

(2) INFORMATION FOR SEQ ID NO: 4:

(i) SEQUENCE CHARACTERISTICS:
        (A) LENGTH: 548 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

```
Met His Thr Phe Leu Arg Ser Thr Ala Leu Val Val Ala Gly Leu Ser
1               5                   10                  15
Ala Arg Ala Leu Ala Ser Ile Gly Pro Val Thr Asp Phe His Ile Val
                20                  25                  30
Asn Ala Ala Val Ser Pro Asp Gly Phe Ser Arg Gln Ala Val Leu Ala
            35                  40                  45
```

```
Glu Gly Val Phe Pro Gly Pro Leu Ile Ala Gly Asn Lys Gly Asp Asn
 50                  55                  60

Phe Gln Ile Asn Val Ile Asp Glu Leu Thr Asn Ala Thr Met Leu Lys
 65                  70                  75                  80

Thr Thr Thr Ile His Trp His Gly Phe Phe Gln His Gly Thr Asn Trp
                     85                  90                  95

Ala Asp Gly Pro Ala Phe Ile Asn Gln Cys Pro Ile Ala Ser Gly Asp
            100                 105                 110

Ser Phe Leu Tyr Asn Phe Gln Val Pro Asp Gln Ala Gly Thr Phe Trp
            115                 120                 125

Tyr His Ser His Leu Ser Thr Gln Tyr Cys Asp Gly Leu Arg Gly Pro
            130                 135                 140

Phe Val Val Tyr Asp Pro Ala Asp Pro Tyr Leu Asp Gln Tyr Asp Val
145                 150                 155                 160

Asp Asp Asp Ser Thr Val Ile Thr Leu Ala Asp Trp Tyr His Thr Ala
                165                 170                 175

Ala Arg Leu Gly Ser Pro Phe Pro Ala Ala Asp Thr Thr Leu Ile Asn
            180                 185                 190

Gly Leu Gly Arg Cys Gly Glu Ala Gly Cys Pro Val Ser Asp Leu Ala
            195                 200                 205

Val Ile Ser Val Thr Lys Gly Lys Arg Tyr Arg Phe Arg Leu Val Ser
210                 215                 220

Ile Ser Cys Asp Ser Phe Phe Thr Phe Ser Ile Asp Gly His Ser Leu
225                 230                 235                 240

Asn Val Ile Glu Val Asp Ala Thr Asn His Gln Pro Leu Thr Val Asp
            245                 250                 255

Glu Leu Thr Ile Tyr Ala Gly Gln Arg Tyr Ser Phe Ile Leu Thr Ala
            260                 265                 270

Asp Gln Asp Val Asp Asn Tyr Trp Ile Arg Ala Asn Pro Gly Ile Gly
            275                 280                 285

Ile Thr Thr Gly Phe Ala Gly Gly Ile Asn Ser Ala Ile Leu Arg Tyr
            290                 295                 300

Asp Gly Ala Asp Val Val Glu Pro Thr Thr Thr Gln Ala Thr Ser Pro
305                 310                 315                 320

Val Val Leu Ser Glu Ser Asn Leu Ala Pro Leu Thr Asn Ala Ala Ala
                325                 330                 335

Pro Gly Leu Pro Glu Val Gly Gly Val Asp Leu Ala Leu Asn Phe Asn
            340                 345                 350

Leu Thr Phe Asp Gly Pro Ser Leu Lys Phe Gln Ile Asn Gly Val Thr
            355                 360                 365

Phe Val Pro Pro Thr Val Pro Val Leu Leu Gln Ile Leu Ser Gly Ala
370                 375                 380

Gln Ser Ala Ala Asp Leu Leu Pro Ser Gly Ser Val Tyr Ala Leu Pro
385                 390                 395                 400

Ser Asn Ala Thr Ile Glu Leu Ser Leu Pro Ala Gly Ala Leu Gly Gly
                405                 410                 415

Pro His Pro Phe His Leu His Gly His Thr Phe Ser Val Val Arg Pro
            420                 425                 430

Ala Gly Ser Thr Thr Tyr Asn Tyr Val Asn Pro Val Gln Arg Asp Val
            435                 440                 445

Val Ser Ile Gly Asn Thr Gly Asp Asn Val Thr Ile Arg Phe Asp Thr
450                 455                 460
```

-continued

```
Asn Asn Pro Gly Pro Trp Phe Leu His Cys His Ile Asp Trp His Leu
465                 470                 475                 480

Glu Ala Ala Leu Pro Leu Ser Ser Leu Arg Thr Ser Leu Thr Leu Arg
                485                 490                 495

Pro Leu Thr Leu Ser Pro Arg Thr Gly Pro Thr Cys Ala Leu Ser Thr
                500                 505                 510

Thr Leu Trp Thr His Leu Ile Thr Ser Gly Phe Ala Ser Ile Ile Gln
            515                 520                 525

Trp Met Met Gly Gly Asn Gly Leu Phe Ala Pro His Ala Leu Ser Phe
            530                 535                 540

Leu Gly Ser Gln
545

(2) INFORMATION FOR SEQ ID NO: 5:

(i) SEQUENCE CHARACTERISTICS:
        (A) LENGTH: 529 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5:

Met Leu Ser Ser Ile Thr Leu Leu Pro Leu Leu Ala Ala Val Ser Thr
1               5                   10                  15

Pro Ala Phe Ala Ala Val Arg Asn Tyr Lys Phe Asp Ile Lys Asn Val
                20                  25                  30

Asn Val Ala Pro Asp Gly Phe Gln Arg Ser Ile Val Ser Val Asn Gly
            35                  40                  45

Leu Val Pro Gly Thr Leu Ile Thr Ala Asn Lys Gly Asp Thr Leu Arg
50                  55                  60

Ile Asn Val Thr Asn Gln Leu Thr Asp Pro Ser Met Arg Arg Ala Thr
65                  70                  75                  80

Thr Ile His Trp His Gly Leu Phe Gln Ala Thr Thr Ala Asp Glu Asp
                85                  90                  95

Gly Pro Ala Phe Val Thr Gln Cys Pro Ile Ala Gln Asn Leu Ser Tyr
                100                 105                 110

Thr Tyr Glu Ile Pro Leu Arg Gly Gln Thr Gly Thr Met Trp Tyr His
            115                 120                 125

Ala His Leu Ala Ser Gln Tyr Val Asp Gly Leu Arg Gly Pro Leu Val
            130                 135                 140

Ile Tyr Asp Pro Asn Asp Pro His Lys Ser Arg Tyr Asp Val Asp Asp
145                 150                 155                 160

Ala Ser Thr Val Val Met Leu Glu Asp Trp Tyr His Thr Pro Ala Pro
                165                 170                 175

Val Leu Glu Lys Gln Met Phe Ser Thr Asn Asn Thr Ala Leu Leu Ser
                180                 185                 190

Pro Val Pro Asp Ser Gly Leu Ile Asn Gly Lys Gly Arg Tyr Val Gly
            195                 200                 205

Gly Pro Ala Val Pro Arg Ser Val Ile Asn Val Lys Arg Gly Lys Arg
210                 215                 220

Tyr Arg Leu Arg Val Ile Asn Ala Ser Ala Ile Gly Ser Phe Thr Phe
225                 230                 235                 240

Ser Ile Glu Gly His Ser Leu Thr Val Ile Glu Ala Asp Gly Ile Leu
                245                 250                 255
```

-continued

His Gln Pro Leu Ala Val Asp Ser Phe Gln Ile Tyr Ala Gly Gln Arg
            260                 265                 270

Tyr Ser Val Ile Val Glu Ala Asn Gln Thr Ala Ala Asn Tyr Trp Ile
        275                 280                 285

Arg Ala Pro Met Thr Val Ala Gly Ala Gly Thr Asn Ala Asn Leu Asp
        290                 295                 300

Pro Thr Asn Val Phe Ala Val Leu His Tyr Glu Gly Ala Pro Asn Ala
305                 310                 315                 320

Glu Pro Thr Thr Glu Gln Gly Ser Ala Ile Gly Thr Ala Leu Val Glu
                325                 330                 335

Glu Asn Leu His Ala Leu Ile Asn Pro Gly Ala Pro Gly Gly Ser Ala
            340                 345                 350

Pro Ala Asp Val Ser Leu Asn Leu Ala Ile Gly Arg Ser Thr Val Asp
            355                 360                 365

Gly Ile Leu Arg Phe Thr Phe Asn Asn Ile Lys Tyr Glu Ala Pro Ser
        370                 375                 380

Leu Pro Thr Leu Leu Lys Ile Leu Ala Asn Asn Ala Ser Asn Asp Ala
385                 390                 395                 400

Asp Phe Thr Pro Asn Glu His Thr Ile Val Leu Pro His Asn Lys Val
                405                 410                 415

Ile Glu Leu Asn Ile Thr Gly Gly Ala Asp His Pro Ile His Leu His
            420                 425                 430

Gly His Val Phe Asp Ile Val Lys Ser Leu Gly Gly Thr Pro Asn Tyr
        435                 440                 445

Val Asn Pro Pro Arg Arg Asp Val Val Arg Val Gly Gly Thr Gly Val
450                 455                 460

Val Leu Arg Phe Lys Thr Asp Asn Pro Gly Pro Trp Phe Val His Cys
465                 470                 475                 480

His Ile Asp Trp His Leu Glu Ala Gly Leu Ala Leu Val Phe Ala Glu
                485                 490                 495

Ala Pro Ser Gln Ile Arg Gln Gly Val Gln Ser Val Gln Pro Asn Asn
            500                 505                 510

Ala Trp Asn Gln Leu Cys Pro Lys Tyr Ala Ala Leu Pro Pro Asp Leu
        515                 520                 525

Gln (2) INFORMATION FOR SEQ ID NO: 6:

(i) SEQUENCE CHARACTERISTICS:
        (A) LENGTH: 599 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

Met Ala Arg Ser Thr Thr Ser Leu Phe Ala Leu Ser Leu Val Ala Ser
1               5                   10                  15

Ala Phe Ala Arg Val Val Asp Tyr Gly Phe Asp Val Ala Asn Gly Ala
            20                  25                  30

Val Ala Pro Asp Gly Val Thr Arg Asn Ala Val Leu Val Asn Gly Arg
        35                  40                  45

Phe Pro Gly Pro Leu Ile Thr Ala Asn Lys Gly Asp Thr Leu Lys Ile
    50                  55                  60

Thr Val Arg Asn Lys Leu Ser Asp Pro Thr Met Arg Arg Ser Thr Thr

```
 65                   70                   75                   80
Ile His Trp His Gly Leu Leu Gln His Arg Thr Ala Glu Glu Asp Gly
                 85                   90                   95

Pro Ala Phe Val Thr Gln Cys Pro Ile Pro Gln Glu Ser Tyr Thr
                100                 105                 110

Tyr Thr Met Pro Leu Gly Glu Gln Thr Gly Thr Tyr Trp Tyr His Ser
                115                 120                 125

His Leu Ser Ser Gln Tyr Val Asp Gly Leu Arg Gly Pro Ile Val Ile
            130                 135                 140

Tyr Asp Pro His Asp Pro Tyr Arg Asn Tyr Asp Val Asp Asp Glu
145                 150                 155                 160

Arg Thr Val Phe Thr Leu Ala Asp Trp Tyr His Thr Pro Ser Glu Ala
                165                 170                 175

Ile Ile Ala Thr His Asp Val Leu Lys Thr Ile Pro Asp Ser Gly Thr
                180                 185                 190

Ile Asn Gly Lys Gly Lys Tyr Asp Pro Ala Ser Ala Asn Thr Asn Asn
            195                 200                 205

Thr Thr Leu Glu Asn Leu Tyr Thr Leu Lys Val Lys Arg Gly Lys Arg
            210                 215                 220

Tyr Arg Leu Arg Ile Ile Asn Ala Ser Ala Ile Ala Ser Phe Arg Phe
225                 230                 235                 240

Gly Val Gln Gly His Lys Cys Thr Ile Ile Glu Ala Asp Gly Val Leu
                245                 250                 255

Thr Lys Pro Ile Glu Val Asp Ala Phe Asp Ile Leu Ala Gly Gln Arg
                260                 265                 270

Tyr Ser Cys Ile Leu Lys Ala Asp Gln Asp Pro Asp Ser Tyr Trp Ile
            275                 280                 285

Asn Ala Pro Ile Thr Asn Val Leu Asn Thr Asn Val Gln Ala Leu Leu
            290                 295                 300

Val Tyr Glu Asp Asp Lys Arg Pro Thr His Tyr Pro Trp Lys Pro Phe
305                 310                 315                 320

Leu Thr Trp Lys Ile Ser Asn Glu Ile Ile Gln Tyr Trp Gln His Lys
                325                 330                 335

His Gly Ser His Gly His Lys Gly Lys Gly His His His Lys Val Arg
                340                 345                 350

Ala Ile Gly Gly Val Ser Gly Leu Ser Ser Arg Val Lys Ser Arg Ala
                355                 360                 365

Ser Asp Leu Ser Lys Lys Ala Val Glu Leu Ala Ala Ala Leu Val Ala
370                 375                 380

Gly Glu Ala Glu Leu Asp Lys Arg Gln Asn Glu Asp Asn Ser Thr Ile
385                 390                 395                 400

Val Leu Asp Glu Thr Lys Leu Ile Pro Leu Val Gln Pro Gly Ala Pro
                405                 410                 415

Gly Gly Ser Arg Pro Ala Asp Val Val Pro Leu Asp Phe Gly Leu
                420                 425                 430

Asn Phe Ala Asn Gly Leu Trp Thr Ile Asn Asn Val Ser Tyr Ser Pro
                435                 440                 445

Pro Asp Val Pro Thr Leu Leu Lys Ile Leu Thr Asp Lys Asp Lys Val
450                 455                 460

Asp Ala Ser Asp Phe Thr Ala Asp Glu His Thr Tyr Ile Leu Pro Lys
465                 470                 475                 480

Asn Gln Val Val Glu Leu His Ile Lys Gly Gln Ala Leu Gly Ile Val
                485                 490                 495
```

```
His Pro Leu His Leu His Gly His Ala Phe Asp Val Val Gln Phe Gly
            500                 505                 510

Asp Asn Ala Pro Asn Tyr Val Asn Pro Pro Arg Arg Asp Val Val Gly
            515                 520                 525

Val Thr Asp Ala Gly Val Arg Ile Gln Phe Arg Thr Asp Asn Pro Gly
            530                 535                 540

Pro Trp Phe Leu His Cys His Ile Asp Trp His Leu Glu Glu Gly Phe
545                 550                 555                 560

Ala Met Val Phe Ala Glu Ala Pro Glu Asp Ile Lys Lys Gly Ser Gln
                565                 570                 575

Ser Val Lys Pro Asp Gly Gln Trp Lys Lys Leu Cys Glu Lys Tyr Glu
            580                 585                 590

Lys Leu Pro Glu Ala Leu Gln
            595
```

(2) INFORMATION FOR SEQ ID NO: 7:

(i) SEQUENCE CHARACTERISTICS:
        (A) LENGTH: 572 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 7:

```
Met Ala Arg Thr Thr Phe Leu Val Ser Val Ser Leu Phe Val Ser Ala
1               5                   10                  15

Val Leu Ala Arg Thr Val Glu Tyr Asn Leu Lys Ile Ser Asn Gly Lys
            20                  25                  30

Ile Ala Pro Asp Gly Val Glu Arg Asp Ala Thr Leu Val Asn Gly Gly
            35                  40                  45

Tyr Pro Gly Pro Leu Ile Phe Ala Asn Lys Gly Asp Thr Leu Lys Val
            50                  55                  60

Lys Val Gln Asn Lys Leu Thr Asn Pro Asp Met Tyr Arg Thr Thr Ser
65                  70                  75                  80

Ile His Trp His Gly Leu Leu Gln His Arg Asn Ala Asp Asp Asp Gly
                85                  90                  95

Pro Ala Phe Val Thr Gln Cys Pro Ile Val Pro Gln Ala Ser Tyr Thr
            100                 105                 110

Tyr Thr Met Pro Leu Gly Asp Gln Thr Gly Thr Tyr Trp Tyr His Ser
            115                 120                 125

His Leu Ser Ser Gln Tyr Val Asp Gly Leu Arg Gly Pro Leu Val Ile
            130                 135                 140

Tyr Asp Pro Lys Asp Pro His Arg Arg Leu Tyr Asp Ile Asp Asp Glu
145                 150                 155                 160

Lys Thr Val Leu Ile Ile Gly Asp Trp Tyr His Thr Ser Ser Lys Ala
            165                 170                 175

Ile Leu Ala Thr Gly Asn Ile Thr Leu Gln Gln Pro Asp Ser Ala Thr
            180                 185                 190

Ile Asn Gly Lys Gly Arg Phe Asp Pro Asp Asn Thr Pro Ala Asn Pro
            195                 200                 205

Asn Thr Leu Tyr Thr Leu Lys Val Lys Arg Gly Lys Arg Tyr Arg Leu
            210                 215                 220

Arg Val Ile Asn Ser Ser Ala Ile Ala Ser Phe Arg Met Ser Ile Gln
225                 230                 235                 240
```

```
Gly His Lys Met Thr Val Ile Ala Ala Asp Gly Val Ser Thr Lys Pro
            245                 250                 255

Tyr Gln Val Asp Ser Phe Asp Ile Leu Ala Gly Gln Arg Ile Asp Ala
            260                 265                 270

Val Val Glu Ala Asn Gln Glu Pro Asp Thr Tyr Trp Ile Asn Ala Pro
            275                 280                 285

Leu Thr Asn Val Ala Asn Lys Thr Ala Gln Ala Leu Leu Ile Tyr Glu
            290                 295                 300

Asp Asp Arg Arg Pro Tyr His Pro Pro Lys Gly Pro Tyr Arg Lys Trp
305                 310                 315                 320

Ser Val Ser Glu Ala Ile Ile Lys Tyr Trp Lys His Lys His Gly Arg
            325                 330                 335

Gly Leu Leu Ser Gly His Gly Leu Lys Ala Arg Met Met Glu Gly
            340                 345                 350

Ser Leu His Leu His Gly Arg Arg Asp Ile Val Lys Arg Gln Asn Glu
            355                 360                 365

Thr Thr Thr Val Val Met Asp Glu Thr Lys Leu Val Pro Leu Glu His
            370                 375                 380

Pro Gly Ala Ala Cys Gly Ser Lys Pro Ala Asp Leu Val Ile Asp Leu
385                 390                 395                 400

Thr Phe Gly Val Asn Phe Thr Thr Gly His Trp Met Ile Asn Gly Ile
            405                 410                 415

Pro His Lys Ser Pro Asp Met Pro Thr Leu Leu Lys Ile Leu Thr Asp
            420                 425                 430

Thr Asp Gly Val Thr Glu Ser Asp Phe Thr Gln Pro Glu His Thr Ile
            435                 440                 445

Ile Leu Pro Lys Asn Lys Cys Val Glu Phe Asn Ile Lys Gly Asn Ser
450                 455                 460

Gly Leu Gly Ile Val His Pro Ile His Leu His Gly His Thr Phe Asp
465                 470                 475                 480

Val Val Gln Phe Gly Asn Asn Pro Pro Asn Tyr Val Asn Pro Pro Arg
            485                 490                 495

Arg Asp Val Val Gly Ala Thr Asp Glu Gly Val Arg Phe Gln Phe Lys
            500                 505                 510

Thr Asp Asn Pro Gly Pro Trp Phe Leu His Cys His Ile Asp Trp His
            515                 520                 525

Leu Glu Glu Gly Phe Ala Met Val Phe Ala Glu Ala Pro Glu Ala Ile
            530                 535                 540

Lys Gly Gly Pro Lys Ser Val Pro Val Asp Arg Gln Trp Lys Asp Leu
545                 550                 555                 560

Cys Arg Lys Tyr Gly Ser Leu Pro Ala Gly Phe Leu
                565                 570

(2) INFORMATION FOR SEQ ID NO: 8:

(i) SEQUENCE CHARACTERISTICS:
        (A) LENGTH: 575 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

Met Ala Arg Thr Thr Phe Leu Val Ser Val Ser Leu Phe Val Ser Ala
1               5                   10                  15
```

-continued

```
Val Leu Ala Arg Thr Val Glu Tyr Gly Leu Lys Ile Ser Asp Gly Glu
             20                  25                  30

Ile Ala Pro Asp Gly Val Lys Arg Asn Ala Thr Leu Val Asn Gly Gly
             35                  40                  45

Tyr Pro Gly Pro Leu Ile Phe Ala Asn Lys Gly Asp Thr Leu Lys Val
             50                  55                  60

Lys Val Gln Asn Lys Leu Thr Asn Pro Glu Met Tyr Arg Thr Thr Ser
 65                  70                  75                  80

Ile His Trp His Gly Leu Leu Gln His Arg Asn Ala Asp Asp Asp Gly
                     85                  90                  95

Pro Ser Phe Val Thr Gln Cys Pro Ile Val Pro Arg Glu Ser Tyr Thr
                    100                 105                 110

Tyr Thr Ile Pro Leu Asp Asp Gln Thr Gly Thr Tyr Trp Tyr His Ser
                115                 120                 125

His Leu Ser Ser Gln Tyr Val Asp Gly Leu Arg Gly Pro Leu Val Ile
            130                 135                 140

Tyr Pro Lys Asp Pro His Arg Arg Leu Tyr Asp Val Asp Asp Glu Lys
145                 150                 155                 160

Thr Val Leu Ile Ile Gly Asp Trp Tyr His Glu Ser Ser Lys Ala Ile
                        165                 170                 175

Leu Ala Ser Gly Asn Ile Thr Arg Gln Arg Pro Val Ser Ala Thr Ile
                180                 185                 190

Asn Gly Lys Gly Arg Phe Asp Pro Asp Asn Thr Pro Ala Asn Pro Asp
            195                 200                 205

Thr Leu Tyr Thr Leu Lys Val Lys Arg Gly Lys Arg Tyr Arg Leu Arg
210                 215                 220

Val Ile Asn Ser Ser Glu Ile Ala Ser Phe Arg Phe Ser Val Glu Gly
225                 230                 235                 240

His Lys Val Thr Val Ile Ala Ala Asp Gly Val Ser Thr Lys Pro Tyr
                    245                 250                 255

Gln Val Asp Ala Phe Asp Ile Leu Ala Gly Gln Arg Ile Asp Cys Val
                260                 265                 270

Val Glu Ala Asn Gln Glu Pro Asp Thr Tyr Trp Ile Asn Ala Pro Leu
            275                 280                 285

Thr Asn Val Pro Asn Lys Thr Ala Gln Ala Leu Leu Val Tyr Glu Glu
290                 295                 300

Asp Arg Arg Pro Tyr His Pro Pro Lys Gly Pro Tyr Arg Lys Trp Ser
305                 310                 315                 320

Val Ser Glu Ala Ile Ile Lys Tyr Trp Asn His Lys His Lys His Gly
                    325                 330                 335

Arg Gly Leu Leu Ser Gly His Gly Leu Lys Ala Arg Met Ile Glu
                340                 345                 350

Gly Ser His His Leu His Ser Arg Ser Val Val Lys Arg Gln Asn Glu
            355                 360                 365

Thr Thr Thr Val Val Met Asp Glu Ser Lys Leu Val Pro Leu Glu Tyr
            370                 375                 380

Pro Gly Ala Ala Cys Gly Ser Lys Pro Ala Asp Leu Val Leu Asp Leu
385                 390                 395                 400

Thr Phe Gly Leu Asn Phe Ala Thr Gly His Trp Met Ile Asn Gly Ile
                405                 410                 415

Pro Tyr Glu Ser Pro Lys Ile Pro Thr Leu Leu Lys Ile Leu Thr Asp
            420                 425                 430
```

-continued

```
Glu Asp Gly Val Thr Glu Ser Asp Phe Thr Lys Glu Glu His Thr Val
        435                 440                 445

Ile Leu Pro Lys Asn Lys Cys Ile Glu Phe Asn Ile Lys Gly Asn Ser
        450                 455                 460

Gly Ile Pro Ile Thr His Pro Val His Leu His Gly His Thr Trp Asp
465                 470                 475                 480

Val Val Gln Phe Gly Asn Asn Pro Pro Asn Tyr Val Asn Pro Pro Arg
                485                 490                 495

Arg Asp Val Val Gly Ser Thr Asp Ala Gly Val Arg Ile Gln Phe Lys
                500                 505                 510

Thr Asp Asn Pro Gly Pro Trp Phe Leu His Cys His Ile Asp Trp His
        515                 520                 525

Leu Glu Glu Gly Phe Ala Met Val Phe Ala Glu Ala Pro Glu Ala Val
        530                 535                 540

Lys Gly Gly Pro Lys Ser Val Ala Val Asp Ser Gln Trp Glu Gly Leu
545                 550                 555                 560

Cys Gly Lys Tyr Asp Asn Trp Leu Lys Ser Asn Pro Gly Gln Leu
                565                 570                 575
```

(2) INFORMATION FOR SEQ ID NO: 9:

(i) SEQUENCE CHARACTERISTICS:
        (A) LENGTH: 616 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 9:

```
Met Lys Arg Phe Phe Ile Asn Ser Leu Leu Leu Ala Gly Leu Leu
1               5                   10                  15

Asn Ser Gly Ala Leu Ala Ala Pro Ser Thr His Pro Arg Ser Asn Pro
                20                  25                  30

Asp Ile Leu Leu Glu Arg Asp His Ser Leu Thr Ser Arg Gln Gly
        35                  40                  45

Ser Cys His Ser Pro Ser Asn Arg Ala Cys Trp Cys Ser Gly Phe Asp
50                  55                  60

Ile Asn Thr Asp Tyr Glu Thr Lys Thr Pro Asn Thr Gly Val Val Arg
65              70                  75                  80

Arg Tyr Thr Phe Asp Ile Thr Glu Val Asp Asn Arg Pro Gly Pro Asp
                85                  90                  95

Gly Val Ile Lys Glu Lys Leu Met Leu Ile Asn Asp Lys Leu Leu Gly
                100                 105                 110

Pro Thr Val Phe Ala Asn Trp Gly Asp Thr Ile Glu Val Thr Val Asn
            115                 120                 125

Asn His Leu Arg Thr Asn Gly Thr Ser Ile His Trp His Gly Leu His
        130                 135                 140

Gln Lys Gly Thr Asn Tyr His Asp Gly Ala Asn Gly Val Thr Glu Cys
145                 150                 155                 160

Pro Ile Pro Pro Gly Gly Ser Arg Val Tyr Ser Phe Arg Ala Arg Gln
                165                 170                 175

Tyr Gly Thr Ser Trp Tyr His Ser His Phe Ser Ala Gln Tyr Gly Asn
                180                 185                 190

Gly Val Ser Gly Ala Ile Gln Ile Asn Gly Pro Ala Ser Leu Pro Tyr
                195                 200                 205
```

```
Asp Ile Asp Leu Gly Val Leu Pro Leu Xaa Asp Trp Tyr Tyr Lys Ser
    210                 215                 220

Ala Asp Gln Leu Val Ile Glu Thr Leu Xaa Lys Gly Asn Ala Pro Phe
225                 230                 235                 240

Ser Asp Asn Val Leu Ile Asn Gly Thr Ala Lys His Pro Thr Thr Gly
                245                 250                 255

Glu Gly Glu Tyr Ala Ile Val Lys Leu Thr Pro Asp Lys Arg His Arg
            260                 265                 270

Leu Arg Leu Ile Asn Met Ser Val Glu Asn His Phe Gln Val Ser Leu
        275                 280                 285

Ala Lys His Thr Met Thr Val Ile Ala Ala Asp Met Val Pro Val Asn
    290                 295                 300

Ala Met Thr Val Asp Ser Leu Phe Met Ala Val Gly Gln Arg Tyr Asp
305                 310                 315                 320

Val Thr Ile Asp Ala Ser Gln Ala Val Gly Asn Tyr Trp Phe Asn Ile
                325                 330                 335

Thr Phe Gly Gly Gln Gln Lys Cys Gly Phe Ser His Asn Pro Ala Pro
            340                 345                 350

Ala Ala Ile Phe Arg Tyr Glu Gly Ala Pro Asp Ala Leu Pro Thr Asp
        355                 360                 365

Pro Gly Ala Ala Pro Lys Asp His Gln Cys Leu Asp Thr Leu Asp Leu
    370                 375                 380

Ser Pro Val Val Gln Lys Asn Val Pro Val Asp Gly Phe Val Lys Glu
385                 390                 395                 400

Pro Gly Asn Thr Leu Pro Val Thr Leu His Val Asp Gln Ala Ala Ala
                405                 410                 415

Pro His Val Phe Thr Trp Lys Ile Asn Gly Ser Ala Ala Asp Val Asp
            420                 425                 430

Trp Asp Arg Pro Val Leu Glu Tyr Val Met Asn Asn Asp Leu Ser Ser
        435                 440                 445

Ile Pro Val Lys Asn Asn Ile Val Arg Val Asp Gly Val Asn Glu Trp
    450                 455                 460

Thr Tyr Trp Leu Val Glu Asn Asp Pro Glu Gly Arg Leu Ser Leu Pro
465                 470                 475                 480

His Pro Met His Leu His Gly His Asp Phe Phe Val Leu Gly Arg Ser
                485                 490                 495

Pro Asp Val Ser Pro Asp Ser Glu Thr Arg Phe Val Phe Asp Pro Ala
            500                 505                 510

Val Asp Leu Pro Arg Leu Arg Gly His Asn Pro Val Arg Arg Asp Val
        515                 520                 525

Thr Met Leu Pro Ala Arg Gly Trp Leu Leu Leu Ala Phe Arg Thr Asp
    530                 535                 540

Asn Pro Gly Ala Trp Leu Phe His Cys His Ile Ala Xaa His Val Ser
545                 550                 555                 560

Gly Gly Leu Ser Val Asp Phe Leu Glu Arg Pro Asp Glu Leu Arg Gly
                565                 570                 575

Gln Leu Thr Gly Glu Ser Lys Ala Glu Leu Glu Arg Val Cys Arg Glu
            580                 585                 590

Trp Lys Asp Trp Glu Ala Lys Ser Pro His Gly Lys Ile Asp Ser Gly
        595                 600                 605

Leu Lys Gln Arg Arg Trp Asp Ala
    610                 615
```

(2) INFORMATION FOR SEQ ID NO: 10:

(i) SEQUENCE CHARACTERISTICS:
       (A) LENGTH: 573 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 10:

```
Gln Gln Ser Cys Asn Thr Pro Ser Asn Arg Ala Cys Trp Thr Asp Gly
1               5                   10                  15

Tyr Asp Ile Asn Thr Asp Tyr Glu Val Asp Ser Pro Asp Thr Gly Val
            20                  25                  30

Val Arg Pro Tyr Thr Leu Thr Leu Thr Glu Val Asp Asn Trp Thr Gly
        35                  40                  45

Pro Asp Gly Val Val Lys Glu Lys Val Met Leu Val Asn Asn Ser Ile
    50                  55                  60

Ile Gly Pro Thr Ile Phe Ala Asp Trp Gly Asp Thr Ile Gln Val Thr
65                  70                  75                  80

Val Ile Asn Asn Leu Glu Thr Asn Gly Thr Ser Ile His Trp His Gly
            85                  90                  95

Leu His Gln Lys Gly Thr Asn Leu His Asp Gly Ala Asn Gly Ile Thr
        100                 105                 110

Glu Cys Pro Ile Pro Lys Gly Gly Arg Lys Val Tyr Arg Phe Lys
    115                 120                 125

Ala Gln Gln Tyr Gly Thr Ser Trp Tyr His Ser His Phe Ser Ala Gln
    130                 135                 140

Tyr Gly Asn Gly Val Val Gly Ala Ile Gln Ile Asn Gly Pro Ala Ser
145                 150                 155                 160

Leu Pro Tyr Asp Thr Asp Leu Gly Val Phe Pro Ile Ser Asp Tyr Tyr
            165                 170                 175

Tyr Ser Ser Ala Asp Glu Leu Val Glu Leu Thr Lys Asn Ser Gly Ala
        180                 185                 190

Pro Phe Ser Asp Asn Val Leu Phe Asn Gly Thr Ala Lys His Pro Glu
    195                 200                 205

Thr Gly Glu Gly Glu Tyr Ala Asn Val Thr Leu Thr Pro Gly Arg Arg
    210                 215                 220

His Arg Leu Arg Leu Ile Asn Thr Ser Val Glu Asn His Phe Gln Val
225                 230                 235                 240

Ser Leu Val Asn His Thr Met Cys Ile Ile Ala Ala Asp Met Val Pro
            245                 250                 255

Val Asn Ala Met Thr Val Asp Ser Leu Phe Leu Gly Val Gly Gln Arg
        260                 265                 270

Tyr Asp Val Val Ile Glu Ala Asn Arg Thr Pro Gly Asn Tyr Trp Phe
    275                 280                 285

Asn Val Thr Phe Gly Gly Gly Leu Leu Cys Gly Gly Ser Arg Asn Pro
    290                 295                 300

Tyr Pro Ala Ala Ile Phe His Tyr Ala Gly Ala Pro Gly Gly Pro Pro
305                 310                 315                 320

Thr Asp Glu Gly Lys Ala Pro Val Asp His Asn Cys Leu Asp Leu Pro
            325                 330                 335

Asn Leu Lys Pro Val Val Ala Arg Asp Val Pro Leu Ser Gly Phe Ala
        340                 345                 350

Lys Arg Ala Asp Asn Thr Leu Asp Val Thr Leu Asp Thr Thr Gly Thr
```

-continued

```
                355                 360                 365

Pro Leu Phe Val Trp Lys Val Asn Gly Ser Ala Ile Asn Ile Asp Trp
        370                 375                 380

Gly Arg Ala Val Val Asp Tyr Val Leu Thr Gln Asn Thr Ser Phe Pro
385                 390                 395                 400

Pro Gly Tyr Asn Ile Val Glu Val Asn Gly Ala Asp Gln Trp Ser Tyr
                405                 410                 415

Trp Leu Ile Glu Asn Asp Pro Gly Ala Pro Phe Thr Leu Pro His Pro
                420                 425                 430

Met His Leu His Gly His Asp Phe Tyr Val Leu Gly Arg Ser Pro Asp
                435                 440                 445

Glu Ser Pro Ala Ser Asn Glu Arg His Val Phe Asp Pro Ala Arg Asp
450                 455                 460

Ala Gly Leu Leu Ser Gly Ala Asn Pro Val Arg Arg Asp Val Ser Met
465                 470                 475                 480

Leu Pro Ala Phe Gly Trp Val Val Leu Ser Phe Arg Ala Asp Asn Pro
                485                 490                 495

Gly Ala Trp Leu Phe His Cys His Ile Ala Trp His Val Ser Gly Gly
                500                 505                 510

Leu Gly Val Val Tyr Leu Glu Arg Ala Asp Asp Leu Arg Gly Ala Val
                515                 520                 525

Ser Asp Ala Asp Ala Asp Asp Leu Asp Arg Leu Cys Ala Asp Trp Arg
    530                 535                 540

Arg Tyr Trp Pro Thr Asn Pro Tyr Pro Lys Ser Asp Ser Gly Leu Lys
545                 550                 555                 560

His Arg Trp Val Glu Glu Gly Glu Trp Leu Val Lys Ala
                565                 570
```

5032-WO

29

Appendix 1:

```
SEQRES  1 A  504  GLN ILE VAL ASN SER VAL ASP THR MET THR LEU THR ASN
SEQRES  2 A  504  ALA ASN VAL SER PRO ASP GLY PHE THR ARG ALA GLY ILE
SEQRES  3 A  504  LEU VAL ASN GLY VAL HIS GLY PRO LEU ILE ARG GLY GLY
SEQRES  4 A  504  LYS ASN ASP ASN PHE GLU LEU ASN VAL VAL ASN ASP LEU
SEQRES  5 A  504  ASP ASN PRO THR MET LEU ARG PRO THR SER ILE HIS TRP
SEQRES  6 A  504  HIS GLY LEU PHE GLN ARG GLY THR ASN TRP ALA ASN GLY
SEQRES  7 A  504  ALA ASP GLY VAL ASN GLN CYS PRO ILE SER PRO GLY HIS
SEQRES  8 A  504  ALA PHE LEU TYR LYS PHE THR PRO ALA GLY HIS ALA GLY
SEQRES  9 A  504  THR PHE TRP TYR HIS SER HIS PHE GLY THR GLN TYR CYS
SEQRES 10 A  504  ASP GLY LEU ARG GLY PRO MET VAL ILE TYR ASP ASP ASN
SEQRES 11 A  504  ASP PRO HIS ALA ALA LEU TYR ASP GLU ASP ASP GLU ASN
SEQRES 12 A  504  THR ILE ILE THR LEU ALA ASP TRP TYR HIS ILE PRO ALA
SEQRES 13 A  504  PRO SER ILE GLN GLY ALA ALA GLN PRO ASP ALA THR LEU
SEQRES 14 A  504  ILE ASN GLY LYS GLY ARG TYR VAL GLY GLY PRO ALA ALA
SEQRES 15 A  504  GLU LEU SER ILE VAL ASN VAL GLU GLN GLY LYS LYS TYR
SEQRES 16 A  504  ARG MET ARG LEU ILE SER LEU SER CYS ASP PRO ASN TRP
SEQRES 17 A  504  GLN PHE SER ILE ASP GLY HIS GLU LEU THR ILE ILE GLU
SEQRES 18 A  504  VAL ASP GLY ASN LEU THR GLU PRO HIS THR VAL ASP ARG
SEQRES 19 A  504  LEU GLN ILE PHE THR GLY GLN ARG TYR SER PHE VAL LEU
SEQRES 20 A  504  ASP ALA ASN GLN PRO VAL ASP ASN TYR TRP ILE ARG ALA
SEQRES 21 A  504  GLN PRO ASN LYS GLY ARG ASN GLY LEU ALA GLY THR PHE
SEQRES 22 A  504  ALA ASN GLY VAL ASN SER ALA ILE LEU ARG TYR ALA GLY
SEQRES 23 A  504  ALA ALA ASN ALA ASP PRO THR THR SER ALA ASN PRO ASN
SEQRES 24 A  504  PRO ALA GLN LEU ASN GLU ALA ASP LEU HIS ALA LEU ILE
SEQRES 25 A  504  ASP PRO ALA ALA PRO GLY ILE PRO THR PRO GLY ALA ALA
SEQRES 26 A  504  ASN VAL ASN LEU ARG PHE GLN LEU GLY PHE SER GLY GLY
SEQRES 27 A  504  ARG PHE THR ILE ASN GLY THR ALA TYR GLU SER PRO SER
SEQRES 28 A  504  VAL PRO THR LEU LEU GLN ILE MET SER GLY ALA GLN SER
SEQRES 29 A  504  ALA ASN ASP LEU LEU PRO ALA GLY SER VAL TYR GLU LEU
SEQRES 30 A  504  PRO ARG ASN GLN VAL VAL GLU LEU VAL VAL PRO ALA GLY
SEQRES 31 A  504  VAL LEU GLY GLY PRO HIS PRO PHE HIS LEU HIS GLY HIS
SEQRES 32 A  504  ALA PHE SER VAL VAL ARG SER ALA GLY SER SER THR TYR
SEQRES 33 A  504  ASN PHE VAL ASN PRO VAL LYS ARG ASP VAL VAL SER LEU
SEQRES 34 A  504  GLY VAL THR GLY ASP GLU VAL THR ILE ARG PHE VAL THR
SEQRES 35 A  504  ASP ASN PRO GLY PRO TRP PHE PHE HIS CYS HIS ILE GLU
SEQRES 36 A  504  PHE HIS LEU MET ASN GLY LEU ALA ILE VAL PHE ALA GLU
```

5032-WO

30

```
      SEQRES  37 A  504  ASP MET ALA ASN THR VAL ASP ALA ASN ASN PRO PRO VAL
      SEQRES  38 A  504  GLU TRP ALA GLN LEU CYS GLU ILE TYR ASP ASP LEU PRO
      SEQRES  39 A  504  PRO GLU ALA THR SER ILE GLN THR VAL VAL
      SSBOND   1 CYS    85   CYS   487
   5  SSBOND   2 CYS   117   CYS   204
      CRYST   45.390  85.720 143.070  90.00  90.00  90.00 P212121
      SCALE1     0.02203  0.00000  0.00000        0.00000
      SCALE2     0.00000  0.01167  0.00000        0.00000
      SCALE3     0.00000  0.00000  0.00699        0.00000
  10  ATOM       1  N   ALA A   1  0     18.748  34.495   5.326  1.00 36.36
      ATOM       2  CA  ALA A   1  0     19.554  35.757   5.185  1.00 35.87
      ATOM       3  C   ALA A   1  0     19.785  36.380   6.558  1.00 34.53
      ATOM       4  O   ALA A   1  0     19.248  35.884   7.577  1.00 35.40
      ATOM       5  CB  ALA A   1  0     19.050  36.675   4.107  1.00 36.65
  15  ATOM       6  N   ILE A   2  0     20.844  37.201   6.659  1.00 31.00
      ATOM       7  CA  ILE A   2  0     21.310  37.654   7.963  1.00 27.71
      ATOM       8  C   ILE A   2  0     21.368  39.165   8.117  1.00 25.19
      ATOM       9  O   ILE A   2  0     21.789  39.861   7.192  1.00 23.77
      ATOM      10  CB  ILE A   2  0     22.744  37.107   8.206  1.00 28.28
  20  ATOM      11  CG1 ILE A   2  0     22.790  35.590   8.022  1.00 28.54
      ATOM      12  CG2 ILE A   2  0     23.285  37.557   9.554  1.00 27.91
      ATOM      13  CD1 ILE A   2  0     23.334  34.738   9.130  1.00 29.32
      ATOM      14  N   VAL A   3  0     20.986  39.659   9.283  1.00 22.31
      ATOM      15  CA  VAL A   3  0     21.093  41.092   9.540  1.00 22.78
  25  ATOM      16  C   VAL A   3  0     22.246  41.297  10.524  1.00 22.62
      ATOM      17  O   VAL A   3  0     22.460  40.556  11.467  1.00 21.74
      ATOM      18  CB  VAL A   3  0     19.801  41.849   9.799  1.00 23.54
      ATOM      19  CG1 VAL A   3  0     18.537  40.985   9.684  1.00 21.30
      ATOM      20  CG2 VAL A   3  0     19.760  42.709  11.055  1.00 21.32
  30  ATOM      21  N   ASN A   4  0     23.122  42.261  10.209  1.00 23.39
      ATOM      22  CA  ASN A   4  0     24.303  42.520  11.021  1.00 23.45
      ATOM      23  C   ASN A   4  0     24.002  43.517  12.126  1.00 24.44
      ATOM      24  O   ASN A   4  0     22.928  44.122  12.160  1.00 23.05
      ATOM      25  CB  ASN A   4  0     25.477  42.965  10.149  1.00 24.77
  35  ATOM      26  CG  ASN A   4  0     25.726  41.991   9.021  1.00 26.62
      ATOM      27  OD1 ASN A   4  0     25.668  42.388   7.849  1.00 30.29
      ATOM      28  ND2 ASN A   4  0     25.923  40.719   9.324  1.00 27.59
      ATOM      29  N   SER A   5  0     24.960  43.707  13.040  1.00 24.28
```

5032-WO

31

```
ATOM   30  CA  SER A   5  0   24.702  44.636  14.143  1.00 25.77
ATOM   31  C   SER A   5  0   24.595  46.090  13.701  1.00 24.41
ATOM   32  O   SER A   5  0   23.973  46.862  14.452  1.00 23.55
ATOM   33  CB  SER A   5  0   25.741  44.405  15.240  1.00 26.18
ATOM   34  OG  SER A   5  0   26.976  44.750  14.641  1.00 27.89
ATOM   35  N   VAL A   6  0   25.104  46.517  12.539  1.00 24.01
ATOM   36  CA  VAL A   6  0   24.770  47.863  12.096  1.00 25.06
ATOM   37  C   VAL A   6  0   24.131  47.617  10.731  1.00 25.57
ATOM   38  O   VAL A   6  0   24.778  47.030   9.874  1.00 28.07
ATOM   39  CB  VAL A   6  0   25.722  49.032  12.155  1.00 26.65
ATOM   40  CG1 VAL A   6  0   26.937  48.759  13.025  1.00 26.73
ATOM   41  CG2 VAL A   6  0   26.098  49.614  10.801  1.00 25.50
ATOM   42  N   ASP A   7  0   22.848  47.952  10.605  1.00 23.82
ATOM   43  CA  ASP A   7  0   22.173  47.543   9.369  1.00 24.07
ATOM   44  C   ASP A   7  0   20.794  48.170   9.276  1.00 23.66
ATOM   45  O   ASP A   7  0   20.342  48.845  10.204  1.00 23.47
ATOM   46  CB  ASP A   7  0   21.996  46.012   9.444  1.00 23.43
ATOM   47  CG  ASP A   7  0   22.017  45.317   8.111  1.00 23.78
ATOM   48  OD1 ASP A   7  0   21.805  45.937   7.055  1.00 23.74
ATOM   49  OD2 ASP A   7  0   22.255  44.089   8.099  1.00 24.62
ATOM   50  N   THR A   8  0   20.155  47.881   8.158  1.00 23.88
ATOM   51  CA  THR A   8  0   18.799  48.359   7.928  1.00 24.45
ATOM   52  C   THR A   8  0   17.813  47.189   7.950  1.00 22.49
ATOM   53  O   THR A   8  0   18.143  46.142   7.377  1.00 22.56
ATOM   54  CB  THR A   8  0   18.694  49.108   6.579  1.00 25.75
ATOM   55  OG1 THR A   8  0   19.573  50.242   6.719  1.00 28.53
ATOM   56  CG2 THR A   8  0   17.295  49.656   6.339  1.00 25.55
ATOM   57  N   MET A   9  0   16.677  47.364   8.602  1.00 19.10
ATOM   58  CA  MET A   9  0   15.650  46.311   8.616  1.00 20.47
ATOM   59  C   MET A   9  0   14.392  46.863   7.925  1.00 21.97
ATOM   60  O   MET A   9  0   13.638  47.638   8.544  1.00 19.49
ATOM   61  CB  MET A   9  0   15.308  45.871  10.022  1.00 20.49
ATOM   62  CG  MET A   9  0   16.351  44.982  10.682  1.00 22.11
ATOM   63  SD  MET A   9  0   16.192  44.917  12.482  1.00 24.71
ATOM   64  CE  MET A   9  0   14.640  44.024  12.635  1.00 22.61
ATOM   65  N   THR A  10  0   14.246  46.516   6.641  1.00 21.81
ATOM   66  CA  THR A  10  0   13.073  47.064   5.926  1.00 23.43
ATOM   67  C   THR A  10  0   11.912  46.081   6.046  1.00 22.90
```

5032-WO

32

```
ATOM   68 O   THR A 10 0  12.056 44.890  5.719 1.00 23.55
ATOM   69 CB  THR A 10 0  13.390 47.384  4.459 1.00 24.69
ATOM   70 OG1 THR A 10 0  14.533 48.261  4.456 1.00 26.08
ATOM   71 CG2 THR A 10 0  12.216 48.028  3.742 1.00 23.95
ATOM   72 N   LEU A 11 0  10.820 46.600  6.583 1.00 21.13
ATOM   73 CA  LEU A 11 0   9.615 45.836  6.846 1.00 21.10
ATOM   74 C   LEU A 11 0   8.607 45.957  5.709 1.00 24.58
ATOM   75 O   LEU A 11 0   8.124 47.056  5.358 1.00 23.89
ATOM   76 CB  LEU A 11 0   9.045 46.411  8.129 1.00 21.29
ATOM   77 CG  LEU A 11 0   9.474 45.955  9.508 1.00 22.26
ATOM   78 CD1 LEU A 11 0  10.952 45.742  9.692 1.00 22.42
ATOM   79 CD2 LEU A 11 0   8.978 46.931 10.583 1.00 22.75
ATOM   80 N   THR A 12 0   8.272 44.836  5.057 1.00 24.01
ATOM   81 CA  THR A 12 0   7.302 44.851  3.980 1.00 24.33
ATOM   82 C   THR A 12 0   6.322 43.677  4.123 1.00 25.34
ATOM   83 O   THR A 12 0   6.480 42.740  4.913 1.00 25.62
ATOM   84 CB  THR A 12 0   7.882 44.776  2.560 1.00 25.12
ATOM   85 OG1 THR A 12 0   8.575 43.548  2.377 1.00 24.05
ATOM   86 CG2 THR A 12 0   8.847 45.905  2.217 1.00 25.26
ATOM   87 N   ASN A 13 0   5.261 43.760  3.335 1.00 24.09
ATOM   88 CA  ASN A 13 0   4.232 42.722  3.299 1.00 22.87
ATOM   89 C   ASN A 13 0   4.422 41.954  1.989 1.00 22.13
ATOM   90 O   ASN A 13 0   4.809 42.600  1.023 1.00 22.32
ATOM   91 CB  ASN A 13 0   2.852 43.355  3.311 1.00 21.58
ATOM   92 CG  ASN A 13 0   2.526 44.060  4.607 1.00 22.50
ATOM   93 OD1 ASN A 13 0   2.187 45.245  4.648 1.00 22.20
ATOM   94 ND2 ASN A 13 0   2.615 43.306  5.705 1.00 21.81
ATOM   95 N   ALA A 14 0   4.218 40.655  1.985 1.00 21.00
ATOM   96 CA  ALA A 14 0   4.270 39.869  0.762 1.00 21.93
ATOM   97 C   ALA A 14 0   3.571 38.533  1.078 1.00 20.77
ATOM   98 O   ALA A 14 0   3.292 38.309  2.259 1.00 20.45
ATOM   99 CB  ALA A 14 0   5.676 39.618  0.248 1.00 23.72
ATOM  100 N   ASN A 15 0   3.366 37.695  0.072 1.00 18.88
ATOM  101 CA  ASN A 15 0   2.748 36.412  0.337 1.00 19.67
ATOM  102 C   ASN A 15 0   3.798 35.457  0.873 1.00 19.19
ATOM  103 O   ASN A 15 0   4.891 35.474  0.338 1.00 19.57
ATOM  104 CB  ASN A 15 0   2.114 35.721 -0.875 1.00 21.13
ATOM  105 CG  ASN A 15 0   0.839 36.457 -1.284 1.00 21.15
```

5032-WO

33

```
ATOM   106  OD1 ASN A 15   0    0.343  37.207  -0.472  1.00 20.87
ATOM   107  ND2 ASN A 15   0    0.379  36.284  -2.501  1.00 20.00
ATOM   108  N   VAL A 16   0    3.358  34.614   1.772  1.00 19.11
ATOM   109  CA  VAL A 16   0    4.322  33.628   2.342  1.00 18.90
ATOM   110  C   VAL A 16   0    3.626  32.293   2.345  1.00 19.25
ATOM   111  O   VAL A 16   0    2.386  32.281   2.406  1.00 16.71
ATOM   112  CB  VAL A 16   0    4.612  34.317   3.691  1.00 19.95
ATOM   113  CG1 VAL A 16   0    3.990  33.749   4.937  1.00 18.58
ATOM   114  CG2 VAL A 16   0    6.091  34.603   3.814  1.00 21.38
ATOM   115  N   SER A 17   0    4.312  31.157   2.303  1.00 18.57
ATOM   116  CA  SER A 17   0    3.678  29.869   2.410  1.00 20.90
ATOM   117  C   SER A 17   0    4.608  28.866   3.065  1.00 21.12
ATOM   118  O   SER A 17   0    5.106  27.939   2.448  1.00 21.24
ATOM   119  CB  SER A 17   0    3.186  29.285   1.080  1.00 23.95
ATOM   120  OG  SER A 17   0    4.204  29.399   0.125  1.00 26.79
ATOM   121  N   PRO A 18   0    4.834  29.051   4.358  1.00 20.78
ATOM   122  CA  PRO A 18   0    5.703  28.216   5.141  1.00 20.02
ATOM   123  C   PRO A 18   0    5.197  26.793   5.376  1.00 19.74
ATOM   124  O   PRO A 18   0    5.978  25.920   5.753  1.00 17.97
ATOM   125  CB  PRO A 18   0    5.889  28.954   6.481  1.00 19.27
ATOM   126  CG  PRO A 18   0    4.701  29.832   6.536  1.00 21.41
ATOM   127  CD  PRO A 18   0    4.249  30.153   5.128  1.00 20.70
ATOM   128  N   ASP A 19   0    3.899  26.534   5.241  1.00 18.82
ATOM   129  CA  ASP A 19   0    3.323  25.227   5.475  1.00 16.87
ATOM   130  C   ASP A 19   0    2.548  24.823   4.237  1.00 17.28
ATOM   131  O   ASP A 19   0    1.713  23.929   4.337  1.00 17.84
ATOM   132  CB  ASP A 19   0    2.419  25.207   6.701  1.00 16.54
ATOM   133  CG  ASP A 19   0    1.192  26.120   6.596  1.00 16.67
ATOM   134  OD1 ASP A 19   0    1.032  26.935   5.654  1.00 14.17
ATOM   135  OD2 ASP A 19   0    0.360  26.045   7.529  1.00 14.56
ATOM   136  N   GLY A 20   0    2.782  25.469   3.100  1.00 17.87
ATOM   137  CA  GLY A 20   0    2.079  25.091   1.890  1.00 19.40
ATOM   138  C   GLY A 20   0    0.732  25.789   1.699  1.00 22.52
ATOM   139  O   GLY A 20   0    0.158  25.619   0.628  1.00 22.87
ATOM   140  N   PHE A 21   0    0.240  26.587   2.631  1.00 21.35
ATOM   141  CA  PHE A 21   0   -0.913  27.443   2.534  1.00 20.39
ATOM   142  C   PHE A 21   0   -0.348  28.855   2.322  1.00 21.23
ATOM   143  O   PHE A 21   0    0.475  29.316   3.122  1.00 21.26
```

5032-WO

34

```
     ATOM    144  CB  PHE A  21  0   -1.742  27.472   3.814  1.00 20.80
     ATOM    145  CG  PHE A  21  0   -3.059  28.180   3.695  1.00 21.91
     ATOM    146  CD1 PHE A  21  0   -3.171  29.527   3.963  1.00 22.49
     ATOM    147  CD2 PHE A  21  0   -4.207  27.470   3.327  1.00 22.51
 5   ATOM    148  CE1 PHE A  21  0   -4.370  30.207   3.845  1.00 22.27
     ATOM    149  CE2 PHE A  21  0   -5.419  28.128   3.203  1.00 22.79
     ATOM    150  CZ  PHE A  21  0   -5.498  29.497   3.474  1.00 23.34
     ATOM    151  N   THR A  22  0   -0.638  29.514   1.225  1.00 20.20
     ATOM    152  CA  THR A  22  0   -0.143  30.850   0.977  1.00 21.36
10   ATOM    153  C   THR A  22  0   -1.083  31.939   1.488  1.00 21.79
     ATOM    154  O   THR A  22  0   -2.271  31.952   1.162  1.00 21.19
     ATOM    155  CB  THR A  22  0    0.045  31.012  -0.553  1.00 21.46
     ATOM    156  OG1 THR A  22  0    0.838  29.881  -0.934  1.00 20.09
     ATOM    157  CG2 THR A  22  0    0.693  32.353  -0.891  1.00 20.94
15   ATOM    158  N   ARG A  23  0   -0.562  32.871   2.257  1.00 20.80
     ATOM    159  CA  ARG A  23  0   -1.230  34.008   2.844  1.00 20.78
     ATOM    160  C   ARG A  23  0   -0.257  35.189   2.960  1.00 21.15
     ATOM    161  O   ARG A  23  0    0.954  35.018   2.740  1.00 20.42
     ATOM    162  CB  ARG A  23  0   -1.874  33.685   4.172  1.00 20.47
20   ATOM    163  CG  ARG A  23  0   -0.964  33.152   5.295  1.00 21.52
     ATOM    164  CD  ARG A  23  0   -0.552  34.357   6.113  1.00 22.75
     ATOM    165  NE  ARG A  23  0   -0.905  34.419   7.477  1.00 21.60
     ATOM    166  CZ  ARG A  23  0   -0.870  35.283   8.464  1.00 19.89
     ATOM    167  NH1 ARG A  23  0   -0.526  36.565   8.453  1.00 20.19
25   ATOM    168  NH2 ARG A  23  0   -1.249  34.744   9.610  1.00 18.64
     ATOM    169  N   ALA A  24  0   -0.784  36.389   3.199  1.00 20.05
     ATOM    170  CA  ALA A  24  0    0.140  37.541   3.243  1.00 22.03
     ATOM    171  C   ALA A  24  0    0.786  37.561   4.635  1.00 21.09
     ATOM    172  O   ALA A  24  0    0.200  37.124   5.637  1.00 21.16
30   ATOM    173  CB  ALA A  24  0   -0.578  38.836   2.902  1.00 22.98
     ATOM    174  N   GLY A  25  0    2.042  37.984   4.683  1.00 20.28
     ATOM    175  CA  GLY A  25  0    2.786  37.993   5.950  1.00 20.29
     ATOM    176  C   GLY A  25  0    3.649  39.254   5.979  1.00 21.38
     ATOM    177  O   GLY A  25  0    3.465  40.229   5.238  1.00 21.06
35   ATOM    178  N   ILE A  26  0    4.604  39.221   6.897  1.00 20.33
     ATOM    179  CA  ILE A  26  0    5.475  40.365   7.145  1.00 20.64
     ATOM    180  C   ILE A  26  0    6.903  39.886   6.932  1.00 20.00
     ATOM    181  O   ILE A  26  0    7.247  38.851   7.485  1.00 21.34
```

5032-WO

35

| | ATOM | 182 | CB | ILE A | 26 | 0 | 5.278 | 40.933 | 8.564 | 1.00 | 20.38 |
|---|---|---|---|---|---|---|---|---|---|---|---|
| | ATOM | 183 | CG1 | ILE A | 26 | 0 | 3.883 | 41.536 | 8.667 | 1.00 | 20.72 |
| | ATOM | 184 | CG2 | ILE A | 26 | 0 | 6.333 | 42.007 | 8.821 | 1.00 | 22.34 |
| | ATOM | 185 | CD1 | ILE A | 26 | 0 | 3.310 | 41.822 | 10.024 | 1.00 | 20.76 |
| 5 | ATOM | 186 | N | LEU A | 27 | 0 | 7.644 | 40.551 | 6.079 | 1.00 | 19.10 |
| | ATOM | 187 | CA | LEU A | 27 | 0 | 9.005 | 40.168 | 5.739 | 1.00 | 19.67 |
| | ATOM | 188 | C | LEU A | 27 | 0 | 9.964 | 41.226 | 6.280 | 1.00 | 19.85 |
| | ATOM | 189 | O | LEU A | 27 | 0 | 9.591 | 42.407 | 6.356 | 1.00 | 19.19 |
| | ATOM | 190 | CB | LEU A | 27 | 0 | 9.138 | 40.172 | 4.219 | 1.00 | 20.26 |
| 10 | ATOM | 191 | CG | LEU A | 27 | 0 | 9.046 | 38.883 | 3.415 | 1.00 | 22.65 |
| | ATOM | 192 | CD1 | LEU A | 27 | 0 | 8.127 | 37.835 | 3.989 | 1.00 | 21.10 |
| | ATOM | 193 | CD2 | LEU A | 27 | 0 | 8.738 | 39.198 | 1.963 | 1.00 | 22.01 |
| | ATOM | 194 | N | VAL A | 28 | 0 | 11.162 | 40.804 | 6.630 | 1.00 | 18.03 |
| | ATOM | 195 | CA | VAL A | 28 | 0 | 12.199 | 41.723 | 7.088 | 1.00 | 17.24 |
| 15 | ATOM | 196 | C | VAL A | 28 | 0 | 13.289 | 41.573 | 6.040 | 1.00 | 18.99 |
| | ATOM | 197 | O | VAL A | 28 | 0 | 13.791 | 40.453 | 5.863 | 1.00 | 20.36 |
| | ATOM | 198 | CB | VAL A | 28 | 0 | 12.762 | 41.415 | 8.491 | 1.00 | 16.50 |
| | ATOM | 199 | CG1 | VAL A | 28 | 0 | 13.899 | 42.361 | 8.845 | 1.00 | 15.41 |
| | ATOM | 200 | CG2 | VAL A | 28 | 0 | 11.681 | 41.517 | 9.558 | 1.00 | 15.42 |
| 20 | ATOM | 201 | N | ASN A | 29 | 0 | 13.575 | 42.601 | 5.256 | 1.00 | 20.78 |
| | ATOM | 202 | CA | ASN A | 29 | 0 | 14.567 | 42.579 | 4.198 | 1.00 | 20.46 |
| | ATOM | 203 | C | ASN A | 29 | 0 | 14.316 | 41.435 | 3.226 | 1.00 | 23.05 |
| | ATOM | 204 | O | ASN A | 29 | 0 | 15.247 | 40.675 | 2.880 | 1.00 | 23.62 |
| | ATOM | 205 | CB | ASN A | 29 | 0 | 15.982 | 42.446 | 4.764 | 1.00 | 21.06 |
| 25 | ATOM | 206 | CG | ASN A | 29 | 0 | 16.475 | 43.654 | 5.522 | 1.00 | 22.44 |
| | ATOM | 207 | OD1 | ASN A | 29 | 0 | 15.870 | 44.722 | 5.434 | 1.00 | 23.47 |
| | ATOM | 208 | ND2 | ASN A | 29 | 0 | 17.560 | 43.507 | 6.288 | 1.00 | 22.23 |
| | ATOM | 209 | N | GLY A | 30 | 0 | 13.053 | 41.215 | 2.878 | 1.00 | 23.18 |
| | ATOM | 210 | CA | GLY A | 30 | 0 | 12.662 | 40.181 | 1.922 | 1.00 | 23.36 |
| 30 | ATOM | 211 | C | GLY A | 30 | 0 | 12.723 | 38.757 | 2.436 | 1.00 | 23.85 |
| | ATOM | 212 | O | GLY A | 30 | 0 | 12.707 | 37.814 | 1.633 | 1.00 | 25.17 |
| | ATOM | 213 | N | VAL A | 31 | 0 | 12.832 | 38.585 | 3.755 | 1.00 | 21.85 |
| | ATOM | 214 | CA | VAL A | 31 | 0 | 12.999 | 37.276 | 4.352 | 1.00 | 20.55 |
| | ATOM | 215 | C | VAL A | 31 | 0 | 12.031 | 37.190 | 5.548 | 1.00 | 19.91 |
| 35 | ATOM | 216 | O | VAL A | 31 | 0 | 11.796 | 38.172 | 6.269 | 1.00 | 17.50 |
| | ATOM | 217 | CB | VAL A | 31 | 0 | 14.436 | 37.020 | 4.856 | 1.00 | 21.36 |
| | ATOM | 218 | CG1 | VAL A | 31 | 0 | 14.556 | 35.709 | 5.626 | 1.00 | 20.79 |
| | ATOM | 219 | CG2 | VAL A | 31 | 0 | 15.495 | 37.005 | 3.757 | 1.00 | 21.84 |

```
ATOM    220  N   HIS A  32  0    11.489  35.984   5.698  1.00 17.05
ATOM    221  CA  HIS A  32  0    10.592  35.729   6.797  1.00 18.61
ATOM    222  C   HIS A  32  0    11.417  35.499   8.050  1.00 17.67
ATOM    223  O   HIS A  32  0    11.873  34.385   8.216  1.00 18.72
ATOM    224  CB  HIS A  32  0     9.676  34.543   6.493  1.00 21.00
ATOM    225  CG  HIS A  32  0     8.639  34.208   7.517  1.00 23.80
ATOM    226  ND1 HIS A  32  0     7.744  33.174   7.332  1.00 25.14
ATOM    227  CD2 HIS A  32  0     8.331  34.720   8.735  1.00 25.32
ATOM    228  CE1 HIS A  32  0     6.942  33.061   8.385  1.00 25.36
ATOM    229  NE2 HIS A  32  0     7.271  33.986   9.260  1.00 26.23
ATOM    230  N   GLY A  33  0    11.522  36.446   8.960  1.00 16.23
ATOM    231  CA  GLY A  33  0    12.276  36.252  10.198  1.00 16.97
ATOM    232  C   GLY A  33  0    13.740  35.869  10.083  1.00 15.54
ATOM    233  O   GLY A  33  0    14.228  34.885  10.609  1.00 15.13
ATOM    234  N   PRO A  34  0    14.555  36.734   9.475  1.00 15.75
ATOM    235  CA  PRO A  34  0    16.012  36.561   9.359  1.00 14.70
ATOM    236  C   PRO A  34  0    16.734  36.660  10.701  1.00 14.02
ATOM    237  O   PRO A  34  0    16.241  37.252  11.673  1.00 10.44
ATOM    238  CB  PRO A  34  0    16.491  37.699   8.435  1.00 14.40
ATOM    239  CG  PRO A  34  0    15.441  38.742   8.783  1.00 15.11
ATOM    240  CD  PRO A  34  0    14.113  38.005   8.905  1.00 13.69
ATOM    241  N   LEU A  35  0    17.925  36.049  10.767  1.00 13.60
ATOM    242  CA  LEU A  35  0    18.748  36.022  11.963  1.00 14.35
ATOM    243  C   LEU A  35  0    19.462  37.359  12.161  1.00 16.25
ATOM    244  O   LEU A  35  0    20.015  37.902  11.210  1.00 14.10
ATOM    245  CB  LEU A  35  0    19.834  34.916  11.862  1.00 15.33
ATOM    246  CG  LEU A  35  0    20.958  34.943  12.911  1.00 17.74
ATOM    247  CD1 LEU A  35  0    20.486  34.698  14.348  1.00 16.30
ATOM    248  CD2 LEU A  35  0    22.052  33.934  12.575  1.00 16.60
ATOM    249  N   ILE A  36  0    19.471  37.855  13.384  1.00 16.71
ATOM    250  CA  ILE A  36  0    20.265  39.027  13.738  1.00 16.66
ATOM    251  C   ILE A  36  0    21.403  38.487  14.620  1.00 17.92
ATOM    252  O   ILE A  36  0    21.183  37.732  15.573  1.00 17.20
ATOM    253  CB  ILE A  36  0    19.560  40.129  14.533  1.00 16.60
ATOM    254  CG1 ILE A  36  0    18.389  40.771  13.771  1.00 16.09
ATOM    255  CG2 ILE A  36  0    20.565  41.226  14.917  1.00 17.67
ATOM    256  CD1 ILE A  36  0    17.590  41.754  14.629  1.00 15.88
ATOM    257  N   ARG A  37  0    22.647  38.829  14.288  1.00 18.72
```

5032-WO

37

```
    ATOM   258 CA  ARG A 37  0   23.754 38.315 15.091 1.00 19.94
    ATOM   259 C   ARG A 37  0   24.839 39.369 15.280 1.00 20.08
    ATOM   260 O   ARG A 37  0   24.979 40.249 14.450 1.00 20.52
    ATOM   261 CB  ARG A 37  0   24.395 37.077 14.465 1.00 21.72
 5  ATOM   262 CG  ARG A 37  0   25.102 37.393 13.171 1.00 24.46
    ATOM   263 CD  ARG A 37  0   26.113 36.339 12.762 1.00 26.90
    ATOM   264 NE  ARG A 37  0   26.584 36.571 11.381 1.00 29.30
    ATOM   265 CZ  ARG A 37  0   26.838 35.571 10.528 1.00 31.29
    ATOM   266 NH1 ARG A 37  0   26.711 34.283 10.851 1.00 31.37
10  ATOM   267 NH2 ARG A 37  0   27.252 35.827  9.291 1.00 31.66
    ATOM   268 N   GLY A 38  0   25.587 39.223 16.361 1.00 20.22
    ATOM   269 CA  GLY A 38  0   26.716 40.121 16.611 1.00 18.98
    ATOM   270 C   GLY A 38  0   27.533 39.545 17.765 1.00 18.08
    ATOM   271 O   GLY A 38  0   27.259 38.421 18.225 1.00 15.92
15  ATOM   272 N   GLY A 39  0   28.436 40.412 18.238 1.00 17.65
    ATOM   273 CA  GLY A 39  0   29.322 40.026 19.351 1.00 16.23
    ATOM   274 C   GLY A 39  0   28.861 40.774 20.592 1.00 17.21
    ATOM   275 O   GLY A 39  0   28.157 41.784 20.489 1.00 17.27
    ATOM   276 N   LYS A 40  0   29.276 40.328 21.764 1.00 16.58
20  ATOM   277 CA  LYS A 40  0   28.839 40.805 23.057 1.00 18.03
    ATOM   278 C   LYS A 40  0   29.185 42.267 23.348 1.00 20.44
    ATOM   279 O   LYS A 40  0   28.562 42.878 24.221 1.00 19.42
    ATOM   280 CB  LYS A 40  0   29.394 39.933 24.185 1.00 16.74
    ATOM   281 CG  LYS A 40  0   30.892 39.997 24.370 1.00 17.98
25  ATOM   282 CD  LYS A 40  0   31.333 39.170 25.569 1.00 20.66
    ATOM   283 CE  LYS A 40  0   32.809 38.768 25.493 1.00 21.70
    ATOM   284 NZ  LYS A 40  0   33.227 38.111 26.757 1.00 23.11
    ATOM   285 N   ASN A 41  0   30.181 42.780 22.645 1.00 21.43
    ATOM   286 CA  ASN A 41  0   30.536 44.171 22.840 1.00 25.14
30  ATOM   287 C   ASN A 41  0   30.092 44.976 21.644 1.00 24.05
    ATOM   288 O   ASN A 41  0   30.409 46.161 21.655 1.00 25.66
    ATOM   289 CB  ASN A 41  0   32.052 44.326 23.111 1.00 27.02
    ATOM   290 CG  ASN A 41  0   32.434 43.606 24.404 1.00 29.76
    ATOM   291 OD1 ASN A 41  0   33.398 42.832 24.431 1.00 31.54
35  ATOM   292 ND2 ASN A 41  0   31.663 43.825 25.473 1.00 30.13
    ATOM   293 N   ASP A 42  0   29.424 44.447 20.631 1.00 23.80
    ATOM   294 CA  ASP A 42  0   29.073 45.325 19.506 1.00 24.12
    ATOM   295 C   ASP A 42  0   28.169 46.484 19.891 1.00 24.24
```

5032-WO

38

```
ATOM   296  O   ASP A  42   0    27.420 46.428 20.872 1.00 22.42
ATOM   297  CB  ASP A  42   0    28.388 44.528 18.392 1.00 26.65
ATOM   298  CG  ASP A  42   0    29.404 43.599 17.773 1.00 28.94
ATOM   299  OD1 ASP A  42   0    30.603 43.754 18.056 1.00 31.45
ATOM   300  OD2 ASP A  42   0    29.026 42.708 17.009 1.00 31.69
ATOM   301  N   ASN A  43   0    28.258 47.547 19.090 1.00 24.72
ATOM   302  CA  ASN A  43   0    27.316 48.660 19.255 1.00 26.50
ATOM   303  C   ASN A  43   0    26.293 48.430 18.128 1.00 26.23
ATOM   304  O   ASN A  43   0    26.723 48.420 16.979 1.00 25.02
ATOM   305  CB  ASN A  43   0    27.934 50.047 19.128 1.00 28.45
ATOM   306  CG  ASN A  43   0    28.858 50.244 20.323 1.00 31.09
ATOM   307  OD1 ASN A  43   0    30.041 50.502 20.106 1.00 33.11
ATOM   308  ND2 ASN A  43   0    28.364 50.055 21.531 1.00 31.18
ATOM   309  N   PHE A  44   0    25.039 48.155 18.468 1.00 24.63
ATOM   310  CA  PHE A  44   0    24.083 47.897 17.393 1.00 23.28
ATOM   311  C   PHE A  44   0    23.450 49.191 16.916 1.00 22.36
ATOM   312  O   PHE A  44   0    23.024 50.008 17.735 1.00 21.07
ATOM   313  CB  PHE A  44   0    22.959 46.965 17.853 1.00 22.04
ATOM   314  CG  PHE A  44   0    23.376 45.525 17.955 1.00 22.96
ATOM   315  CD1 PHE A  44   0    22.779 44.562 17.153 1.00 23.91
ATOM   316  CD2 PHE A  44   0    24.330 45.120 18.869 1.00 22.03
ATOM   317  CE1 PHE A  44   0    23.131 43.230 17.253 1.00 24.42
ATOM   318  CE2 PHE A  44   0    24.689 43.797 18.974 1.00 23.25
ATOM   319  CZ  PHE A  44   0    24.095 42.837 18.168 1.00 24.02
ATOM   320  N   GLU A  45   0    23.350 49.343 15.604 1.00 22.78
ATOM   321  CA  GLU A  45   0    22.611 50.482 15.054 1.00 24.47
ATOM   322  C   GLU A  45   0    21.619 49.884 14.055 1.00 23.79
ATOM   323  O   GLU A  45   0    22.017 49.587 12.924 1.00 24.40
ATOM   324  CB  GLU A  45   0    23.543 51.473 14.368 1.00 27.07
ATOM   325  CG  GLU A  45   0    24.474 52.130 15.374 1.00 31.60
ATOM   326  CD  GLU A  45   0    25.380 53.179 14.772 1.00 33.90
ATOM   327  OE1 GLU A  45   0    25.354 53.438 13.559 1.00 35.62
ATOM   328  OE2 GLU A  45   0    26.155 53.748 15.565 1.00 36.42
ATOM   329  N   LEU A  46   0    20.369 49.684 14.465 1.00 22.18
ATOM   330  CA  LEU A  46   0    19.419 49.044 13.556 1.00 21.22
ATOM   331  C   LEU A  46   0    18.348 50.001 13.077 1.00 21.27
ATOM   332  O   LEU A  46   0    17.464 50.429 13.812 1.00 21.60
ATOM   333  CB  LEU A  46   0    18.837 47.811 14.262 1.00 20.72
```

5032-WO

39

```
   ATOM   334 CG  LEU A  46  0   19.827 46.658 14.403 1.00 21.28
   ATOM   335 CD1 LEU A  46  0   19.334 45.621 15.397 1.00 20.83
   ATOM   336 CD2 LEU A  46  0   20.148 46.034 13.052 1.00 18.33
   ATOM   337 N   ASN A  47  0   18.438 50.403 11.823 1.00 21.09
 5 ATOM   338 CA  ASN A  47  0   17.498 51.344 11.252 1.00 22.37
   ATOM   339 C   ASN A  47  0   16.273 50.558 10.803 1.00 22.18
   ATOM   340 O   ASN A  47  0   16.390 49.810  9.847 1.00 23.41
   ATOM   341 CB  ASN A  47  0   18.131 52.104 10.066 1.00 24.01
   ATOM   342 CG  ASN A  47  0   17.226 53.243  9.615 1.00 25.54
10 ATOM   343 OD1 ASN A  47  0   16.443 53.772 10.413 1.00 26.53
   ATOM   344 ND2 ASN A  47  0   17.332 53.612  8.346 1.00 26.01
   ATOM   345 N   VAL A  48  0   15.147 50.692 11.475 1.00 22.04
   ATOM   346 CA  VAL A  48  0   13.918 49.995 11.140 1.00 21.99
   ATOM   347 C   VAL A  48  0   13.026 50.879 10.269 1.00 21.82
15 ATOM   348 O   VAL A  48  0   12.532 51.910 10.699 1.00 20.61
   ATOM   349 CB  VAL A  48  0   13.176 49.579 12.430 1.00 22.64
   ATOM   350 CG1 VAL A  48  0   11.819 48.931 12.148 1.00 21.99
   ATOM   351 CG2 VAL A  48  0   14.098 48.631 13.216 1.00 21.68
   ATOM   352 N   VAL A  49  0   12.931 50.512  9.009 1.00 21.79
20 ATOM   353 CA  VAL A  49  0   12.164 51.167  7.966 1.00 21.34
   ATOM   354 C   VAL A  49  0   10.816 50.460  7.795 1.00 21.12
   ATOM   355 O   VAL A  49  0   10.703 49.308  7.365 1.00 19.76
   ATOM   356 CB  VAL A  49  0   12.983 51.189  6.665 1.00 22.02
   ATOM   357 CG1 VAL A  49  0   12.267 51.913  5.519 1.00 21.70
25 ATOM   358 CG2 VAL A  49  0   14.312 51.933  6.906 1.00 21.47
   ATOM   359 N   ASN A  50  0    9.767 51.112  8.257 1.00 20.26
   ATOM   360 CA  ASN A  50  0    8.424 50.611  8.215 1.00 22.70
   ATOM   361 C   ASN A  50  0    7.751 50.899  6.869 1.00 25.99
   ATOM   362 O   ASN A  50  0    7.043 51.925  6.735 1.00 27.06
30 ATOM   363 CB  ASN A  50  0    7.549 51.230  9.318 1.00 21.92
   ATOM   364 CG  ASN A  50  0    6.198 50.569  9.471 1.00 22.44
   ATOM   365 OD1 ASN A  50  0    5.818 49.801  8.572 1.00 24.19
   ATOM   366 ND2 ASN A  50  0    5.435 50.833 10.526 1.00 20.19
   ATOM   367 N   ASP A  51  0    7.915 49.959  5.926 1.00 26.42
35 ATOM   368 CA  ASP A  51  0    7.208 50.071  4.641 1.00 26.35
   ATOM   369 C   ASP A  51  0    5.951 49.200  4.600 1.00 24.86
   ATOM   370 O   ASP A  51  0    5.542 48.810  3.511 1.00 25.19
   ATOM   371 CB  ASP A  51  0    8.126 49.698  3.481 1.00 26.75
```

5032-WO

40

```
   ATOM   372 CG  ASP A  51  0    9.152 50.761  3.158 1.00 29.77
   ATOM   373 OD1 ASP A  51  0    8.944 51.904  3.617 1.00 31.03
   ATOM   374 OD2 ASP A  51  0   10.166 50.509  2.465 1.00 30.42
   ATOM   375 N   LEU A  52  0    5.332 48.801  5.700 1.00 25.05
 5 ATOM   376 CA  LEU A  52  0    4.172 47.911  5.640 1.00 25.44
   ATOM   377 C   LEU A  52  0    2.934 48.624  5.094 1.00 26.65
   ATOM   378 O   LEU A  52  0    2.553 49.696  5.586 1.00 24.56
   ATOM   379 CB  LEU A  52  0    3.837 47.374  7.029 1.00 24.19
   ATOM   380 CG  LEU A  52  0    4.896 46.503  7.699 1.00 24.60
10 ATOM   381 CD1 LEU A  52  0    4.611 46.424  9.196 1.00 24.05
   ATOM   382 CD2 LEU A  52  0    4.891 45.119  7.061 1.00 23.49
   ATOM   383 N   ASP A  53  0    2.242 47.980  4.169 1.00 28.79
   ATOM   384 CA  ASP A  53  0    1.049 48.602  3.581 1.00 29.91
   ATOM   385 C   ASP A  53  0   -0.135 47.658  3.492 1.00 29.90
15 ATOM   386 O   ASP A  53  0   -1.152 48.082  2.951 1.00 30.40
   ATOM   387 CB  ASP A  53  0    1.367 49.190  2.197 1.00 29.26
   ATOM   388 CG  ASP A  53  0    1.838 48.140  1.218 1.00 31.28
   ATOM   389 OD1 ASP A  53  0    1.865 46.926  1.540 1.00 31.64
   ATOM   390 OD2 ASP A  53  0    2.233 48.474  0.074 1.00 32.42
20 ATOM   391 N   ASN A  54  0   -0.060 46.437  4.014 1.00 29.44
   ATOM   392 CA  ASN A  54  0   -1.237 45.554  3.983 1.00 26.89
   ATOM   393 C   ASN A  54  0   -2.089 45.832  5.192 1.00 27.37
   ATOM   394 O   ASN A  54  0   -1.772 45.528  6.350 1.00 27.99
   ATOM   395 CB  ASN A  54  0   -0.831 44.095  3.913 1.00 25.11
25 ATOM   396 CG  ASN A  54  0   -1.978 43.141  3.690 1.00 24.20
   ATOM   397 OD1 ASN A  54  0   -1.874 42.344  2.746 1.00 25.13
   ATOM   398 ND2 ASN A  54  0   -3.030 43.182  4.481 1.00 23.26
   ATOM   399 N   PRO A  55  0   -3.337 46.256  4.961 1.00 28.44
   ATOM   400 CA  PRO A  55  0   -4.286 46.589  6.014 1.00 26.57
30 ATOM   401 C   PRO A  55  0   -4.909 45.414  6.723 1.00 27.10
   ATOM   402 O   PRO A  55  0   -5.671 45.624  7.687 1.00 26.05
   ATOM   403 CB  PRO A  55  0   -5.368 47.465  5.334 1.00 28.18
   ATOM   404 CG  PRO A  55  0   -5.249 47.049  3.899 1.00 27.50
   ATOM   405 CD  PRO A  55  0   -3.844 46.564  3.625 1.00 27.56
35 ATOM   406 N   THR A  56  0   -4.603 44.160  6.345 1.00 25.55
   ATOM   407 CA  THR A  56  0   -5.214 43.024  7.065 1.00 25.52
   ATOM   408 C   THR A  56  0   -4.446 42.647  8.326 1.00 24.87
   ATOM   409 O   THR A  56  0   -4.766 41.764  9.115 1.00 23.97
```

```
ATOM  410 CB  THR A 56 0  -5.393 41.807  6.154 1.00 25.10
ATOM  411 OG1 THR A 56 0  -4.100 41.345  5.763 1.00 24.26
ATOM  412 CG2 THR A 56 0  -6.178 42.123  4.861 1.00 25.63
ATOM  413 N   MET A 57 0  -3.317 43.311  8.558 1.00 26.01
ATOM  414 CA  MET A 57 0  -2.553 43.099  9.801 1.00 26.57
ATOM  415 C   MET A 57 0  -2.026 44.475 10.201 1.00 25.88
ATOM  416 O   MET A 57 0  -2.026 45.416  9.397 1.00 25.18
ATOM  417 CB  MET A 57 0  -1.561 41.939  9.698 1.00 25.42
ATOM  418 CG  MET A 57 0  -0.639 41.868  8.554 1.00 24.37
ATOM  419 SD  MET A 57 0  -0.034 40.288  7.916 1.00 22.34
ATOM  420 CE  MET A 57 0  -0.275 40.640  6.167 1.00 19.23
ATOM  421 N   LEU A 58 0  -1.694 44.601 11.476 1.00 25.98
ATOM  422 CA  LEU A 58 0  -1.180 45.850 12.036 1.00 25.57
ATOM  423 C   LEU A 58 0  -0.053 46.425 11.195 1.00 24.52
ATOM  424 O   LEU A 58 0   0.824 45.739 10.638 1.00 23.63
ATOM  425 CB  LEU A 58 0  -0.757 45.535 13.463 1.00 26.67
ATOM  426 CG  LEU A 58 0  -1.628 45.817 14.657 1.00 28.97
ATOM  427 CD1 LEU A 58 0  -3.107 45.995 14.312 1.00 30.99
ATOM  428 CD2 LEU A 58 0  -1.488 44.756 15.736 1.00 28.36
ATOM  429 N   ARG A 59 0  -0.078 47.741 11.030 1.00 24.96
ATOM  430 CA  ARG A 59 0   0.918 48.434 10.231 1.00 26.92
ATOM  431 C   ARG A 59 0   1.932 49.229 11.014 1.00 26.31
ATOM  432 O   ARG A 59 0   3.120 49.198 10.699 1.00 28.82
ATOM  433 CB  ARG A 59 0   0.260 49.277  9.132 1.00 28.35
ATOM  434 CG  ARG A 59 0  -0.252 48.385  7.986 1.00 29.50
ATOM  435 CD  ARG A 59 0  -0.986 49.274  6.996 1.00 30.33
ATOM  436 NE  ARG A 59 0  -2.333 49.604  7.459 1.00 32.26
ATOM  437 CZ  ARG A 59 0  -3.121 50.525  6.883 1.00 33.24
ATOM  438 NH1 ARG A 59 0  -2.679 51.233  5.845 1.00 32.27
ATOM  439 NH2 ARG A 59 0  -4.340 50.712  7.389 1.00 32.65
ATOM  440 N   PRO A 60 0   1.542 49.961 12.020 1.00 26.30
ATOM  441 CA  PRO A 60 0   2.460 50.669 12.916 1.00 26.19
ATOM  442 C   PRO A 60 0   3.312 49.591 13.595 1.00 25.29
ATOM  443 O   PRO A 60 0   2.879 48.432 13.668 1.00 24.63
ATOM  444 CB  PRO A 60 0   1.623 51.464 13.925 1.00 25.93
ATOM  445 CG  PRO A 60 0   0.235 51.357 13.325 1.00 26.19
ATOM  446 CD  PRO A 60 0   0.165 50.073 12.508 1.00 26.23
ATOM  447 N   THR A 61 0   4.544 49.932 13.976 1.00 24.60
```

42

|  | ATOM | 448 | CA | THR A 61 | 0 | 5.365 | 48.871 | 14.587 | 1.00 | 23.49 |
|---|---|---|---|---|---|---|---|---|---|---|
|  | ATOM | 449 | C | THR A 61 | 0 | 6.204 | 49.400 | 15.743 | 1.00 | 22.83 |
|  | ATOM | 450 | O | THR A 61 | 0 | 6.390 | 50.601 | 15.921 | 1.00 | 20.77 |
|  | ATOM | 451 | CB | THR A 61 | 0 | 6.245 | 48.170 | 13.535 | 1.00 | 22.69 |
| 5 | ATOM | 452 | OG1 | THR A 61 | 0 | 6.668 | 46.918 | 14.096 | 1.00 | 23.55 |
|  | ATOM | 453 | CG2 | THR A 61 | 0 | 7.444 | 48.976 | 13.119 | 1.00 | 20.92 |
|  | ATOM | 454 | N | SER A 62 | 0 | 6.702 | 48.449 | 16.507 | 1.00 | 22.38 |
|  | ATOM | 455 | CA | SER A 62 | 0 | 7.599 | 48.672 | 17.633 | 1.00 | 22.47 |
|  | ATOM | 456 | C | SER A 62 | 0 | 8.381 | 47.380 | 17.893 | 1.00 | 22.12 |
| 10 | ATOM | 457 | O | SER A 62 | 0 | 7.763 | 46.331 | 18.124 | 1.00 | 20.53 |
|  | ATOM | 458 | CB | SER A 62 | 0 | 6.784 | 49.033 | 18.882 | 1.00 | 22.02 |
|  | ATOM | 459 | OG | SER A 62 | 0 | 7.666 | 49.570 | 19.832 | 1.00 | 21.19 |
|  | ATOM | 460 | N | ILE A 63 | 0 | 9.716 | 47.451 | 17.806 | 1.00 | 21.17 |
|  | ATOM | 461 | CA | ILE A 63 | 0 | 10.513 | 46.240 | 17.960 | 1.00 | 18.32 |
| 15 | ATOM | 462 | C | ILE A 63 | 0 | 11.095 | 46.034 | 19.354 | 1.00 | 18.28 |
|  | ATOM | 463 | O | ILE A 63 | 0 | 11.832 | 46.909 | 19.826 | 1.00 | 19.63 |
|  | ATOM | 464 | CB | ILE A 63 | 0 | 11.642 | 46.234 | 16.924 | 1.00 | 16.68 |
|  | ATOM | 465 | CG1 | ILE A 63 | 0 | 11.166 | 46.509 | 15.508 | 1.00 | 18.51 |
|  | ATOM | 466 | CG2 | ILE A 63 | 0 | 12.319 | 44.848 | 16.906 | 1.00 | 16.78 |
| 20 | ATOM | 467 | CD1 | ILE A 63 | 0 | 10.055 | 45.625 | 14.994 | 1.00 | 18.25 |
|  | ATOM | 468 | N | HIS A 64 | 0 | 10.880 | 44.890 | 19.985 | 1.00 | 15.18 |
|  | ATOM | 469 | CA | HIS A 64 | 0 | 11.478 | 44.539 | 21.261 | 1.00 | 15.51 |
|  | ATOM | 470 | C | HIS A 64 | 0 | 12.648 | 43.559 | 21.029 | 1.00 | 16.73 |
|  | ATOM | 471 | O | HIS A 64 | 0 | 12.491 | 42.591 | 20.279 | 1.00 | 16.85 |
| 25 | ATOM | 472 | CB | HIS A 64 | 0 | 10.512 | 43.912 | 22.239 | 1.00 | 14.37 |
|  | ATOM | 473 | CG | HIS A 64 | 0 | 11.033 | 43.420 | 23.546 | 1.00 | 14.47 |
|  | ATOM | 474 | ND1 | HIS A 64 | 0 | 11.763 | 44.191 | 24.410 | 1.00 | 12.89 |
|  | ATOM | 475 | CD2 | HIS A 64 | 0 | 10.883 | 42.223 | 24.193 | 1.00 | 14.85 |
|  | ATOM | 476 | CE1 | HIS A 64 | 0 | 12.067 | 43.518 | 25.498 | 1.00 | 11.53 |
| 30 | ATOM | 477 | NE2 | HIS A 64 | 0 | 11.547 | 42.325 | 25.423 | 1.00 | 13.63 |
|  | ATOM | 478 | N | TRP A 65 | 0 | 13.761 | 43.781 | 21.723 | 1.00 | 14.37 |
|  | ATOM | 479 | CA | TRP A 65 | 0 | 14.966 | 42.926 | 21.577 | 1.00 | 13.92 |
|  | ATOM | 480 | C | TRP A 65 | 0 | 14.987 | 42.084 | 22.840 | 1.00 | 13.50 |
|  | ATOM | 481 | O | TRP A 65 | 0 | 15.482 | 42.538 | 23.901 | 1.00 | 12.84 |
| 35 | ATOM | 482 | CB | TRP A 65 | 0 | 16.189 | 43.825 | 21.371 | 1.00 | 13.50 |
|  | ATOM | 483 | CG | TRP A 65 | 0 | 15.890 | 45.020 | 20.492 | 1.00 | 13.19 |
|  | ATOM | 484 | CD1 | TRP A 65 | 0 | 15.453 | 46.247 | 20.913 | 1.00 | 12.42 |
|  | ATOM | 485 | CD2 | TRP A 65 | 0 | 15.908 | 45.087 | 19.068 | 1.00 | 13.61 |

5032-WO

43

```
    ATOM   486  NE1 TRP A  65  0   15.234  47.067  19.862  1.00 11.49
    ATOM   487  CE2 TRP A  65  0   15.511  46.390  18.710  1.00 13.77
    ATOM   488  CE3 TRP A  65  0   16.251  44.174  18.061  1.00 14.35
    ATOM   489  CZ2 TRP A  65  0   15.439  46.815  17.378  1.00 14.99
 5  ATOM   490  CZ3 TRP A  65  0   16.169  44.572  16.735  1.00 13.99
    ATOM   491  CH2 TRP A  65  0   15.756  45.869  16.411  1.00 15.82
    ATOM   492  N   HIS A  66  0   14.295  40.941  22.747  1.00 10.39
    ATOM   493  CA  HIS A  66  0   13.939  40.200  23.966  1.00 12.00
    ATOM   494  C   HIS A  66  0   15.158  39.653  24.698  1.00 11.34
10  ATOM   495  O   HIS A  66  0   15.889  38.859  24.130  1.00 11.51
    ATOM   496  CB  HIS A  66  0   12.923  39.069  23.629  1.00 10.76
    ATOM   497  CG  HIS A  66  0   12.418  38.308  24.808  1.00 11.26
    ATOM   498  ND1 HIS A  66  0   11.106  38.085  25.092  1.00 13.10
    ATOM   499  CD2 HIS A  66  0   13.050  37.676  25.824  1.00 13.49
15  ATOM   500  CE1 HIS A  66  0   10.919  37.407  26.191  1.00 12.50
    ATOM   501  NE2 HIS A  66  0   12.116  37.146  26.683  1.00 13.71
    ATOM   502  N   GLY A  67  0   15.345  39.971  25.948  1.00 12.84
    ATOM   503  CA  GLY A  67  0   16.492  39.469  26.719  1.00 13.36
    ATOM   504  C   GLY A  67  0   17.596  40.500  26.914  1.00 13.11
20  ATOM   505  O   GLY A  67  0   18.435  40.289  27.788  1.00 13.36
    ATOM   506  N   LEU A  68  0   17.641  41.558  26.131  1.00 12.89
    ATOM   507  CA  LEU A  68  0   18.659  42.598  26.300  1.00 15.22
    ATOM   508  C   LEU A  68  0   18.235  43.501  27.448  1.00 16.14
    ATOM   509  O   LEU A  68  0   17.029  43.842  27.505  1.00 16.50
25  ATOM   510  CB  LEU A  68  0   18.929  43.320  24.988  1.00 15.98
    ATOM   511  CG  LEU A  68  0   20.002  42.638  24.114  1.00 19.57
    ATOM   512  CD1 LEU A  68  0   19.719  41.185  23.809  1.00 20.39
    ATOM   513  CD2 LEU A  68  0   20.188  43.316  22.758  1.00 19.59
    ATOM   514  N   PHE A  69  0   19.125  43.848  28.386  1.00 13.24
30  ATOM   515  CA  PHE A  69  0   18.700  44.657  29.526  1.00 13.85
    ATOM   516  C   PHE A  69  0   18.499  46.128  29.205  1.00 14.34
    ATOM   517  O   PHE A  69  0   17.806  46.879  29.895  1.00 15.02
    ATOM   518  CB  PHE A  69  0   19.770  44.579  30.637  1.00 16.02
    ATOM   519  CG  PHE A  69  0   20.112  43.187  31.072  1.00 16.45
35  ATOM   520  CD1 PHE A  69  0   19.172  42.162  31.026  1.00 16.68
    ATOM   521  CD2 PHE A  69  0   21.381  42.927  31.578  1.00 16.78
    ATOM   522  CE1 PHE A  69  0   19.504  40.883  31.448  1.00 18.86
    ATOM   523  CE2 PHE A  69  0   21.717  41.652  32.001  1.00 17.34
```

5032-WO

44

```
ATOM   524  CZ  PHE A  69  0   20.782  40.628  31.932  1.00 18.09
ATOM   525  N   GLN A  70  0   19.081  46.611  28.130  1.00 12.22
ATOM   526  CA  GLN A  70  0   18.919  47.990  27.708  1.00 15.20
ATOM   527  C   GLN A  70  0   19.242  49.004  28.799  1.00 16.76
ATOM   528  O   GLN A  70  0   18.555  50.016  28.919  1.00 16.08
ATOM   529  CB  GLN A  70  0   17.488  48.115  27.232  1.00 15.52
ATOM   530  CG  GLN A  70  0   17.168  47.303  26.003  1.00 17.37
ATOM   531  CD  GLN A  70  0   17.781  47.744  24.709  1.00 17.70
ATOM   532  OE1 GLN A  70  0   17.557  47.090  23.676  1.00 21.63
ATOM   533  NE2 GLN A  70  0   18.549  48.805  24.620  1.00 16.79
ATOM   534  N   ARG A  71  0   20.338  48.804  29.518  1.00 16.49
ATOM   535  CA  ARG A  71  0   20.765  49.712  30.588  1.00 18.41
ATOM   536  C   ARG A  71  0   21.239  51.011  29.970  1.00 16.23
ATOM   537  O   ARG A  71  0   22.059  50.998  29.027  1.00 14.48
ATOM   538  CB  ARG A  71  0   21.827  48.942  31.382  1.00 22.65
ATOM   539  CG  ARG A  71  0   22.273  49.589  32.671  1.00 29.50
ATOM   540  CD  ARG A  71  0   23.286  48.756  33.457  1.00 32.92
ATOM   541  NE  ARG A  71  0   22.712  47.550  34.035  1.00 38.11
ATOM   542  CZ  ARG A  71  0   22.551  46.358  33.452  1.00 40.14
ATOM   543  NH1 ARG A  71  0   22.939  46.138  32.190  1.00 41.23
ATOM   544  NH2 ARG A  71  0   22.022  45.333  34.130  1.00 40.89
ATOM   545  N   GLY A  72  0   20.613  52.145  30.311  1.00 14.82
ATOM   546  CA  GLY A  72  0   20.981  53.414  29.676  1.00 14.51
ATOM   547  C   GLY A  72  0   20.268  53.606  28.338  1.00 15.55
ATOM   548  O   GLY A  72  0   20.401  54.706  27.777  1.00 16.32
ATOM   549  N   THR A  73  0   19.503  52.651  27.804  1.00 12.12
ATOM   550  CA  THR A  73  0   18.857  52.781  26.516  1.00 12.50
ATOM   551  C   THR A  73  0   17.418  52.252  26.621  1.00 13.98
ATOM   552  O   THR A  73  0   16.890  51.534  25.776  1.00 13.81
ATOM   553  CB  THR A  73  0   19.577  52.086  25.346  1.00 12.21
ATOM   554  OG1 THR A  73  0   19.854  50.711  25.666  1.00 12.83
ATOM   555  CG2 THR A  73  0   20.944  52.711  25.000  1.00  9.81
ATOM   556  N   ASN A  74  0   16.744  52.617  27.708  1.00 12.97
ATOM   557  CA  ASN A  74  0   15.354  52.273  27.951  1.00 14.93
ATOM   558  C   ASN A  74  0   14.469  52.718  26.784  1.00 15.92
ATOM   559  O   ASN A  74  0   13.501  52.030  26.455  1.00 16.56
ATOM   560  CB  ASN A  74  0   14.851  52.821  29.271  1.00 13.06
ATOM   561  CG  ASN A  74  0   13.385  52.519  29.556  1.00 15.47
```

5032-WO

45

```
   ATOM   562 OD1 ASN A  74  0    12.557 53.250 29.021  1.00 13.99
   ATOM   563 ND2 ASN A  74  0    13.063 51.500 30.367  1.00 13.91
   ATOM   564 N   TRP A  75  0    14.806 53.765 26.041  1.00 16.16
   ATOM   565 CA  TRP A  75  0    14.036 54.262 24.917  1.00 16.49
 5 ATOM   566 C   TRP A  75  0    14.050 53.345 23.701  1.00 17.29
   ATOM   567 O   TRP A  75  0    13.235 53.529 22.776  1.00 16.34
   ATOM   568 CB  TRP A  75  0    14.516 55.657 24.509  1.00 15.90
   ATOM   569 CG  TRP A  75  0    15.990 55.705 24.207  1.00 16.04
   ATOM   570 CD1 TRP A  75  0    17.011 55.972 25.072  1.00 14.90
10 ATOM   571 CD2 TRP A  75  0    16.584 55.475 22.916  1.00 15.94
   ATOM   572 NE1 TRP A  75  0    18.210 55.917 24.384  1.00 15.89
   ATOM   573 CE2 TRP A  75  0    17.977 55.624 23.076  1.00 15.80
   ATOM   574 CE3 TRP A  75  0    16.060 55.171 21.656  1.00 14.88
   ATOM   575 CZ2 TRP A  75  0    18.867 55.459 22.016  1.00 17.60
15 ATOM   576 CZ3 TRP A  75  0    16.928 55.025 20.603  1.00 16.64
   ATOM   577 CH2 TRP A  75  0    18.321 55.153 20.785  1.00 18.16
   ATOM   578 N   ALA A  76  0    14.962 52.372 23.675  1.00 15.12
   ATOM   579 CA  ALA A  76  0    15.075 51.430 22.578  1.00 14.61
   ATOM   580 C   ALA A  76  0    14.569 50.047 22.971  1.00 13.98
20 ATOM   581 O   ALA A  76  0    14.617 49.132 22.159  1.00 14.20
   ATOM   582 CB  ALA A  76  0    16.554 51.354 22.157  1.00 13.68
   ATOM   583 N   ASP A  77  0    13.941 49.885 24.121  1.00 14.47
   ATOM   584 CA  ASP A  77  0    13.409 48.605 24.586  1.00 14.23
   ATOM   585 C   ASP A  77  0    12.198 48.167 23.762  1.00 15.04
25 ATOM   586 O   ASP A  77  0    11.982 46.946 23.638  1.00 13.78
   ATOM   587 CB  ASP A  77  0    13.112 48.567 26.072  1.00 13.41
   ATOM   588 CG  ASP A  77  0    12.945 47.155 26.612  1.00 14.93
   ATOM   589 OD1 ASP A  77  0    11.943 46.986 27.345  1.00 15.07
   ATOM   590 OD2 ASP A  77  0    13.744 46.217 26.334  1.00 13.73
30 ATOM   591 N   GLY A  78  0    11.458 49.095 23.160  1.00 13.63
   ATOM   592 CA  GLY A  78  0    10.442 48.686 22.210  1.00 14.96
   ATOM   593 C   GLY A  78  0     9.040 48.309 22.631  1.00 16.75
   ATOM   594 O   GLY A  78  0     8.276 47.865 21.755  1.00 16.49
   ATOM   595 N   ALA A  79  0     8.631 48.436 23.886  1.00 15.34
35 ATOM   596 CA  ALA A  79  0     7.252 48.176 24.270  1.00 14.70
   ATOM   597 C   ALA A  79  0     6.490 49.495 24.084  1.00 17.51
   ATOM   598 O   ALA A  79  0     6.690 50.486 24.807  1.00 17.05
   ATOM   599 CB  ALA A  79  0     7.145 47.701 25.708  1.00 14.78
```

5032-WO

46

```
ATOM   600  N   ASP A 80  0    5.641 49.536 23.053 1.00 18.56
ATOM   601  CA  ASP A 80  0    4.859 50.741 22.798 1.00 19.52
ATOM   602  C   ASP A 80  0    3.959 50.963 24.010 1.00 17.61
ATOM   603  O   ASP A 80  0    3.530 49.999 24.664 1.00 16.72
ATOM   604  CB  ASP A 80  0    4.044 50.714 21.510 1.00 24.02
ATOM   605  CG  ASP A 80  0    3.003 49.607 21.549 1.00 28.13
ATOM   606  OD1 ASP A 80  0    3.410 48.417 21.541 1.00 30.66
ATOM   607  OD2 ASP A 80  0    1.803 49.959 21.603 1.00 30.61
ATOM   608  N   GLY A 81  0    3.776 52.242 24.337 1.00 15.85
ATOM   609  CA  GLY A 81  0    2.991 52.566 25.532 1.00 16.27
ATOM   610  C   GLY A 81  0    3.846 52.615 26.784 1.00 18.72
ATOM   611  O   GLY A 81  0    3.405 52.983 27.890 1.00 20.61
ATOM   612  N   VAL A 82  0    5.108 52.173 26.725 1.00 19.11
ATOM   613  CA  VAL A 82  0    5.978 52.119 27.890 1.00 19.14
ATOM   614  C   VAL A 82  0    7.288 52.851 27.590 1.00 18.41
ATOM   615  O   VAL A 82  0    7.594 53.839 28.242 1.00 16.79
ATOM   616  CB  VAL A 82  0    6.266 50.697 28.390 1.00 19.82
ATOM   617  CG1 VAL A 82  0    7.059 50.741 29.710 1.00 21.37
ATOM   618  CG2 VAL A 82  0    4.995 49.894 28.640 1.00 19.27
ATOM   619  N   ASN A 83  0    7.982 52.408 26.551 1.00 17.90
ATOM   620  CA  ASN A 83  0    9.271 52.926 26.147 1.00 16.94
ATOM   621  C   ASN A 83  0    9.226 53.778 24.886 1.00 18.32
ATOM   622  O   ASN A 83  0   10.175 54.551 24.634 1.00 20.58
ATOM   623  CB  ASN A 83  0   10.249 51.747 25.937 1.00 15.23
ATOM   624  CG  ASN A 83  0   10.112 50.745 27.063 1.00 16.00
ATOM   625  OD1 ASN A 83  0    9.493 49.676 26.879 1.00 14.98
ATOM   626  ND2 ASN A 83  0   10.583 51.131 28.249 1.00 13.17
ATOM   627  N   GLN A 84  0    8.183 53.668 24.066 1.00 16.40
ATOM   628  CA  GLN A 84  0    8.080 54.464 22.867 1.00 16.34
ATOM   629  C   GLN A 84  0    6.658 54.465 22.309 1.00 17.95
ATOM   630  O   GLN A 84  0    5.816 53.679 22.728 1.00 17.69
ATOM   631  CB  GLN A 84  0    8.995 53.953 21.754 1.00 17.98
ATOM   632  CG  GLN A 84  0    8.456 52.654 21.127 1.00 16.63
ATOM   633  CD  GLN A 84  0    9.272 52.225 19.938 1.00 18.17
ATOM   634  OE1 GLN A 84  0    8.994 52.601 18.792 1.00 20.91
ATOM   635  NE2 GLN A 84  0   10.279 51.385 20.096 1.00 18.70
ATOM   636  N   CYS A 85  0    6.419 55.350 21.365 1.00 18.60
ATOM   637  CA  CYS A 85  0    5.140 55.344 20.622 1.00 20.25
```

```
   ATOM   638  C   CYS A 85  0    5.512 54.555 19.375 1.00 19.55
   ATOM   639  O   CYS A 85  0    6.690 54.546 18.995 1.00 18.92
   ATOM   640  CB  CYS A 85  0    4.772 56.786 20.228 1.00 22.20
   ATOM   641  SG  CYS A 85  0    3.899 57.783 21.481 1.00 24.65
 5 ATOM   642  N   PRO A 86  0    4.589 53.951 18.674 1.00 21.19
   ATOM   643  CA  PRO A 86  0    4.869 53.152 17.498 1.00 20.78
   ATOM   644  C   PRO A 86  0    5.560 53.930 16.394 1.00 21.46
   ATOM   645  O   PRO A 86  0    5.453 55.137 16.298 1.00 23.08
   ATOM   646  CB  PRO A 86  0    3.530 52.555 17.028 1.00 19.94
10 ATOM   647  CG  PRO A 86  0    2.667 52.720 18.252 1.00 19.59
   ATOM   648  CD  PRO A 86  0    3.174 53.872 19.062 1.00 20.46
   ATOM   649  N   ILE A 87  0    6.318 53.259 15.550 1.00 20.95
   ATOM   650  CA  ILE A 87  0    6.907 53.773 14.337 1.00 22.43
   ATOM   651  C   ILE A 87  0    5.768 53.641 13.292 1.00 22.80
15 ATOM   652  O   ILE A 87  0    5.148 52.562 13.228 1.00 21.61
   ATOM   653  CB  ILE A 87  0    8.105 52.954 13.844 1.00 21.99
   ATOM   654  CG1 ILE A 87  0    9.130 52.696 14.944 1.00 24.18
   ATOM   655  CG2 ILE A 87  0    8.773 53.656 12.674 1.00 22.91
   ATOM   656  CD1 ILE A 87  0   10.256 51.776 14.514 1.00 23.87
20 ATOM   657  N   SER A 88  0    5.464 54.702 12.570 1.00 22.64
   ATOM   658  CA  SER A 88  0    4.338 54.709 11.647 1.00 22.85
   ATOM   659  C   SER A 88  0    4.751 54.268 10.249 1.00 23.35
   ATOM   660  O   SER A 88  0    5.870 54.489  9.764 1.00 23.30
   ATOM   661  CB  SER A 88  0    3.767 56.137 11.518 1.00 24.00
25 ATOM   662  OG  SER A 88  0    3.379 56.770 12.720 1.00 23.93
   ATOM   663  N   PRO A 89  0    3.778 53.752  9.514 1.00 23.60
   ATOM   664  CA  PRO A 89  0    3.955 53.382  8.116 1.00 25.19
   ATOM   665  C   PRO A 89  0    4.579 54.556  7.361 1.00 26.58
   ATOM   666  O   PRO A 89  0    4.177 55.699  7.585 1.00 26.66
30 ATOM   667  CB  PRO A 89  0    2.566 53.065  7.555 1.00 23.59
   ATOM   668  CG  PRO A 89  0    1.740 52.856  8.798 1.00 22.37
   ATOM   669  CD  PRO A 89  0    2.415 53.513  9.970 1.00 23.25
   ATOM   670  N   GLY A 90  0    5.588 54.311  6.550 1.00 27.73
   ATOM   671  CA  GLY A 90  0    6.223 55.338  5.748 1.00 30.55
35 ATOM   672  C   GLY A 90  0    7.384 56.032  6.438 1.00 32.38
   ATOM   673  O   GLY A 90  0    8.050 56.894  5.879 1.00 32.53
   ATOM   674  N   HIS A 91  0    7.639 55.693  7.702 1.00 32.77
   ATOM   675  CA  HIS A 91  0    8.691 56.283  8.494 1.00 32.55
```

```
ATOM   676  C   HIS A 91  0    9.649 55.179  8.982 1.00 32.36
ATOM   677  O   HIS A 91  0    9.381 53.972  8.961 1.00 31.30
ATOM   678  CB  HIS A 91  0    8.118 57.016  9.722 1.00 33.75
ATOM   679  CG  HIS A 91  0    7.147 58.073  9.295 1.00 34.64
ATOM   680  ND1 HIS A 91  0    7.519 59.381  9.072 1.00 34.41
ATOM   681  CD2 HIS A 91  0    5.822 57.977  9.002 1.00 34.89
ATOM   682  CE1 HIS A 91  0    6.450 60.050  8.679 1.00 34.87
ATOM   683  NE2 HIS A 91  0    5.410 59.233  8.628 1.00 35.14
ATOM   684  N   ALA A 92  0   10.786 55.668  9.437 1.00 29.57
ATOM   685  CA  ALA A 92  0   11.895 54.898  9.937 1.00 27.71
ATOM   686  C   ALA A 92  0   12.316 55.347 11.337 1.00 27.41
ATOM   687  O   ALA A 92  0   12.076 56.484 11.741 1.00 26.12
ATOM   688  CB  ALA A 92  0   13.051 55.057  8.967 1.00 25.23
ATOM   689  N   PHE A 93  0   12.931 54.418 12.081 1.00 26.87
ATOM   690  CA  PHE A 93  0   13.441 54.760 13.405 1.00 25.87
ATOM   691  C   PHE A 93  0   14.746 54.008 13.632 1.00 25.21
ATOM   692  O   PHE A 93  0   14.797 52.810 13.347 1.00 25.80
ATOM   693  CB  PHE A 93  0   12.457 54.456 14.526 1.00 25.30
ATOM   694  CG  PHE A 93  0   12.964 54.955 15.847 1.00 25.41
ATOM   695  CD1 PHE A 93  0   13.154 56.309 16.061 1.00 25.36
ATOM   696  CD2 PHE A 93  0   13.276 54.057 16.853 1.00 25.31
ATOM   697  CE1 PHE A 93  0   13.637 56.753 17.285 1.00 26.54
ATOM   698  CE2 PHE A 93  0   13.754 54.503 18.078 1.00 25.39
ATOM   699  CZ  PHE A 93  0   13.935 55.857 18.302 1.00 25.01
ATOM   700  N   LEU A 94  0   15.756 54.699 14.136 1.00 23.39
ATOM   701  CA  LEU A 94  0   17.046 54.058 14.361 1.00 23.35
ATOM   702  C   LEU A 94  0   17.191 53.611 15.804 1.00 23.22
ATOM   703  O   LEU A 94  0   17.261 54.431 16.714 1.00 23.47
ATOM   704  CB  LEU A 94  0   18.186 54.994 13.943 1.00 24.96
ATOM   705  CG  LEU A 94  0   19.630 54.555 14.170 1.00 26.28
ATOM   706  CD1 LEU A 94  0   19.979 53.313 13.352 1.00 25.99
ATOM   707  CD2 LEU A 94  0   20.627 55.678 13.887 1.00 26.06
ATOM   708  N   TYR A 95  0   17.261 52.293 16.023 1.00 21.81
ATOM   709  CA  TYR A 95  0   17.481 51.780 17.379 1.00 19.72
ATOM   710  C   TYR A 95  0   18.991 51.663 17.585 1.00 20.90
ATOM   711  O   TYR A 95  0   19.690 51.248 16.656 1.00 20.74
ATOM   712  CB  TYR A 95  0   16.831 50.448 17.609 1.00 17.86
ATOM   713  CG  TYR A 95  0   15.329 50.411 17.691 1.00 16.35
```

5032-WO

49

```
    ATOM   714 CD1 TYR A 95  0   14.541 50.288 16.535 1.00 16.89
    ATOM   715 CD2 TYR A 95  0   14.701 50.442 18.911 1.00 15.71
    ATOM   716 CE1 TYR A 95  0   13.157 50.205 16.621 1.00 17.21
    ATOM   717 CE2 TYR A 95  0   13.325 50.362 19.033 1.00 16.25
 5  ATOM   718 CZ  TYR A 95  0   12.568 50.266 17.874 1.00 17.97
    ATOM   719 OH  TYR A 95  0   11.205 50.189 18.001 1.00 18.61
    ATOM   720 N   LYS A 96  0   19.475 52.105 18.752 1.00 20.56
    ATOM   721 CA  LYS A 96  0   20.917 52.058 18.975 1.00 21.77
    ATOM   722 C   LYS A 96  0   21.139 51.519 20.386 1.00 20.91
10  ATOM   723 O   LYS A 96  0   20.558 52.122 21.286 1.00 21.98
    ATOM   724 CB  LYS A 96  0   21.565 53.427 18.960 1.00 22.89
    ATOM   725 CG  LYS A 96  0   21.857 54.046 17.609 1.00 26.39
    ATOM   726 CD  LYS A 96  0   22.749 55.251 17.923 1.00 30.80
    ATOM   727 CE  LYS A 96  0   22.732 56.348 16.884 1.00 32.90
15  ATOM   728 NZ  LYS A 96  0   23.767 57.378 17.277 1.00 36.06
    ATOM   729 N   PHE A 97  0   21.871 50.437 20.520 1.00 18.14
    ATOM   730 CA  PHE A 97  0   22.062 49.863 21.854 1.00 18.19
    ATOM   731 C   PHE A 97  0   23.276 48.928 21.805 1.00 16.76
    ATOM   732 O   PHE A 97  0   23.870 48.700 20.747 1.00 14.19
20  ATOM   733 CB  PHE A 97  0   20.816 49.067 22.307 1.00 17.34
    ATOM   734 CG  PHE A 97  0   20.379 48.026 21.304 1.00 17.56
    ATOM   735 CD1 PHE A 97  0   20.873 46.732 21.348 1.00 16.27
    ATOM   736 CD2 PHE A 97  0   19.451 48.343 20.326 1.00 18.65
    ATOM   737 CE1 PHE A 97  0   20.476 45.801 20.398 1.00 17.76
25  ATOM   738 CE2 PHE A 97  0   19.026 47.408 19.386 1.00 18.64
    ATOM   739 CZ  PHE A 97  0   19.546 46.120 19.416 1.00 17.55
    ATOM   740 N   THR A 98  0   23.552 48.348 22.971 1.00 17.45
    ATOM   741 CA  THR A 98  0   24.644 47.359 22.992 1.00 17.00
    ATOM   742 C   THR A 98  0   24.304 46.333 24.042 1.00 16.63
30  ATOM   743 O   THR A 98  0   23.725 46.631 25.090 1.00 15.86
    ATOM   744 CB  THR A 98  0   26.028 47.990 23.256 1.00 17.53
    ATOM   745 OG1 THR A 98  0   27.017 46.924 23.372 1.00 19.01
    ATOM   746 CG2 THR A 98  0   26.088 48.807 24.525 1.00 14.85
    ATOM   747 N   PRO A 99  0   24.740 45.097 23.831 1.00 15.98
35  ATOM   748 CA  PRO A 99  0   24.601 44.019 24.787 1.00 15.11
    ATOM   749 C   PRO A 99  0   25.445 44.270 26.020 1.00 15.99
    ATOM   750 O   PRO A 99  0   25.260 43.633 27.064 1.00 15.94
    ATOM   751 CB  PRO A 99  0   25.025 42.717 24.098 1.00 15.83
```

5032-WO

50

```
   ATOM  752 CG  PRO A 99  0  25.042 43.140 22.644 1.00 17.12
   ATOM  753 CD  PRO A 99  0  25.362 44.627 22.601 1.00 15.68
   ATOM  754 N   ALA A 100 0  26.452 45.149 25.932 1.00 17.29
   ATOM  755 CA  ALA A 100 0  27.316 45.501 27.050 1.00 16.88
 5 ATOM  756 C   ALA A 100 0  27.919 44.293 27.754 1.00 16.16
   ATOM  757 O   ALA A 100 0  27.779 44.187 28.977 1.00 18.13
   ATOM  758 CB  ALA A 100 0  26.498 46.292 28.084 1.00 14.96
   ATOM  759 N   GLY A 101 0  28.474 43.360 27.033 1.00 16.41
   ATOM  760 CA  GLY A 101 0  29.063 42.172 27.599 1.00 17.49
10 ATOM  761 C   GLY A 101 0  28.130 40.994 27.769 1.00 16.15
   ATOM  762 O   GLY A 101 0  28.593 39.930 28.137 1.00 16.57
   ATOM  763 N   HIS A 102 0  26.838 41.120 27.521 1.00 17.58
   ATOM  764 CA  HIS A 102 0  25.858 40.058 27.804 1.00 15.77
   ATOM  765 C   HIS A 102 0  25.707 39.165 26.600 1.00 15.28
15 ATOM  766 O   HIS A 102 0  25.087 39.641 25.662 1.00 17.64
   ATOM  767 CB  HIS A 102 0  24.498 40.666 28.186 1.00 17.95
   ATOM  768 CG  HIS A 102 0  23.432 39.661 28.493 1.00 20.00
   ATOM  769 ND1 HIS A 102 0  22.099 40.005 28.547 1.00 20.59
   ATOM  770 CD2 HIS A 102 0  23.475 38.323 28.772 1.00 20.09
20 ATOM  771 CE1 HIS A 102 0  21.398 38.937 28.866 1.00 20.77
   ATOM  772 NE2 HIS A 102 0  22.201 37.896 29.016 1.00 20.56
   ATOM  773 N   ALA A 103 0  26.277 37.958 26.584 1.00 13.32
   ATOM  774 CA  ALA A 103 0  26.141 37.127 25.415 1.00 13.99
   ATOM  775 C   ALA A 103 0  24.974 36.156 25.649 1.00 13.43
25 ATOM  776 O   ALA A 103 0  24.571 35.905 26.784 1.00 11.81
   ATOM  777 CB  ALA A 103 0  27.418 36.329 25.151 1.00 16.36
   ATOM  778 N   GLY A 104 0  24.459 35.610 24.554 1.00 12.38
   ATOM  779 CA  GLY A 104 0  23.381 34.632 24.778 1.00 12.85
   ATOM  780 C   GLY A 104 0  22.480 34.451 23.581 1.00 11.06
30 ATOM  781 O   GLY A 104 0  22.674 35.057 22.515 1.00 10.91
   ATOM  782 N   THR A 105 0  21.442 33.650 23.794 1.00 10.14
   ATOM  783 CA  THR A 105 0  20.490 33.394 22.704 1.00 10.04
   ATOM  784 C   THR A 105 0  19.238 34.236 22.989 1.00  9.52
   ATOM  785 O   THR A 105 0  18.738 34.194 24.125 1.00  7.52
35 ATOM  786 CB  THR A 105 0  20.114 31.913 22.665 1.00 12.67
   ATOM  787 OG1 THR A 105 0  21.273 31.075 22.593 1.00 13.47
   ATOM  788 CG2 THR A 105 0  19.187 31.684 21.468 1.00 12.75
   ATOM  789 N   PHE A 106 0  18.842 35.065 22.044 1.00  7.76
```

5032-WO

51

| | ATOM | 790 | CA | PHE A 106 | 0 | 17.731 | 35.992 | 22.243 | 1.00 | 10.15 |
|---|---|---|---|---|---|---|---|---|---|---|
| | ATOM | 791 | C | PHE A 106 | 0 | 16.756 | 35.910 | 21.068 | 1.00 | 8.42 |
| | ATOM | 792 | O | PHE A 106 | 0 | 16.941 | 35.083 | 20.166 | 1.00 | 8.33 |
| | ATOM | 793 | CB | PHE A 106 | 0 | 18.283 | 37.460 | 22.369 | 1.00 | 10.19 |
| 5 | ATOM | 794 | CG | PHE A 106 | 0 | 19.291 | 37.577 | 23.506 | 1.00 | 12.95 |
| | ATOM | 795 | CD1 | PHE A 106 | 0 | 18.905 | 37.443 | 24.815 | 1.00 | 11.44 |
| | ATOM | 796 | CD2 | PHE A 106 | 0 | 20.654 | 37.775 | 23.230 | 1.00 | 12.37 |
| | ATOM | 797 | CE1 | PHE A 106 | 0 | 19.855 | 37.531 | 25.822 | 1.00 | 14.20 |
| | ATOM | 798 | CE2 | PHE A 106 | 0 | 21.574 | 37.857 | 24.273 | 1.00 | 11.56 |
| 10 | ATOM | 799 | CZ | PHE A 106 | 0 | 21.202 | 37.733 | 25.599 | 1.00 | 9.45 |
| | ATOM | 800 | N | TRP A 107 | 0 | 15.869 | 36.887 | 20.917 | 1.00 | 6.61 |
| | ATOM | 801 | CA | TRP A 107 | 0 | 15.062 | 36.977 | 19.713 | 1.00 | 10.20 |
| | ATOM | 802 | C | TRP A 107 | 0 | 14.511 | 38.398 | 19.625 | 1.00 | 10.63 |
| | ATOM | 803 | O | TRP A 107 | 0 | 14.463 | 39.036 | 20.657 | 1.00 | 13.71 |
| 15 | ATOM | 804 | CB | TRP A 107 | 0 | 13.928 | 35.966 | 19.636 | 1.00 | 7.49 |
| | ATOM | 805 | CG | TRP A 107 | 0 | 12.945 | 35.916 | 20.755 | 1.00 | 9.41 |
| | ATOM | 806 | CD1 | TRP A 107 | 0 | 13.136 | 35.804 | 22.106 | 1.00 | 10.53 |
| | ATOM | 807 | CD2 | TRP A 107 | 0 | 11.509 | 36.004 | 20.581 | 1.00 | 9.17 |
| | ATOM | 808 | NE1 | TRP A 107 | 0 | 11.929 | 35.784 | 22.768 | 1.00 | 10.63 |
| 20 | ATOM | 809 | CE2 | TRP A 107 | 0 | 10.924 | 35.926 | 21.842 | 1.00 | 9.90 |
| | ATOM | 810 | CE3 | TRP A 107 | 0 | 10.698 | 36.144 | 19.444 | 1.00 | 8.77 |
| | ATOM | 811 | CZ2 | TRP A 107 | 0 | 9.538 | 35.947 | 22.025 | 1.00 | 10.01 |
| | ATOM | 812 | CZ3 | TRP A 107 | 0 | 9.336 | 36.167 | 19.613 | 1.00 | 8.60 |
| | ATOM | 813 | CH2 | TRP A 107 | 0 | 8.774 | 36.061 | 20.890 | 1.00 | 10.09 |
| 25 | ATOM | 814 | N | TYR A 108 | 0 | 14.117 | 38.847 | 18.464 | 1.00 | 10.72 |
| | ATOM | 815 | CA | TYR A 108 | 0 | 13.498 | 40.148 | 18.302 | 1.00 | 12.19 |
| | ATOM | 816 | C | TYR A 108 | 0 | 12.030 | 39.869 | 17.875 | 1.00 | 13.62 |
| | ATOM | 817 | O | TYR A 108 | 0 | 11.752 | 38.837 | 17.245 | 1.00 | 13.85 |
| | ATOM | 818 | CB | TYR A 108 | 0 | 14.182 | 40.994 | 17.259 | 1.00 | 11.05 |
| 30 | ATOM | 819 | CG | TYR A 108 | 0 | 14.176 | 40.413 | 15.857 | 1.00 | 13.89 |
| | ATOM | 820 | CD1 | TYR A 108 | 0 | 15.087 | 39.464 | 15.423 | 1.00 | 12.99 |
| | ATOM | 821 | CD2 | TYR A 108 | 0 | 13.257 | 40.897 | 14.920 | 1.00 | 14.94 |
| | ATOM | 822 | CE1 | TYR A 108 | 0 | 15.064 | 38.979 | 14.130 | 1.00 | 13.64 |
| | ATOM | 823 | CE2 | TYR A 108 | 0 | 13.216 | 40.409 | 13.624 | 1.00 | 15.34 |
| 35 | ATOM | 824 | CZ | TYR A 108 | 0 | 14.123 | 39.443 | 13.236 | 1.00 | 14.99 |
| | ATOM | 825 | OH | TYR A 108 | 0 | 14.063 | 38.960 | 11.946 | 1.00 | 16.68 |
| | ATOM | 826 | N | HIS A 109 | 0 | 11.123 | 40.752 | 18.254 | 1.00 | 12.81 |
| | ATOM | 827 | CA | HIS A 109 | 0 | 9.735 | 40.630 | 17.826 | 1.00 | 14.92 |

```
   ATOM  828  C   HIS A 109 0   9.057 41.988 17.991 1.00 15.96
   ATOM  829  O   HIS A 109 0   9.392 42.800 18.875 1.00 15.67
   ATOM  830  CB  HIS A 109 0   8.903 39.566 18.550 1.00 12.30
   ATOM  831  CG  HIS A 109 0   8.804 39.727 20.036 1.00 12.30
 5 ATOM  832  ND1 HIS A 109 0   7.788 40.429 20.666 1.00  9.89
   ATOM  833  CD2 HIS A 109 0   9.614 39.264 21.034 1.00 10.76
   ATOM  834  CE1 HIS A 109 0   7.982 40.379 21.971 1.00  8.49
   ATOM  835  NE2 HIS A 109 0   9.086 39.679 22.224 1.00  7.92
   ATOM  836  N   SER A 110 0   8.070 42.203 17.122 1.00 16.26
10 ATOM  837  CA  SER A 110 0   7.244 43.404 17.300 1.00 14.55
   ATOM  838  C   SER A 110 0   6.548 43.283 18.646 1.00 13.56
   ATOM  839  O   SER A 110 0   6.219 42.191 19.140 1.00 13.54
   ATOM  840  CB  SER A 110 0   6.219 43.543 16.159 1.00 16.69
   ATOM  841  OG  SER A 110 0   5.212 44.481 16.508 1.00 15.32
15 ATOM  842  N   HIS A 111 0   6.396 44.395 19.359 1.00 14.60
   ATOM  843  CA  HIS A 111 0   5.724 44.397 20.645 1.00 16.23
   ATOM  844  C   HIS A 111 0   4.349 45.070 20.478 1.00 18.61
   ATOM  845  O   HIS A 111 0   3.713 45.391 21.473 1.00 21.72
   ATOM  846  CB  HIS A 111 0   6.478 45.166 21.721 1.00 14.37
20 ATOM  847  CG  HIS A 111 0   6.392 44.519 23.077 1.00 15.33
   ATOM  848  ND1 HIS A 111 0   5.341 44.660 23.947 1.00 14.55
   ATOM  849  CD2 HIS A 111 0   7.265 43.676 23.680 1.00 14.72
   ATOM  850  CE1 HIS A 111 0   5.589 43.936 25.040 1.00 16.29
   ATOM  851  NE2 HIS A 111 0   6.773 43.326 24.920 1.00 15.35
25 ATOM  852  N   PHE A 112 0   3.950 45.382 19.258 1.00 18.67
   ATOM  853  CA  PHE A 112 0   2.725 46.139 19.037 1.00 19.61
   ATOM  854  C   PHE A 112 0   1.540 45.219 18.777 1.00 19.06
   ATOM  855  O   PHE A 112 0   1.521 44.630 17.707 1.00 17.50
   ATOM  856  CB  PHE A 112 0   2.971 47.113 17.875 1.00 21.16
30 ATOM  857  CG  PHE A 112 0   1.798 48.019 17.611 1.00 23.12
   ATOM  858  CD1 PHE A 112 0   1.456 49.007 18.509 1.00 24.59
   ATOM  859  CD2 PHE A 112 0   1.034 47.886 16.466 1.00 24.82
   ATOM  860  CE1 PHE A 112 0   0.387 49.852 18.312 1.00 24.29
   ATOM  861  CE2 PHE A 112 0  -0.063 48.714 16.243 1.00 25.87
35 ATOM  862  CZ  PHE A 112 0  -0.378 49.698 17.161 1.00 25.17
   ATOM  863  N   GLY A 113 0   0.599 45.092 19.707 1.00 18.05
   ATOM  864  CA  GLY A 113 0  -0.554 44.236 19.433 1.00 19.69
   ATOM  865  C   GLY A 113 0  -0.085 42.819 19.096 1.00 22.25
```

5032-WO

53

| | ATOM | 866 | O | GLY A 113 | 0 | 0.937 | 42.333 | 19.593 | 1.00 | 20.55 |
|---|---|---|---|---|---|---|---|---|---|---|
| | ATOM | 867 | N | THR A 114 | 0 | -0.817 | 42.173 | 18.186 | 1.00 | 20.91 |
| | ATOM | 868 | CA | THR A 114 | 0 | -0.493 | 40.816 | 17.749 | 1.00 | 20.85 |
| | ATOM | 869 | C | THR A 114 | 0 | 0.296 | 40.774 | 16.471 | 1.00 | 18.04 |
| 5 | ATOM | 870 | O | THR A 114 | 0 | 0.243 | 39.783 | 15.743 | 1.00 | 18.26 |
| | ATOM | 871 | CB | THR A 114 | 0 | -1.847 | 40.095 | 17.487 | 1.00 | 23.93 |
| | ATOM | 872 | OG1 | THR A 114 | 0 | -2.609 | 40.910 | 16.554 | 1.00 | 25.68 |
| | ATOM | 873 | CG2 | THR A 114 | 0 | -2.571 | 39.928 | 18.792 | 1.00 | 23.72 |
| | ATOM | 874 | N | GLN A 115 | 0 | 1.023 | 41.819 | 16.095 | 1.00 | 17.04 |
| 10 | ATOM | 875 | CA | GLN A 115 | 0 | 1.792 | 41.842 | 14.853 | 1.00 | 16.88 |
| | ATOM | 876 | C | GLN A 115 | 0 | 2.881 | 40.775 | 14.744 | 1.00 | 17.94 |
| | ATOM | 877 | O | GLN A 115 | 0 | 3.203 | 40.263 | 13.649 | 1.00 | 17.18 |
| | ATOM | 878 | CB | GLN A 115 | 0 | 2.391 | 43.244 | 14.757 | 1.00 | 17.55 |
| | ATOM | 879 | CG | GLN A 115 | 0 | 3.026 | 43.601 | 13.418 | 1.00 | 17.65 |
| 15 | ATOM | 880 | CD | GLN A 115 | 0 | 3.558 | 45.024 | 13.418 | 1.00 | 17.73 |
| | ATOM | 881 | OE1 | GLN A 115 | 0 | 3.257 | 45.782 | 12.482 | 1.00 | 19.19 |
| | ATOM | 882 | NE2 | GLN A 115 | 0 | 4.334 | 45.421 | 14.422 | 1.00 | 14.70 |
| | ATOM | 883 | N | TYR A 116 | 0 | 3.515 | 40.416 | 15.881 | 1.00 | 16.32 |
| | ATOM | 884 | CA | TYR A 116 | 0 | 4.561 | 39.386 | 15.859 | 1.00 | 15.92 |
| 20 | ATOM | 885 | C | TYR A 116 | 0 | 3.935 | 38.042 | 15.479 | 1.00 | 17.17 |
| | ATOM | 886 | O | TYR A 116 | 0 | 4.584 | 37.258 | 14.786 | 1.00 | 16.70 |
| | ATOM | 887 | CB | TYR A 116 | 0 | 5.411 | 39.312 | 17.096 | 1.00 | 13.45 |
| | ATOM | 888 | CG | TYR A 116 | 0 | 5.209 | 38.487 | 18.314 | 1.00 | 10.97 |
| | ATOM | 889 | CD1 | TYR A 116 | 0 | 5.581 | 37.146 | 18.394 | 1.00 | 11.02 |
| 25 | ATOM | 890 | CD2 | TYR A 116 | 0 | 4.665 | 39.052 | 19.460 | 1.00 | 12.18 |
| | ATOM | 891 | CE1 | TYR A 116 | 0 | 5.364 | 36.399 | 19.532 | 1.00 | 10.02 |
| | ATOM | 892 | CE2 | TYR A 116 | 0 | 4.491 | 38.345 | 20.642 | 1.00 | 12.25 |
| | ATOM | 893 | CZ | TYR A 116 | 0 | 4.838 | 36.996 | 20.649 | 1.00 | 11.73 |
| | ATOM | 894 | OH | TYR A 116 | 0 | 4.642 | 36.295 | 21.821 | 1.00 | 12.72 |
| 30 | ATOM | 895 | N | CYS A 117 | 0 | 2.654 | 37.829 | 15.842 | 1.00 | 17.70 |
| | ATOM | 896 | CA | CYS A 117 | 0 | 1.965 | 36.617 | 15.424 | 1.00 | 18.01 |
| | ATOM | 897 | C | CYS A 117 | 0 | 1.883 | 36.496 | 13.911 | 1.00 | 17.55 |
| | ATOM | 898 | O | CYS A 117 | 0 | 1.796 | 35.352 | 13.450 | 1.00 | 17.50 |
| | ATOM | 899 | CB | CYS A 117 | 0 | 0.565 | 36.528 | 16.042 | 1.00 | 17.90 |
| 35 | ATOM | 900 | SG | CYS A 117 | 0 | 0.463 | 36.895 | 17.810 | 1.00 | 19.72 |
| | ATOM | 901 | N | ASP A 118 | 0 | 2.001 | 37.568 | 13.136 | 1.00 | 15.51 |
| | ATOM | 902 | CA | ASP A 118 | 0 | 1.953 | 37.509 | 11.696 | 1.00 | 17.74 |
| | ATOM | 903 | C | ASP A 118 | 0 | 3.341 | 37.445 | 11.061 | 1.00 | 18.72 |

```
    ATOM  904 O   ASP A 118  0   3.494 37.770  9.865 1.00 17.47
    ATOM  905 CB  ASP A 118  0   1.142 38.696 11.131 1.00 18.61
    ATOM  906 CG  ASP A 118  0  -0.356 38.448 11.378 1.00 21.44
    ATOM  907 OD1 ASP A 118  0  -0.826 37.331 11.082 1.00 21.55
 5  ATOM  908 OD2 ASP A 118  0  -1.064 39.333 11.885 1.00 21.54
    ATOM  909 N   GLY A 119  0   4.355 37.095 11.882 1.00 18.19
    ATOM  910 CA  GLY A 119  0   5.671 36.889 11.313 1.00 19.00
    ATOM  911 C   GLY A 119  0   6.751 37.898 11.590 1.00 19.79
    ATOM  912 O   GLY A 119  0   7.909 37.640 11.213 1.00 19.97
10  ATOM  913 N   LEU A 120  0   6.445 39.011 12.280 1.00 18.24
    ATOM  914 CA  LEU A 120  0   7.484 39.991 12.569 1.00 16.08
    ATOM  915 C   LEU A 120  0   8.210 39.565 13.848 1.00 16.53
    ATOM  916 O   LEU A 120  0   7.933 40.051 14.939 1.00 15.31
    ATOM  917 CB  LEU A 120  0   6.918 41.389 12.654 1.00 16.22
15  ATOM  918 CG  LEU A 120  0   7.916 42.540 12.830 1.00 17.73
    ATOM  919 CD1 LEU A 120  0   9.188 42.293 12.043 1.00 17.73
    ATOM  920 CD2 LEU A 120  0   7.302 43.880 12.448 1.00 16.66
    ATOM  921 N   ARG A 121  0   9.144 38.622 13.682 1.00 14.23
    ATOM  922 CA  ARG A 121  0   9.859 37.985 14.773 1.00 14.19
20  ATOM  923 C   ARG A 121  0  11.007 37.152 14.159 1.00 14.09
    ATOM  924 O   ARG A 121  0  10.936 36.787 12.978 1.00 13.72
    ATOM  925 CB  ARG A 121  0   8.934 37.061 15.581 1.00 12.30
    ATOM  926 CG  ARG A 121  0   8.253 35.999 14.728 1.00 12.44
    ATOM  927 CD  ARG A 121  0   7.303 35.098 15.518 1.00 11.94
25  ATOM  928 NE  ARG A 121  0   6.507 34.269 14.604 1.00 12.92
    ATOM  929 CZ  ARG A 121  0   5.413 33.570 14.933 1.00 10.55
    ATOM  930 NH1 ARG A 121  0   4.897 33.483 16.137 1.00  8.12
    ATOM  931 NH2 ARG A 121  0   4.803 32.946 13.930 1.00 10.40
    ATOM  932 N   GLY A 122  0  12.045 36.848 14.937 1.00 12.29
30  ATOM  933 CA  GLY A 122  0  13.162 36.078 14.364 1.00 11.42
    ATOM  934 C   GLY A 122  0  14.185 35.918 15.486 1.00 12.42
    ATOM  935 O   GLY A 122  0  14.095 36.604 16.509 1.00 11.47
    ATOM  936 N   PRO A 123  0  15.164 35.075 15.246 1.00 11.82
    ATOM  937 CA  PRO A 123  0  16.226 34.778 16.190 1.00 12.81
35  ATOM  938 C   PRO A 123  0  17.288 35.857 16.258 1.00 12.41
    ATOM  939 O   PRO A 123  0  17.565 36.580 15.302 1.00 12.03
    ATOM  940 CB  PRO A 123  0  16.833 33.416 15.713 1.00 12.34
    ATOM  941 CG  PRO A 123  0  16.567 33.494 14.223 1.00 12.19
```

```
    ATOM   942 CD  PRO A 123  0   15.283 34.289 14.021 1.00 11.35
    ATOM   943 N   MET A 124  0   17.903 36.027 17.431 1.00 14.30
    ATOM   944 CA  MET A 124  0   18.959 37.024 17.628 1.00 14.19
    ATOM   945 C   MET A 124  0   20.040 36.414 18.528 1.00 15.37
  5 ATOM   946 O   MET A 124  0   19.788 36.067 19.690 1.00 15.41
    ATOM   947 CB  MET A 124  0   18.411 38.290 18.242 1.00 15.94
    ATOM   948 CG  MET A 124  0   19.464 39.345 18.604 1.00 19.30
    ATOM   949 SD  MET A 124  0   18.646 40.875 19.164 1.00 21.94
    ATOM   950 CE  MET A 124  0   19.918 42.061 18.729 1.00 23.64
 10 ATOM   951 N   VAL A 125  0   21.212 36.178 17.939 1.00 13.74
    ATOM   952 CA  VAL A 125  0   22.282 35.479 18.658 1.00 13.87
    ATOM   953 C   VAL A 125  0   23.478 36.390 18.872 1.00 13.68
    ATOM   954 O   VAL A 125  0   24.004 36.976 17.945 1.00 14.01
    ATOM   955 CB  VAL A 125  0   22.672 34.139 18.005 1.00 12.58
 15 ATOM   956 CG1 VAL A 125  0   23.787 33.383 18.749 1.00 11.23
    ATOM   957 CG2 VAL A 125  0   21.448 33.212 18.033 1.00 12.14
    ATOM   958 N   ILE A 126  0   23.860 36.535 20.135 1.00 14.48
    ATOM   959 CA  ILE A 126  0   25.016 37.295 20.557 1.00 14.53
    ATOM   960 C   ILE A 126  0   26.131 36.348 21.054 1.00 13.58
 20 ATOM   961 O   ILE A 126  0   26.061 35.791 22.154 1.00 12.93
    ATOM   962 CB  ILE A 126  0   24.649 38.295 21.662 1.00 14.95
    ATOM   963 CG1 ILE A 126  0   23.563 39.302 21.254 1.00 15.29
    ATOM   964 CG2 ILE A 126  0   25.901 39.014 22.174 1.00 14.24
    ATOM   965 CD1 ILE A 126  0   23.703 39.905 19.896 1.00 15.84
 25 ATOM   966 N   TYR A 127  0   27.142 36.146 20.236 1.00 13.66
    ATOM   967 CA  TYR A 127  0   28.278 35.258 20.529 1.00 14.62
    ATOM   968 C   TYR A 127  0   29.328 35.778 21.507 1.00 15.97
    ATOM   969 O   TYR A 127  0   29.626 36.977 21.669 1.00 15.27
    ATOM   970 CB  TYR A 127  0   28.965 34.939 19.176 1.00 14.97
 30 ATOM   971 CG  TYR A 127  0   28.057 34.136 18.272 1.00 16.10
    ATOM   972 CD1 TYR A 127  0   27.823 32.782 18.496 1.00 14.96
    ATOM   973 CD2 TYR A 127  0   27.428 34.753 17.177 1.00 16.64
    ATOM   974 CE1 TYR A 127  0   26.995 32.057 17.650 1.00 16.16
    ATOM   975 CE2 TYR A 127  0   26.576 34.039 16.356 1.00 17.32
 35 ATOM   976 CZ  TYR A 127  0   26.374 32.692 16.592 1.00 18.16
    ATOM   977 OH  TYR A 127  0   25.540 31.971 15.756 1.00 20.32
    ATOM   978 N   ASP A 128  0   29.892 34.895 22.312 1.00 14.36
    ATOM   979 CA  ASP A 128  0   30.825 35.269 23.365 1.00 16.80
```

5032-WO

56

```
ATOM    980  C   ASP A 128  0   32.222 34.863 22.939 1.00 20.11
ATOM    981  O   ASP A 128  0   32.508 33.656 22.777 1.00 21.41
ATOM    982  CB  ASP A 128  0   30.398 34.568 24.649 1.00 16.65
ATOM    983  CG  ASP A 128  0   31.136 35.055 25.874 1.00 18.36
ATOM    984  OD1 ASP A 128  0   32.194 35.708 25.750 1.00 18.72
ATOM    985  OD2 ASP A 128  0   30.710 34.819 27.024 1.00 20.03
ATOM    986  N   ASP A 129  0   33.148 35.798 22.771 1.00 22.30
ATOM    987  CA  ASP A 129  0   34.511 35.389 22.377 1.00 24.39
ATOM    988  C   ASP A 129  0   35.282 34.740 23.509 1.00 22.47
ATOM    989  O   ASP A 129  0   36.275 34.096 23.209 1.00 23.18
ATOM    990  CB  ASP A 129  0   35.298 36.490 21.707 1.00 28.46
ATOM    991  CG  ASP A 129  0   35.372 37.764 22.516 1.00 31.10
ATOM    992  OD1 ASP A 129  0   35.254 37.652 23.747 1.00 32.87
ATOM    993  OD2 ASP A 129  0   35.553 38.824 21.891 1.00 34.70
ATOM    994  N   ASN A 130  0   34.829 34.684 24.736 1.00 21.92
ATOM    995  CA  ASN A 130  0   35.368 34.015 25.874 1.00 23.74
ATOM    996  C   ASN A 130  0   34.382 32.976 26.417 1.00 23.02
ATOM    997  O   ASN A 130  0   34.352 32.684 27.616 1.00 20.14
ATOM    998  CB  ASN A 130  0   35.686 35.002 27.028 1.00 26.41
ATOM    999  CG  ASN A 130  0   36.583 36.127 26.550 1.00 30.99
ATOM   1000  OD1 ASN A 130  0   36.187 37.309 26.486 1.00 33.20
ATOM   1001  ND2 ASN A 130  0   37.818 35.769 26.175 1.00 30.96
ATOM   1002  N   ASP A 131  0   33.533 32.401 25.561 1.00 23.32
ATOM   1003  CA  ASP A 131  0   32.476 31.543 26.127 1.00 21.63
ATOM   1004  C   ASP A 131  0   33.010 30.514 27.103 1.00 19.56
ATOM   1005  O   ASP A 131  0   33.704 29.569 26.766 1.00 19.71
ATOM   1006  CB  ASP A 131  0   31.594 30.877 25.063 1.00 22.97
ATOM   1007  CG  ASP A 131  0   30.220 30.487 25.591 1.00 24.48
ATOM   1008  OD1 ASP A 131  0   30.181 29.525 26.397 1.00 26.42
ATOM   1009  OD2 ASP A 131  0   29.166 31.051 25.212 1.00 22.66
ATOM   1010  N   PRO A 132  0   32.491 30.548 28.315 1.00 18.77
ATOM   1011  CA  PRO A 132  0   32.759 29.611 29.381 1.00 19.41
ATOM   1012  C   PRO A 132  0   32.523 28.141 29.031 1.00 20.89
ATOM   1013  O   PRO A 132  0   33.112 27.250 29.672 1.00 19.99
ATOM   1014  CB  PRO A 132  0   31.799 29.990 30.531 1.00 18.42
ATOM   1015  CG  PRO A 132  0   31.589 31.470 30.263 1.00 16.87
ATOM   1016  CD  PRO A 132  0   31.645 31.673 28.778 1.00 16.73
ATOM   1017  N   HIS A 133  0   31.668 27.836 28.063 1.00 19.47
```

```
ATOM  1018 CA  HIS A 133  0   31.331 26.465 27.700 1.00 18.79
ATOM  1019 C   HIS A 133  0   31.887 26.014 26.372 1.00 19.35
ATOM  1020 O   HIS A 133  0   31.503 24.954 25.826 1.00 18.60
ATOM  1021 CB  HIS A 133  0   29.789 26.428 27.536 1.00 18.91
ATOM  1022 CG  HIS A 133  0   29.065 26.242 28.815 1.00 18.13
ATOM  1023 ND1 HIS A 133  0   29.566 25.551 29.877 1.00 19.52
ATOM  1024 CD2 HIS A 133  0   27.817 26.625 29.183 1.00 19.38
ATOM  1025 CE1 HIS A 133  0   28.679 25.530 30.855 1.00 20.08
ATOM  1026 NE2 HIS A 133  0   27.587 26.180 30.457 1.00 19.60
ATOM  1027 N   ALA A 134  0   32.840 26.801 25.852 1.00 19.40
ATOM  1028 CA  ALA A 134  0   33.413 26.465 24.552 1.00 21.88
ATOM  1029 C   ALA A 134  0   34.080 25.107 24.525 1.00 21.69
ATOM  1030 O   ALA A 134  0   34.120 24.514 23.439 1.00 21.61
ATOM  1031 CB  ALA A 134  0   34.418 27.548 24.128 1.00 22.55
ATOM  1032 N   ALA A 135  0   34.582 24.527 25.622 1.00 21.96
ATOM  1033 CA  ALA A 135  0   35.178 23.192 25.483 1.00 23.53
ATOM  1034 C   ALA A 135  0   34.144 22.096 25.232 1.00 24.47
ATOM  1035 O   ALA A 135  0   34.488 20.936 24.989 1.00 24.77
ATOM  1036 CB  ALA A 135  0   35.910 22.820 26.776 1.00 21.92
ATOM  1037 N   LEU A 136  0   32.862 22.375 25.457 1.00 24.95
ATOM  1038 CA  LEU A 136  0   31.800 21.376 25.404 1.00 23.15
ATOM  1039 C   LEU A 136  0   31.284 21.076 24.016 1.00 20.31
ATOM  1040 O   LEU A 136  0   30.609 20.054 23.924 1.00 19.62
ATOM  1041 CB  LEU A 136  0   30.665 21.845 26.318 1.00 24.43
ATOM  1042 CG  LEU A 136  0   30.501 21.211 27.686 1.00 27.55
ATOM  1043 CD1 LEU A 136  0   31.803 20.721 28.285 1.00 25.75
ATOM  1044 CD2 LEU A 136  0   29.747 22.129 28.644 1.00 26.92
ATOM  1045 N   TYR A 137  0   31.565 21.888 22.998 1.00 17.05
ATOM  1046 CA  TYR A 137  0   31.085 21.612 21.662 1.00 16.65
ATOM  1047 C   TYR A 137  0   32.076 22.054 20.599 1.00 17.99
ATOM  1048 O   TYR A 137  0   32.965 22.891 20.794 1.00 18.69
ATOM  1049 CB  TYR A 137  0   29.724 22.319 21.402 1.00 16.73
ATOM  1050 CG  TYR A 137  0   29.711 23.760 21.857 1.00 16.24
ATOM  1051 CD1 TYR A 137  0   29.302 24.108 23.150 1.00 16.00
ATOM  1052 CD2 TYR A 137  0   30.159 24.754 21.001 1.00 14.76
ATOM  1053 CE1 TYR A 137  0   29.355 25.448 23.551 1.00 15.32
ATOM  1054 CE2 TYR A 137  0   30.165 26.081 21.396 1.00 15.52
ATOM  1055 CZ  TYR A 137  0   29.759 26.410 22.675 1.00 15.61
```

```
ATOM   1056  OH  TYR A 137  0   29.782  27.731  23.055  1.00 17.56
ATOM   1057  N   ASP A 138  0   31.903  21.549  19.393  1.00 19.04
ATOM   1058  CA  ASP A 138  0   32.733  21.859  18.253  1.00 20.02
ATOM   1059  C   ASP A 138  0   32.139  22.933  17.364  1.00 21.05
ATOM   1060  O   ASP A 138  0   32.911  23.553  16.631  1.00 21.98
ATOM   1061  CB  ASP A 138  0   32.836  20.628  17.315  1.00 20.66
ATOM   1062  CG  ASP A 138  0   33.355  19.455  18.089  1.00 22.79
ATOM   1063  OD1 ASP A 138  0   32.744  18.404  18.318  1.00 24.88
ATOM   1064  OD2 ASP A 138  0   34.481  19.675  18.581  1.00 25.34
ATOM   1065  N   GLU A 139  0   30.825  22.957  17.184  1.00 19.73
ATOM   1066  CA  GLU A 139  0   30.223  23.865  16.213  1.00 21.27
ATOM   1067  C   GLU A 139  0   29.086  24.668  16.825  1.00 18.97
ATOM   1068  O   GLU A 139  0   28.306  24.143  17.608  1.00 16.95
ATOM   1069  CB  GLU A 139  0   29.617  23.164  15.000  1.00 24.71
ATOM   1070  CG  GLU A 139  0   30.509  22.149  14.311  1.00 30.89
ATOM   1071  CD  GLU A 139  0   31.633  22.868  13.587  1.00 34.42
ATOM   1072  OE1 GLU A 139  0   31.340  23.869  12.898  1.00 36.87
ATOM   1073  OE2 GLU A 139  0   32.794  22.457  13.705  1.00 37.60
ATOM   1074  N   ASP A 140  0   29.057  25.933  16.408  1.00 19.38
ATOM   1075  CA  ASP A 140  0   28.026  26.847  16.912  1.00 17.89
ATOM   1076  C   ASP A 140  0   27.858  27.901  15.837  1.00 18.87
ATOM   1077  O   ASP A 140  0   28.705  28.780  15.768  1.00 21.31
ATOM   1078  CB  ASP A 140  0   28.438  27.399  18.268  1.00 16.26
ATOM   1079  CG  ASP A 140  0   27.445  28.399  18.858  1.00 16.73
ATOM   1080  OD1 ASP A 140  0   27.854  29.143  19.781  1.00 14.86
ATOM   1081  OD2 ASP A 140  0   26.287  28.446  18.401  1.00 13.82
ATOM   1082  N   ASP A 141  0   26.862  27.844  14.972  1.00 17.34
ATOM   1083  CA  ASP A 141  0   26.750  28.859  13.937  1.00 19.52
ATOM   1084  C   ASP A 141  0   25.301  29.031  13.520  1.00 19.33
ATOM   1085  O   ASP A 141  0   24.342  28.513  14.115  1.00 17.91
ATOM   1086  CB  ASP A 141  0   27.681  28.509  12.772  1.00 21.66
ATOM   1087  CG  ASP A 141  0   27.384  27.151  12.193  1.00 24.87
ATOM   1088  OD1 ASP A 141  0   28.280  26.521  11.567  1.00 28.90
ATOM   1089  OD2 ASP A 141  0   26.271  26.604  12.302  1.00 25.89
ATOM   1090  N   GLU A 142  0   25.102  29.688  12.387  1.00 19.21
ATOM   1091  CA  GLU A 142  0   23.775  29.945  11.880  1.00 20.84
ATOM   1092  C   GLU A 142  0   23.052  28.636  11.592  1.00 19.95
ATOM   1093  O   GLU A 142  0   21.844  28.656  11.665  1.00 18.73
```

```
   ATOM 1094 CB  GLU A 142 0  23.771 30.894 10.699 1.00 23.40
   ATOM 1095 CG  GLU A 142 0  24.295 30.301  9.407 1.00 27.22
   ATOM 1096 CD  GLU A 142 0  25.718 30.826  9.221 1.00 32.36
   ATOM 1097 OE1 GLU A 142 0  26.513 30.920 10.206 1.00 31.87
 5 ATOM 1098 OE2 GLU A 142 0  25.968 31.136  8.023 1.00 35.76
   ATOM 1099 N   ASN A 143 0  23.723 27.508 11.378 1.00 20.40
   ATOM 1100 CA  ASN A 143 0  23.105 26.227 11.151 1.00 19.61
   ATOM 1101 C   ASN A 143 0  22.785 25.468 12.421 1.00 18.35
   ATOM 1102 O   ASN A 143 0  22.317 24.337 12.325 1.00 15.65
10 ATOM 1103 CB  ASN A 143 0  24.024 25.401 10.229 1.00 23.57
   ATOM 1104 CG  ASN A 143 0  24.133 26.067  8.857 1.00 26.63
   ATOM 1105 OD1 ASN A 143 0  25.220 26.376  8.356 1.00 29.89
   ATOM 1106 ND2 ASN A 143 0  23.049 26.342  8.175 1.00 25.46
   ATOM 1107 N   THR A 144 0  23.067 25.974 13.632 1.00 16.76
15 ATOM 1108 CA  THR A 144 0  22.678 25.257 14.825 1.00 15.40
   ATOM 1109 C   THR A 144 0  21.556 25.976 15.577 1.00 15.58
   ATOM 1110 O   THR A 144 0  21.361 25.776 16.789 1.00 17.88
   ATOM 1111 CB  THR A 144 0  23.848 25.018 15.785 1.00 16.43
   ATOM 1112 OG1 THR A 144 0  24.296 26.270 16.297 1.00 14.82
20 ATOM 1113 CG2 THR A 144 0  24.935 24.215 15.104 1.00 15.98
   ATOM 1114 N   ILE A 145 0  20.821 26.834 14.898 1.00 13.92
   ATOM 1115 CA  ILE A 145 0  19.697 27.550 15.500 1.00 14.31
   ATOM 1116 C   ILE A 145 0  18.392 26.835 15.139 1.00 13.84
   ATOM 1117 O   ILE A 145 0  18.127 26.478 13.996 1.00 12.32
25 ATOM 1118 CB  ILE A 145 0  19.641 29.016 15.011 1.00 15.15
   ATOM 1119 CG1 ILE A 145 0  20.881 29.726 15.608 1.00 16.27
   ATOM 1120 CG2 ILE A 145 0  18.346 29.736 15.375 1.00 13.14
   ATOM 1121 CD1 ILE A 145 0  21.256 31.006 14.892 1.00 16.72
   ATOM 1122 N   ILE A 146 0  17.550 26.644 16.141 1.00 13.54
30 ATOM 1123 CA  ILE A 146 0  16.263 25.983 15.926 1.00 13.70
   ATOM 1124 C   ILE A 146 0  15.167 26.899 16.494 1.00 12.67
   ATOM 1125 O   ILE A 146 0  15.155 27.082 17.714 1.00 10.09
   ATOM 1126 CB  ILE A 146 0  16.183 24.580 16.553 1.00 15.97
   ATOM 1127 CG1 ILE A 146 0  17.280 23.621 16.012 1.00 17.29
35 ATOM 1128 CG2 ILE A 146 0  14.831 23.937 16.207 1.00 14.52
   ATOM 1129 CD1 ILE A 146 0  17.359 22.340 16.832 1.00 18.45
   ATOM 1130 N   THR A 147 0  14.360 27.507 15.610 1.00 10.81
   ATOM 1131 CA  THR A 147 0  13.240 28.310 16.102 1.00 12.54
```

5032-WO

60

```
   ATOM  1132 C   THR A 147  0   11.912 27.526 15.988 1.00 13.55
   ATOM  1133 O   THR A 147  0   11.655 26.724 15.076 1.00 12.65
   ATOM  1134 CB  THR A 147  0   13.078 29.642 15.351 1.00 12.37
   ATOM  1135 OG1 THR A 147  0   12.728 29.311 14.005 1.00 10.17
 5 ATOM  1136 CG2 THR A 147  0   14.381 30.479 15.402 1.00 11.93
   ATOM  1137 N   LEU A 148  0   11.062 27.715 16.972 1.00 12.48
   ATOM  1138 CA  LEU A 148  0    9.719 27.171 17.039 1.00 13.90
   ATOM  1139 C   LEU A 148  0    8.719 28.350 16.916 1.00 15.44
   ATOM  1140 O   LEU A 148  0    8.860 29.383 17.579 1.00 15.28
10 ATOM  1141 CB  LEU A 148  0    9.501 26.419 18.340 1.00 12.83
   ATOM  1142 CG  LEU A 148  0   10.502 25.293 18.669 1.00 12.45
   ATOM  1143 CD1 LEU A 148  0   10.154 24.669 19.997 1.00 11.49
   ATOM  1144 CD2 LEU A 148  0   10.552 24.203 17.597 1.00 11.82
   ATOM  1145 N   ALA A 149  0    7.726 28.241 16.053 1.00 14.08
15 ATOM  1146 CA  ALA A 149  0    6.725 29.256 15.825 1.00 15.37
   ATOM  1147 C   ALA A 149  0    5.336 28.658 15.521 1.00 16.78
   ATOM  1148 O   ALA A 149  0    5.198 27.637 14.841 1.00 15.78
   ATOM  1149 CB  ALA A 149  0    7.068 30.127 14.628 1.00 13.22
   ATOM  1150 N   ASP A 150  0    4.337 29.344 16.065 1.00 16.39
20 ATOM  1151 CA  ASP A 150  0    2.941 28.995 15.864 1.00 15.96
   ATOM  1152 C   ASP A 150  0    2.515 29.758 14.624 1.00 16.53
   ATOM  1153 O   ASP A 150  0    2.960 30.905 14.483 1.00 18.17
   ATOM  1154 CB  ASP A 150  0    2.066 29.440 17.027 1.00 16.78
   ATOM  1155 CG  ASP A 150  0    2.345 30.836 17.561 1.00 18.15
25 ATOM  1156 OD1 ASP A 150  0    3.410 31.472 17.347 1.00 16.29
   ATOM  1157 OD2 ASP A 150  0    1.414 31.311 18.264 1.00 17.83
   ATOM  1158 N   TRP A 151  0    1.776 29.157 13.726 1.00 15.62
   ATOM  1159 CA  TRP A 151  0    1.366 29.828 12.499 1.00 14.37
   ATOM  1160 C   TRP A 151  0   -0.140 29.688 12.226 1.00 14.78
30 ATOM  1161 O   TRP A 151  0   -0.679 28.607 12.425 1.00 13.41
   ATOM  1162 CB  TRP A 151  0    2.229 29.239 11.373 1.00 13.56
   ATOM  1163 CG  TRP A 151  0    2.046 30.004 10.097 1.00 13.31
   ATOM  1164 CD1 TRP A 151  0    1.385 29.545  8.991 1.00 13.60
   ATOM  1165 CD2 TRP A 151  0    2.484 31.316  9.806 1.00 15.46
35 ATOM  1166 NE1 TRP A 151  0    1.412 30.497  8.017 1.00 14.49
   ATOM  1167 CE2 TRP A 151  0    2.061 31.605  8.473 1.00 15.53
   ATOM  1168 CE3 TRP A 151  0    3.189 32.294 10.522 1.00 16.28
   ATOM  1169 CZ2 TRP A 151  0    2.306 32.822  7.846 1.00 16.57
```

```
ATOM   1170  CZ3 TRP A 151  0    3.436  33.505   9.881  1.00 18.22
ATOM   1171  CH2 TRP A 151  0    3.003  33.766   8.560  1.00 18.00
ATOM   1172  N   TYR A 152  0   -0.818  30.745  11.812  1.00 15.59
ATOM   1173  CA  TYR A 152  0   -2.266  30.813  11.614  1.00 17.47
ATOM   1174  C   TYR A 152  0   -2.556  31.086  10.149  1.00 18.79
ATOM   1175  O   TYR A 152  0   -1.830  31.856   9.521  1.00 19.15
ATOM   1176  CB  TYR A 152  0   -2.981  31.930  12.434  1.00 16.37
ATOM   1177  CG  TYR A 152  0   -2.539  31.776  13.887  1.00 16.24
ATOM   1178  CD1 TYR A 152  0   -1.313  32.303  14.318  1.00 15.22
ATOM   1179  CD2 TYR A 152  0   -3.267  30.998  14.767  1.00 15.29
ATOM   1180  CE1 TYR A 152  0   -0.889  32.135  15.626  1.00 14.67
ATOM   1181  CE2 TYR A 152  0   -2.831  30.799  16.054  1.00 16.52
ATOM   1182  CZ  TYR A 152  0   -1.632  31.369  16.474  1.00 16.12
ATOM   1183  OH  TYR A 152  0   -1.219  31.139  17.771  1.00 16.36
ATOM   1184  N   HIS A 153  0   -3.590  30.445   9.599  1.00 20.39
ATOM   1185  CA  HIS A 153  0   -3.899  30.683   8.181  1.00 21.90
ATOM   1186  C   HIS A 153  0   -4.642  31.988   7.952  1.00 21.94
ATOM   1187  O   HIS A 153  0   -4.750  32.386   6.784  1.00 22.32
ATOM   1188  CB  HIS A 153  0   -4.592  29.483   7.549  1.00 22.29
ATOM   1189  CG  HIS A 153  0   -3.651  28.319   7.385  1.00 24.52
ATOM   1190  ND1 HIS A 153  0   -4.071  27.022   7.258  1.00 24.25
ATOM   1191  CD2 HIS A 153  0   -2.286  28.274   7.338  1.00 23.32
ATOM   1192  CE1 HIS A 153  0   -3.034  26.220   7.124  1.00 24.15
ATOM   1193  NE2 HIS A 153  0   -1.956  26.965   7.178  1.00 24.30
ATOM   1194  N   ILE A 154  0   -5.084  32.718   8.972  1.00 21.86
ATOM   1195  CA  ILE A 154  0   -5.611  34.046   8.686  1.00 24.39
ATOM   1196  C   ILE A 154  0   -4.904  35.051   9.597  1.00 22.15
ATOM   1197  O   ILE A 154  0   -4.517  34.732  10.698  1.00 20.15
ATOM   1198  CB  ILE A 154  0   -7.120  34.281   8.693  1.00 26.43
ATOM   1199  CG1 ILE A 154  0   -7.682  34.498  10.099  1.00 27.66
ATOM   1200  CG2 ILE A 154  0   -7.947  33.251   7.928  1.00 26.60
ATOM   1201  CD1 ILE A 154  0   -7.312  33.468  11.125  1.00 28.86
ATOM   1202  N   PRO A 155  0   -4.723  36.255   9.105  1.00 23.79
ATOM   1203  CA  PRO A 155  0   -4.108  37.361   9.816  1.00 23.66
ATOM   1204  C   PRO A 155  0   -4.604  37.435  11.252  1.00 24.59
ATOM   1205  O   PRO A 155  0   -5.814  37.317  11.539  1.00 24.53
ATOM   1206  CB  PRO A 155  0   -4.546  38.634   9.077  1.00 24.20
ATOM   1207  CG  PRO A 155  0   -4.990  38.162   7.733  1.00 23.40
```

```
ATOM  1208 CD  PRO A 155  0  -5.207 36.672  7.776 1.00 23.41
ATOM  1209 N   ALA A 156  0  -3.704 37.776 12.178 1.00 24.03
ATOM  1210 CA  ALA A 156  0  -4.066 37.806 13.588 1.00 25.45
ATOM  1211 C   ALA A 156  0  -5.262 38.667 13.992 1.00 24.85
ATOM  1212 O   ALA A 156  0  -6.083 38.217 14.798 1.00 22.79
ATOM  1213 CB  ALA A 156  0  -2.866 38.045 14.492 1.00 24.30
ATOM  1214 N   PRO A 157  0  -5.393 39.873 13.518 1.00 25.98
ATOM  1215 CA  PRO A 157  0  -6.521 40.741 13.807 1.00 28.77
ATOM  1216 C   PRO A 157  0  -7.840 40.092 13.406 1.00 30.78
ATOM  1217 O   PRO A 157  0  -8.798 40.416 14.105 1.00 34.62
ATOM  1218 CB  PRO A 157  0  -6.324 42.071 13.068 1.00 26.56
ATOM  1219 CG  PRO A 157  0  -4.859 42.013 12.762 1.00 25.98
ATOM  1220 CD  PRO A 157  0  -4.480 40.547 12.585 1.00 25.96
ATOM  1221 N   SER A 158  0  -7.950 39.207 12.430 1.00 30.95
ATOM  1222 CA  SER A 158  0  -9.174 38.549 12.047 1.00 31.32
ATOM  1223 C   SER A 158  0  -9.450 37.288 12.851 1.00 33.61
ATOM  1224 O   SER A 158  0 -10.472 36.633 12.575 1.00 34.71
ATOM  1225 CB  SER A 158  0  -9.176 38.118 10.577 1.00 30.14
ATOM  1226 OG  SER A 158  0  -8.942 39.187  9.665 1.00 31.20
ATOM  1227 N   ILE A 159  0  -8.588 36.875 13.773 1.00 34.23
ATOM  1228 CA  ILE A 159  0  -8.918 35.642 14.491 1.00 36.40
ATOM  1229 C   ILE A 159  0 -10.189 35.896 15.309 1.00 39.20
ATOM  1230 O   ILE A 159  0 -10.294 36.875 16.046 1.00 39.00
ATOM  1231 CB  ILE A 159  0  -7.769 35.121 15.360 1.00 35.56
ATOM  1232 CG1 ILE A 159  0  -6.713 34.408 14.485 1.00 35.58
ATOM  1233 CG2 ILE A 159  0  -8.262 34.184 16.452 1.00 34.97
ATOM  1234 CD1 ILE A 159  0  -5.388 34.268 15.212 1.00 34.91
ATOM  1235 N   GLN A 160  0 -11.137 34.969 15.196 1.00 41.53
ATOM  1236 CA  GLN A 160  0 -12.398 35.056 15.946 1.00 42.57
ATOM  1237 C   GLN A 160  0 -12.466 33.914 16.949 1.00 40.51
ATOM  1238 O   GLN A 160  0 -12.308 32.741 16.585 1.00 41.96
ATOM  1239 CB  GLN A 160  0 -13.542 35.062 14.937 1.00 45.52
ATOM  1240 CG  GLN A 160  0 -14.814 34.319 15.267 1.00 48.48
ATOM  1241 CD  GLN A 160  0 -15.570 33.799 14.055 1.00 50.12
ATOM  1242 OE1 GLN A 160  0 -16.204 32.737 14.118 1.00 50.77
ATOM  1243 NE2 GLN A 160  0 -15.504 34.520 12.940 1.00 51.22
ATOM  1244 N   GLY A 161  0 -12.667 34.191 18.225 1.00 37.10
ATOM  1245 CA  GLY A 161  0 -12.722 33.112 19.208 1.00 34.91
```

```
ATOM  1246 C   GLY A 161  0  -11.305 32.826 19.696 1.00 34.13
ATOM  1247 O   GLY A 161  0  -10.412 33.648 19.451 1.00 32.40
ATOM  1248 N   ALA A 162  0  -11.158 31.738 20.433 1.00 33.01
ATOM  1249 CA  ALA A 162  0   -9.864 31.355 20.988 1.00 32.39
ATOM  1250 C   ALA A 162  0   -8.927 30.902 19.880 1.00 31.53
ATOM  1251 O   ALA A 162  0   -9.285 30.132 19.013 1.00 30.73
ATOM  1252 CB  ALA A 162  0  -10.058 30.263 22.010 1.00 34.12
ATOM  1253 N   ALA A 163  0   -7.731 31.475 19.851 1.00 32.06
ATOM  1254 CA  ALA A 163  0   -6.740 31.202 18.814 1.00 30.85
ATOM  1255 C   ALA A 163  0   -6.219 29.774 18.897 1.00 29.40
ATOM  1256 O   ALA A 163  0   -5.967 29.223 19.965 1.00 30.49
ATOM  1257 CB  ALA A 163  0   -5.607 32.217 18.911 1.00 30.29
ATOM  1258 N   GLN A 164  0   -6.101 29.130 17.754 1.00 28.69
ATOM  1259 CA  GLN A 164  0   -5.616 27.769 17.612 1.00 28.24
ATOM  1260 C   GLN A 164  0   -4.720 27.744 16.370 1.00 25.02
ATOM  1261 O   GLN A 164  0   -5.157 28.046 15.260 1.00 23.64
ATOM  1262 CB  GLN A 164  0   -6.732 26.756 17.361 1.00 31.99
ATOM  1263 CG  GLN A 164  0   -7.885 26.640 18.319 1.00 36.24
ATOM  1264 CD  GLN A 164  0   -7.535 25.809 19.540 1.00 40.95
ATOM  1265 OE1 GLN A 164  0   -7.863 26.166 20.684 1.00 43.34
ATOM  1266 NE2 GLN A 164  0   -6.864 24.672 19.328 1.00 41.86
ATOM  1267 N   PRO A 165  0   -3.446 27.406 16.549 1.00 22.68
ATOM  1268 CA  PRO A 165  0   -2.501 27.360 15.463 1.00 20.43
ATOM  1269 C   PRO A 165  0   -2.856 26.294 14.429 1.00 18.89
ATOM  1270 O   PRO A 165  0   -3.286 25.176 14.715 1.00 18.00
ATOM  1271 CB  PRO A 165  0   -1.126 27.075 16.088 1.00 20.83
ATOM  1272 CG  PRO A 165  0   -1.476 26.651 17.479 1.00 22.05
ATOM  1273 CD  PRO A 165  0   -2.873 27.081 17.851 1.00 21.57
ATOM  1274 N   ASP A 166  0   -2.667 26.608 13.169 1.00 17.50
ATOM  1275 CA  ASP A 166  0   -2.829 25.677 12.059 1.00 19.82
ATOM  1276 C   ASP A 166  0   -1.591 24.788 11.930 1.00 19.47
ATOM  1277 O   ASP A 166  0   -1.692 23.649 11.506 1.00 19.38
ATOM  1278 CB  ASP A 166  0   -3.005 26.413 10.727 1.00 19.75
ATOM  1279 CG  ASP A 166  0   -4.347 27.162 10.728 1.00 21.69
ATOM  1280 OD1 ASP A 166  0   -5.376 26.480 10.593 1.00 22.24
ATOM  1281 OD2 ASP A 166  0   -4.384 28.392 10.885 1.00 22.13
ATOM  1282 N   ALA A 167  0   -0.435 25.386 12.231 1.00 18.54
ATOM  1283 CA  ALA A 167  0    0.806 24.614 12.142 1.00 18.74
```

```
ATOM 1284  C   ALA A 167  0   1.867 25.056 13.148 1.00 17.69
ATOM 1285  O   ALA A 167  0   1.874 26.147 13.715 1.00 15.83
ATOM 1286  CB  ALA A 167  0   1.387 24.767 10.735 1.00 17.32
ATOM 1287  N   THR A 168  0   2.826 24.166 13.335 1.00 18.40
ATOM 1288  CA  THR A 168  0   4.087 24.402 14.027 1.00 14.85
ATOM 1289  C   THR A 168  0   5.180 24.553 12.955 1.00 15.24
ATOM 1290  O   THR A 168  0   5.402 23.737 12.071 1.00 12.99
ATOM 1291  CB  THR A 168  0   4.530 23.235 14.900 1.00 14.31
ATOM 1292  OG1 THR A 168  0   3.558 23.068 15.920 1.00 12.30
ATOM 1293  CG2 THR A 168  0   5.921 23.516 15.524 1.00 13.60
ATOM 1294  N   LEU A 169  0   5.867 25.686 12.973 1.00 16.69
ATOM 1295  CA  LEU A 169  0   6.976 26.002 12.071 1.00 14.74
ATOM 1296  C   LEU A 169  0   8.285 25.747 12.833 1.00 14.34
ATOM 1297  O   LEU A 169  0   8.497 26.259 13.942 1.00 12.34
ATOM 1298  CB  LEU A 169  0   6.890 27.471 11.652 1.00 14.90
ATOM 1299  CG  LEU A 169  0   6.071 27.845 10.428 1.00 17.83
ATOM 1300  CD1 LEU A 169  0   4.978 26.825 10.133 1.00 15.89
ATOM 1301  CD2 LEU A 169  0   5.500 29.254 10.443 1.00 16.43
ATOM 1302  N   ILE A 170  0   9.141 24.923 12.255 1.00 14.06
ATOM 1303  CA  ILE A 170  0  10.472 24.659 12.819 1.00 14.01
ATOM 1304  C   ILE A 170  0  11.397 25.312 11.784 1.00 15.19
ATOM 1305  O   ILE A 170  0  11.307 25.009 10.585 1.00 14.73
ATOM 1306  CB  ILE A 170  0  10.807 23.179 13.025 1.00 14.75
ATOM 1307  CG1 ILE A 170  0   9.849 22.605 14.069 1.00 13.74
ATOM 1308  CG2 ILE A 170  0  12.268 22.983 13.468 1.00 13.47
ATOM 1309  CD1 ILE A 170  0   9.915 21.134 14.385 1.00 15.26
ATOM 1310  N   ASN A 171  0  12.166 26.317 12.208 1.00 13.13
ATOM 1311  CA  ASN A 171  0  12.992 27.042 11.250 1.00 13.74
ATOM 1312  C   ASN A 171  0  12.163 27.517 10.083 1.00 13.71
ATOM 1313  O   ASN A 171  0  12.562 27.381  8.921 1.00 13.20
ATOM 1314  CB  ASN A 171  0  14.220 26.209 10.793 1.00 14.42
ATOM 1315  CG  ASN A 171  0  15.236 26.157 11.940 1.00 16.29
ATOM 1316  OD1 ASN A 171  0  15.123 26.983 12.875 1.00 16.78
ATOM 1317  ND2 ASN A 171  0  16.203 25.259 11.964 1.00 14.32
ATOM 1318  N   GLY A 172  0  10.967 28.074 10.337 1.00 14.17
ATOM 1319  CA  GLY A 172  0  10.157 28.619  9.270 1.00 11.74
ATOM 1320  C   GLY A 172  0   9.387 27.636  8.433 1.00 14.40
ATOM 1321  O   GLY A 172  0   8.783 28.064  7.441 1.00 15.60
```

```
ATOM 1322  N   LYS A 173  0   9.430 26.319  8.669 1.00 13.84
ATOM 1323  CA  LYS A 173  0   8.777 25.363  7.794 1.00 13.67
ATOM 1324  C   LYS A 173  0   8.038 24.303  8.589 1.00 13.59
ATOM 1325  O   LYS A 173  0   8.445 24.027  9.723 1.00 11.70
ATOM 1326  CB  LYS A 173  0   9.775 24.645  6.875 1.00 17.03
ATOM 1327  CG  LYS A 173  0  10.704 25.577  6.118 1.00 17.63
ATOM 1328  CD  LYS A 173  0  11.508 24.796  5.094 1.00 20.84
ATOM 1329  CE  LYS A 173  0  12.213 25.821  4.198 1.00 22.63
ATOM 1330  NZ  LYS A 173  0  13.304 25.087  3.499 1.00 28.08
ATOM 1331  N   GLY A 174  0   6.922 23.821  8.014 1.00 12.28
ATOM 1332  CA  GLY A 174  0   6.178 22.768  8.753 1.00 11.45
ATOM 1333  C   GLY A 174  0   4.958 22.409  7.896 1.00 13.55
ATOM 1334  O   GLY A 174  0   4.823 22.877  6.760 1.00 13.37
ATOM 1335  N   ARG A 175  0   4.042 21.619  8.432 1.00 14.54
ATOM 1336  CA  ARG A 175  0   2.859 21.201  7.687 1.00 16.62
ATOM 1337  C   ARG A 175  0   1.598 21.336  8.541 1.00 17.67
ATOM 1338  O   ARG A 175  0   1.727 21.264  9.769 1.00 18.41
ATOM 1339  CB  ARG A 175  0   2.985 19.718  7.292 1.00 16.05
ATOM 1340  CG  ARG A 175  0   3.894 19.472  6.116 1.00 16.55
ATOM 1341  CD  ARG A 175  0   4.358 18.009  6.108 1.00 17.70
ATOM 1342  NE  ARG A 175  0   5.421 17.861  5.097 1.00 17.74
ATOM 1343  CZ  ARG A 175  0   5.971 16.667  4.792 1.00 17.63
ATOM 1344  NH1 ARG A 175  0   6.918 16.665  3.866 1.00 17.25
ATOM 1345  NH2 ARG A 175  0   5.594 15.538  5.375 1.00 14.80
ATOM 1346  N   TYR A 176  0   0.429 21.438  7.908 1.00 18.08
ATOM 1347  CA  TYR A 176  0  -0.800 21.481  8.746 1.00 18.67
ATOM 1348  C   TYR A 176  0  -1.613 20.200  8.509 1.00 18.24
ATOM 1349  O   TYR A 176  0  -1.417 19.534  7.483 1.00 17.67
ATOM 1350  CB  TYR A 176  0  -1.635 22.709  8.462 1.00 17.21
ATOM 1351  CG  TYR A 176  0  -2.102 22.931  7.053 1.00 16.36
ATOM 1352  CD1 TYR A 176  0  -1.246 23.433  6.089 1.00 14.84
ATOM 1353  CD2 TYR A 176  0  -3.441 22.676  6.677 1.00 17.26
ATOM 1354  CE1 TYR A 176  0  -1.640 23.686  4.796 1.00 16.01
ATOM 1355  CE2 TYR A 176  0  -3.862 22.908  5.361 1.00 16.65
ATOM 1356  CZ  TYR A 176  0  -2.967 23.407  4.432 1.00 17.65
ATOM 1357  OH  TYR A 176  0  -3.347 23.678  3.131 1.00 17.81
ATOM 1358  N   VAL A 177  0  -2.427 19.815  9.464 1.00 18.46
ATOM 1359  CA  VAL A 177  0  -3.200 18.571  9.303 1.00 21.18
```

```
ATOM   1360 C   VAL A 177  0  -4.090 18.639  8.073 1.00 21.50
ATOM   1361 O   VAL A 177  0  -4.788 19.620  7.858 1.00 21.85
ATOM   1362 CB  VAL A 177  0  -4.072 18.306 10.532 1.00 22.29
ATOM   1363 CG1 VAL A 177  0  -4.802 16.974 10.370 1.00 21.70
ATOM   1364 CG2 VAL A 177  0  -3.205 18.289 11.784 1.00 22.43
ATOM   1365 N   GLY A 178  0  -3.989 17.707  7.142 1.00 21.84
ATOM   1366 CA  GLY A 178  0  -4.761 17.742  5.918 1.00 20.35
ATOM   1367 C   GLY A 178  0  -4.047 18.602  4.900 1.00 22.84
ATOM   1368 O   GLY A 178  0  -4.576 18.673  3.774 1.00 23.86
ATOM   1369 N   GLY A 179  0  -2.887 19.220  5.210 1.00 21.49
ATOM   1370 CA  GLY A 179  0  -2.291 20.060  4.149 1.00 19.94
ATOM   1371 C   GLY A 179  0  -1.389 19.250  3.242 1.00 18.86
ATOM   1372 O   GLY A 179  0  -1.192 18.052  3.399 1.00 19.35
ATOM   1373 N   PRO A 180  0  -0.800 19.905  2.268 1.00 19.42
ATOM   1374 CA  PRO A 180  0   0.150 19.328  1.335 1.00 19.92
ATOM   1375 C   PRO A 180  0   1.430 18.922  2.041 1.00 20.56
ATOM   1376 O   PRO A 180  0   1.731 19.399  3.145 1.00 20.66
ATOM   1377 CB  PRO A 180  0   0.503 20.399  0.298 1.00 19.52
ATOM   1378 CG  PRO A 180  0  -0.144 21.639  0.829 1.00 19.70
ATOM   1379 CD  PRO A 180  0  -0.930 21.356  2.081 1.00 19.79
ATOM   1380 N   ALA A 181  0   2.213 18.059  1.403 1.00 21.19
ATOM   1381 CA  ALA A 181  0   3.489 17.644  2.007 1.00 23.04
ATOM   1382 C   ALA A 181  0   4.548 18.723  1.772 1.00 21.24
ATOM   1383 O   ALA A 181  0   5.465 18.522  0.986 1.00 23.93
ATOM   1384 CB  ALA A 181  0   3.928 16.305  1.435 1.00 21.73
ATOM   1385 N   ALA A 182  0   4.398 19.905  2.315 1.00 19.30
ATOM   1386 CA  ALA A 182  0   5.357 20.987  2.183 1.00 18.39
ATOM   1387 C   ALA A 182  0   6.706 20.549  2.791 1.00 17.36
ATOM   1388 O   ALA A 182  0   6.858 19.712  3.701 1.00 16.16
ATOM   1389 CB  ALA A 182  0   4.826 22.209  2.932 1.00 17.68
ATOM   1390 N   GLU A 183  0   7.739 21.103  2.210 1.00 18.23
ATOM   1391 CA  GLU A 183  0   9.134 20.882  2.599 1.00 20.90
ATOM   1392 C   GLU A 183  0   9.381 21.078  4.093 1.00 18.87
ATOM   1393 O   GLU A 183  0   8.976 22.073  4.699 1.00 17.80
ATOM   1394 CB  GLU A 183  0   9.990 21.875  1.820 1.00 25.16
ATOM   1395 CG  GLU A 183  0  11.508 21.760  1.962 1.00 31.31
ATOM   1396 CD  GLU A 183  0  12.075 22.803  0.998 1.00 34.38
ATOM   1397 OE1 GLU A 183  0  11.901 22.609 -0.229 1.00 36.88
```

```
ATOM  1398 OE2 GLU A 183  0  12.619 23.809  1.484 1.00 36.18
ATOM  1399 N   LEU A 184  0  10.010 20.093  4.691 1.00 17.33
ATOM  1400 CA  LEU A 184  0  10.388 20.155  6.098 1.00 18.77
ATOM  1401 C   LEU A 184  0  11.780 20.743  6.255 1.00 19.44
ATOM  1402 O   LEU A 184  0  12.582 20.687  5.314 1.00 20.95
ATOM  1403 CB  LEU A 184  0  10.331 18.735  6.673 1.00 18.11
ATOM  1404 CG  LEU A 184  0   8.915 18.125  6.577 1.00 19.10
ATOM  1405 CD1 LEU A 184  0   8.887 16.734  7.178 1.00 18.87
ATOM  1406 CD2 LEU A 184  0   7.868 19.026  7.229 1.00 18.69
ATOM  1407 N   SER A 185  0  12.054 21.342  7.398 1.00 18.46
ATOM  1408 CA  SER A 185  0  13.366 21.883  7.699 1.00 17.73
ATOM  1409 C   SER A 185  0  14.298 20.699  8.018 1.00 16.95
ATOM  1410 O   SER A 185  0  13.883 19.710  8.629 1.00 15.84
ATOM  1411 CB  SER A 185  0  13.303 22.786  8.934 1.00 17.34
ATOM  1412 OG  SER A 185  0  12.846 24.073  8.560 1.00 18.09
ATOM  1413 N   ILE A 186  0  15.533 20.845  7.587 1.00 16.43
ATOM  1414 CA  ILE A 186  0  16.595 19.858  7.821 1.00 16.85
ATOM  1415 C   ILE A 186  0  17.725 20.491  8.626 1.00 15.86
ATOM  1416 O   ILE A 186  0  18.178 21.605  8.387 1.00 11.67
ATOM  1417 CB  ILE A 186  0  17.193 19.390  6.471 1.00 18.77
ATOM  1418 CG1 ILE A 186  0  16.048 18.895  5.557 1.00 19.78
ATOM  1419 CG2 ILE A 186  0  18.167 18.241  6.697 1.00 18.53
ATOM  1420 CD1 ILE A 186  0  16.464 18.731  4.110 1.00 22.35
ATOM  1421 N   VAL A 187  0  18.114 19.840  9.703 1.00 16.18
ATOM  1422 CA  VAL A 187  0  19.243 20.287 10.505 1.00 16.63
ATOM  1423 C   VAL A 187  0  20.362 19.239 10.231 1.00 17.36
ATOM  1424 O   VAL A 187  0  20.158 18.046 10.505 1.00 15.19
ATOM  1425 CB  VAL A 187  0  18.928 20.323 11.984 1.00 16.68
ATOM  1426 CG1 VAL A 187  0  20.198 20.622 12.796 1.00 16.82
ATOM  1427 CG2 VAL A 187  0  17.874 21.375 12.275 1.00 17.07
ATOM  1428 N   ASN A 188  0  21.449 19.695  9.634 1.00 16.45
ATOM  1429 CA  ASN A 188  0  22.528 18.766  9.272 1.00 19.84
ATOM  1430 C   ASN A 188  0  23.598 18.597 10.349 1.00 19.41
ATOM  1431 O   ASN A 188  0  24.051 19.618 10.862 1.00 21.31
ATOM  1432 CB  ASN A 188  0  23.209 19.246  7.976 1.00 18.78
ATOM  1433 CG  ASN A 188  0  22.249 19.186  6.797 1.00 20.77
ATOM  1434 OD1 ASN A 188  0  21.734 20.201  6.305 1.00 21.70
ATOM  1435 ND2 ASN A 188  0  21.995 17.985  6.286 1.00 20.52
```

```
ATOM 1436 N   VAL A 189  0   24.024 17.389 10.681 1.00 17.35
ATOM 1437 CA  VAL A 189  0   25.098 17.164 11.617 1.00 17.93
ATOM 1438 C   VAL A 189  0   26.091 16.135 11.046 1.00 19.82
ATOM 1439 O   VAL A 189  0   25.773 15.392 10.109 1.00 18.90
ATOM 1440 CB  VAL A 189  0   24.660 16.684 13.009 1.00 18.43
ATOM 1441 CG1 VAL A 189  0   23.931 17.796 13.766 1.00 18.89
ATOM 1442 CG2 VAL A 189  0   23.760 15.449 12.965 1.00 15.94
ATOM 1443 N   GLU A 190  0   27.242 15.993 11.688 1.00 21.48
ATOM 1444 CA  GLU A 190  0   28.220 14.972 11.274 1.00 24.63
ATOM 1445 C   GLU A 190  0   28.514 14.065 12.469 1.00 23.06
ATOM 1446 O   GLU A 190  0   28.797 14.650 13.522 1.00 21.04
ATOM 1447 CB  GLU A 190  0   29.569 15.551 10.860 1.00 26.79
ATOM 1448 CG  GLU A 190  0   29.571 16.355  9.567 1.00 32.24
ATOM 1449 CD  GLU A 190  0   30.951 16.990  9.351 1.00 34.67
ATOM 1450 OE1 GLU A 190  0   31.927 16.199  9.305 1.00 35.41
ATOM 1451 OE2 GLU A 190  0   30.999 18.236  9.264 1.00 35.78
ATOM 1452 N   GLN A 191  0   28.490 12.752 12.256 1.00 21.94
ATOM 1453 CA  GLN A 191  0   28.768 11.824 13.357 1.00 21.92
ATOM 1454 C   GLN A 191  0   30.121 12.151 13.984 1.00 22.68
ATOM 1455 O   GLN A 191  0   31.052 12.516 13.251 1.00 23.08
ATOM 1456 CB  GLN A 191  0   28.797 10.400 12.820 1.00 22.01
ATOM 1457 CG  GLN A 191  0   28.795  9.347 13.917 1.00 23.87
ATOM 1458 CD  GLN A 191  0   28.846  7.966 13.259 1.00 26.64
ATOM 1459 OE1 GLN A 191  0   29.745  7.761 12.427 1.00 28.86
ATOM 1460 NE2 GLN A 191  0   27.909  7.080 13.563 1.00 26.40
ATOM 1461 N   GLY A 192  0   30.224 12.119 15.290 1.00 21.84
ATOM 1462 CA  GLY A 192  0   31.418 12.469 15.996 1.00 22.91
ATOM 1463 C   GLY A 192  0   31.564 13.910 16.446 1.00 23.87
ATOM 1464 O   GLY A 192  0   32.394 14.174 17.322 1.00 25.80
ATOM 1465 N   LYS A 193  0   30.839 14.867 15.922 1.00 23.54
ATOM 1466 CA  LYS A 193  0   30.899 16.259 16.362 1.00 22.84
ATOM 1467 C   LYS A 193  0   29.840 16.584 17.404 1.00 21.67
ATOM 1468 O   LYS A 193  0   28.826 15.882 17.538 1.00 20.99
ATOM 1469 CB  LYS A 193  0   30.682 17.155 15.143 1.00 24.53
ATOM 1470 CG  LYS A 193  0   31.900 17.149 14.217 1.00 27.82
ATOM 1471 CD  LYS A 193  0   31.739 18.261 13.199 1.00 30.02
ATOM 1472 CE  LYS A 193  0   33.060 19.001 12.990 1.00 31.93
ATOM 1473 NZ  LYS A 193  0   33.392 18.906 11.540 1.00 33.14
```

5032-WO

```
ATOM   1474  N   LYS A 194   0   30.067  17.626  18.169  1.00 19.25
ATOM   1475  CA  LYS A 194   0   29.168  18.115  19.187  1.00 19.49
ATOM   1476  C   LYS A 194   0   28.722  19.523  18.780  1.00 19.40
ATOM   1477  O   LYS A 194   0   29.512  20.285  18.235  1.00 19.29
ATOM   1478  CB  LYS A 194   0   29.771  18.115  20.576  1.00 21.88
ATOM   1479  CG  LYS A 194   0   30.338  16.748  20.999  1.00 25.59
ATOM   1480  CD  LYS A 194   0   31.054  16.902  22.331  1.00 29.48
ATOM   1481  CE  LYS A 194   0   31.455  15.582  22.970  1.00 33.58
ATOM   1482  NZ  LYS A 194   0   30.363  15.049  23.868  1.00 35.93
ATOM   1483  N   TYR A 195   0   27.418  19.818  18.910  1.00 16.92
ATOM   1484  CA  TYR A 195   0   26.858  21.068  18.431  1.00 15.60
ATOM   1485  C   TYR A 195   0   26.143  21.838  19.530  1.00 14.20
ATOM   1486  O   TYR A 195   0   25.394  21.232  20.295  1.00 13.75
ATOM   1487  CB  TYR A 195   0   25.814  20.880  17.300  1.00 16.13
ATOM   1488  CG  TYR A 195   0   26.424  20.225  16.066  1.00 15.41
ATOM   1489  CD1 TYR A 195   0   26.663  18.851  16.091  1.00 15.91
ATOM   1490  CD2 TYR A 195   0   26.786  20.942  14.945  1.00 14.73
ATOM   1491  CE1 TYR A 195   0   27.244  18.204  15.010  1.00 16.55
ATOM   1492  CE2 TYR A 195   0   27.331  20.312  13.839  1.00 15.60
ATOM   1493  CZ  TYR A 195   0   27.570  18.947  13.888  1.00 16.18
ATOM   1494  OH  TYR A 195   0   28.144  18.287  12.831  1.00 15.64
ATOM   1495  N   ARG A 196   0   26.366  23.136  19.561  1.00 12.74
ATOM   1496  CA  ARG A 196   0   25.619  23.980  20.482  1.00 13.63
ATOM   1497  C   ARG A 196   0   24.343  24.369  19.711  1.00 13.86
ATOM   1498  O   ARG A 196   0   24.343  25.218  18.802  1.00 13.81
ATOM   1499  CB  ARG A 196   0   26.379  25.187  20.991  1.00 13.96
ATOM   1500  CG  ARG A 196   0   25.520  26.162  21.796  1.00 14.22
ATOM   1501  CD  ARG A 196   0   26.337  27.238  22.438  1.00 15.27
ATOM   1502  NE  ARG A 196   0   25.649  28.138  23.319  1.00 17.38
ATOM   1503  CZ  ARG A 196   0   26.203  29.034  24.140  1.00 18.86
ATOM   1504  NH1 ARG A 196   0   27.540  29.141  24.217  1.00 16.30
ATOM   1505  NH2 ARG A 196   0   25.377  29.788  24.869  1.00 16.73
ATOM   1506  N   MET A 197   0   23.266  23.624  20.002  1.00 13.86
ATOM   1507  CA  MET A 197   0   21.980  23.932  19.340  1.00 12.98
ATOM   1508  C   MET A 197   0   21.293  25.055  20.127  1.00 12.50
ATOM   1509  O   MET A 197   0   21.285  24.997  21.359  1.00 13.93
ATOM   1510  CB  MET A 197   0   21.118  22.693  19.266  1.00 12.50
ATOM   1511  CG  MET A 197   0   21.762  21.567  18.447  1.00 13.94
```

```
ATOM 1512 SD  MET A 197 0  21.860 22.033 16.735 1.00 16.62
ATOM 1513 CE  MET A 197 0  22.157 20.467 15.927 1.00 16.37
ATOM 1514 N   ARG A 198 0  20.768 26.064 19.450 1.00 11.00
ATOM 1515 CA  ARG A 198 0  20.131 27.191 20.137 1.00 11.83
ATOM 1516 C   ARG A 198 0  18.624 27.130 19.868 1.00 12.36
ATOM 1517 O   ARG A 198 0  18.145 27.304 18.731 1.00 10.03
ATOM 1518 CB  ARG A 198 0  20.804 28.460 19.629 1.00 13.98
ATOM 1519 CG  ARG A 198 0  22.282 28.567 20.065 1.00 16.25
ATOM 1520 CD  ARG A 198 0  22.932 29.863 19.626 1.00 16.68
ATOM 1521 NE  ARG A 198 0  24.350 29.957 20.042 1.00 16.91
ATOM 1522 CZ  ARG A 198 0  24.812 30.691 21.055 1.00 15.76
ATOM 1523 NH1 ARG A 198 0  24.031 31.456 21.820 1.00 13.44
ATOM 1524 NH2 ARG A 198 0  26.123 30.721 21.316 1.00 15.41
ATOM 1525 N   LEU A 199 0  17.871 26.807 20.908 1.00 10.44
ATOM 1526 CA  LEU A 199 0  16.426 26.568 20.708 1.00 10.69
ATOM 1527 C   LEU A 199 0  15.598 27.772 21.169 1.00 10.07
ATOM 1528 O   LEU A 199 0  15.682 28.216 22.317 1.00 10.07
ATOM 1529 CB  LEU A 199 0  16.003 25.317 21.491 1.00  8.67
ATOM 1530 CG  LEU A 199 0  14.499 24.942 21.391 1.00 10.33
ATOM 1531 CD1 LEU A 199 0  14.193 24.333 20.023 1.00  8.13
ATOM 1532 CD2 LEU A 199 0  14.170 23.907 22.485 1.00  9.10
ATOM 1533 N   ILE A 200 0  14.857 28.370 20.242 1.00 10.46
ATOM 1534 CA  ILE A 200 0  14.104 29.572 20.585 1.00 11.72
ATOM 1535 C   ILE A 200 0  12.627 29.428 20.310 1.00 13.84
ATOM 1536 O   ILE A 200 0  12.254 29.059 19.192 1.00 13.22
ATOM 1537 CB  ILE A 200 0  14.628 30.755 19.735 1.00 12.89
ATOM 1538 CG1 ILE A 200 0  16.165 30.899 19.824 1.00 12.38
ATOM 1539 CG2 ILE A 200 0  13.998 32.091 20.065 1.00 13.13
ATOM 1540 CD1 ILE A 200 0  16.811 31.634 18.671 1.00 12.54
ATOM 1541 N   SER A 201 0  11.829 29.825 21.312 1.00 14.64
ATOM 1542 CA  SER A 201 0  10.379 29.849 21.023 1.00 13.89
ATOM 1543 C   SER A 201 0  10.018 31.280 20.608 1.00 11.10
ATOM 1544 O   SER A 201 0  10.250 32.261 21.320 1.00  8.85
ATOM 1545 CB  SER A 201 0   9.539 29.367 22.202 1.00 13.01
ATOM 1546 OG  SER A 201 0   8.313 30.047 22.207 1.00 12.19
ATOM 1547 N   LEU A 202 0   9.428 31.376 19.438 1.00  9.64
ATOM 1548 CA  LEU A 202 0   8.959 32.637 18.881 1.00  9.06
ATOM 1549 C   LEU A 202 0   7.415 32.740 19.046 1.00 10.40
```

```
ATOM  1550 O   LEU A 202 0    6.802 33.528 18.351 1.00  9.36
ATOM  1551 CB  LEU A 202 0    9.239 32.618 17.379 1.00  9.09
ATOM  1552 CG  LEU A 202 0   10.691 32.451 16.888 1.00 10.90
ATOM  1553 CD1 LEU A 202 0   10.637 32.470 15.367 1.00 10.05
ATOM  1554 CD2 LEU A 202 0   11.617 33.559 17.414 1.00  8.56
ATOM  1555 N   SER A 203 0    6.821 31.942 19.892 1.00  9.59
ATOM  1556 CA  SER A 203 0    5.414 31.756 20.017 1.00 15.31
ATOM  1557 C   SER A 203 0    4.624 32.960 20.544 1.00 16.67
ATOM  1558 O   SER A 203 0    4.964 33.676 21.483 1.00 16.42
ATOM  1559 CB  SER A 203 0    5.130 30.505 20.867 1.00 15.21
ATOM  1560 OG  SER A 203 0    3.742 30.240 21.004 1.00 17.14
ATOM  1561 N   CYS A 204 0    3.428 33.051 19.984 1.00 17.18
ATOM  1562 CA  CYS A 204 0    2.442 34.018 20.470 1.00 18.43
ATOM  1563 C   CYS A 204 0    1.599 33.316 21.522 1.00 17.02
ATOM  1564 O   CYS A 204 0    0.867 34.039 22.200 1.00 17.27
ATOM  1565 CB  CYS A 204 0    1.524 34.508 19.334 1.00 18.60
ATOM  1566 SG  CYS A 204 0    2.135 36.038 18.612 1.00 20.23
ATOM  1567 N   ASP A 205 0    1.687 31.989 21.665 1.00 16.38
ATOM  1568 CA  ASP A 205 0    0.776 31.392 22.683 1.00 12.26
ATOM  1569 C   ASP A 205 0    1.123 30.002 23.087 1.00 11.34
ATOM  1570 O   ASP A 205 0    1.432 29.687 24.255 1.00 11.40
ATOM  1571 CB  ASP A 205 0   -0.622 31.516 22.076 1.00 14.87
ATOM  1572 CG  ASP A 205 0   -1.729 30.881 22.892 1.00 16.61
ATOM  1573 OD1 ASP A 205 0   -2.884 30.999 22.433 1.00 18.48
ATOM  1574 OD2 ASP A 205 0   -1.534 30.263 23.966 1.00 17.48
ATOM  1575 N   PRO A 206 0    1.036 29.030 22.205 1.00 11.79
ATOM  1576 CA  PRO A 206 0    1.313 27.639 22.542 1.00 11.91
ATOM  1577 C   PRO A 206 0    2.739 27.411 23.045 1.00 14.01
ATOM  1578 O   PRO A 206 0    3.676 28.135 22.661 1.00 14.38
ATOM  1579 CB  PRO A 206 0    1.124 26.816 21.262 1.00 11.87
ATOM  1580 CG  PRO A 206 0    1.112 27.893 20.191 1.00 12.83
ATOM  1581 CD  PRO A 206 0    0.749 29.241 20.766 1.00 11.09
ATOM  1582 N   ASN A 207 0    2.888 26.439 23.911 1.00 13.06
ATOM  1583 CA  ASN A 207 0    4.128 25.919 24.429 1.00 15.01
ATOM  1584 C   ASN A 207 0    4.332 24.591 23.677 1.00 15.84
ATOM  1585 O   ASN A 207 0    3.376 24.095 23.038 1.00 16.22
ATOM  1586 CB  ASN A 207 0    4.144 25.682 25.933 1.00 15.12
ATOM  1587 CG  ASN A 207 0    3.054 24.708 26.395 1.00 19.36
```

| | ATOM | 1588 | OD1 | ASN A 207 | 0 | 2.062 | 25.161 | 27.014 | 1.00 | 19.36 |
|---|---|---|---|---|---|---|---|---|---|---|
| | ATOM | 1589 | ND2 | ASN A 207 | 0 | 3.174 | 23.408 | 26.203 | 1.00 | 16.49 |
| | ATOM | 1590 | N | TRP A 208 | 0 | 5.557 | 24.077 | 23.634 | 1.00 | 14.46 |
| | ATOM | 1591 | CA | TRP A 208 | 0 | 5.827 | 22.865 | 22.892 | 1.00 | 12.04 |
| 5 | ATOM | 1592 | C | TRP A 208 | 0 | 6.638 | 21.921 | 23.783 | 1.00 | 13.85 |
| | ATOM | 1593 | O | TRP A 208 | 0 | 7.482 | 22.385 | 24.558 | 1.00 | 13.02 |
| | ATOM | 1594 | CB | TRP A 208 | 0 | 6.654 | 23.136 | 21.628 | 1.00 | 11.91 |
| | ATOM | 1595 | CG | TRP A 208 | 0 | 5.951 | 23.769 | 20.465 | 1.00 | 11.27 |
| | ATOM | 1596 | CD1 | TRP A 208 | 0 | 5.149 | 23.164 | 19.561 | 1.00 | 10.33 |
| 10 | ATOM | 1597 | CD2 | TRP A 208 | 0 | 5.988 | 25.158 | 20.092 | 1.00 | 10.29 |
| | ATOM | 1598 | NE1 | TRP A 208 | 0 | 4.698 | 24.078 | 18.625 | 1.00 | 10.91 |
| | ATOM | 1599 | CE2 | TRP A 208 | 0 | 5.201 | 25.313 | 18.954 | 1.00 | 9.64 |
| | ATOM | 1600 | CE3 | TRP A 208 | 0 | 6.634 | 26.294 | 20.625 | 1.00 | 10.25 |
| | ATOM | 1601 | CZ2 | TRP A 208 | 0 | 5.011 | 26.553 | 18.344 | 1.00 | 8.53 |
| 15 | ATOM | 1502 | CZ3 | TRP A 208 | 0 | 6.494 | 27.514 | 20.019 | 1.00 | 10.02 |
| | ATOM | 1603 | CH2 | TRP A 208 | 0 | 5.668 | 27.633 | 18.881 | 1.00 | 11.79 |
| | ATOM | 1604 | N | GLN A 209 | 0 | 6.420 | 20.620 | 23.580 | 1.00 | 13.82 |
| | ATOM | 1605 | CA | GLN A 209 | 0 | 7.240 | 19.588 | 24.192 | 1.00 | 13.83 |
| | ATOM | 1606 | C | GLN A 209 | 0 | 8.251 | 19.281 | 23.075 | 1.00 | 13.07 |
| 20 | ATOM | 1607 | O | GLN A 209 | 0 | 7.848 | 18.968 | 21.948 | 1.00 | 14.18 |
| | ATOM | 1608 | CB | GLN A 209 | 0 | 6.441 | 18.319 | 24.487 | 1.00 | 15.65 |
| | ATOM | 1609 | CG | GLN A 209 | 0 | 5.449 | 18.481 | 25.649 | 1.00 | 17.26 |
| | ATOM | 1610 | CD | GLN A 209 | 0 | 6.177 | 18.514 | 26.975 | 1.00 | 18.17 |
| | ATOM | 1611 | OE1 | GLN A 209 | 0 | 7.414 | 18.471 | 27.002 | 1.00 | 20.00 |
| 25 | ATOM | 1612 | NE2 | GLN A 209 | 0 | 5.462 | 18.570 | 28.085 | 1.00 | 16.89 |
| | ATOM | 1613 | N | PHE A 210 | 0 | 9.538 | 19.461 | 23.351 | 1.00 | 11.26 |
| | ATOM | 1614 | CA | PHE A 210 | 0 | 10.526 | 19.329 | 22.287 | 1.00 | 10.01 |
| | ATOM | 1615 | C | PHE A 210 | 0 | 11.457 | 18.153 | 22.585 | 1.00 | 9.18 |
| | ATOM | 1616 | O | PHE A 210 | 0 | 11.894 | 17.999 | 23.732 | 1.00 | 10.07 |
| 30 | ATOM | 1617 | CB | PHE A 210 | 0 | 11.370 | 20.629 | 22.292 | 1.00 | 10.86 |
| | ATOM | 1618 | CG | PHE A 210 | 0 | 12.489 | 20.581 | 21.292 | 1.00 | 9.63 |
| | ATOM | 1619 | CD1 | PHE A 210 | 0 | 13.760 | 20.179 | 21.674 | 1.00 | 9.95 |
| | ATOM | 1620 | CD2 | PHE A 210 | 0 | 12.251 | 20.922 | 19.984 | 1.00 | 8.54 |
| | ATOM | 1621 | CE1 | PHE A 210 | 0 | 14.778 | 20.150 | 20.738 | 1.00 | 9.23 |
| 35 | ATOM | 1622 | CE2 | PHE A 210 | 0 | 13.243 | 20.862 | 19.023 | 1.00 | 7.93 |
| | ATOM | 1623 | CZ | PHE A 210 | 0 | 14.520 | 20.491 | 19.426 | 1.00 | 8.71 |
| | ATOM | 1624 | N | SER A 211 | 0 | 11.741 | 17.384 | 21.545 | 1.00 | 8.62 |
| | ATOM | 1625 | CA | SER A 211 | 0 | 12.645 | 16.255 | 21.716 | 1.00 | 10.71 |

```
ATOM 1626 C   SER A 211 0  13.142 15.844 20.347 1.00 11.36
ATOM 1627 O   SER A 211 0  12.661 16.323 19.315 1.00  9.99
ATOM 1628 CB  SER A 211 0  11.970 15.070 22.427 1.00 10.56
ATOM 1629 OG  SER A 211 0  10.899 14.731 21.513 1.00 12.92
ATOM 1630 N   ILE A 212 0  14.268 15.122 20.390 1.00 13.67
ATOM 1631 CA  ILE A 212 0  14.883 14.680 19.131 1.00 14.79
ATOM 1632 C   ILE A 212 0  15.013 13.166 19.220 1.00 15.44
ATOM 1633 O   ILE A 212 0  15.624 12.689 20.177 1.00 15.98
ATOM 1634 CB  ILE A 212 0  16.255 15.341 18.887 1.00 17.04
ATOM 1635 CG1 ILE A 212 0  16.082 16.859 18.756 1.00 15.64
ATOM 1636 CG2 ILE A 212 0  16.935 14.722 17.648 1.00 15.24
ATOM 1637 CD1 ILE A 212 0  17.352 17.648 18.553 1.00 16.57
ATOM 1638 N   ASP A 213 0  14.453 12.418 18.281 1.00 15.53
ATOM 1639 CA  ASP A 213 0  14.549 10.952 18.401 1.00 16.50
ATOM 1640 C   ASP A 213 0  16.004 10.469 18.541 1.00 16.69
ATOM 1641 O   ASP A 213 0  16.948 10.902 17.851 1.00 14.36
ATOM 1642 CB  ASP A 213 0  13.884 10.359 17.173 1.00 17.15
ATOM 1643 CG  ASP A 213 0  12.369 10.467 17.144 1.00 18.12
ATOM 1644 OD1 ASP A 213 0  11.751 10.995 18.092 1.00 16.90
ATOM 1645 OD2 ASP A 213 0  11.801  9.990 16.129 1.00 17.35
ATOM 1646 N   GLY A 214 0  16.198  9.559 19.477 1.00 15.76
ATOM 1647 CA  GLY A 214 0  17.457  8.900 19.747 1.00 17.22
ATOM 1648 C   GLY A 214 0  18.548  9.757 20.368 1.00 18.54
ATOM 1649 O   GLY A 214 0  19.680  9.277 20.404 1.00 18.20
ATOM 1650 N   HIS A 215 0  18.341 11.024 20.738 1.00 18.17
ATOM 1651 CA  HIS A 215 0  19.422 11.880 21.229 1.00 17.59
ATOM 1652 C   HIS A 215 0  19.096 12.505 22.577 1.00 17.92
ATOM 1653 O   HIS A 215 0  17.917 12.696 22.898 1.00 20.45
ATOM 1654 CB  HIS A 215 0  19.705 13.008 20.221 1.00 15.73
ATOM 1655 CG  HIS A 215 0  20.309 12.543 18.936 1.00 16.90
ATOM 1656 ND1 HIS A 215 0  19.589 11.864 17.963 1.00 17.35
ATOM 1657 CD2 HIS A 215 0  21.574 12.658 18.444 1.00 16.15
ATOM 1658 CE1 HIS A 215 0  20.376 11.576 16.933 1.00 17.63
ATOM 1659 NE2 HIS A 215 0  21.599 12.046 17.216 1.00 17.73
ATOM 1660 N   GLU A 216 0  20.104 12.815 23.382 1.00 17.22
ATOM 1661 CA  GLU A 216 0  19.876 13.479 24.665 1.00 15.86
ATOM 1662 C   GLU A 216 0  20.070 14.976 24.456 1.00 15.61
ATOM 1663 O   GLU A 216 0  20.684 15.386 23.453 1.00 14.96
```

```
     ATOM   1664 CB  GLU A 216   0    20.817  12.901  25.694  1.00 15.38
     ATOM   1665 CG  GLU A 216   0    20.440  11.520  26.166  1.00 16.53
     ATOM   1666 CD  GLU A 216   0    21.242  11.058  27.357  1.00 17.23
     ATOM   1667 OE1 GLU A 216   0    22.378  10.619  27.129  1.00 20.31
  5  ATOM   1668 OE2 GLU A 216   0    20.813  11.119  28.519  1.00 16.06
     ATOM   1669 N   LEU A 217   0    19.623  15.792  25.394  1.00 14.64
     ATOM   1670 CA  LEU A 217   0    19.738  17.243  25.251  1.00 14.91
     ATOM   1671 C   LEU A 217   0    20.512  17.792  26.446  1.00 14.71
     ATOM   1672 O   LEU A 217   0    19.950  17.734  27.539  1.00 15.67
 10  ATOM   1673 CB  LEU A 217   0    18.362  17.931  25.229  1.00 14.75
     ATOM   1674 CG  LEU A 217   0    17.276  17.349  24.306  1.00 15.40
     ATOM   1675 CD1 LEU A 217   0    15.939  18.075  24.505  1.00 15.08
     ATOM   1676 CD2 LEU A 217   0    17.723  17.453  22.849  1.00 15.22
     ATOM   1677 N   THR A 218   0    21.732  18.278  26.229  1.00 13.65
 15  ATOM   1678 CA  THR A 218   0    22.507  18.714  27.402  1.00 13.26
     ATOM   1679 C   THR A 218   0    22.427  20.232  27.505  1.00 13.27
     ATOM   1680 O   THR A 218   0    23.142  20.955  26.805  1.00 12.91
     ATOM   1681 CB  THR A 218   0    23.955  18.216  27.304  1.00 12.08
     ATOM   1682 OG1 THR A 218   0    23.935  16.782  27.331  1.00 15.48
 20  ATOM   1683 CG2 THR A 218   0    24.767  18.721  28.470  1.00 11.46
     ATOM   1684 N   ILE A 219   0    21.522  20.649  28.385  1.00 13.30
     ATOM   1685 CA  ILE A 219   0    21.259  22.068  28.547  1.00 14.53
     ATOM   1686 C   ILE A 219   0    22.420  22.818  29.180  1.00 12.72
     ATOM   1687 O   ILE A 219   0    22.795  22.492  30.292  1.00 13.08
 25  ATOM   1688 CB  ILE A 219   0    19.930  22.268  29.323  1.00 14.74
     ATOM   1689 CG1 ILE A 219   0    18.761  21.699  28.441  1.00 17.33
     ATOM   1690 CG2 ILE A 219   0    19.666  23.717  29.656  1.00 13.40
     ATOM   1691 CD1 ILE A 219   0    17.597  21.481  29.412  1.00 19.42
     ATOM   1692 N   ILE A 220   0    22.898  23.869  28.510  1.00 12.55
 30  ATOM   1693 CA  ILE A 220   0    23.994  24.696  29.019  1.00 13.25
     ATOM   1694 C   ILE A 220   0    23.686  26.193  29.085  1.00 15.11
     ATOM   1695 O   ILE A 220   0    24.477  27.001  29.618  1.00 14.73
     ATOM   1696 CB  ILE A 220   0    25.239  24.507  28.125  1.00 11.80
     ATOM   1697 CG1 ILE A 220   0    24.954  24.871  26.671  1.00 10.93
 35  ATOM   1698 CG2 ILE A 220   0    25.770  23.072  28.291  1.00  9.59
     ATOM   1699 CD1 ILE A 220   0    26.249  25.231  25.928  1.00 12.07
     ATOM   1700 N   GLU A 221   0    22.490  26.573  28.597  1.00 13.30
     ATOM   1701 CA  GLU A 221   0    22.048  27.951  28.624  1.00 12.96
```

5032-WO

75

```
   ATOM 1702 C   GLU A 221  0   20.522 28.066 28.727 1.00 13.77
   ATOM 1703 O   GLU A 221  0   19.799 27.301 28.068 1.00 14.06
   ATOM 1704 CB  GLU A 221  0   22.436 28.666 27.318 1.00 12.73
   ATOM 1705 CG  GLU A 221  0   22.280 30.178 27.325 1.00 12.94
 5 ATOM 1706 CD  GLU A 221  0   22.018 30.783 25.969 1.00 13.84
   ATOM 1707 OE1 GLU A 221  0   22.345 30.269 24.887 1.00 12.66
   ATOM 1708 OE2 GLU A 221  0   21.386 31.862 25.936 1.00 14.80
   ATOM 1709 N   VAL A 222  0   20.062 29.091 29.434 1.00 13.89
   ATOM 1710 CA  VAL A 222  0   18.632 29.350 29.534 1.00 14.13
10 ATOM 1711 C   VAL A 222  0   18.409 30.853 29.493 1.00 13.87
   ATOM 1712 O   VAL A 222  0   18.900 31.657 30.300 1.00 11.55
   ATOM 1713 CB  VAL A 222  0   18.003 28.649 30.737 1.00 16.86
   ATOM 1714 CG1 VAL A 222  0   18.730 28.941 32.017 1.00 19.16
   ATOM 1715 CG2 VAL A 222  0   16.575 29.120 31.033 1.00 18.45
15 ATOM 1716 N   ASP A 223  0   17.631 31.267 28.481 1.00 11.69
   ATOM 1717 CA  ASP A 223  0   17.245 32.673 28.386 1.00 13.60
   ATOM 1718 C   ASP A 223  0   18.472 33.598 28.548 1.00 14.44
   ATOM 1719 O   ASP A 223  0   18.423 34.552 29.336 1.00 12.75
   ATOM 1720 CB  ASP A 223  0   16.161 33.033 29.417 1.00 12.59
20 ATOM 1721 CG  ASP A 223  0   14.845 32.279 29.364 1.00 14.64
   ATOM 1722 OD1 ASP A 223  0   14.697 31.397 28.493 1.00 13.34
   ATOM 1723 OD2 ASP A 223  0   13.858 32.463 30.156 1.00 13.85
   ATOM 1724 N   GLY A 224  0   19.544 33.372 27.767 1.00 13.49
   ATOM 1725 CA  GLY A 224  0   20.728 34.213 27.770 1.00 12.85
25 ATOM 1726 C   GLY A 224  0   21.562 34.112 29.049 1.00 13.00
   ATOM 1727 O   GLY A 224  0   22.326 35.040 29.317 1.00 13.97
   ATOM 1728 N   GLU A 225  0   21.370 33.105 29.875 1.00 11.78
   ATOM 1729 CA  GLU A 225  0   22.068 32.888 31.114 1.00 14.97
   ATOM 1730 C   GLU A 225  0   22.609 31.447 31.106 1.00 16.73
30 ATOM 1731 O   GLU A 225  0   21.858 30.498 30.849 1.00 15.88
   ATOM 1732 CB  GLU A 225  0   21.174 33.062 32.358 1.00 16.54
   ATOM 1733 CG  GLU A 225  0   20.509 34.424 32.534 1.00 16.30
   ATOM 1734 CD  GLU A 225  0   21.492 35.546 32.823 1.00 17.57
   ATOM 1735 OE1 GLU A 225  0   22.450 35.254 33.561 1.00 18.76
35 ATOM 1736 OE2 GLU A 225  0   21.360 36.711 32.360 1.00 17.77
   ATOM 1737 N   LEU A 226  0   23.922 31.285 31.324 1.00 16.90
   ATOM 1738 CA  LEU A 226  0   24.526 29.955 31.318 1.00 15.50
   ATOM 1739 C   LEU A 226  0   24.183 29.127 32.540 1.00 15.04
```

```
ATOM  1740  O   LEU A 226  0   24.002 29.648 33.652 1.00 15.17
ATOM  1741  CB  LEU A 226  0   26.062 30.008 31.216 1.00 15.36
ATOM  1742  CG  LEU A 226  0   26.567 30.741 29.958 1.00 17.95
ATOM  1743  CD1 LEU A 226  0   28.076 30.876 29.979 1.00 18.77
ATOM  1744  CD2 LEU A 226  0   26.111 30.029 28.687 1.00 17.36
ATOM  1745  N   THR A 227  0   24.119 27.799 32.332 1.00 13.62
ATOM  1746  CA  THR A 227  0   23.848 26.930 33.479 1.00 13.72
ATOM  1747  C   THR A 227  0   24.936 25.851 33.528 1.00 14.30
ATOM  1748  O   THR A 227  0   25.732 25.629 32.592 1.00 14.28
ATOM  1749  CB  THR A 227  0   22.478 26.217 33.352 1.00 14.35
ATOM  1750  OG1 THR A 227  0   22.506 25.385 32.178 1.00 13.68
ATOM  1751  CG2 THR A 227  0   21.284 27.161 33.180 1.00 12.29
ATOM  1752  N   GLU A 228  0   24.960 25.136 34.625 1.00 14.73
ATOM  1753  CA  GLU A 228  0   25.765 23.907 34.714 1.00 17.32
ATOM  1754  C   GLU A 228  0   25.110 22.971 33.680 1.00 17.30
ATOM  1755  O   GLU A 228  0   23.917 23.035 33.472 1.00 16.97
ATOM  1756  CB  GLU A 228  0   25.617 23.315 36.114 1.00 16.58
ATOM  1757  CG  GLU A 228  0   26.493 23.979 37.186 1.00 18.10
ATOM  1758  CD  GLU A 228  0   26.236 23.458 38.575 1.00 20.92
ATOM  1759  OE1 GLU A 228  0   25.469 22.470 38.755 1.00 23.38
ATOM  1760  OE2 GLU A 228  0   26.769 23.997 39.564 1.00 21.26
ATOM  1761  N   PRO A 229  0   25.867 22.158 32.984 1.00 16.91
ATOM  1762  CA  PRO A 229  0   25.369 21.207 31.992 1.00 16.37
ATOM  1763  C   PRO A 229  0   24.351 20.275 32.599 1.00 16.24
ATOM  1764  O   PRO A 229  0   24.624 19.652 33.619 1.00 15.76
ATOM  1765  CB  PRO A 229  0   26.612 20.469 31.419 1.00 15.97
ATOM  1766  CG  PRO A 229  0   27.701 21.509 31.741 1.00 15.92
ATOM  1767  CD  PRO A 229  0   27.337 22.141 33.083 1.00 14.86
ATOM  1768  N   HIS A 230  0   23.140 20.164 32.038 1.00 15.58
ATOM  1769  CA  HIS A 230  0   22.090 19.325 32.618 1.00 15.01
ATOM  1770  C   HIS A 230  0   21.354 18.610 31.488 1.00 13.55
ATOM  1771  O   HIS A 230  0   20.756 19.192 30.590 1.00 13.47
ATOM  1772  CB  HIS A 230  0   21.172 20.164 33.510 1.00 15.89
ATOM  1773  CG  HIS A 230  0   20.045 19.341 34.064 1.00 18.32
ATOM  1774  ND1 HIS A 230  0   20.252 18.347 35.004 1.00 18.14
ATOM  1775  CD2 HIS A 230  0   18.713 19.328 33.791 1.00 17.75
ATOM  1776  CE1 HIS A 230  0   19.121 17.768 35.310 1.00 16.33
ATOM  1777  NE2 HIS A 230  0   18.173 18.344 34.609 1.00 17.85
```

5032-WO

77

```
   ATOM 1778 N   THR A 231 0  21.496 17.304 31.458 1.00 12.94
   ATOM 1779 CA  THR A 231 0  20.995 16.474 30.346 1.00 14.15
   ATOM 1780 C   THR A 231 0  19.620 15.890 30.547 1.00 13.41
   ATOM 1781 O   THR A 231 0  19.293 15.401 31.616 1.00 14.89
 5 ATOM 1782 CB  THR A 231 0  22.040 15.364 30.060 1.00 13.73
   ATOM 1783 OG1 THR A 231 0  23.314 16.023 29.852 1.00 14.77
   ATOM 1784 CG2 THR A 231 0  21.655 14.600 28.818 1.00 13.06
   ATOM 1785 N   VAL A 232 0  18.776 15.954 29.549 1.00 12.86
   ATOM 1786 CA  VAL A 232 0  17.374 15.505 29.665 1.00 13.44
10 ATOM 1787 C   VAL A 232 0  16.999 14.966 28.319 1.00 14.96
   ATOM 1788 O   VAL A 232 0  17.790 15.258 27.390 1.00 14.12
   ATOM 1789 CB  VAL A 232 0  16.771 16.910 30.000 1.00 17.41
   ATOM 1790 CG1 VAL A 232 0  16.075 17.587 28.856 1.00 14.66
   ATOM 1791 CG2 VAL A 232 0  16.158 16.935 31.371 1.00 15.66
15 ATOM 1792 N   ASP A 233 0  15.874 14.277 28.153 1.00 14.01
   ATOM 1793 CA  ASP A 233 0  15.405 13.803 26.874 1.00 14.73
   ATOM 1794 C   ASP A 233 0  14.353 14.718 26.245 1.00 14.74
   ATOM 1795 O   ASP A 233 0  14.187 14.731 25.027 1.00 13.41
   ATOM 1796 CB  ASP A 233 0  14.640 12.465 27.046 1.00 16.54
20 ATOM 1797 CG  ASP A 233 0  15.637 11.417 27.536 1.00 19.27
   ATOM 1798 OD1 ASP A 233 0  16.543 11.145 26.732 1.00 20.98
   ATOM 1799 OD2 ASP A 233 0  15.536 10.945 28.667 1.00 19.27
   ATOM 1800 N   ARG A 234 0  13.595 15.386 27.122 1.00 13.79
   ATOM 1801 CA  ARG A 234 0  12.514 16.199 26.598 1.00 16.36
25 ATOM 1802 C   ARG A 234 0  12.258 17.426 27.472 1.00 15.17
   ATOM 1803 O   ARG A 234 0  12.418 17.390 28.686 1.00 13.96
   ATOM 1804 CB  ARG A 234 0  11.265 15.330 26.482 1.00 19.23
   ATOM 1805 CG  ARG A 234 0  10.104 16.036 25.788 1.00 22.25
   ATOM 1806 CD  ARG A 234 0   8.981 15.023 25.506 1.00 24.68
30 ATOM 1807 NE  ARG A 234 0   8.157 14.983 26.705 1.00 28.27
   ATOM 1808 CZ  ARG A 234 0   6.845 14.828 26.719 1.00 28.66
   ATOM 1809 NH1 ARG A 234 0   6.291 14.833 27.909 1.00 30.08
   ATOM 1810 NH2 ARG A 234 0   6.191 14.662 25.587 1.00 30.24
   ATOM 1811 N   LEU A 235 0  11.874 18.524 26.816 1.00 13.90
35 ATOM 1812 CA  LEU A 235 0  11.619 19.742 27.607 1.00 13.15
   ATOM 1813 C   LEU A 235 0  10.390 20.430 27.041 1.00 11.49
   ATOM 1814 O   LEU A 235 0  10.025 20.304 25.873 1.00 11.08
   ATOM 1815 CB  LEU A 235 0  12.825 20.630 27.695 1.00 14.39
```

```
ATOM 1816 CG  LEU A 235  0  13.459 21.645 26.801 1.00 17.19
ATOM 1817 CD1 LEU A 235  0  14.795 21.218 26.197 1.00 16.98
ATOM 1818 CD2 LEU A 235  0  12.586 22.219 25.685 1.00 18.24
ATOM 1819 N   GLN A 236  0   9.769 21.152 27.949 1.00 12.74
ATOM 1820 CA  GLN A 236  0   8.576 21.944 27.616 1.00 13.45
ATOM 1821 C   GLN A 236  0   9.005 23.390 27.459 1.00 12.21
ATOM 1822 O   GLN A 236  0   9.606 23.939 28.406 1.00 13.90
ATOM 1823 CB  GLN A 236  0   7.525 21.770 28.741 1.00 12.06
ATOM 1824 CG  GLN A 236  0   6.197 22.276 28.238 1.00 14.12
ATOM 1825 CD  GLN A 236  0   5.025 22.108 29.205 1.00 13.35
ATOM 1826 OE1 GLN A 236  0   3.893 22.215 28.721 1.00 15.61
ATOM 1827 NE2 GLN A 236  0   5.226 21.912 30.463 1.00 12.00
ATOM 1828 N   ILE A 237  0   8.748 24.011 26.311 1.00 12.17
ATOM 1829 CA  ILE A 237. 0   9.213 25.390 26.156 1.00 12.41
ATOM 1830 C   ILE A 237  0   8.061 26.376 25.953 1.00 13.14
ATOM 1831 O   ILE A 237  0   7.283 26.310 24.990 1.00 13.64
ATOM 1832 CB  ILE A 237  0  10.255 25.437 25.022 1.00 11.03
ATOM 1833 CG1 ILE A 237  0  10.947 26.793 24.960 1.00 11.84
ATOM 1834 CG2 ILE A 237  0   9.615 25.086 23.662 1.00 10.02
ATOM 1835 CD1 ILE A 237  0  12.041 26.953 23.902 1.00 11.23
ATOM 1836 N   PHE A 238  0   8.037 27.414 26.765 1.00 12.83
ATOM 1837 CA  PHE A 238  0   6.979 28.431 26.714 1.00 13.23
ATOM 1838 C   PHE A 238  0   7.382 29.683 25.957 1.00 13.99
ATOM 1839 O   PHE A 238  0   8.530 29.848 25.545 1.00 13.87
ATOM 1840 CB  PHE A 238  0   6.592 28.848 28.145 1.00 12.72
ATOM 1841 CG  PHE A 238  0   6.176 27.691 28.993 1.00 14.51
ATOM 1842 CD1 PHE A 238  0   7.098 26.957 29.710 1.00 14.84
ATOM 1843 CD2 PHE A 238  0   4.836 27.314 29.078 1.00 15.50
ATOM 1844 CE1 PHE A 238  0   6.748 25.882 30.497 1.00 13.87
ATOM 1845 CE2 PHE A 238  0   4.468 26.236 29.862 1.00 14.62
ATOM 1846 CZ  PHE A 238  0   5.423 25.528 30.568 1.00 15.15
ATOM 1847 N   THR A 239  0   6.388 30.494 25.604 1.00 14.16
ATOM 1848 CA  THR A 239  0   6.543 31.678 24.806 1.00 13.44
ATOM 1849 C   THR A 239  0   7.832 32.453 25.106 1.00 11.74
ATOM 1850 O   THR A 239  0   8.012 32.950 26.218 1.00 10.47
ATOM 1851 CB  THR A 239  0   5.381 32.695 24.978 1.00 15.55
ATOM 1852 OG1 THR A 239  0   5.258 33.008 26.359 1.00 17.88
ATOM 1853 CG2 THR A 239  0   4.055 32.131 24.478 1.00 16.75
```

```
   ATOM  1854 N   GLY A 240  0   8.672 32.593 24.078 1.00  7.94
   ATOM  1855 CA  GLY A 240  0   9.877 33.348 24.193 1.00 10.08
   ATOM  1856 C   GLY A 240  0  11.039 32.865 25.041 1.00 11.34
   ATOM  1857 O   GLY A 240  0  11.977 33.650 25.216 1.00 11.02
 5 ATOM  1858 N   GLN A 241  0  10.990 31.646 25.592 1.00  9.73
   ATOM  1859 CA  GLN A 241  0  12.067 31.090 26.364 1.00  9.59
   ATOM  1860 C   GLN A 241  0  13.114 30.587 25.342 1.00 10.56
   ATOM  1861 O   GLN A 241  0  12.823 30.467 24.126 1.00  8.44
   ATOM  1862 CB  GLN A 241  0  11.604 29.965 27.285 1.00 10.57
10 ATOM  1863 CG  GLN A 241  0  10.820 30.363 28.523 1.00 10.54
   ATOM  1864 CD  GLN A 241  0  10.341 29.190 29.341 1.00 12.22
   ATOM  1865 OE1 GLN A 241  0  10.118 28.077 28.815 1.00 13.21
   ATOM  1866 NE2 GLN A 241  0  10.220 29.466 30.639 1.00 11.74
   ATOM  1867 N   ARG A 242  0  14.372 30.492 25.774 1.00  9.00
15 ATOM  1868 CA  ARG A 242  0  15.388 29.992 24.834 1.00 11.01
   ATOM  1869 C   ARG A 242  0  16.210 28.966 25.609 1.00 11.30
   ATOM  1870 O   ARG A 242  0  16.292 29.133 26.816 1.00  9.51
   ATOM  1871 CB  ARG A 242  0  16.324 31.043 24.265 1.00 12.77
   ATOM  1872 CG  ARG A 242  0  15.694 32.128 23.364 1.00 12.52
20 ATOM  1873 CD  ARG A 242  0  15.066 33.249 24.138 1.00 10.81
   ATOM  1874 NE  ARG A 242  0  15.957 34.126 24.892 1.00 10.80
   ATOM  1875 CZ  ARG A 242  0  15.630 34.761 26.002 1.00 11.36
   ATOM  1876 NH1 ARG A 242  0  16.486 35.548 26.648 1.00  7.98
   ATOM  1877 NH2 ARG A 242  0  14.365 34.589 26.489 1.00 12.78
25 ATOM  1878 N   TYR A 243  0  16.717 27.934 24.942 1.00 11.61
   ATOM  1879 CA  TYR A 243  0  17.631 27.009 25.610 1.00 12.54
   ATOM  1880 C   TYR A 243  0  18.819 26.762 24.650 1.00 14.46
   ATOM  1881 O   TYR A 243  0  18.568 26.656 23.435 1.00 16.11
   ATOM  1882 CB  TYR A 243  0  17.015 25.638 25.934 1.00 11.09
30 ATOM  1883 CG  TYR A 243  0  16.007 25.667 27.054 1.00 12.11
   ATOM  1884 CD1 TYR A 243  0  14.641 25.825 26.843 1.00 12.88
   ATOM  1885 CD2 TYR A 243  0  16.440 25.575 28.371 1.00 12.11
   ATOM  1886 CE1 TYR A 243  0  13.748 25.869 27.915 1.00 12.71
   ATOM  1887 CE2 TYR A 243  0  15.560 25.582 29.436 1.00 12.50
35 ATOM  1888 CZ  TYR A 243  0  14.205 25.738 29.188 1.00 12.29
   ATOM  1889 OH  TYR A 243  0  13.379 25.789 30.286 1.00 13.65
   ATOM  1890 N   SER A 244  0  20.059 26.734 25.144 1.00 12.78
   ATOM  1891 CA  SER A 244  0  21.117 26.212 24.268 1.00 13.22
```

```
ATOM  1892 C   SER A 244  0   21.333 24.779 24.814 1.00 11.06
ATOM  1893 O   SER A 244  0   21.377 24.604 26.018 1.00 11.27
ATOM  1894 CB  SER A 244  0   22.485 26.907 24.308 1.00 14.46
ATOM  1895 OG  SER A 244  0   22.551 28.029 23.463 1.00 13.59
ATOM  1896 N   PHE A 245  0   21.484 23.780 23.983 1.00 11.89
ATOM  1897 CA  PHE A 245  0   21.772 22.437 24.452 1.00 13.14
ATOM  1898 C   PHE A 245  0   22.867 21.857 23.546 1.00 12.32
ATOM  1899 O   PHE A 245  0   22.890 22.128 22.354 1.00 11.11
ATOM  1900 CB  PHE A 245  0   20.554 21.495 24.526 1.00 11.40
ATOM  1901 CG  PHE A 245  0   19.915 21.236 23.195 1.00 11.98
ATOM  1902 CD1 PHE A 245  0   18.815 21.993 22.813 1.00 13.38
ATOM  1903 CD2 PHE A 245  0   20.349 20.236 22.351 1.00 11.45
ATOM  1904 CE1 PHE A 245  0   18.216 21.773 21.588 1.00 12.84
ATOM  1905 CE2 PHE A 245  0   19.759 20.000 21.129 1.00 11.48
ATOM  1906 CZ  PHE A 245  0   18.705 20.796 20.743 1.00 12.65
ATOM  1907 N   VAL A 246  0   23.742 21.073 24.169 1.00 13.51
ATOM  1908 CA  VAL A 246  0   24.775 20.427 23.341 1.00 13.37
ATOM  1909 C   VAL A 246  0   24.096 19.177 22.783 1.00 12.47
ATOM  1910 O   VAL A 246  0   23.505 18.425 23.540 1.00 11.41
ATOM  1911 CB  VAL A 246  0   25.990 19.984 24.190 1.00 14.96
ATOM  1912 CG1 VAL A 246  0   26.995 19.186 23.364 1.00 13.75
ATOM  1913 CG2 VAL A 246  0   26.681 21.165 24.841 1.00 15.92
ATOM  1914 N   LEU A 247  0   24.160 18.996 21.490 1.00 12.97
ATOM  1915 CA  LEU A 247  0   23.766 17.833 20.785 1.00 14.32
ATOM  1916 C   LEU A 247  0   25.071 17.077 20.395 1.00 14.22
ATOM  1917 O   LEU A 247  0   25.954 17.529 19.664 1.00 12.45
ATOM  1918 CB  LEU A 247  0   22.980 18.109 19.505 1.00 16.00
ATOM  1919 CG  LEU A 247  0   22.514 16.786 18.835 1.00 16.80
ATOM  1920 CD1 LEU A 247  0   21.266 16.306 19.513 1.00 18.30
ATOM  1921 CD2 LEU A 247  0   22.207 16.988 17.373 1.00 18.70
ATOM  1922 N   ASP A 248  0   25.144 15.886 20.926 1.00 13.56
ATOM  1923 CA  ASP A 248  0   26.278 14.980 20.727 1.00 16.65
ATOM  1924 C   ASP A 248  0   25.916 14.072 19.581 1.00 16.18
ATOM  1925 O   ASP A 248  0   25.095 13.166 19.813 1.00 17.60
ATOM  1926 CB  ASP A 248  0   26.536 14.229 22.036 1.00 17.83
ATOM  1927 CG  ASP A 248  0   27.798 13.359 22.024 1.00 21.77
ATOM  1928 OD1 ASP A 248  0   28.231 12.967 23.140 1.00 24.11
ATOM  1929 OD2 ASP A 248  0   28.345 13.060 20.950 1.00 21.25
```

```
   ATOM 1930  N   ALA A 249  0    26.414  14.277  18.369  1.00 15.85
   ATOM 1931  CA  ALA A 249  0    25.982  13.416  17.255  1.00 17.99
   ATOM 1932  C   ALA A 249  0    26.698  12.049  17.306  1.00 20.21
   ATOM 1933  O   ALA A 249  0    27.569  11.766  16.485  1.00 19.11
 5 ATOM 1934  CB  ALA A 249  0    26.165  14.126  15.930  1.00 14.57
   ATOM 1935  N   ASN A 250  0    26.273  11.223  18.253  1.00 21.66
   ATOM 1936  CA  ASN A 250  0    26.861   9.961  18.581  1.00 25.53
   ATOM 1937  C   ASN A 250  0    26.061   8.721  18.202  1.00 27.30
   ATOM 1938  O   ASN A 250  0    26.344   7.645  18.756  1.00 29.42
10 ATOM 1939  CB  ASN A 250  0    27.108   9.912  20.104  1.00 25.83
   ATOM 1940  CG  ASN A 250  0    25.888   9.968  20.978  1.00 28.76
   ATOM 1941  OD1 ASN A 250  0    24.757  10.156  20.527  1.00 29.90
   ATOM 1942  ND2 ASN A 250  0    26.042   9.826  22.306  1.00 29.52
   ATOM 1943  N   GLN A 251  0    25.089   8.841  17.302  1.00 26.74
15 ATOM 1944  CA  GLN A 251  0    24.239   7.712  16.934  1.00 23.48
   ATOM 1945  C   GLN A 251  0    24.583   7.311  15.510  1.00 21.73
   ATOM 1946  O   GLN A 251  0    25.333   8.009  14.843  1.00 19.39
   ATOM 1947  CB  GLN A 251  0    22.757   8.104  17.022  1.00 24.79
   ATOM 1948  CG  GLN A 251  0    22.333   8.701  18.360  1.00 25.14
20 ATOM 1949  CD  GLN A 251  0    22.430   7.693  19.480  1.00 26.76
   ATOM 1950  OE1 GLN A 251  0    21.762   6.654  19.405  1.00 28.78
   ATOM 1951  NE2 GLN A 251  0    23.202   7.986  20.514  1.00 26.02
   ATOM 1952  N   PRO A 252  0    24.058   6.177  15.076  1.00 20.53
   ATOM 1953  CA  PRO A 252  0    24.293   5.637  13.755  1.00 20.06
25 ATOM 1954  C   PRO A 252  0    23.940   6.671  12.702  1.00 21.83
   ATOM 1955  O   PRO A 252  0    22.973   7.424  12.940  1.00 22.51
   ATOM 1956  CB  PRO A 252  0    23.417   4.367  13.647  1.00 19.98
   ATOM 1957  CG  PRO A 252  0    23.288   3.997  15.096  1.00 19.94
   ATOM 1958  CD  PRO A 252  0    23.223   5.289  15.902  1.00 19.68
30 ATOM 1959  N   VAL A 253  0    24.663   6.728  11.584  1.00 20.85
   ATOM 1960  CA  VAL A 253  0    24.302   7.741  10.604  1.00 22.29
   ATOM 1961  C   VAL A 253  0    22.897   7.414  10.108  1.00 23.02
   ATOM 1962  O   VAL A 253  0    22.593   6.289   9.753  1.00 21.37
   ATOM 1963  CB  VAL A 253  0    25.298   8.065   9.494  1.00 23.22
35 ATOM 1964  CG1 VAL A 253  0    26.696   7.582   9.827  1.00 22.25
   ATOM 1965  CG2 VAL A 253  0    24.859   7.680   8.101  1.00 22.26
   ATOM 1966  N   ASP A 254  0    22.012   8.422  10.159  1.00 24.32
   ATOM 1967  CA  ASP A 254  0    20.613   8.176   9.786  1.00 22.09
```

```
ATOM  1968 C   ASP A 254  0   19.782  9.448  9.821 1.00 20.71
ATOM  1969 O   ASP A 254  0   20.365 10.481 10.099 1.00 18.92
ATOM  1970 CB  ASP A 254  0   20.048  7.211 10.830 1.00 23.39
ATOM  1971 CG  ASP A 254  0   18.964  6.331 10.251 1.00 24.43
ATOM  1972 OD1 ASP A 254  0   18.355  6.663  9.239 1.00 23.21
ATOM  1973 OD2 ASP A 254  0   18.736  5.244 10.816 1.00 28.26
ATOM  1974 N   ASN A 255  0   18.485  9.338  9.496 1.00 18.97
ATOM  1975 CA  ASN A 255  0   17.583 10.479  9.599 1.00 17.69
ATOM  1976 C   ASN A 255  0   16.785 10.335 10.889 1.00 17.64
ATOM  1977 O   ASN A 255  0   16.390  9.204 11.249 1.00 17.75
ATOM  1978 CB  ASN A 255  0   16.663 10.554  8.386 1.00 17.19
ATOM  1979 CG  ASN A 255  0   17.467 10.882  7.143 1.00 17.33
ATOM  1980 OD1 ASN A 255  0   17.891 12.023  6.932 1.00 18.05
ATOM  1981 ND2 ASN A 255  0   17.649  9.913  6.263 1.00 15.98
ATOM  1982 N   TYR A 256  0   16.657 11.403 11.684 1.00 14.89
ATOM  1983 CA  TYR A 256  0   15.983 11.364 12.961 1.00 12.56
ATOM  1984 C   TYR A 256  0   14.966 12.520 12.991 1.00 15.02
ATOM  1985 O   TYR A 256  0   15.208 13.637 12.509 1.00 14.49
ATOM  1986 CB  TYR A 256  0   16.867 11.479 14.216 1.00 14.85
ATOM  1987 CG  TYR A 256  0   17.883 10.349 14.316 1.00 13.96
ATOM  1988 CD1 TYR A 256  0   19.030 10.427 13.529 1.00 13.97
ATOM  1989 CD2 TYR A 256  0   17.712  9.245 15.129 1.00 14.62
ATOM  1990 CE1 TYR A 256  0   19.986  9.422 13.534 1.00 13.83
ATOM  1991 CE2 TYR A 256  0   18.667  8.224 15.170 1.00 15.31
ATOM  1992 CZ  TYR A 256  0   19.795  8.336 14.346 1.00 15.90
ATOM  1993 OH  TYR A 256  0   20.763  7.341 14.337 1.00 17.15
ATOM  1994 N   TRP A 257  0   13.801 12.198 13.564 1.00 13.58
ATOM  1995 CA  TRP A 257  0   12.742 13.196 13.657 1.00 14.21
ATOM  1996 C   TRP A 257  0   13.041 14.198 14.769 1.00 12.04
ATOM  1997 O   TRP A 257  0   13.382 13.811 15.878 1.00 10.46
ATOM  1998 CB  TRP A 257  0   11.363 12.592 13.988 1.00 12.49
ATOM  1999 CG  TRP A 257  0   10.648 11.906 12.865 1.00 13.06
ATOM  2000 CD1 TRP A 257  0   10.315 10.568 12.879 1.00 12.86
ATOM  2001 CD2 TRP A 257  0   10.161 12.437 11.633 1.00 12.33
ATOM  2002 NE1 TRP A 257  0    9.640 10.267 11.720 1.00 13.75
ATOM  2003 CE2 TRP A 257  0    9.530 11.388 10.940 1.00 13.78
ATOM  2004 CE3 TRP A 257  0   10.173 13.691 11.035 1.00 14.13
ATOM  2005 CZ2 TRP A 257  0    8.940 11.538  9.681 1.00 13.24
```

```
ATOM 2006 CZ3 TRP A 257 0    9.590 13.868  9.786 1.00 14.34
ATOM 2007 CH2 TRP A 257 0    8.963 12.789  9.127 1.00 13.64
ATOM 2008 N   ILE A 258 0   12.790 15.463 14.454 1.00 12.29
ATOM 2009 CA  ILE A 258 0   12.886 16.498 15.508 1.00 12.44
ATOM 2010 C   ILE A 258 0   11.391 16.840 15.769 1.00 12.40
ATOM 2011 O   ILE A 258 0   10.629 17.039 14.812 1.00 12.43
ATOM 2012 CB  ILE A 258 0   13.617 17.777 15.048 1.00 13.32
ATOM 2013 CG1 ILE A 258 0   15.107 17.477 14.854 1.00 14.52
ATOM 2014 CG2 ILE A 258 0   13.365 18.888 16.052 1.00 12.32
ATOM 2015 CD1 ILE A 258 0   15.839 18.474 13.994 1.00 14.35
ATOM 2016 N   ARG A 259 0   11.017 16.764 17.013 1.00 11.51
ATOM 2017 CA  ARG A 259 0    9.610 16.832 17.407 1.00 13.43
ATOM 2018 C   ARG A 259 0    9.254 18.019 18.274 1.00 12.74
ATOM 2019 O   ARG A 259 0    9.931 18.246 19.280 1.00 12.62
ATOM 2020 CB  ARG A 259 0    9.326 15.567 18.253 1.00 12.43
ATOM 2021 CG  ARG A 259 0    9.308 14.290 17.414 1.00 15.81
ATOM 2022 CD  ARG A 259 0    8.910 13.054 18.244 1.00 16.58
ATOM 2023 NE  ARG A 259 0    9.204 11.818 17.528 1.00 16.91
ATOM 2024 CZ  ARG A 259 0    8.475 11.187 16.616 1.00 18.43
ATOM 2025 NH1 ARG A 259 0    7.285 11.657 16.239 1.00 19.39
ATOM 2026 NH2 ARG A 259 0    8.907 10.070 16.045 1.00 17.95
ATOM 2027 N   ALA A 260 0    8.226 18.764 17.884 1.00 13.12
ATOM 2028 CA  ALA A 260 0    7.768 19.882 18.727 1.00 12.65
ATOM 2029 C   ALA A 260 0    6.237 19.763 18.802 1.00 14.47
ATOM 2030 O   ALA A 260 0    5.545 20.140 17.868 1.00 14.73
ATOM 2031 CB  ALA A 260 0    8.281 21.188 18.165 1.00  9.58
ATOM 2032 N   GLN A 261 0    5.690 19.225 19.870 1.00 14.78
ATOM 2033 CA  GLN A 261 0    4.272 19.004 20.060 1.00 16.99
ATOM 2034 C   GLN A 261 0    3.606 20.154 20.803 1.00 15.01
ATOM 2035 O   GLN A 261 0    3.914 20.389 21.961 1.00 13.86
ATOM 2036 CB  GLN A 261 0    4.118 17.747 20.924 1.00 20.94
ATOM 2037 CG  GLN A 261 0    2.717 17.131 20.940 1.00 27.53
ATOM 2038 CD  GLN A 261 0    2.721 15.991 21.947 1.00 29.63
ATOM 2039 OE1 GLN A 261 0    3.152 14.887 21.682 1.00 31.60
ATOM 2040 NE2 GLN A 261 0    2.331 16.255 23.188 1.00 34.91
ATOM 2041 N   PRO A 262 0    2.663 20.820 20.167 1.00 14.60
ATOM 2042 CA  PRO A 262 0    1.974 21.969 20.739 1.00 15.72
ATOM 2043 C   PRO A 262 0    0.921 21.568 21.757 1.00 16.25
```

5032-WO

84

```
    ATOM  2044 O   PRO A 262  0    0.498 20.409 21.814  1.00 15.61
    ATOM  2045 CB  PRO A 262  0    1.401 22.752 19.539  1.00 13.88
    ATOM  2046 CG  PRO A 262  0    1.168 21.608 18.563  1.00 13.62
    ATOM  2047 CD  PRO A 262  0    2.257 20.570 18.772  1.00 13.23
 5  ATOM  2048 N   ASN A 263  0    0.570 22.481 22.665  1.00 17.25
    ATOM  2049 CA  ASN A 263  0   -0.471 22.203 23.648  1.00 17.50
    ATOM  2050 C   ASN A 263  0   -1.834 22.460 22.981  1.00 18.43
    ATOM  2051 O   ASN A 263  0   -2.810 22.121 23.608  1.00 19.35
    ATOM  2052 CB  ASN A 263  0   -0.422 22.990 24.954  1.00 16.12
10  ATOM  2053 CG  ASN A 263  0   -0.333 24.493 24.728  1.00 16.97
    ATOM  2054 OD1 ASN A 263  0    0.236 25.002 23.751  1.00 15.54
    ATOM  2055 ND2 ASN A 263  0   -0.905 25.269 25.653  1.00 16.31
    ATOM  2056 N   LYS A 264  0   -1.947 23.055 21.818  1.00 20.51
    ATOM  2057 CA  LYS A 264  0   -3.256 23.208 21.180  1.00 24.76
15  ATOM  2058 C   LYS A 264  0   -3.055 23.395 19.683  1.00 23.64
    ATOM  2059 O   LYS A 264  0   -1.909 23.572 19.267  1.00 24.23
    ATOM  2060 CB  LYS A 264  0   -4.038 24.393 21.775  1.00 25.87
    ATOM  2061 CG  LYS A 264  0   -3.266 25.702 21.602  1.00 28.62
    ATOM  2062 CD  LYS A 264  0   -3.579 26.624 22.772  1.00 30.65
20  ATOM  2063 CE  LYS A 264  0   -4.114 27.960 22.283  1.00 32.62
    ATOM  2064 NZ  LYS A 264  0   -4.593 28.753 23.459  1.00 34.39
    ATOM  2065 N   GLY A 265  0   -4.112 23.386 18.892  1.00 22.60
    ATOM  2066 CA  GLY A 265  0   -3.959 23.591 17.452  1.00 22.98
    ATOM  2067 C   GLY A 265  0   -5.190 23.002 16.758  1.00 23.95
25  ATOM  2068 O   GLY A 265  0   -5.904 22.202 17.362  1.00 22.64
    ATOM  2069 N   ARG A 266  0   -5.398 23.434 15.537  1.00 24.60
    ATOM  2070 CA  ARG A 266  0   -6.527 23.051 14.734  1.00 26.24
    ATOM  2071 C   ARG A 266  0   -6.412 21.605 14.272  1.00 27.29
    ATOM  2072 O   ARG A 266  0   -5.329 21.074 14.015  1.00 25.41
30  ATOM  2073 CB  ARG A 266  0   -6.628 23.903 13.469  1.00 30.71
    ATOM  2074 CG  ARG A 266  0   -7.065 25.334 13.563  1.00 35.66
    ATOM  2075 CD  ARG A 266  0   -8.161 25.673 12.539  1.00 40.48
    ATOM  2076 NE  ARG A 266  0   -9.379 25.957 13.286  1.00 45.08
    ATOM  2077 CZ  ARG A 266  0  -10.551 25.334 13.319  1.00 47.09
35  ATOM  2078 NH1 ARG A 266  0  -10.921 24.294 12.577  1.00 48.10
    ATOM  2079 NH2 ARG A 266  0  -11.452 25.828 14.165  1.00 47.80
    ATOM  2080 N   ASN A 267  0   -7.586 20.983 14.141  1.00 25.17
    ATOM  2081 CA  ASN A 267  0   -7.727 19.669 13.602  1.00 23.96
```

```
    ATOM  2082  C   ASN A 267  0   -6.859  18.625  14.244  1.00 22.35
    ATOM  2083  O   ASN A 267  0   -6.306  17.864  13.448  1.00 23.57
    ATOM  2084  CB  ASN A 267  0   -7.390  19.695  12.098  1.00 26.46
    ATOM  2085  CG  ASN A 267  0   -8.461  20.426  11.309  1.00 29.21
  5 ATOM  2086  OD1 ASN A 267  0   -8.190  21.226  10.405  1.00 30.18
    ATOM  2087  ND2 ASN A 267  0   -9.681  20.075  11.701  1.00 28.77
    ATOM  2088  N   GLY A 268  0   -6.706  18.594  15.550  1.00 21.85
    ATOM  2089  CA  GLY A 268  0   -5.890  17.533  16.121  1.00 22.47
    ATOM  2090  C   GLY A 268  0   -4.383  17.760  16.118  1.00 23.29
 10 ATOM  2091  O   GLY A 268  0   -3.652  16.898  16.632  1.00 23.28
    ATOM  2092  N   LEU A 269  0   -3.880  18.901  15.676  1.00 22.69
    ATOM  2093  CA  LEU A 269  0   -2.454  19.222  15.684  1.00 22.62
    ATOM  2094  C   LEU A 269  0   -1.753  18.890  16.990  1.00 23.26
    ATOM  2095  O   LEU A 269  0   -0.650  18.335  17.035  1.00 23.42
 15 ATOM  2096  CB  LEU A 269  0   -2.311  20.713  15.472  1.00 22.28
    ATOM  2097  CG  LEU A 269  0   -1.183  21.414  14.745  1.00 23.42
    ATOM  2098  CD1 LEU A 269  0   -0.508  22.380  15.682  1.00 19.64
    ATOM  2099  CD2 LEU A 269  0   -0.213  20.492  14.009  1.00 21.26
    ATOM  2100  N   ALA A 270  0   -2.371  19.199  18.135  1.00 21.51
 20 ATOM  2101  CA  ALA A 270  0   -1.784  18.899  19.419  1.00 22.26
    ATOM  2102  C   ALA A 270  0   -1.612  17.415  19.680  1.00 23.22
    ATOM  2103  O   ALA A 270  0   -0.898  17.077  20.637  1.00 21.81
    ATOM  2104  CB  ALA A 270  0   -2.632  19.518  20.542  1.00 21.06
    ATOM  2105  N   GLY A 271  0   -2.337  16.521  18.996  1.00 23.75
 25 ATOM  2106  CA  GLY A 271  0   -2.190  15.125  19.372  1.00 24.98
    ATOM  2107  C   GLY A 271  0   -1.507  14.267  18.328  1.00 26.07
    ATOM  2108  O   GLY A 271  0   -1.501  13.045  18.523  1.00 26.26
    ATOM  2109  N   THR A 272  0   -0.906  14.825  17.278  1.00 26.48
    ATOM  2110  CA  THR A 272  0   -0.327  13.901  16.294  1.00 25.27
 30 ATOM  2111  C   THR A 272  0    0.986  14.362  15.701  1.00 25.58
    ATOM  2112  O   THR A 272  0    1.216  15.567  15.701  1.00 24.46
    ATOM  2113  CB  THR A 272  0   -1.380  13.759  15.164  1.00 24.40
    ATOM  2114  OG1 THR A 272  0   -0.931  12.737  14.275  1.00 26.32
    ATOM  2115  CG2 THR A 272  0   -1.575  15.022  14.347  1.00 22.50
 35 ATOM  2116  N   PHE A 273  0    1.714  13.443  15.062  1.00 24.01
    ATOM  2117  CA  PHE A 273  0    2.897  13.755  14.271  1.00 23.99
    ATOM  2118  C   PHE A 273  0    2.663  13.201  12.858  1.00 24.84
    ATOM  2119  O   PHE A 273  0    3.534  13.207  11.987  1.00 24.73
```

```
    ATOM  2120  CB  PHE A 273  0    4.175 13.094 14.812 1.00 22.16
    ATOM  2121  CG  PHE A 273  0    4.550 13.676 16.153 1.00 21.84
    ATOM  2122  CD1 PHE A 273  0    4.190 13.037 17.327 1.00 20.67
    ATOM  2123  CD2 PHE A 273  0    5.221 14.881 16.216 1.00 20.98
  5 ATOM  2124  CE1 PHE A 273  0    4.538 13.574 18.554 1.00 21.75
    ATOM  2125  CE2 PHE A 273  0    5.559 15.428 17.440 1.00 21.65
    ATOM  2126  CZ  PHE A 273  0    5.216 14.787 18.616 1.00 22.38
    ATOM  2127  N   ALA A 274  0    1.440 12.718 12.647 1.00 24.38
    ATOM  2128  CA  ALA A 274  0    1.094 12.053 11.397 1.00 24.29
 10 ATOM  2129  C   ALA A 274  0    1.399 12.920 10.194 1.00 24.15
    ATOM  2130  O   ALA A 274  0    0.990 14.078 10.161 1.00 23.07
    ATOM  2131  CB  ALA A 274  0   -0.385 11.681 11.387 1.00 23.53
    ATOM  2132  N   ASN A 275  0    2.075 12.355  9.204 1.00 23.41
    ATOM  2133  CA  ASN A 275  0    2.389 13.068  7.987 1.00 24.88
 15 ATOM  2134  C   ASN A 275  0    3.498 14.093  8.191 1.00 22.73
    ATOM  2135  O   ASN A 275  0    3.708 14.947  7.337 1.00 21.57
    ATOM  2136  CB  ASN A 275  0    1.138 13.806  7.516 1.00 30.04
    ATOM  2137  CG  ASN A 275  0    0.194 13.070  6.633 1.00 35.28
    ATOM  2138  OD1 ASN A 275  0   -0.458 12.071  6.985 1.00 36.92
 20 ATOM  2139  ND2 ASN A 275  0    0.156 13.655  5.427 1.00 37.87
    ATOM  2140  N   GLY A 276  0    4.185 14.083  9.322 1.00 22.10
    ATOM  2141  CA  GLY A 276  0    5.278 15.025  9.503 1.00 20.95
    ATOM  2142  C   GLY A 276  0    4.801 16.392  9.962 1.00 19.61
    ATOM  2143  O   GLY A 276  0    5.587 17.325  9.816 1.00 19.96
 25 ATOM  2144  N   VAL A 277  0    3.600 16.504 10.540 1.00 16.82
    ATOM  2145  CA  VAL A 277  0    3.207 17.796 11.107 1.00 15.06
    ATOM  2146  C   VAL A 277  0    4.033 17.942 12.379 1.00 13.80
    ATOM  2147  O   VAL A 277  0    4.454 16.912 12.926 1.00 13.80
    ATOM  2148  CB  VAL A 277  0    1.676 17.849 11.397 1.00 14.37
 30 ATOM  2149  CG1 VAL A 277  0    0.882 17.824 10.099 1.00 13.37
    ATOM  2150  CG2 VAL A 277  0    1.213 16.763 12.330 1.00 11.77
    ATOM  2151  N   ASN A 278  0    4.307 19.100 12.936 1.00 14.25
    ATOM  2152  CA  ASN A 278  0    5.026 19.262 14.209 1.00 13.80
    ATOM  2153  C   ASN A 278  0    6.443 18.640 14.208 1.00 13.80
 35 ATOM  2154  O   ASN A 278  0    7.020 18.228 15.229 1.00 11.81
    ATOM  2155  CB  ASN A 278  0    4.216 18.607 15.312 1.00 14.24
    ATOM  2156  CG  ASN A 278  0    2.890 19.288 15.659 1.00 15.35
    ATOM  2157  OD1 ASN A 278  0    1.952 18.531 16.009 1.00 14.81
```

```
ATOM  2158  ND2 ASN A 278  0   2.821 20.591 15.593 1.00 10.69
ATOM  2159  N   SER A 279  0   7.044 18.595 13.025 1.00 12.68
ATOM  2160  CA  SER A 279  0   8.296 17.892 12.860 1.00 15.48
ATOM  2161  C   SER A 279  0   9.323 18.571 11.964 1.00 15.07
ATOM  2162  O   SER A 279  0   8.995 19.309 11.044 1.00 12.20
ATOM  2163  CB  SER A 279  0   7.976 16.549 12.122 1.00 14.76
ATOM  2164  OG  SER A 279  0   7.268 15.722 13.054 1.00 19.57
ATOM  2165  N   ALA A 280  0  10.570 18.152 12.229 1.00 15.67
ATOM  2166  CA  ALA A 280  0  11.664 18.548 11.327 1.00 16.75
ATOM  2167  C   ALA A 280  0  12.620 17.341 11.287 1.00 15.83
ATOM  2168  O   ALA A 280  0  12.438 16.346 11.997 1.00 15.55
ATOM  2169  CB  ALA A 280  0  12.363 19.828 11.745 1.00 16.40
ATOM  2170  N   ILE A 281  0  13.669 17.478 10.485 1.00 14.79
ATOM  2171  CA  ILE A 281  0  14.569 16.346 10.257 1.00 15.55
ATOM  2172  C   ILE A 281  0  16.002 16.610 10.699 1.00 15.92
ATOM  2173  O   ILE A 281  0  16.649 17.577 10.284 1.00 14.96
ATOM  2174  CB  ILE A 281  0  14.557 16.013  8.735 1.00 16.44
ATOM  2175  CG1 ILE A 281  0  13.147 15.573  8.275 1.00 16.42
ATOM  2176  CG2 ILE A 281  0  15.615 14.959  8.421 1.00 15.71
ATOM  2177  CD1 ILE A 281  0  12.981 15.376  6.771 1.00 14.22
ATOM  2178  N   LEU A 282  0  16.505 15.698 11.515 1.00 16.76
ATOM  2179  CA  LEU A 282  0  17.920 15.736 11.912 1.00 15.82
ATOM  2180  C   LEU A 282  0  18.655 14.747 10.990 1.00 16.16
ATOM  2181  O   LEU A 282  0  18.409 13.530 11.034 1.00 16.41
ATOM  2182  CB  LEU A 282  0  18.129 15.400 13.379 1.00 14.54
ATOM  2183  CG  LEU A 282  0  19.632 15.346 13.773 1.00 16.00
ATOM  2184  CD1 LEU A 282  0  20.100 16.767 14.052 1.00 16.10
ATOM  2185  CD2 LEU A 282  0  19.865 14.469 14.970 1.00 13.21
ATOM  2186  N   ARG A 283  0  19.490 15.254 10.100 1.00 15.20
ATOM  2187  CA  ARG A 283  0  20.160 14.377  9.141 1.00 16.98
ATOM  2188  C   ARG A 283  0  21.683 14.326  9.279 1.00 17.31
ATOM  2189  O   ARG A 283  0  22.398 15.330  9.203 1.00 17.82
ATOM  2190  CB  ARG A 283  0  19.844 14.861  7.736 1.00 17.30
ATOM  2191  CG  ARG A 283  0  20.417 13.978  6.641 1.00 19.94
ATOM  2192  CD  ARG A 283  0  19.860 14.446  5.301 1.00 20.04
ATOM  2193  NE  ARG A 283  0  18.474 14.010  5.208 1.00 21.56
ATOM  2194  CZ  ARG A 283  0  17.479 14.530  4.505 1.00 21.81
ATOM  2195  NH1 ARG A 283  0  16.287 13.922  4.564 1.00 21.52
```

5032-WO

88

```
   ATOM  2196  NH2 ARG A 283  0   17.653  15.634   3.797  1.00 21.84
   ATOM  2197  N   TYR A 284  0   22.163  13.136   9.567  1.00 16.79
   ATOM  2198  CA  TYR A 284  0   23.581  12.821   9.620  1.00 16.35
   ATOM  2199  C   TYR A 284  0   24.155  12.787   8.198  1.00 16.52
 5 ATOM  2200  O   TYR A 284  0   23.556  12.226   7.271  1.00 16.33
   ATOM  2201  CB  TYR A 284  0   23.730  11.444  10.252  1.00 16.51
   ATOM  2202  CG  TYR A 284  0   23.727  11.460  11.755  1.00 17.09
   ATOM  2203  CD1 TYR A 284  0   24.910  11.178  12.437  1.00 17.37
   ATOM  2204  CD2 TYR A 284  0   22.601  11.753  12.504  1.00 17.15
10 ATOM  2205  CE1 TYR A 284  0   24.937  11.163  13.817  1.00 17.64
   ATOM  2206  CE2 TYR A 284  0   22.623  11.770  13.892  1.00 15.66
   ATOM  2207  CZ  TYR A 284  0   23.796  11.476  14.542  1.00 15.99
   ATOM  2208  OH  TYR A 284  0   23.873  11.448  15.919  1.00 14.03
   ATOM  2209  N   ALA A 285  0   25.276  13.463   7.992  1.00 17.42
15 ATOM  2210  CA  ALA A 285  0   25.950  13.461   6.692  1.00 19.35
   ATOM  2211  C   ALA A 285  0   26.186  11.994   6.328  1.00 19.20
   ATOM  2212  O   ALA A 285  0   26.692  11.237   7.146  1.00 17.18
   ATOM  2213  CB  ALA A 285  0   27.293  14.194   6.770  1.00 19.86
   ATOM  2214  N   GLY A 286  0   25.724  11.614   5.153  1.00 20.01
20 ATOM  2215  CA  GLY A 286  0   25.851  10.224   4.747  1.00 21.88
   ATOM  2216  C   GLY A 286  0   24.507   9.510   4.754  1.00 22.87
   ATOM  2217  O   GLY A 286  0   24.406   8.418   4.197  1.00 23.06
   ATOM  2218  N   ALA A 287  0   23.504  10.076   5.423  1.00 22.81
   ATOM  2219  CA  ALA A 287  0   22.176   9.449   5.364  1.00 21.50
25 ATOM  2220  C   ALA A 287  0   21.482   9.880   4.079  1.00 20.58
   ATOM  2221  O   ALA A 287  0   21.647  11.032   3.629  1.00 19.44
   ATOM  2222  CB  ALA A 287  0   21.340   9.890   6.562  1.00 21.34
   ATOM  2223  N   ALA A 288  0   20.632   9.041   3.523  1.00 21.20
   ATOM  2224  CA  ALA A 288  0   19.899   9.450   2.310  1.00 23.46
30 ATOM  2225  C   ALA A 288  0   18.965  10.629   2.513  1.00 24.70
   ATOM  2226  O   ALA A 288  0   18.494  10.929   3.621  1.00 25.30
   ATOM  2227  CB  ALA A 288  0   19.012   8.298   1.827  1.00 24.84
   ATOM  2228  N   ASN A 289  0   18.638  11.300   1.411  1.00 25.98
   ATOM  2229  CA  ASN A 289  0   17.674  12.398   1.439  1.00 27.16
35 ATOM  2230  C   ASN A 289  0   16.303  11.707   1.505  1.00 27.36
   ATOM  2231  O   ASN A 289  0   15.761  11.330   0.477  1.00 27.56
   ATOM  2232  CB  ASN A 289  0   17.784  13.250   0.189  1.00 29.01
   ATOM  2233  CG  ASN A 289  0   18.808  14.364   0.299  1.00 30.44
```

```
ATOM  2234 OD1 ASN A 289  0   20.005 14.168  0.545 1.00 30.40
ATOM  2235 ND2 ASN A 289  0   18.340 15.591  0.121 1.00 31.98
ATOM  2236 N   ALA A 290  0   15.837 11.426  2.703 1.00 25.22
ATOM  2237 CA  ALA A 290  0   14.600 10.727  2.955 1.00 25.09
ATOM  2238 C   ALA A 290  0   14.087 11.057  4.363 1.00 22.98
ATOM  2239 O   ALA A 290  0   14.830 11.555  5.205 1.00 22.02
ATOM  2240 CB  ALA A 290  0   14.764  9.210  2.823 1.00 24.89
ATOM  2241 N   ASP A 291  0   12.822 10.718  4.597 1.00 21.88
ATOM  2242 CA  ASP A 291  0   12.223 10.985  5.907 1.00 21.71
ATOM  2243 C   ASP A 291  0   12.724  9.965  6.916 1.00 18.93
ATOM  2244 O   ASP A 291  0   12.911  8.814  6.596 1.00 19.66
ATOM  2245 CB  ASP A 291  0   10.695 10.862  5.834 1.00 22.63
ATOM  2246 CG  ASP A 291  0   10.088 12.005  5.076 1.00 25.41
ATOM  2247 OD1 ASP A 291  0   10.781 12.988  4.735 1.00 27.11
ATOM  2248 OD2 ASP A 291  0    8.885 11.932  4.812 1.00 27.47
ATOM  2249 N   PRO A 292  0   12.863 10.362  8.164 1.00 16.14
ATOM  2250 CA  PRO A 292  0   13.229  9.473  9.230 1.00 15.27
ATOM  2251 C   PRO A 292  0   12.087  8.484  9.389 1.00 19.40
ATOM  2252 O   PRO A 292  0   10.925  8.785  9.063 1.00 20.36
ATOM  2253 CB  PRO A 292  0   13.257 10.335 10.511 1.00 14.68
ATOM  2254 CG  PRO A 292  0   13.291 11.739  9.941 1.00 14.39
ATOM  2255 CD  PRO A 292  0   12.606 11.735  8.593 1.00 14.02
ATOM  2256 N   THR A 293  0   12.357  7.361 10.024 1.00 19.91
ATOM  2257 CA  THR A 293  0   11.360  6.379 10.373 1.00 20.62
ATOM  2258 C   THR A 293  0   11.589  6.055 11.847 1.00 20.83
ATOM  2259 O   THR A 293  0   11.323  4.943 12.287 1.00 23.91
ATOM  2260 CB  THR A 293  0   11.556  5.088  9.557 1.00 23.41
ATOM  2261 OG1 THR A 293  0   12.874  4.577  9.836 1.00 24.50
ATOM  2262 CG2 THR A 293  0   11.438  5.341  8.058 1.00 23.72
ATOM  2263 N   THR A 294  0   12.172  6.958 12.624 1.00 19.30
ATOM  2264 CA  THR A 294  0   12.440  6.634 14.017 1.00 19.42
ATOM  2265 C   THR A 294  0   11.214  6.896 14.878 1.00 20.66
ATOM  2266 O   THR A 294  0   10.240  7.485 14.411 1.00 19.89
ATOM  2267 CB  THR A 294  0   13.565  7.548 14.553 1.00 19.28
ATOM  2268 OG1 THR A 294  0   13.174  8.889 14.251 1.00 17.55
ATOM  2269 CG2 THR A 294  0   14.860  7.214 13.822 1.00 19.27
ATOM  2270 N   SER A 295  0   11.359  6.576 16.159 1.00 23.85
ATOM  2271 CA  SER A 295  0   10.274  6.851 17.095 1.00 27.18
```

```
ATOM  2272 C   SER A 295  0  10.781  7.484 18.375 1.00 27.92
ATOM  2273 O   SER A 295  0  11.900  7.292 18.844 1.00 27.09
ATOM  2274 CB  SER A 295  0   9.513  5.546 17.367 1.00 28.92
ATOM  2275 OG  SER A 295  0  10.389  4.761 18.160 1.00 33.04
ATOM  2276 N   ALA A 296  0   9.930  8.331 18.965 1.00 30.04
ATOM  2277 CA  ALA A 296  0  10.295  9.003 20.207 1.00 29.82
ATOM  2278 C   ALA A 296  0  10.552  8.011 21.327 1.00 30.83
ATOM  2279 O   ALA A 296  0  10.114  6.861 21.328 1.00 30.67
ATOM  2280 CB  ALA A 296  0   9.187  9.968 20.599 1.00 30.16
ATOM  2281 N   ASN A 297  0  11.286  8.489 22.328 1.00 31.65
ATOM  2282 CA  ASN A 297  0  11.543  7.750 23.549 1.00 32.16
ATOM  2283 C   ASN A 297  0  10.200  7.650 24.285 1.00 32.80
ATOM  2284 O   ASN A 297  0   9.492  8.616 24.565 1.00 31.30
ATOM  2285 CB  ASN A 297  0  12.522  8.497 24.443 1.00 33.07
ATOM  2286 CG  ASN A 297  0  12.869  7.742 25.706 1.00 35.21
ATOM  2287 OD1 ASN A 297  0  12.116  6.965 26.284 1.00 35.45
ATOM  2288 ND2 ASN A 297  0  14.106  7.982 26.162 1.00 37.10
ATOM  2289 N   PRO A 298  0   9.865  6.430 24.647 1.00 33.40
ATOM  2290 CA  PRO A 298  0   8.626  6.116 25.331 1.00 33.89
ATOM  2291 C   PRO A 298  0   8.580  6.690 26.732 1.00 32.60
ATOM  2292 O   PRO A 298  0   7.522  7.155 27.173 1.00 32.72
ATOM  2293 CB  PRO A 298  0   8.505  4.576 25.358 1.00 35.13
ATOM  2294 CG  PRO A 298  0   9.932  4.147 25.128 1.00 34.52
ATOM  2295 CD  PRO A 298  0  10.630  5.222 24.323 1.00 34.10
ATOM  2296 N   ASN A 299  0   9.689  6.721 27.461 1.00 29.60
ATOM  2297 CA  ASN A 299  0   9.701  7.229 28.834 1.00 28.47
ATOM  2298 C   ASN A 299  0  10.818  8.251 29.006 1.00 27.18
ATOM  2299 O   ASN A 299  0  11.906  7.967 29.528 1.00 25.69
ATOM  2300 CB  ASN A 299  0   9.964  6.017 29.747 1.00 29.50
ATOM  2301 CG  ASN A 299  0   8.907  4.935 29.673 1.00 32.34
ATOM  2302 OD1 ASN A 299  0   9.090  3.873 29.075 1.00 33.50
ATOM  2303 ND2 ASN A 299  0   7.735  5.182 30.251 1.00 33.04
ATOM  2304 N   PRO A 300  0  10.629  9.450 28.498 1.00 26.02
ATOM  2305 CA  PRO A 300  0  11.668 10.486 28.498 1.00 23.99
ATOM  2306 C   PRO A 300  0  11.987 11.054 29.860 1.00 21.16
ATOM  2307 O   PRO A 300  0  11.051 11.174 30.649 1.00 20.81
ATOM  2308 CB  PRO A 300  0  11.137 11.623 27.594 1.00 23.33
ATOM  2309 CG  PRO A 300  0   9.645 11.422 27.729 1.00 24.68
```

5032-WO

91

```
   ATOM 2310 CD  PRO A 300  0   9.387  9.918 27.882 1.00 25.22
   ATOM 2311 N   ALA A 301  0  13.242 11.361 30.179 1.00 19.17
   ATOM 2312 CA  ALA A 301  0  13.538 12.139 31.410 1.00 17.57
   ATOM 2313 C   ALA A 301  0  13.159 13.588 31.084 1.00 16.53
 5 ATOM 2314 O   ALA A 301  0  13.613 14.235 30.131 1.00 16.24
   ATOM 2315 CB  ALA A 301  0  15.006 11.982 31.774 1.00 17.17
   ATOM 2316 N   GLN A 302  0  12.139 14.131 31.723 1.00 18.15
   ATOM 2317 CA  GLN A 302  0  11.580 15.446 31.441 1.00 19.34
   ATOM 2318 C   GLN A 302  0  12.335 16.580 32.124 1.00 19.16
10 ATOM 2319 O   GLN A 302  0  12.577 16.444 33.324 1.00 19.07
   ATOM 2320 CB  GLN A 302  0  10.122 15.483 31.937 1.00 19.10
   ATOM 2321 CG  GLN A 302  0   9.304 16.666 31.478 1.00 20.55
   ATOM 2322 CD  GLN A 302  0   8.960 16.738 30.009 1.00 20.18
   ATOM 2323 OE1 GLN A 302  0   8.843 15.721 29.331 1.00 22.29
15 ATOM 2324 NE2 GLN A 302  0   8.813 17.936 29.436 1.00 18.46
   ATOM 2325 N   LEU A 303  0  12.629 17.681 31.444 1.00 17.92
   ATOM 2326 CA  LEU A 303  0  13.241 18.824 32.139 1.00 17.32
   ATOM 2327 C   LEU A 303  0  12.316 19.357 33.232 1.00 17.65
   ATOM 2328 O   LEU A 303  0  11.140 19.664 33.021 1.00 17.55
20 ATOM 2329 CB  LEU A 303  0  13.489 19.988 31.168 1.00 15.14
   ATOM 2330 CG  LEU A 303  0  13.919 21.317 31.797 1.00 16.94
   ATOM 2331 CD1 LEU A 303  0  15.262 21.146 32.504 1.00 17.30
   ATOM 2332 CD2 LEU A 303  0  13.988 22.432 30.764 1.00 12.82
   ATOM 2333 N   ASN A 304  0  12.868 19.580 34.399 1.00 17.34
25 ATOM 2334 CA  ASN A 304  0  12.199 20.212 35.531 1.00 19.12
   ATOM 2335 C   ASN A 304  0  13.071 21.435 35.833 1.00 19.06
   ATOM 2336 O   ASN A 304  0  14.265 21.349 36.122 1.00 20.37
   ATOM 2337 CB  ASN A 304  0  12.073 19.244 36.704 1.00 22.16
   ATOM 2338 CG  ASN A 304  0  11.748 19.900 38.024 1.00 25.02
30 ATOM 2339 OD1 ASN A 304  0  11.506 21.111 38.146 1.00 26.72
   ATOM 2340 ND2 ASN A 304  0  11.766 19.133 39.114 1.00 25.99
   ATOM 2341 N   GLU A 305  0  12.541 22.629 35.662 1.00 17.64
   ATOM 2342 CA  GLU A 305  0  13.204 23.890 35.840 1.00 16.64
   ATOM 2343 C   GLU A 305  0  13.884 23.977 37.194 1.00 16.06
35 ATOM 2344 O   GLU A 305  0  14.965 24.564 37.208 1.00 14.78
   ATOM 2345 CB  GLU A 305  0  12.286 25.085 35.567 1.00 15.91
   ATOM 2346 CG  GLU A 305  0  12.898 26.484 35.831 1.00 14.81
   ATOM 2347 CD  GLU A 305  0  11.794 27.546 35.666 1.00 15.72
```

```
ATOM 2348 OE1 GLU A 305 0  11.584 28.026 34.527 1.00 14.63
ATOM 2349 OE2 GLU A 305 0  11.154 27.861 36.685 1.00 13.05
ATOM 2350 N   ALA A 306 0  13.416 23.432 38.298 1.00 15.83
ATOM 2351 CA  ALA A 306 0  14.131 23.509 39.565 1.00 17.92
ATOM 2352 C   ALA A 306 0  15.437 22.682 39.532 1.00 18.62
ATOM 2353 O   ALA A 306 0  16.213 22.867 40.464 1.00 18.37
ATOM 2354 CB  ALA A 306 0  13.283 22.993 40.711 1.00 16.23
ATOM 2355 N   ASP A 307 0  15.721 21.860 38.523 1.00 18.04
ATOM 2356 CA  ASP A 307 0  16.988 21.164 38.409 1.00 18.68
ATOM 2357 C   ASP A 307 0  18.035 22.039 37.707 1.00 19.89
ATOM 2358 O   ASP A 307 0  19.239 21.695 37.739 1.00 20.36
ATOM 2359 CB  ASP A 307 0  16.904 19.863 37.592 1.00 17.64
ATOM 2360 CG  ASP A 307 0  15.980 18.873 38.290 1.00 18.17
ATOM 2361 OD1 ASP A 307 0  15.918 18.919 39.535 1.00 18.27
ATOM 2362 OD2 ASP A 307 0  15.311 18.094 37.592 1.00 17.32
ATOM 2363 N   LEU A 308 0  17.583 23.110 37.052 1.00 16.43
ATOM 2364 CA  LEU A 308 0  18.581 23.962 36.377 1.00 16.80
ATOM 2365 C   LEU A 308 0  19.327 24.827 37.384 1.00 16.94
ATOM 2366 O   LEU A 308 0  18.784 25.320 38.380 1.00 17.28
ATOM 2367 CB  LEU A 308 0  17.925 24.775 35.257 1.00 12.52
ATOM 2368 CG  LEU A 308 0  17.436 23.936 34.073 1.00 12.15
ATOM 2369 CD1 LEU A 308 0  16.692 24.834 33.101 1.00 11.67
ATOM 2370 CD2 LEU A 308 0  18.547 23.186 33.341 1.00 12.23
ATOM 2371 N   HIS A 309 0  20.640 24.968 37.243 1.00 18.01
ATOM 2372 CA  HIS A 309 0  21.430 25.802 38.158 1.00 18.47
ATOM 2373 C   HIS A 309 0  22.328 26.770 37.394 1.00 17.36
ATOM 2374 O   HIS A 309 0  23.015 26.378 36.459 1.00 17.82
ATOM 2375 CB  HIS A 309 0  22.267 24.997 39.140 1.00 18.51
ATOM 2376 CG  HIS A 309 0  21.470 24.052 39.965 1.00 20.71
ATOM 2377 ND1 HIS A 309 0  21.526 22.684 39.790 1.00 21.77
ATOM 2378 CD2 HIS A 309 0  20.578 24.285 40.956 1.00 22.07
ATOM 2379 CE1 HIS A 309 0  20.701 22.115 40.657 1.00 22.85
ATOM 2380 NE2 HIS A 309 0  20.120 23.059 41.377 1.00 22.67
ATOM 2381 N   ALA A 310 0  22.352 28.005 37.837 1.00 17.27
ATOM 2382 CA  ALA A 310 0  23.173 29.068 37.228 1.00 17.74
ATOM 2383 C   ALA A 310 0  24.663 28.775 37.342 1.00 18.13
ATOM 2384 O   ALA A 310 0  25.103 28.233 38.369 1.00 19.61
ATOM 2385 CB  ALA A 310 0  22.869 30.356 37.985 1.00 16.92
```

5032-WO

93

```
   ATOM 2386 N   LEU A 311  0  25.427 29.021 36.304 1.00 19.30
   ATOM 2387 CA  LEU A 311  0  26.856 28.762 36.277 1.00 20.71
   ATOM 2388 C   LEU A 311  0  27.655 29.922 36.881 1.00 22.67
   ATOM 2389 O   LEU A 311  0  28.581 29.788 37.682 1.00 23.06
 5 ATOM 2390 CB  LEU A 311  0  27.305 28.591 34.817 1.00 20.57
   ATOM 2391 CG  LEU A 311  0  28.796 28.196 34.684 1.00 21.52
   ATOM 2392 CD1 LEU A 311  0  28.993 26.783 35.229 1.00 20.80
   ATOM 2393 CD2 LEU A 311  0  29.319 28.282 33.254 1.00 20.17
   ATOM 2394 N   ILE A 312  0  27.333 31.142 36.449 1.00 23.42
10 ATOM 2395 CA  ILE A 312  0  28.092 32.311 36.899 1.00 24.86
   ATOM 2396 C   ILE A 312  0  27.337 33.157 37.914 1.00 26.54
   ATOM 2397 O   ILE A 312  0  26.154 33.467 37.739 1.00 25.31
   ATOM 2398 CB  ILE A 312  0  28.397 33.179 35.670 1.00 24.45
   ATOM 2399 CG1 ILE A 312  0  28.998 32.330 34.576 1.00 25.60
15 ATOM 2400 CG2 ILE A 312  0  29.261 34.373 36.075 1.00 26.44
   ATOM 2401 CD1 ILE A 312  0  30.462 32.026 34.512 1.00 24.51
   ATOM 2402 N   ASP A 313  0  28.008 33.523 39.003 1.00 28.70
   ATOM 2403 CA  ASP A 313  0  27.432 34.339 40.071 1.00 30.99
   ATOM 2404 C   ASP A 313  0  26.065 33.763 40.417 1.00 29.83
20 ATOM 2405 O   ASP A 313  0  25.024 34.385 40.235 1.00 28.51
   ATOM 2406 CB  ASP A 313  0  27.266 35.777 39.576 1.00 35.88
   ATOM 2407 CG  ASP A 313  0  28.532 36.505 39.187 1.00 40.21
   ATOM 2408 OD1 ASP A 313  0  29.577 36.243 39.847 1.00 42.99
   ATOM 2409 OD2 ASP A 313  0  28.525 37.346 38.252 1.00 40.95
25 ATOM 2410 N   PRO A 314  0  26.041 32.517 40.863 1.00 28.77
   ATOM 2411 CA  PRO A 314  0  24.841 31.743 41.074 1.00 27.80
   ATOM 2412 C   PRO A 314  0  23.865 32.198 42.137 1.00 26.49
   ATOM 2413 O   PRO A 314  0  22.671 31.857 42.032 1.00 27.17
   ATOM 2414 CB  PRO A 314  0  25.297 30.311 41.479 1.00 27.61
30 ATOM 2415 CG  PRO A 314  0  26.711 30.573 41.929 1.00 29.37
   ATOM 2416 CD  PRO A 314  0  27.248 31.726 41.111 1.00 28.10
   ATOM 2417 N   ALA A 315  0  24.364 32.818 43.206 1.00 23.45
   ATOM 2418 CA  ALA A 315  0  23.505 33.092 44.336 1.00 22.34
   ATOM 2419 C   ALA A 315  0  22.414 34.111 44.008 1.00 22.46
35 ATOM 2420 O   ALA A 315  0  22.678 35.127 43.370 1.00 22.52
   ATOM 2421 CB  ALA A 315  0  24.294 33.617 45.532 1.00 21.68
   ATOM 2422 N   ALA A 316  0  21.226 33.838 44.534 1.00 20.85
   ATOM 2423 CA  ALA A 316  0  20.133 34.805 44.422 1.00 20.78
```

```
   ATOM 2424 C   ALA A 316 0  20.547 36.010 45.271 1.00 20.55
   ATOM 2425 O   ALA A 316 0  21.143 35.846 46.333 1.00 21.47
   ATOM 2426 CB  ALA A 316 0  18.897 34.166 45.043 1.00 18.32
   ATOM 2427 N   PRO A 317 0  20.237 37.212 44.864 1.00 20.84
 5 ATOM 2428 CA  PRO A 317 0  20.539 38.410 45.634 1.00 20.82
   ATOM 2429 C   PRO A 317 0  19.766 38.449 46.945 1.00 20.96
   ATOM 2430 O   PRO A 317 0  18.668 37.885 47.030 1.00 21.42
   ATOM 2431 CB  PRO A 317 0  20.064 39.590 44.758 1.00 21.64
   ATOM 2432 CG  PRO A 317 0  19.178 38.938 43.746 1.00 21.69
10 ATOM 2433 CD  PRO A 317 0  19.517 37.466 43.619 1.00 20.10
   ATOM 2434 N   GLY A 318 0  20.269 39.080 47.988 1.00 20.69
   ATOM 2435 CA  GLY A 318 0  19.533 39.282 49.225 1.00 21.68
   ATOM 2436 C   GLY A 318 0  19.631 38.218 50.283 1.00 22.93
   ATOM 2437 O   GLY A 318 0  20.344 37.221 50.101 1.00 23.87
15 ATOM 2438 N   ILE A 319 0  18.895 38.398 51.368 1.00 22.20
   ATOM 2439 CA  ILE A 319 0  18.879 37.432 52.454 1.00 24.16
   ATOM 2440 C   ILE A 319 0  18.169 36.189 51.956 1.00 25.28
   ATOM 2441 O   ILE A 319 0  17.071 36.271 51.405 1.00 26.26
   ATOM 2442 CB  ILE A 319 0  18.208 38.030 53.704 1.00 24.54
20 ATOM 2443 CG1 ILE A 319 0  19.075 39.176 54.213 1.00 25.08
   ATOM 2444 CG2 ILE A 319 0  17.944 37.012 54.793 1.00 24.03
   ATOM 2445 CD1 ILE A 319 0  18.262 40.183 55.006 1.00 27.56
   ATOM 2446 N   PRO A 320 0  18.762 35.030 52.159 1.00 26.23
   ATOM 2447 CA  PRO A 320 0  18.273 33.748 51.684 1.00 26.64
25 ATOM 2448 C   PRO A 320 0  17.105 33.172 52.453 1.00 26.74
   ATOM 2449 O   PRO A 320 0  17.140 32.025 52.896 1.00 27.54
   ATOM 2450 CB  PRO A 320 0  19.501 32.801 51.772 1.00 27.16
   ATOM 2451 CG  PRO A 320 0  20.216 33.388 52.985 1.00 25.20
   ATOM 2452 CD  PRO A 320 0  20.061 34.891 52.837 1.00 25.62
30 ATOM 2453 N   THR A 321 0  16.022 33.909 52.611 1.00 27.35
   ATOM 2454 CA  THR A 321 0  14.820 33.550 53.329 1.00 28.07
   ATOM 2455 C   THR A 321 0  13.632 34.190 52.603 1.00 27.48
   ATOM 2456 O   THR A 321 0  13.597 35.383 52.302 1.00 27.13
   ATOM 2457 CB  THR A 321 0  14.824 34.085 54.780 1.00 29.87
35 ATOM 2458 OG1 THR A 321 0  15.957 33.582 55.511 1.00 31.85
   ATOM 2459 CG2 THR A 321 0  13.548 33.687 55.507 1.00 31.06
   ATOM 2460 N   PRO A 322 0  12.630 33.378 52.326 1.00 26.63
   ATOM 2461 CA  PRO A 322 0  11.428 33.824 51.637 1.00 25.91
```

```
ATOM   2462  C   PRO A 322   0    10.892  35.072  52.313  1.00 25.37
ATOM   2463  O   PRO A 322   0    10.945  35.194  53.542  1.00 25.02
ATOM   2464  CB  PRO A 322   0    10.456  32.638  51.661  1.00 26.11
ATOM   2465  CG  PRO A 322   0    11.370  31.477  51.931  1.00 26.67
ATOM   2466  CD  PRO A 322   0    12.592  31.961  52.691  1.00 26.21
ATOM   2467  N   GLY A 323   0    10.432  36.075  51.573  1.00 24.30
ATOM   2468  CA  GLY A 323   0     9.943  37.288  52.197  1.00 24.13
ATOM   2469  C   GLY A 323   0    11.013  38.161  52.842  1.00 25.48
ATOM   2470  O   GLY A 323   0    10.603  39.128  53.512  1.00 25.28
ATOM   2471  N   ALA A 324   0    12.320  37.959  52.688  1.00 24.80
ATOM   2472  CA  ALA A 324   0    13.278  38.831  53.377  1.00 24.61
ATOM   2473  C   ALA A 324   0    14.034  39.773  52.451  1.00 23.92
ATOM   2474  O   ALA A 324   0    15.148  40.225  52.748  1.00 24.53
ATOM   2475  CB  ALA A 324   0    14.255  38.012  54.204  1.00 23.79
ATOM   2476  N   ALA A 325   0    13.423  40.081  51.315  1.00 22.22
ATOM   2477  CA  ALA A 325   0    14.033  40.985  50.341  1.00 20.42
ATOM   2478  C   ALA A 325   0    13.825  42.423  50.803  1.00 19.97
ATOM   2479  O   ALA A 325   0    12.987  42.648  51.677  1.00 18.14
ATOM   2480  CB  ALA A 325   0    13.272  40.763  49.018  1.00 19.40
ATOM   2481  N   ASP A 326   0    14.422  43.421  50.161  1.00 20.69
ATOM   2482  CA  ASP A 326   0    14.141  44.804  50.529  1.00 22.54
ATOM   2483  C   ASP A 326   0    12.702  45.158  50.220  1.00 22.83
ATOM   2484  O   ASP A 326   0    12.015  45.754  51.030  1.00 23.68
ATOM   2485  CB  ASP A 326   0    15.089  45.767  49.789  1.00 22.32
ATOM   2486  CG  ASP A 326   0    16.494  45.378  50.238  1.00 23.83
ATOM   2487  OD1 ASP A 326   0    16.650  45.284  51.475  1.00 24.78
ATOM   2488  OD2 ASP A 326   0    17.393  45.171  49.409  1.00 24.90
ATOM   2489  N   VAL A 327   0    12.254  44.821  49.026  1.00 24.29
ATOM   2490  CA  VAL A 327   0    10.914  45.064  48.503  1.00 23.57
ATOM   2491  C   VAL A 327   0    10.246  43.721  48.170  1.00 23.46
ATOM   2492  O   VAL A 327   0    10.785  42.933  47.386  1.00 22.62
ATOM   2493  CB  VAL A 327   0    10.946  45.898  47.220  1.00 24.70
ATOM   2494  CG1 VAL A 327   0     9.554  46.274  46.751  1.00 24.11
ATOM   2495  CG2 VAL A 327   0    11.773  47.173  47.420  1.00 26.30
ATOM   2496  N   ASN A 328   0     9.113  43.463  48.811  1.00 21.44
ATOM   2497  CA  ASN A 328   0     8.390  42.212  48.717  1.00 23.21
ATOM   2498  C   ASN A 328   0     6.986  42.410  48.158  1.00 23.12
ATOM   2499  O   ASN A 328   0     6.140  43.030  48.799  1.00 22.76
```

5032-WO

96

```
   ATOM 2500 CB  ASN A 328  0   8.223 41.603 50.121 1.00 23.09
   ATOM 2501 CG  ASN A 328  0   9.569 41.204 50.693 1.00 24.61
   ATOM 2502 OD1 ASN A 328  0  10.181 40.188 50.295 1.00 25.87
   ATOM 2503 ND2 ASN A 328  0  10.017 42.029 51.617 1.00 21.47
 5 ATOM 2504 N   LEU A 329  0   6.776 42.000 46.923 1.00 23.14
   ATOM 2505 CA  LEU A 329  0   5.497 42.179 46.268 1.00 24.23
   ATOM 2506 C   LEU A 329  0   4.859 40.822 45.953 1.00 25.21
   ATOM 2507 O   LEU A 329  0   5.489 39.876 45.469 1.00 24.20
   ATOM 2508 CB  LEU A 329  0   5.622 42.963 44.948 1.00 24.33
10 ATOM 2509 CG  LEU A 329  0   6.369 44.279 45.082 1.00 26.30
   ATOM 2510 CD1 LEU A 329  0   6.778 44.884 43.757 1.00 26.24
   ATOM 2511 CD2 LEU A 329  0   5.550 45.249 45.913 1.00 27.07
   ATOM 2512 N   ARG A 330  0   3.562 40.806 46.204 1.00 25.13
   ATOM 2513 CA  ARG A 330  0   2.740 39.641 45.899 1.00 27.48
15 ATOM 2514 C   ARG A 330  0   1.628 40.116 44.965 1.00 27.52
   ATOM 2515 O   ARG A 330  0   0.988 41.132 45.257 1.00 27.17
   ATOM 2516 CB  ARG A 330  0   2.200 39.017 47.166 1.00 29.82
   ATOM 2517 CG  ARG A 330  0   1.351 37.794 46.932 1.00 33.18
   ATOM 2518 CD  ARG A 330  0   0.880 37.251 48.284 1.00 37.06
20 ATOM 2519 NE  ARG A 330  0   0.305 35.914 48.038 1.00 40.34
   ATOM 2520 CZ  ARG A 330  0   1.009 34.803 48.298 1.00 40.82
   ATOM 2521 NH1 ARG A 330  0   2.229 34.903 48.812 1.00 40.36
   ATOM 2522 NH2 ARG A 330  0   0.415 33.642 48.040 1.00 41.33
   ATOM 2523 N   PHE A 331  0   1.507 39.481 43.795 1.00 25.88
25 ATOM 2524 CA  PHE A 331  0   0.475 39.937 42.855 1.00 25.87
   ATOM 2525 C   PHE A 331  0  -0.657 38.919 42.779 1.00 25.94
   ATOM 2526 O   PHE A 331  0  -0.441 37.697 42.824 1.00 24.61
   ATOM 2527 CB  PHE A 331  0   1.102 40.269 41.511 1.00 25.94
   ATOM 2528 CG  PHE A 331  0   1.884 41.565 41.496 1.00 28.66
30 ATOM 2529 CD1 PHE A 331  0   1.282 42.782 41.759 1.00 28.04
   ATOM 2530 CD2 PHE A 331  0   3.246 41.569 41.214 1.00 29.71
   ATOM 2531 CE1 PHE A 331  0   1.988 43.963 41.744 1.00 29.21
   ATOM 2532 CE2 PHE A 331  0   3.975 42.753 41.181 1.00 30.61
   ATOM 2533 CZ  PHE A 331  0   3.348 43.965 41.453 1.00 30.66
35 ATOM 2534 N   GLN A 332  0  -1.873 39.446 42.676 1.00 25.58
   ATOM 2535 CA  GLN A 332  0  -3.085 38.628 42.608 1.00 26.60
   ATOM 2536 C   GLN A 332  0  -3.672 38.698 41.203 1.00 23.61
   ATOM 2537 O   GLN A 332  0  -4.136 39.739 40.755 1.00 21.73
```

5032-WO

```
   ATOM 2538 CB  GLN A 332 0 -4.110 39.094 43.630 1.00 30.32
   ATOM 2539 CG  GLN A 332 0 -5.412 38.299 43.642 1.00 35.72
   ATOM 2540 CD  GLN A 332 0 -5.199 36.961 44.325 1.00 39.98
   ATOM 2541 OE1 GLN A 332 0 -5.859 35.961 44.007 1.00 42.32
 5 ATOM 2542 NE2 GLN A 332 0 -4.257 36.915 45.270 1.00 42.27
   ATOM 2543 N   LEU A 333 0 -3.612 37.576 40.504 1.00 23.60
   ATOM 2544 CA  LEU A 333 0 -4.105 37.565 39.118 1.00 26.25
   ATOM 2545 C   LEU A 333 0 -5.627 37.373 39.123 1.00 26.55
   ATOM 2546 O   LEU A 333 0 -6.107 36.655 39.998 1.00 25.70
10 ATOM 2547 CB  LEU A 333 0 -3.424 36.465 38.304 1.00 25.25
   ATOM 2548 CG  LEU A 333 0 -1.919 36.608 38.052 1.00 25.72
   ATOM 2549 CD1 LEU A 333 0 -1.431 35.565 37.067 1.00 23.66
   ATOM 2550 CD2 LEU A 333 0 -1.551 38.000 37.558 1.00 25.25
   ATOM 2551 N   GLY A 334 0 -6.327 37.976 38.188 1.00 27.85
15 ATOM 2552 CA  GLY A 334 0 -7.770 37.782 38.118 1.00 29.96
   ATOM 2553 C   GLY A 334 0 -8.253 37.802 36.672 1.00 32.36
   ATOM 2554 O   GLY A 334 0 -7.559 38.175 35.719 1.00 30.74
   ATOM 2555 N   PHE A 335 0 -9.502 37.377 36.544 1.00 34.76
   ATOM 2556 CA  PHE A 335 0 -10.181 37.360 35.260 1.00 38.54
20 ATOM 2557 C   PHE A 335 0 -11.625 37.806 35.514 1.00 41.05
   ATOM 2558 O   PHE A 335 0 -12.443 37.028 36.021 1.00 41.53
   ATOM 2559 CB  PHE A 335 0 -10.183 36.003 34.586 1.00 39.00
   ATOM 2560 CG  PHE A 335 0 -10.772 36.105 33.197 1.00 40.61
   ATOM 2561 CD1 PHE A 335 0 -10.052 36.686 32.175 1.00 40.45
25 ATOM 2562 CD2 PHE A 335 0 -12.045 35.614 32.942 1.00 41.39
   ATOM 2563 CE1 PHE A 335 0 -10.580 36.778 30.901 1.00 40.81
   ATOM 2564 CE2 PHE A 335 0 -12.588 35.697 31.671 1.00 41.51
   ATOM 2565 CZ  PHE A 335 0 -11.849 36.281 30.652 1.00 41.87
   ATOM 2566 N   SER A 336 0 -11.861 39.075 35.193 1.00 42.39
30 ATOM 2567 CA  SER A 336 0 -13.203 39.582 35.445 1.00 44.12
   ATOM 2568 C   SER A 336 0 -13.704 40.525 34.370 1.00 44.31
   ATOM 2569 O   SER A 336 0 -13.028 41.440 33.903 1.00 44.49
   ATOM 2570 CB  SER A 336 0 -13.214 40.206 36.842 1.00 45.46
   ATOM 2571 OG  SER A 336 0 -13.727 39.233 37.758 1.00 47.11
35 ATOM 2572 N   GLY A 337 0 -14.963 40.267 33.983 1.00 44.12
   ATOM 2573 CA  GLY A 337 0 -15.630 41.067 32.959 1.00 41.89
   ATOM 2574 C   GLY A 337 0 -14.963 40.920 31.608 1.00 40.08
   ATOM 2575 O   GLY A 337 0 -14.712 41.891 30.888 1.00 41.35
```

5032-WO

98

```
   ATOM  2576  N   GLY A 338  0  -14.583  39.699  31.263  1.00 39.12
   ATOM  2577  CA  GLY A 338  0  -13.899  39.364  30.034  1.00 36.11
   ATOM  2578  C   GLY A 338  0  -12.503  39.970  29.929  1.00 34.97
   ATOM  2579  O   GLY A 338  0  -12.005  40.116  28.806  1.00 33.64
 5 ATOM  2580  N   ARG A 339  0  -11.885  40.355  31.048  1.00 33.21
   ATOM  2581  CA  ARG A 339  0  -10.538  40.916  30.982  1.00 32.04
   ATOM  2582  C   ARG A 339  0   -9.724  40.397  32.164  1.00 29.23
   ATOM  2583  O   ARG A 339  0  -10.260  40.053  33.210  1.00 26.38
   ATOM  2584  CB  ARG A 339  0  -10.495  42.419  30.845  1.00 36.52
10 ATOM  2585  CG  ARG A 339  0  -11.291  43.281  31.790  1.00 42.08
   ATOM  2586  CD  ARG A 339  0  -11.895  44.502  31.127  1.00 45.03
   ATOM  2587  NE  ARG A 339  0  -11.046  45.380  30.351  1.00 47.77
   ATOM  2588  CZ  ARG A 339  0  -10.635  46.616  30.664  1.00 49.55
   ATOM  2589  NH1 ARG A 339  0  -10.935  47.242  31.799  1.00 49.60
15 ATOM  2590  NH2 ARG A 339  0   -9.862  47.295  29.805  1.00 49.96
   ATOM  2591  N   PHE A 340  0   -8.425  40.181  31.900  1.00 25.50
   ATOM  2592  CA  PHE A 340  0   -7.526  39.713  32.938  1.00 22.68
   ATOM  2593  C   PHE A 340  0   -7.171  40.945  33.774  1.00 22.15
   ATOM  2594  O   PHE A 340  0   -7.069  42.069  33.266  1.00 21.26
20 ATOM  2595  CB  PHE A 340  0   -6.210  39.135  32.397  1.00 22.39
   ATOM  2596  CG  PHE A 340  0   -6.333  37.792  31.736  1.00 20.74
   ATOM  2597  CD1 PHE A 340  0   -6.338  37.710  30.357  1.00 20.97
   ATOM  2598  CD2 PHE A 340  0   -6.448  36.644  32.468  1.00 21.19
   ATOM  2599  CE1 PHE A 340  0   -6.449  36.488  29.721  1.00 21.61
25 ATOM  2600  CE2 PHE A 340  0   -6.585  35.408  31.826  1.00 22.99
   ATOM  2601  CZ  PHE A 340  0   -6.578  35.334  30.444  1.00 19.90
   ATOM  2602  N   THR A 341  0   -7.000  40.736  35.069  1.00 20.76
   ATOM  2603  CA  THR A 341  0   -6.605  41.879  35.889  1.00 21.55
   ATOM  2604  C   THR A 341  0   -5.400  41.509  36.759  1.00 21.00
30 ATOM  2605  O   THR A 341  0   -5.236  40.329  37.089  1.00 20.70
   ATOM  2606  CB  THR A 341  0   -7.757  42.255  36.853  1.00 21.12
   ATOM  2607  OG1 THR A 341  0   -8.014  41.102  37.668  1.00 21.26
   ATOM  2608  CG2 THR A 341  0   -9.050  42.630  36.150  1.00 21.74
   ATOM  2609  N   ILE A 342  0   -4.750  42.529  37.308  1.00 20.28
35 ATOM  2610  CA  ILE A 342  0   -3.739  42.273  38.333  1.00 20.34
   ATOM  2611  C   ILE A 342  0   -4.026  43.212  39.496  1.00 18.92
   ATOM  2612  O   ILE A 342  0   -4.004  44.437  39.327  1.00 16.42
   ATOM  2613  CB  ILE A 342  0   -2.306  42.439  37.820  1.00 21.04
```

```
ATOM 2614 CG1 ILE A 342  0  -1.337 42.721 38.988 1.00 21.39
ATOM 2615 CG2 ILE A 342  0  -2.250 43.540 36.800 1.00 24.57
ATOM 2616 CD1 ILE A 342  0  -0.260 41.661 38.949 1.00 24.53
ATOM 2617 N   ASN A 343  0  -4.282 42.601 40.650 1.00 17.77
ATOM 2618 CA  ASN A 343  0  -4.702 43.413 41.782 1.00 21.51
ATOM 2619 C   ASN A 343  0  -5.881 44.287 41.394 1.00 21.43
ATOM 2620 O   ASN A 343  0  -5.903 45.495 41.598 1.00 20.26
ATOM 2621 CB  ASN A 343  0  -3.513 44.231 42.356 1.00 22.34
ATOM 2622 CG  ASN A 343  0  -2.685 43.190 43.073 1.00 25.38
ATOM 2623 OD1 ASN A 343  0  -2.075 42.218 42.598 1.00 26.90
ATOM 2624 ND2 ASN A 343  0  -2.652 43.238 44.425 1.00 25.34
ATOM 2625 N   GLY A 344  0  -6.875 43.703 40.730 1.00 23.77
ATOM 2626 CA  GLY A 344  0  -8.078 44.406 40.324 1.00 25.28
ATOM 2627 C   GLY A 344  0  -7.954 45.280 39.111 1.00 26.82
ATOM 2628 O   GLY A 344  0  -9.029 45.728 38.672 1.00 29.56
ATOM 2629 N   THR A 345  0  -6.798 45.561 38.527 1.00 26.28
ATOM 2630 CA  THR A 345  0  -6.766 46.440 37.366 1.00 25.48
ATOM 2631 C   THR A 345  0  -6.343 45.703 36.109 1.00 26.49
ATOM 2632 O   THR A 345  0  -5.385 44.925 36.122 1.00 28.22
ATOM 2633 CB  THR A 345  0  -5.829 47.648 37.589 1.00 26.17
ATOM 2634 OG1 THR A 345  0  -6.191 48.334 38.788 1.00 25.32
ATOM 2635 CG2 THR A 345  0  -5.867 48.677 36.462 1.00 24.83
ATOM 2636 N   ALA A 346  0  -7.017 46.012 35.008 1.00 24.80
ATOM 2637 CA  ALA A 346  0  -6.768 45.491 33.688 1.00 23.82
ATOM 2638 C   ALA A 346  0  -5.862 46.511 32.997 1.00 23.77
ATOM 2639 O   ALA A 346  0  -6.098 47.711 33.088 1.00 22.93
ATOM 2640 CB  ALA A 346  0  -8.031 45.353 32.841 1.00 24.13
ATOM 2641 N   TYR A 347  0  -4.793 46.023 32.392 1.00 22.69
ATOM 2642 CA  TYR A 347  0  -3.862 46.949 31.792 1.00 22.75
ATOM 2643 C   TYR A 347  0  -4.483 47.532 30.527 1.00 23.42
ATOM 2644 O   TYR A 347  0  -4.954 46.753 29.709 1.00 22.19
ATOM 2645 CB  TYR A 347  0  -2.521 46.274 31.455 1.00 21.25
ATOM 2646 CG  TYR A 347  0  -1.584 47.221 30.732 1.00 18.93
ATOM 2647 CD1 TYR A 347  0  -0.819 48.137 31.442 1.00 18.17
ATOM 2648 CD2 TYR A 347  0  -1.473 47.176 29.353 1.00 19.30
ATOM 2649 CE1 TYR A 347  0   0.034 49.003 30.763 1.00 18.37
ATOM 2650 CE2 TYR A 347  0  -0.650 48.063 28.664 1.00 18.40
ATOM 2651 CZ  TYR A 347  0   0.102 48.962 29.394 1.00 18.99
```

5032-WO

100

```
   ATOM 2652 OH  TYR A 347 0   0.947 49.802 28.706 1.00 19.65
   ATOM 2653 N   GLU A 348 0  -4.378 48.833 30.359 1.00 25.22
   ATOM 2654 CA  GLU A 348 0  -4.769 49.453 29.098 1.00 28.77
   ATOM 2655 C   GLU A 348 0  -3.659 50.470 28.805 1.00 27.38
 5 ATOM 2656 O   GLU A 348 0  -3.297 51.229 29.704 1.00 28.49
   ATOM 2657 CB  GLU A 348 0  -6.114 50.134 29.110 1.00 32.95
   ATOM 2658 CG  GLU A 348 0  -7.391 49.302 29.072 1.00 39.29
   ATOM 2659 CD  GLU A 348 0  -8.562 50.170 29.559 1.00 43.20
   ATOM 2660 OE1 GLU A 348 0  -8.825 51.211 28.900 1.00 45.31
10 ATOM 2661 OE2 GLU A 348 0  -9.175 49.855 30.601 1.00 44.11
   ATOM 2662 N   SER A 349 0  -3.168 50.541 27.621 1.00 25.73
   ATOM 2663 CA  SER A 349 0  -2.080 51.410 27.201 1.00 28.25
   ATOM 2664 C   SER A 349 0  -2.401 52.887 27.194 1.00 28.71
   ATOM 2665 O   SER A 349 0  -3.279 53.399 26.526 1.00 29.13
15 ATOM 2666 CB  SER A 349 0  -1.743 50.818 25.838 1.00 28.54
   ATOM 2667 OG  SER A 349 0  -0.850 51.499 25.026 1.00 33.31
   ATOM 2668 N   PRO A 350 0  -1.623 53.700 27.898 1.00 29.56
   ATOM 2669 CA  PRO A 350 0  -1.770 55.145 27.997 1.00 28.53
   ATOM 2670 C   PRO A 350 0  -1.480 55.825 26.679 1.00 28.01
20 ATOM 2671 O   PRO A 350 0  -0.787 55.217 25.856 1.00 26.93
   ATOM 2672 CB  PRO A 350 0  -0.752 55.632 29.063 1.00 27.91
   ATOM 2673 CG  PRO A 350 0   0.309 54.560 28.863 1.00 28.03
   ATOM 2674 CD  PRO A 350 0  -0.461 53.245 28.688 1.00 28.76
   ATOM 2675 N   SER A 351 0  -1.951 57.066 26.485 1.00 28.89
25 ATOM 2676 CA  SER A 351 0  -1.630 57.718 25.206 1.00 29.67
   ATOM 2677 C   SER A 351 0  -0.213 58.287 25.257 1.00 27.67
   ATOM 2678 O   SER A 351 0   0.320 58.524 24.177 1.00 28.18
   ATOM 2679 CB  SER A 351 0  -2.566 58.860 24.790 1.00 31.71
   ATOM 2680 OG  SER A 351 0  -2.793 59.679 25.938 1.00 34.19
30 ATOM 2681 N   VAL A 352 0   0.316 58.529 26.449 1.00 25.32
   ATOM 2682 CA  VAL A 352 0   1.703 58.997 26.534 1.00 25.27
   ATOM 2683 C   VAL A 352 0   2.503 57.872 27.211 1.00 23.63
   ATOM 2684 O   VAL A 352 0   2.181 57.493 28.323 1.00 23.26
   ATOM 2685 CB  VAL A 352 0   1.934 60.300 27.303 1.00 24.91
35 ATOM 2686 CG1 VAL A 352 0   1.129 61.436 26.658 1.00 24.41
   ATOM 2687 CG2 VAL A 352 0   3.424 60.635 27.281 1.00 23.35
   ATOM 2688 N   PRO A 353 0   3.498 57.375 26.510 1.00 22.39
   ATOM 2689 CA  PRO A 353 0   4.342 56.300 26.983 1.00 21.86
```

5032-WO

101

```
   ATOM  2690  C   PRO A 353  0    4.978 56.699 28.300 1.00 20.91
   ATOM  2691  O   PRO A 353  0    5.393 57.852 28.483 1.00 21.91
   ATOM  2692  CB  PRO A 353  0    5.417 56.054 25.916 1.00 23.95
   ATOM  2693  CG  PRO A 353  0    5.181 57.123 24.878 1.00 23.79
 5 ATOM  2694  CD  PRO A 353  0    3.882 57.848 25.180 1.00 23.03
   ATOM  2695  N   THR A 354  0    5.043 55.778 29.234 1.00 18.66
   ATOM  2696  CA  THR A 354  0    5.646 56.015 30.530 1.00 18.05
   ATOM  2697  C   THR A 354  0    6.981 56.739 30.478 1.00 18.33
   ATOM  2698  O   THR A 354  0    7.168 57.630 31.319 1.00 19.46
10 ATOM  2699  CB  THR A 354  0    5.871 54.661 31.242 1.00 17.10
   ATOM  2700  OG1 THR A 354  0    4.903 53.710 30.797 1.00 17.24
   ATOM  2701  CG2 THR A 354  0    5.772 54.852 32.741 1.00 16.43
   ATOM  2702  N   LEU A 355  0    7.940 56.380 29.618 1.00 17.49
   ATOM  2703  CA  LEU A 355  0    9.215 57.076 29.604 1.00 18.84
15 ATOM  2704  C   LEU A 355  0    9.013 58.579 29.284 1.00 19.80
   ATOM  2705  O   LEU A 355  0    9.722 59.417 29.849 1.00 17.13
   ATOM  2706  CB  LEU A 355  0   10.200 56.498 28.622 1.00 17.89
   ATOM  2707  CG  LEU A 355  0   11.703 56.488 28.819 1.00 18.66
   ATOM  2708  CD1 LEU A 355  0   12.436 56.851 27.547 1.00 18.37
20 ATOM  2709  CD2 LEU A 355  0   12.199 57.204 30.056 1.00 16.79
   ATOM  2710  N   LEU A 356  0    8.134 58.883 28.328 1.00 20.48
   ATOM  2711  CA  LEU A 356  0    7.812 60.274 27.993 1.00 21.62
   ATOM  2712  C   LEU A 356  0    7.085 60.932 29.163 1.00 21.28
   ATOM  2713  O   LEU A 356  0    7.497 62.042 29.506 1.00 22.01
25 ATOM  2714  CB  LEU A 356  0    7.028 60.474 26.700 1.00 22.08
   ATOM  2715  CG  LEU A 356  0    6.850 61.939 26.239 1.00 23.98
   ATOM  2716  CD1 LEU A 356  0    8.157 62.709 26.207 1.00 23.11
   ATOM  2717  CD2 LEU A 356  0    6.191 61.985 24.864 1.00 24.74
   ATOM  2718  N   GLN A 357  0    6.219 60.267 29.922 1.00 21.37
30 ATOM  2719  CA  GLN A 357  0    5.669 60.893 31.120 1.00 21.87
   ATOM  2720  C   GLN A 357  0    6.759 61.254 32.128 1.00 24.12
   ATOM  2721  O   GLN A 357  0    6.674 62.277 32.811 1.00 24.92
   ATOM  2722  CB  GLN A 357  0    4.636 60.015 31.822 1.00 20.63
   ATOM  2723  CG  GLN A 357  0    3.447 59.674 30.906 1.00 19.17
35 ATOM  2724  CD  GLN A 357  0    2.547 58.643 31.540 1.00 18.85
   ATOM  2725  OE1 GLN A 357  0    2.162 58.748 32.713 1.00 19.06
   ATOM  2726  NE2 GLN A 357  0    2.262 57.600 30.742 1.00 18.49
   ATOM  2727  N   ILE A 358  0    7.735 60.371 32.346 1.00 25.66
```

```
    ATOM  2728 CA  ILE A 358  0   8.822 60.651 33.263 1.00 26.19
    ATOM  2729 C   ILE A 358  0   9.699 61.800 32.762 1.00 27.66
    ATOM  2730 O   ILE A 358  0   9.940 62.725 33.551 1.00 26.65
    ATOM  2731 CB  ILE A 358  0   9.692 59.420 33.578 1.00 24.79
  5 ATOM  2732 CG1 ILE A 358  0   8.807 58.395 34.304 1.00 24.09
    ATOM  2733 CG2 ILE A 358  0  10.865 59.841 34.451 1.00 23.78
    ATOM  2734 CD1 ILE A 358  0   9.251 56.954 34.234 1.00 23.34
    ATOM  2735 N   MET A 359  0  10.054 61.844 31.486 1.00 29.63
    ATOM  2736 CA  MET A 359  0  10.893 62.910 30.965 1.00 33.02
 10 ATOM  2737 C   MET A 359  0  10.174 64.260 31.027 1.00 34.46
    ATOM  2738 O   MET A 359  0  10.801 65.324 31.026 1.00 33.77
    ATOM  2739 CB  MET A 359  0  11.346 62.664 29.537 1.00 35.67
    ATOM  2740 CG  MET A 359  0  12.065 61.403 29.138 1.00 40.75
    ATOM  2741 SD  MET A 359  0  13.764 61.153 29.671 1.00 44.90
 15 ATOM  2742 CE  MET A 359  0  14.594 62.592 29.007 1.00 44.24
    ATOM  2743 N   SER A 360  0   8.835 64.238 31.070 1.00 33.43
    ATOM  2744 CA  SER A 360  0   8.024 65.430 31.088 1.00 32.92
    ATOM  2745 C   SER A 360  0   7.761 65.995 32.474 1.00 33.24
    ATOM  2746 O   SER A 360  0   6.989 66.966 32.556 1.00 34.08
 20 ATOM  2747 CB  SER A 360  0   6.678 65.134 30.393 1.00 31.34
    ATOM  2748 OG  SER A 360  0   6.928 65.109 28.996 1.00 31.06
    ATOM  2749 N   GLY A 361  0   8.288 65.360 33.517 1.00 32.06
    ATOM  2750 CA  GLY A 361  0   8.072 65.868 34.847 1.00 31.80
    ATOM  2751 C   GLY A 361  0   7.487 64.955 35.880 1.00 32.48
 25 ATOM  2752 O   GLY A 361  0   7.420 65.377 37.043 1.00 33.20
    ATOM  2753 N   ALA A 362  0   6.991 63.769 35.535 1.00 33.69
    ATOM  2754 CA  ALA A 362  0   6.406 62.926 36.601 1.00 35.10
    ATOM  2755 C   ALA A 362  0   7.475 62.615 37.650 1.00 34.45
    ATOM  2756 O   ALA A 362  0   8.598 62.306 37.286 1.00 33.60
 30 ATOM  2757 CB  ALA A 362  0   5.789 61.658 36.043 1.00 34.88
    ATOM  2758 N   GLN A 363  0   7.146 62.676 38.920 1.00 36.22
    ATOM  2759 CA  GLN A 363  0   8.083 62.458 40.007 1.00 37.87
    ATOM  2760 C   GLN A 363  0   7.776 61.189 40.787 1.00 37.20
    ATOM  2761 O   GLN A 363  0   8.620 60.777 41.587 1.00 36.79
 35 ATOM  2762 CB  GLN A 363  0   8.012 63.619 41.022 1.00 40.41
    ATOM  2763 CG  GLN A 363  0   8.986 64.740 40.721 1.00 44.07
    ATOM  2764 CD  GLN A 363  0   8.586 66.154 41.092 1.00 45.77
    ATOM  2765 OE1 GLN A 363  0   7.697 66.473 41.901 1.00 46.53
```

5032-WO

```
ATOM 2766 NE2 GLN A 363 0   9.294 67.089 40.435 1.00 46.12
ATOM 2767 N   SER A 364 0   6.579 60.632 40.610 1.00 35.74
ATOM 2768 CA  SER A 364 0   6.249 59.434 41.381 1.00 34.54
ATOM 2769 C   SER A 364 0   5.225 58.588 40.653 1.00 34.32
ATOM 2770 O   SER A 364 0   4.605 59.037 39.692 1.00 33.71
ATOM 2771 CB  SER A 364 0   5.774 59.835 42.769 1.00 35.68
ATOM 2772 OG  SER A 364 0   4.396 60.095 42.928 1.00 35.86
ATOM 2773 N   ALA A 365 0   5.015 57.372 41.146 1.00 33.95
ATOM 2774 CA  ALA A 365 0   4.017 56.486 40.564 1.00 34.62
ATOM 2775 C   ALA A 365 0   2.637 57.148 40.560 1.00 34.46
ATOM 2776 O   ALA A 365 0   1.906 56.995 39.582 1.00 34.37
ATOM 2777 CB  ALA A 365 0   3.963 55.155 41.301 1.00 33.51
ATOM 2778 N   ASN A 366 0   2.261 57.916 41.571 1.00 34.45
ATOM 2779 CA  ASN A 366 0   1.003 58.619 41.632 1.00 36.37
ATOM 2780 C   ASN A 366 0   0.708 59.524 40.447 1.00 35.60
ATOM 2781 O   ASN A 366 0  -0.462 59.719 40.131 1.00 36.50
ATOM 2782 CB  ASN A 366 0   0.904 59.464 42.918 1.00 38.72
ATOM 2783 CG  ASN A 366 0   0.794 58.558 44.126 1.00 41.08
ATOM 2784 OD1 ASN A 366 0   0.863 58.966 45.284 1.00 43.39
ATOM 2785 ND2 ASN A 366 0   0.646 57.256 43.914 1.00 42.72
ATOM 2786 N   ASP A 367 0   1.694 60.046 39.752 1.00 34.06
ATOM 2787 CA  ASP A 367 0   1.571 60.899 38.610 1.00 33.37
ATOM 2788 C   ASP A 367 0   1.566 60.122 37.293 1.00 32.09
ATOM 2789 O   ASP A 367 0   1.430 60.762 36.247 1.00 31.74
ATOM 2790 CB  ASP A 367 0   2.768 61.841 38.483 1.00 35.96
ATOM 2791 CG  ASP A 367 0   3.048 62.818 39.602 1.00 37.69
ATOM 2792 OD1 ASP A 367 0   2.123 63.209 40.336 1.00 37.23
ATOM 2793 OD2 ASP A 367 0   4.258 63.194 39.705 1.00 39.62
ATOM 2794 N   LEU A 368 0   1.791 58.814 37.371 1.00 30.39
ATOM 2795 CA  LEU A 368 0   1.897 58.055 36.123 1.00 28.74
ATOM 2796 C   LEU A 368 0   0.586 57.386 35.745 1.00 28.85
ATOM 2797 O   LEU A 368 0  -0.214 56.947 36.555 1.00 28.17
ATOM 2798 CB  LEU A 368 0   3.043 57.046 36.194 1.00 26.94
ATOM 2799 CG  LEU A 368 0   4.436 57.668 36.422 1.00 27.05
ATOM 2800 CD1 LEU A 368 0   5.455 56.581 36.765 1.00 25.41
ATOM 2801 CD2 LEU A 368 0   4.882 58.499 35.236 1.00 24.44
ATOM 2802 N   LEU A 369 0   0.392 57.332 34.446 1.00 28.81
ATOM 2803 CA  LEU A 369 0  -0.753 56.671 33.834 1.00 29.65
```

5032-WO

104

```
   ATOM 2804 C   LEU A 369 0  -0.238 55.398 33.162 1.00 28.29
   ATOM 2805 O   LEU A 369 0   0.875 55.356 32.660 1.00 25.59
   ATOM 2806 CB  LEU A 369 0  -1.333 57.668 32.821 1.00 30.27
   ATOM 2807 CG  LEU A 369 0  -1.800 58.998 33.456 1.00 32.06
 5 ATOM 2808 CD1 LEU A 369 0  -2.220 59.979 32.370 1.00 31.87
   ATOM 2809 CD2 LEU A 369 0  -2.932 58.787 34.455 1.00 30.89
   ATOM 2810 N   PRO A 370 0  -1.054 54.361 33.157 1.00 27.87
   ATOM 2811 CA  PRO A 370 0  -2.396 54.379 33.688 1.00 26.71
   ATOM 2812 C   PRO A 370 0  -2.513 54.112 35.169 1.00 26.73
10 ATOM 2813 O   PRO A 370 0  -1.872 53.184 35.668 1.00 26.55
   ATOM 2814 CB  PRO A 370 0  -3.126 53.222 32.958 1.00 27.28
   ATOM 2815 CG  PRO A 370 0  -2.003 52.317 32.557 1.00 27.38
   ATOM 2816 CD  PRO A 370 0  -0.720 53.102 32.482 1.00 27.24
   ATOM 2817 N   ALA A 371 0  -3.414 54.810 35.870 1.00 26.16
15 ATOM 2818 CA  ALA A 371 0  -3.581 54.556 37.302 1.00 25.73
   ATOM 2819 C   ALA A 371 0  -3.892 53.103 37.616 1.00 24.59
   ATOM 2820 O   ALA A 371 0  -4.758 52.533 36.946 1.00 25.05
   ATOM 2821 CB  ALA A 371 0  -4.718 55.394 37.903 1.00 26.42
   ATOM 2822 N   GLY A 372 0  -3.261 52.524 38.625 1.00 22.47
20 ATOM 2823 CA  GLY A 372 0  -3.519 51.187 39.087 1.00 21.06
   ATOM 2824 C   GLY A 372 0  -2.691 50.096 38.427 1.00 23.01
   ATOM 2825 O   GLY A 372 0  -2.758 48.928 38.831 1.00 23.85
   ATOM 2826 N   SER A 373 0  -1.910 50.428 37.421 1.00 23.30
   ATOM 2827 CA  SER A 373 0  -1.054 49.459 36.736 1.00 24.36
25 ATOM 2828 C   SER A 373 0   0.429 49.746 36.919 1.00 24.76
   ATOM 2829 O   SER A 373 0   1.257 49.103 36.270 1.00 25.75
   ATOM 2830 CB  SER A 373 0  -1.371 49.584 35.233 1.00 23.25
   ATOM 2831 OG  SER A 373 0  -2.638 49.014 34.952 1.00 23.80
   ATOM 2832 N   VAL A 374 0   0.779 50.799 37.657 1.00 23.87
30 ATOM 2833 CA  VAL A 374 0   2.176 51.255 37.706 1.00 22.95
   ATOM 2834 C   VAL A 374 0   2.739 51.109 39.105 1.00 21.72
   ATOM 2835 O   VAL A 374 0   2.093 51.518 40.059 1.00 21.03
   ATOM 2836 CB  VAL A 374 0   2.317 52.687 37.169 1.00 23.05
   ATOM 2837 CG1 VAL A 374 0   3.720 53.273 37.323 1.00 24.13
35 ATOM 2838 CG2 VAL A 374 0   1.945 52.771 35.698 1.00 21.58
   ATOM 2839 N   TYR A 375 0   3.862 50.402 39.246 1.00 20.52
   ATOM 2840 CA  TYR A 375 0   4.445 50.184 40.573 1.00 22.02
   ATOM 2841 C   TYR A 375 0   5.873 50.743 40.549 1.00 22.56
```

```
ATOM  2842 O   TYR A 375  0    6.665 50.524 39.639 1.00 21.82
ATOM  2843 CB  TYR A 375  0    4.467 48.729 41.067 1.00 21.98
ATOM  2844 CG  TYR A 375  0    3.042 48.217 41.226 1.00 24.04
ATOM  2845 CD1 TYR A 375  0    2.398 48.261 42.445 1.00 23.57
ATOM  2846 CD2 TYR A 375  0    2.339 47.760 40.115 1.00 24.92
ATOM  2847 CE1 TYR A 375  0    1.100 47.831 42.575 1.00 25.65
ATOM  2848 CE2 TYR A 375  0    1.034 47.327 40.220 1.00 25.89
ATOM  2849 CZ  TYR A 375  0    0.429 47.352 41.464 1.00 26.65
ATOM  2850 OH  TYR A 375  0   -0.869 46.916 41.593 1.00 27.26
ATOM  2851 N   GLU A 376  0    6.130 51.563 41.546 1.00 22.36
ATOM  2852 CA  GLU A 376  0    7.403 52.214 41.718 1.00 23.62
ATOM  2853 C   GLU A 376  0    8.411 51.289 42.387 1.00 22.40
ATOM  2854 O   GLU A 376  0    8.062 50.578 43.324 1.00 21.88
ATOM  2855 CB  GLU A 376  0    7.211 53.465 42.614 1.00 25.13
ATOM  2856 CG  GLU A 376  0    8.500 54.255 42.720 1.00 27.91
ATOM  2857 CD  GLU A 376  0    8.376 55.725 43.046 1.00 29.20
ATOM  2858 OE1 GLU A 376  0    7.247 56.268 43.109 1.00 30.01
ATOM  2859 OE2 GLU A 376  0    9.458 56.336 43.219 1.00 28.05
ATOM  2860 N   LEU A 377  0    9.669 51.353 41.954 1.00 21.23
ATOM  2861 CA  LEU A 377  0   10.705 50.535 42.626 1.00 19.95
ATOM  2862 C   LEU A 377  0   11.838 51.478 42.982 1.00 20.30
ATOM  2863 O   LEU A 377  0   12.220 52.350 42.197 1.00 20.12
ATOM  2864 CB  LEU A 377  0   11.129 49.419 41.692 1.00 20.77
ATOM  2865 CG  LEU A 377  0   10.668 47.964 41.818 1.00 20.49
ATOM  2866 CD1 LEU A 377  0    9.439 47.739 42.629 1.00 17.77
ATOM  2867 CD2 LEU A 377  0   10.617 47.242 40.483 1.00 19.28
ATOM  2868 N   PRO A 378  0   12.407 51.334 44.162 1.00 19.69
ATOM  2869 CA  PRO A 378  0   13.523 52.117 44.631 1.00 19.91
ATOM  2870 C   PRO A 378  0   14.797 51.650 43.937 1.00 19.81
ATOM  2871 O   PRO A 378  0   14.795 50.645 43.241 1.00 17.74
ATOM  2872 CB  PRO A 378  0   13.611 51.893 46.157 1.00 20.21
ATOM  2873 CG  PRO A 378  0   12.957 50.546 46.291 1.00 20.73
ATOM  2874 CD  PRO A 378  0   12.050 50.292 45.114 1.00 19.74
ATOM  2875 N   ARG A 379  0   15.877 52.410 44.059 1.00 19.68
ATOM  2876 CA  ARG A 379  0   17.172 52.135 43.449 1.00 18.58
ATOM  2877 C   ARG A 379  0   18.027 51.129 44.193 1.00 18.68
ATOM  2878 O   ARG A 379  0   18.151 51.126 45.432 1.00 17.60
ATOM  2879 CB  ARG A 379  0   17.946 53.487 43.431 1.00 18.33
```

5032-WO

106

```
ATOM  2880 CG  ARG A 379  0   19.406 53.348 43.030 1.00 19.33
ATOM  2881 CD  ARG A 379  0   20.026 54.710 42.729 1.00 19.06
ATOM  2882 NE  ARG A 379  0   21.413 54.561 42.295 1.00 16.65
ATOM  2883 CZ  ARG A 379  0   21.794 54.681 41.031 1.00 15.60
ATOM  2884 NH1 ARG A 379  0   20.964 54.904 40.038 1.00 14.29
ATOM  2885 NH2 ARG A 379  0   23.096 54.505 40.783 1.00 17.29
ATOM  2886 N   ASN A 380  0   18.701 50.263 43.441 1.00 20.11
ATOM  2887 CA  ASN A 380  0   19.658 49.328 44.011 1.00 21.97
ATOM  2888 C   ASN A 380  0   19.129 48.604 45.227 1.00 22.44
ATOM  2889 O   ASN A 380  0   19.712 48.630 46.317 1.00 22.53
ATOM  2890 CB  ASN A 380  0   20.995 50.045 44.345 1.00 23.30
ATOM  2891 CG  ASN A 380  0   21.860 50.231 43.107 1.00 25.83
ATOM  2892 OD1 ASN A 380  0   22.636 51.186 42.877 1.00 27.14
ATOM  2893 ND2 ASN A 380  0   21.767 49.271 42.185 1.00 24.91
ATOM  2894 N   GLN A 381  0   17.974 47.936 45.097 1.00 21.39
ATOM  2895 CA  GLN A 381  0   17.468 47.162 46.220 1.00 20.88
ATOM  2896 C   GLN A 381  0   17.169 45.760 45.679 1.00 19.96
ATOM  2897 O   GLN A 381  0   17.000 45.635 44.471 1.00 19.90
ATOM  2898 CB  GLN A 381  0   16.219 47.722 46.871 1.00 22.84
ATOM  2899 CG  GLN A 381  0   16.326 49.172 47.318 1.00 27.28
ATOM  2900 CD  GLN A 381  0   16.065 49.297 48.792 1.00 30.24
ATOM  2901 OE1 GLN A 381  0   15.067 49.917 49.171 1.00 34.48
ATOM  2902 NE2 GLN A 381  0   16.929 48.742 49.611 1.00 30.80
ATOM  2903 N   VAL A 382  0   17.046 44.825 46.594 1.00 18.67
ATOM  2904 CA  VAL A 382  0   16.665 43.472 46.248 1.00 18.98
ATOM  2905 C   VAL A 382  0   15.139 43.327 46.212 1.00 19.75
ATOM  2906 O   VAL A 382  0   14.443 43.550 47.225 1.00 18.76
ATOM  2907 CB  VAL A 382  0   17.252 42.491 47.278 1.00 19.03
ATOM  2908 CG1 VAL A 382  0   16.811 41.065 46.960 1.00 18.87
ATOM  2909 CG2 VAL A 382  0   18.779 42.637 47.344 1.00 17.54
ATOM  2910 N   VAL A 383  0   14.601 42.954 45.046 1.00 17.58
ATOM  2911 CA  VAL A 383  0   13.151 42.715 45.037 1.00 17.76
ATOM  2912 C   VAL A 383  0   12.777 41.254 44.883 1.00 17.50
ATOM  2913 O   VAL A 383  0   13.348 40.472 44.153 1.00 16.42
ATOM  2914 CB  VAL A 383  0   12.306 43.626 44.145 1.00 17.69
ATOM  2915 CG1 VAL A 383  0   13.111 44.759 43.585 1.00 15.33
ATOM  2916 CG2 VAL A 383  0   11.400 43.009 43.126 1.00 17.79
ATOM  2917 N   GLU A 384  0   11.743 40.861 45.638 1.00 18.47
```

5032-WO

107

```
   ATOM 2918 CA  GLU A 384 0  11.173 39.529 45.542 1.00 18.27
   ATOM 2919 C   GLU A 384 0   9.711 39.683 45.096 1.00 18.94
   ATOM 2920 O   GLU A 384 0   8.956 40.311 45.816 1.00 19.06
   ATOM 2921 CB  GLU A 384 0  11.253 38.764 46.852 1.00 17.12
 5 ATOM 2922 CG  GLU A 384 0  10.717 37.345 46.738 1.00 17.52
   ATOM 2923 CD  GLU A 384 0  10.979 36.551 47.998 1.00 19.10
   ATOM 2924 OE1 GLU A 384 0  12.101 36.050 48.218 1.00 20.69
   ATOM 2925 OE2 GLU A 384 0  10.018 36.405 48.773 1.00 21.22
   ATOM 2926 N   LEU A 385 0   9.326 39.182 43.948 1.00 19.78
10 ATOM 2927 CA  LEU A 385 0   7.966 39.153 43.463 1.00 21.07
   ATOM 2928 C   LEU A 385 0   7.391 37.738 43.591 1.00 20.91
   ATOM 2929 O   LEU A 385 0   8.043 36.790 43.113 1.00 21.40
   ATOM 2930 CB  LEU A 385 0   7.881 39.466 41.959 1.00 20.92
   ATOM 2931 CG  LEU A 385 0   8.393 40.795 41.457 1.00 23.75
15 ATOM 2932 CD1 LEU A 385 0   8.118 40.984 39.962 1.00 23.01
   ATOM 2933 CD2 LEU A 385 0   7.827 41.977 42.244 1.00 22.40
   ATOM 2934 N   VAL A 386 0   6.182 37.574 44.099 1.00 20.91
   ATOM 2935 CA  VAL A 386 0   5.510 36.274 44.189 1.00 19.03
   ATOM 2936 C   VAL A 386 0   4.228 36.334 43.356 1.00 21.11
20 ATOM 2937 O   VAL A 386 0   3.465 37.326 43.516 1.00 20.56
   ATOM 2938 CB  VAL A 386 0   5.159 35.967 45.654 1.00 20.91
   ATOM 2939 CG1 VAL A 386 0   4.518 34.575 45.739 1.00 20.40
   ATOM 2940 CG2 VAL A 386 0   6.321 36.044 46.625 1.00 19.89
   ATOM 2941 N   VAL A 387 0   4.011 35.469 42.358 1.00 20.02
25 ATOM 2942 CA  VAL A 387 0   2.817 35.515 41.491 1.00 20.83
   ATOM 2943 C   VAL A 387 0   2.119 34.152 41.385 1.00 21.15
   ATOM 2944 O   VAL A 387 0   2.369 33.285 40.528 1.00 19.97
   ATOM 2945 CB  VAL A 387 0   3.163 36.076 40.104 1.00 20.91
   ATOM 2946 CG1 VAL A 387 0   1.917 36.472 39.297 1.00 22.49
30 ATOM 2947 CG2 VAL A 387 0   3.959 37.393 40.171 1.00 22.24
   ATOM 2948 N   PRO A 388 0   1.262 33.832 42.358 1.00 20.55
   ATOM 2949 CA  PRO A 388 0   0.570 32.548 42.483 1.00 20.93
   ATOM 2950 C   PRO A 388 0  -0.271 32.226 41.264 1.00 20.76
   ATOM 2951 O   PRO A 388 0  -0.928 33.118 40.715 1.00 19.53
35 ATOM 2952 CB  PRO A 388 0  -0.310 32.559 43.757 1.00 20.54
   ATOM 2953 CG  PRO A 388 0   0.280 33.766 44.482 1.00 21.86
   ATOM 2954 CD  PRO A 388 0   0.841 34.707 43.438 1.00 20.83
   ATOM 2955 N   ALA A 389 0  -0.160 30.986 40.807 1.00 21.68
```

5032-WO

108

```
   ATOM 2956 CA  ALA A 389  0  -0.983 30.617 39.640 1.00 24.20
   ATOM 2957 C   ALA A 389  0  -2.394 30.320 40.148 1.00 25.02
   ATOM 2958 O   ALA A 389  0  -2.619 30.162 41.350 1.00 24.19
   ATOM 2959 CB  ALA A 389  0  -0.383 29.403 38.968 1.00 23.67
 5 ATOM 2960 N   GLY A 390  0  -3.309 30.143 39.222 1.00 28.43
   ATOM 2961 CA  GLY A 390  0  -4.713 29.811 39.539 1.00 28.47
   ATOM 2962 C   GLY A 390  0  -5.624 30.325 38.431 1.00 28.63
   ATOM 2963 O   GLY A 390  0  -6.512 29.630 37.937 1.00 31.26
   ATOM 2964 N   VAL A 391  0  -5.402 31.531 37.961 1.00 27.11
10 ATOM 2965 CA  VAL A 391  0  -6.234 32.164 36.962 1.00 26.51
   ATOM 2966 C   VAL A 391  0  -6.246 31.377 35.666 1.00 29.59
   ATOM 2967 O   VAL A 391  0  -5.274 30.775 35.181 1.00 30.61
   ATOM 2968 CB  VAL A 391  0  -5.835 33.634 36.788 1.00 25.83
   ATOM 2969 CG1 VAL A 391  0  -4.584 33.787 35.937 1.00 24.18
15 ATOM 2970 CG2 VAL A 391  0  -7.017 34.419 36.219 1.00 24.11
   ATOM 2971 N   LEU A 392  0  -7.439 31.392 35.058 1.00 30.83
   ATOM 2972 CA  LEU A 392  0  -7.705 30.604 33.867 1.00 30.29
   ATOM 2973 C   LEU A 392  0  -6.809 31.004 32.710 1.00 27.38
   ATOM 2974 O   LEU A 392  0  -6.316 32.113 32.665 1.00 24.62
20 ATOM 2975 CB  LEU A 392  0  -9.173 30.726 33.436 1.00 32.58
   ATOM 2976 CG  LEU A 392  0  -9.711 32.126 33.189 1.00 33.97
   ATOM 2977 CD1 LEU A 392  0  -9.411 32.626 31.786 1.00 34.78
   ATOM 2978 CD2 LEU A 392  0 -11.225 32.122 33.463 1.00 36.03
   ATOM 2979 N   GLY A 393  0  -6.725 30.074 31.754 1.00 26.24
25 ATOM 2980 CA  GLY A 393  0  -5.936 30.302 30.554 1.00 25.54
   ATOM 2981 C   GLY A 393  0  -4.458 29.994 30.710 1.00 25.81
   ATOM 2982 O   GLY A 393  0  -3.686 30.361 29.820 1.00 26.67
   ATOM 2983 N   GLY A 394  0  -4.033 29.379 31.803 1.00 25.84
   ATOM 2984 CA  GLY A 394  0  -2.615 29.112 32.035 1.00 25.94
30 ATOM 2985 C   GLY A 394  0  -2.140 27.844 31.348 1.00 26.00
   ATOM 2986 O   GLY A 394  0  -2.884 27.193 30.625 1.00 25.18
   ATOM 2987 N   PRO A 395  0  -0.860 27.527 31.517 1.00 24.26
   ATOM 2988 CA  PRO A 395  0   0.051 28.258 32.364 1.00 21.79
   ATOM 2989 C   PRO A 395  0   0.517 29.518 31.660 1.00 19.29
35 ATOM 2990 O   PRO A 395  0   0.704 29.597 30.445 1.00 17.41
   ATOM 2991 CB  PRO A 395  0   1.159 27.279 32.794 1.00 22.52
   ATOM 2992 CG  PRO A 395  0   1.062 26.223 31.758 1.00 24.35
   ATOM 2993 CD  PRO A 395  0  -0.241 26.312 30.973 1.00 24.87
```

```
ATOM 2994  N   HIS A 396  0    0.586 30.591 32.451 1.00 16.97
ATOM 2995  CA  HIS A 396  0    0.970 31.917 31.980 1.00 15.05
ATOM 2996  C   HIS A 396  0    2.477 32.137 32.186 1.00 15.41
ATOM 2997  O   HIS A 396  0    3.039 32.025 33.275 1.00 14.21
ATOM 2998  CB  HIS A 396  0    0.288 32.989 32.842 1.00 15.40
ATOM 2999  CG  HIS A 396  0   -1.224 32.924 32.737 1.00 18.23
ATOM 3000  ND1 HIS A 396  0   -1.942 33.504 31.702 1.00 16.23
ATOM 3001  CD2 HIS A 396  0   -2.109 32.319 33.557 1.00 17.00
ATOM 3002  CE1 HIS A 396  0   -3.218 33.262 31.906 1.00 18.22
ATOM 3003  NE2 HIS A 396  0   -3.343 32.526 33.014 1.00 19.08
ATOM 3004  N   PRO A 397  0    3.143 32.403 31.090 1.00 14.69
ATOM 3005  CA  PRO A 397  0    4.593 32.617 31.080 1.00 16.91
ATOM 3006  C   PRO A 397  0    4.818 34.129 31.202 1.00 17.59
ATOM 3007  O   PRO A 397  0    4.524 34.843 30.235 1.00 17.59
ATOM 3008  CB  PRO A 397  0    5.076 32.040 29.757 1.00 16.63
ATOM 3009  CG  PRO A 397  0    3.785 31.844 28.978 1.00 17.83
ATOM 3010  CD  PRO A 397  0    2.620 32.464 29.736 1.00 14.36
ATOM 3011  N   PHE A 398  0    5.242 34.590 32.377 1.00 16.39
ATOM 3012  CA  PHE A 398  0    5.462 36.019 32.529 1.00 15.95
ATOM 3013  C   PHE A 398  0    6.906 36.365 32.168 1.00 15.74
ATOM 3014  O   PHE A 398  0    7.846 35.619 32.444 1.00 15.78
ATOM 3015  CB  PHE A 398  0    5.173 36.455 33.963 1.00 17.20
ATOM 3016  CG  PHE A 398  0    3.817 37.073 34.169 1.00 19.23
ATOM 3017  CD1 PHE A 398  0    2.673 36.299 34.005 1.00 19.58
ATOM 3018  CD2 PHE A 398  0    3.688 38.403 34.537 1.00 19.42
ATOM 3019  CE1 PHE A 398  0    1.409 36.832 34.198 1.00 19.83
ATOM 3020  CE2 PHE A 398  0    2.405 38.933 34.709 1.00 21.46
ATOM 3021  CZ  PHE A 398  0    1.260 38.162 34.539 1.00 19.65
ATOM 3022  N   HIS A 399  0    7.080 37.562 31.640 1.00 14.77
ATOM 3023  CA  HIS A 399  0    8.374 38.089 31.333 1.00 14.75
ATOM 3024  C   HIS A 399  0    8.580 39.496 31.872 1.00 17.67
ATOM 3025  O   HIS A 399  0    7.635 40.308 31.925 1.00 18.29
ATOM 3026  CB  HIS A 399  0    8.582 37.968 29.861 1.00 14.01
ATOM 3027  CG  HIS A 399  0    8.747 39.105 28.962 1.00 16.26
ATOM 3028  ND1 HIS A 399  0    9.957 39.511 28.446 1.00 15.35
ATOM 3029  CD2 HIS A 399  0    7.788 39.903 28.386 1.00 17.58
ATOM 3030  CE1 HIS A 399  0    9.764 40.507 27.593 1.00 15.61
ATOM 3031  NE2 HIS A 399  0    8.457 40.770 27.548 1.00 17.52
```

```
5032-WO

110

ATOM   3032  N   LEU A 400  0    9.837  39.771  32.201  1.00 15.57
     ATOM   3033  CA  LEU A 400  0   10.220  41.061  32.745  1.00 16.93
     ATOM   3034  C   LEU A 400  0   11.207  41.732  31.788  1.00 16.51
     ATOM   3035  O   LEU A 400  0   12.268  41.175  31.510  1.00 15.77
  5  ATOM   3036  CB  LEU A 400  0   10.913  40.825  34.084  1.00 18.17
     ATOM   3037  CG  LEU A 400  0   10.877  41.741  35.288  1.00 21.27
     ATOM   3038  CD1 LEU A 400  0   12.130  41.638  36.151  1.00 19.27
     ATOM   3039  CD2 LEU A 400  0   10.536  43.166  34.926  1.00 19.86
     ATOM   3040  N   HIS A 401  0   10.945  42.916  31.321  1.00 14.34
 10  ATOM   3041  CA  HIS A 401  0   11.830  43.707  30.508  1.00 16.06
     ATOM   3042  C   HIS A 401  0   12.924  44.300  31.428  1.00 16.15
     ATOM   3043  O   HIS A 401  0   12.644  44.543  32.600  1.00 13.61
     ATOM   3044  CB  HIS A 401  0   11.105  44.884  29.843  1.00 13.27
     ATOM   3045  CG  HIS A 401  0   10.184  44.441  28.751  1.00 14.50
 15  ATOM   3046  ND1 HIS A 401  0   10.201  44.973  27.479  1.00 14.96
     ATOM   3047  CD2 HIS A 401  0    9.202  43.492  28.750  1.00 12.35
     ATOM   3048  CE1 HIS A 401  0    9.263  44.387  26.725  1.00 12.61
     ATOM   3049  NE2 HIS A 401  0    8.677  43.507  27.492  1.00 12.41
     ATOM   3050  N   GLY A 402  0   14.103  44.549  30.855  1.00 15.59
 20  ATOM   3051  CA  GLY A 402  0   15.152  45.209  31.598  1.00 15.18
     ATOM   3052  C   GLY A 402  0   16.009  44.351  32.510  1.00 15.96
     ATOM   3053  O   GLY A 402  0   16.927  44.898  33.170  1.00 16.30
     ATOM   3054  N   HIS A 403  0   15.618  43.147  32.893  1.00 12.96
     ATOM   3055  CA  HIS A 403  0   16.282  42.337  33.873  1.00 15.00
 25  ATOM   3056  C   HIS A 403  0   16.226  40.839  33.586  1.00 15.22
     ATOM   3057  O   HIS A 403  0   15.253  40.381  32.971  1.00 16.16
     ATOM   3058  CB  HIS A 403  0   15.525  42.478  35.227  1.00 14.13
     ATOM   3059  CG  HIS A 403  0   15.571  43.829  35.827  1.00 16.69
     ATOM   3060  ND1 HIS A 403  0   16.604  44.253  36.649  1.00 16.13
 30  ATOM   3061  CD2 HIS A 403  0   14.744  44.911  35.659  1.00 15.50
     ATOM   3062  CE1 HIS A 403  0   16.425  45.520  37.002  1.00 15.02
     ATOM   3063  NE2 HIS A 403  0   15.285  45.905  36.430  1.00 16.15
     ATOM   3064  N   ALA A 404  0   17.138  40.054  34.113  1.00 13.71
     ATOM   3065  CA  ALA A 404  0   17.039  38.607  34.158  1.00 12.60
 35  ATOM   3066  C   ALA A 404  0   16.771  38.370  35.649  1.00 12.31
     ATOM   3067  O   ALA A 404  0   17.156  39.291  36.373  1.00 13.94
     ATOM   3068  CB  ALA A 404  0   18.249  37.819  33.721  1.00 13.84
     ATOM   3069  N   PHE A 405  0   16.085  37.356  36.126  1.00 12.21
```

5032-WO

111

```
ATOM 3070 CA  PHE A 405 0  15.813 37.235 37.559 1.00 11.64
ATOM 3071 C   PHE A 405 0  16.177 35.821 38.008 1.00 12.55
ATOM 3072 O   PHE A 405 0  16.196 34.883 37.201 1.00 12.23
ATOM 3073 CB  PHE A 405 0  14.325 37.487 37.907 1.00 11.82
ATOM 3074 CG  PHE A 405 0  13.382 36.893 36.879 1.00 11.75
ATOM 3075 CD1 PHE A 405 0  13.030 35.557 36.933 1.00 10.76
ATOM 3076 CD2 PHE A 405 0  12.917 37.663 35.824 1.00 11.55
ATOM 3077 CE1 PHE A 405 0  12.189 35.002 35.978 1.00 11.52
ATOM 3078 CE2 PHE A 405 0  12.087 37.112 34.862 1.00 13.32
ATOM 3079 CZ  PHE A 405 0  11.692 35.767 34.946 1.00 11.45
ATOM 3080 N   SER A 406 0  16.414 35.625 39.288 1.00 12.86
ATOM 3081 CA  SER A 406 0  16.660 34.286 39.796 1.00 13.43
ATOM 3082 C   SER A 406 0  15.276 33.712 40.130 1.00 13.49
ATOM 3083 O   SER A 406 0  14.518 34.375 40.847 1.00 10.13
ATOM 3084 CB  SER A 406 0  17.433 34.290 41.123 1.00 13.78
ATOM 3085 OG  SER A 406 0  18.708 34.834 40.938 1.00 16.72
ATOM 3086 N   VAL A 407 0  15.100 32.453 39.741 1.00 14.53
ATOM 3087 CA  VAL A 407 0  13.853 31.777 40.093 1.00 13.90
ATOM 3088 C   VAL A 407 0  14.160 30.943 41.325 1.00 14.53
ATOM 3089 O   VAL A 407 0  14.513 29.753 41.262 1.00 14.62
ATOM 3090 CB  VAL A 407 0  13.333 30.903 38.941 1.00 16.43
ATOM 3091 CG1 VAL A 407 0  11.969 30.317 39.341 1.00 16.69
ATOM 3092 CG2 VAL A 407 0  13.272 31.682 37.626 1.00 14.90
ATOM 3093 N   VAL A 408 0  13.971 31.544 42.485 1.00 14.32
ATOM 3094 CA  VAL A 408 0  14.173 30.947 43.780 1.00 15.47
ATOM 3095 C   VAL A 408 0  13.115 29.870 44.049 1.00 16.51
ATOM 3096 O   VAL A 408 0  13.387 28.927 44.812 1.00 17.39
ATOM 3097 CB  VAL A 408 0  14.280 31.967 44.932 1.00 15.75
ATOM 3098 CG1 VAL A 408 0  15.345 33.015 44.600 1.00 14.81
ATOM 3099 CG2 VAL A 408 0  12.952 32.693 45.189 1.00 15.99
ATOM 3100 N   ARG A 409 0  11.972 29.940 43.387 1.00 16.28
ATOM 3101 CA  ARG A 409 0  10.960 28.900 43.570 1.00 17.67
ATOM 3102 C   ARG A 409 0  10.217 28.757 42.236 1.00 17.09
ATOM 3103 O   ARG A 409 0   9.585 29.698 41.763 1.00 15.25
ATOM 3104 CB  ARG A 409 0   9.993 29.143 44.718 1.00 17.87
ATOM 3105 CG  ARG A 409 0   8.796 28.188 44.663 1.00 21.12
ATOM 3106 CD  ARG A 409 0   8.008 28.181 45.945 1.00 22.10
ATOM 3107 NE  ARG A 409 0   6.801 27.370 45.955 1.00 24.80
```

```
ATOM 3108 CZ  ARG A 409 0   5.918 27.361 46.961 1.00 25.93
ATOM 3109 NH1 ARG A 409 0   4.859 26.569 46.877 1.00 27.14
ATOM 3110 NH2 ARG A 409 0   6.068 28.117 48.046 1.00 25.44
ATOM 3111 N   SER A 410 0  10.366 27.576 41.668 1.00 16.33
ATOM 3112 CA  SER A 410 0   9.802 27.245 40.373 1.00 18.33
ATOM 3113 C   SER A 410 0   8.406 26.612 40.492 1.00 18.60
ATOM 3114 O   SER A 410 0   7.941 26.223 41.566 1.00 16.94
ATOM 3115 CB  SER A 410 0  10.724 26.199 39.705 1.00 19.51
ATOM 3116 OG  SER A 410 0  11.718 26.865 38.933 1.00 20.28
ATOM 3117 N   ALA A 411 0   7.754 26.551 39.343 1.00 18.19
ATOM 3118 CA  ALA A 411 0   6.458 25.899 39.231 1.00 19.76
ATOM 3119 C   ALA A 411 0   6.667 24.406 39.474 1.00 22.62
ATOM 3120 O   ALA A 411 0   7.636 23.759 39.067 1.00 20.97
ATOM 3121 CB  ALA A 411 0   5.873 26.075 37.841 1.00 17.13
ATOM 3122 N   GLY A 412 0   5.710 23.856 40.229 1.00 26.30
ATOM 3123 CA  GLY A 412 0   5.714 22.442 40.558 1.00 27.05
ATOM 3124 C   GLY A 412 0   6.692 22.150 41.677 1.00 29.22
ATOM 3125 O   GLY A 412 0   6.917 20.959 41.944 1.00 32.10
ATOM 3126 N   SER A 413 0   7.293 23.139 42.322 1.00 28.66
ATOM 3127 CA  SER A 413 0   8.223 22.871 43.400 1.00 28.58
ATOM 3128 C   SER A 413 0   7.757 23.600 44.642 1.00 29.64
ATOM 3129 O   SER A 413 0   7.279 24.735 44.524 1.00 30.66
ATOM 3130 CB  SER A 413 0   9.610 23.407 43.015 1.00 30.12
ATOM 3131 OG  SER A 413 0  10.484 23.233 44.127 1.00 31.74
ATOM 3132 N   SER A 414 0   7.902 23.031 45.819 1.00 29.19
ATOM 3133 CA  SER A 414 0   7.523 23.753 47.033 1.00 30.71
ATOM 3134 C   SER A 414 0   8.762 24.124 47.834 1.00 30.51
ATOM 3135 O   SER A 414 0   8.746 24.453 49.017 1.00 31.90
ATOM 3136 CB  SER A 414 0   6.612 22.832 47.853 1.00 31.10
ATOM 3137 OG  SER A 414 0   7.438 21.764 48.299 1.00 34.24
ATOM 3138 N   THR A 415 0   9.919 24.063 47.194 1.00 30.60
ATOM 3139 CA  THR A 415 0  11.194 24.336 47.860 1.00 30.60
ATOM 3140 C   THR A 415 0  11.819 25.614 47.291 1.00 27.71
ATOM 3141 O   THR A 415 0  11.582 25.998 46.137 1.00 27.49
ATOM 3142 CB  THR A 415 0  12.089 23.095 47.747 1.00 32.16
ATOM 3143 OG1 THR A 415 0  13.411 23.441 47.285 1.00 35.60
ATOM 3144 CG2 THR A 415 0  11.599 22.103 46.710 1.00 34.11
ATOM 3145 N   TYR A 416 0  12.662 26.268 48.053 1.00 24.34
```

```
ATOM 3146 CA  TYR A 416  0  13.288 27.513 47.621 1.00 25.69
ATOM 3147 C   TYR A 416  0  14.782 27.297 47.392 1.00 24.69
ATOM 3148 O   TYR A 416  0  15.364 26.603 48.211 1.00 25.96
ATOM 3149 CB  TYR A 416  0  13.129 28.633 48.659 1.00 23.79
ATOM 3150 CG  TYR A 416  0  11.690 29.091 48.794 1.00 24.53
ATOM 3151 CD1 TYR A 416  0  10.789 28.387 49.596 1.00 24.14
ATOM 3152 CD2 TYR A 416  0  11.230 30.219 48.131 1.00 23.99
ATOM 3153 CE1 TYR A 416  0   9.474 28.799 49.713 1.00 23.70
ATOM 3154 CE2 TYR A 416  0   9.922 30.641 48.248 1.00 23.96
ATOM 3155 CZ  TYR A 416  0   9.050 29.929 49.054 1.00 23.73
ATOM 3156 OH  TYR A 416  0   7.744 30.337 49.152 1.00 23.53
ATOM 3157 N   ASN A 417  0  15.360 27.867 46.353 1.00 22.34
ATOM 3158 CA  ASN A 417  0  16.810 27.702 46.223 1.00 20.83
ATOM 3159 C   ASN A 417  0  17.425 29.089 46.092 1.00 20.43
ATOM 3160 O   ASN A 417  0  17.247 29.761 45.082 1.00 20.00
ATOM 3161 CB  ASN A 417  0  17.179 26.763 45.086 1.00 19.72
ATOM 3162 CG  ASN A 417  0  18.660 26.716 44.758 1.00 19.50
ATOM 3163 OD1 ASN A 417  0  19.485 27.313 45.465 1.00 20.18
ATOM 3164 ND2 ASN A 417  0  18.981 26.043 43.660 1.00 17.21
ATOM 3165 N   PHE A 418  0  18.153 29.508 47.119 1.00 20.79
ATOM 3166 CA  PHE A 418  0  18.831 30.797 47.049 1.00 20.77
ATOM 3167 C   PHE A 418  0  20.314 30.613 46.725 1.00 20.47
ATOM 3168 O   PHE A 418  0  20.973 31.618 46.517 1.00 19.47
ATOM 3169 CB  PHE A 418  0  18.764 31.542 48.384 1.00 20.52
ATOM 3170 CG  PHE A 418  0  17.332 31.821 48.753 1.00 22.19
ATOM 3171 CD1 PHE A 418  0  16.644 30.947 49.578 1.00 21.36
ATOM 3172 CD2 PHE A 418  0  16.697 32.951 48.244 1.00 21.95
ATOM 3173 CE1 PHE A 418  0  15.320 31.208 49.919 1.00 21.64
ATOM 3174 CE2 PHE A 418  0  15.386 33.198 48.599 1.00 22.81
ATOM 3175 CZ  PHE A 418  0  14.694 32.325 49.419 1.00 22.57
ATOM 3176 N   VAL A 419  0  20.816 29.380 46.732 1.00 19.72
ATOM 3177 CA  VAL A 419  0  22.272 29.235 46.564 1.00 19.96
ATOM 3178 C   VAL A 419  0  22.682 29.261 45.114 1.00 20.65
ATOM 3179 O   VAL A 419  0  23.634 29.875 44.671 1.00 21.02
ATOM 3180 CB  VAL A 419  0  22.708 27.888 47.200 1.00 21.81
ATOM 3181 CG1 VAL A 419  0  23.954 27.291 46.588 1.00 21.97
ATOM 3182 CG2 VAL A 419  0  22.885 28.098 48.713 1.00 21.55
ATOM 3183 N   ASN A 420  0  21.867 28.585 44.327 1.00 19.77
```

```
ATOM 3184 CA  ASN A 420  0   22.076 28.232 42.967 1.00 21.81
ATOM 3185 C   ASN A 420  0   21.028 28.263 41.891 1.00 20.21
ATOM 3186 O   ASN A 420  0   21.046 27.407 41.004 1.00 20.13
ATOM 3187 CB  ASN A 420  0   22.166 26.587 43.207 1.00 21.91
ATOM 3188 CG  ASN A 420  0   23.441 26.231 42.529 1.00 24.12
ATOM 3189 OD1 ASN A 420  0   23.933 25.113 42.403 1.00 26.75
ATOM 3190 ND2 ASN A 420  0   24.051 27.318 42.027 1.00 25.42
ATOM 3191 N   PRO A 421  0   19.987 29.034 42.038 1.00 20.27
ATOM 3192 CA  PRO A 421  0   18.808 28.951 41.183 1.00 17.57
ATOM 3193 C   PRO A 421  0   19.100 29.369 39.778 1.00 15.76
ATOM 3194 O   PRO A 421  0   19.907 30.281 39.586 1.00 15.13
ATOM 3195 CB  PRO A 421  0   17.769 29.850 41.894 1.00 19.52
ATOM 3196 CG  PRO A 421  0   18.674 30.863 42.589 1.00 19.88
ATOM 3197 CD  PRO A 421  0   19.847 30.057 43.095 1.00 20.45
ATOM 3198 N   VAL A 422  0   18.385 28.803 38.820 1.00 15.28
ATOM 3199 CA  VAL A 422  0   18.502 29.239 37.420 1.00 13.48
ATOM 3200 C   VAL A 422  0   18.157 30.721 37.397 1.00 14.53
ATOM 3201 O   VAL A 422  0   17.340 31.208 38.183 1.00 14.44
ATOM 3202 CB  VAL A 422  0   17.498 28.435 36.585 1.00 15.23
ATOM 3203 CG1 VAL A 422  0   16.032 28.747 36.937 1.00 13.85
ATOM 3204 CG2 VAL A 422  0   17.681 28.514 35.089 1.00 13.26
ATOM 3205 N   LYS A 423  0   18.691 31.447 36.451 1.00 15.35
ATOM 3206 CA  LYS A 423  0   18.366 32.831 36.189 1.00 17.23
ATOM 3207 C   LYS A 423  0   17.759 32.891 34.784 1.00 16.55
ATOM 3208 O   LYS A 423  0   18.284 32.189 33.909 1.00 16.92
ATOM 3209 CB  LYS A 423  0   19.627 33.681 36.174 1.00 19.33
ATOM 3210 CG  LYS A 423  0   20.118 33.985 37.565 1.00 24.09
ATOM 3211 CD  LYS A 423  0   21.065 35.206 37.466 1.00 27.32
ATOM 3212 CE  LYS A 423  0   22.470 34.596 37.263 1.00 28.78
ATOM 3213 NZ  LYS A 423  0   23.128 34.482 38.595 1.00 29.50
ATOM 3214 N   ARG A 424  0   16.630 33.570 34.617 1.00 15.85
ATOM 3215 CA  ARG A 424  0   16.016 33.592 33.294 1.00 16.20
ATOM 3216 C   ARG A 424  0   15.235 34.890 33.105 1.00 14.86
ATOM 3217 O   ARG A 424  0   15.354 35.771 33.959 1.00 14.64
ATOM 3218 CB  ARG A 424  0   15.158 32.367 32.994 1.00 16.11
ATOM 3219 CG  ARG A 424  0   14.036 31.864 33.849 1.00 14.06
ATOM 3220 CD  ARG A 424  0   13.447 30.506 33.427 1.00 11.65
ATOM 3221 NE  ARG A 424  0   13.422 30.395 31.961 1.00  9.03
```

```
ATOM 3222 CZ  ARG A 424 0  13.312 29.234 31.319 1.00 10.63
ATOM 3223 NH1 ARG A 424 0  13.185 28.133 32.082 1.00 11.02
ATOM 3224 NH2 ARG A 424 0  13.403 29.213 29.988 1.00  8.52
ATOM 3225 N   ASP A 425 0  14.519 34.975 31.995 1.00 13.83
ATOM 3226 CA  ASP A 425 0  13.751 36.209 31.752 1.00 15.00
ATOM 3227 C   ASP A 425 0  12.298 35.929 31.359 1.00 15.65
ATOM 3228 O   ASP A 425 0  11.474 36.850 31.271 1.00 15.11
ATOM 3229 CB  ASP A 425 0  14.499 37.130 30.797 1.00 12.96
ATOM 3230 CG  ASP A 425 0  14.609 36.652 29.371 1.00 14.32
ATOM 3231 OD1 ASP A 425 0  13.697 35.957 28.818 1.00 13.30
ATOM 3232 OD2 ASP A 425 0  15.632 37.003 28.729 1.00 13.76
ATOM 3233 N   VAL A 426 0  11.883 34.675 31.206 1.00 15.21
ATOM 3234 CA  VAL A 426 0  10.530 34.229 30.984 1.00 13.92
ATOM 3235 C   VAL A 426 0  10.247 33.000 31.865 1.00 13.98
ATOM 3236 O   VAL A 426 0  10.891 31.965 31.696 1.00 15.56
ATOM 3237 CB  VAL A 426 0  10.128 33.807 29.567 1.00 12.49
ATOM 3238 CG1 VAL A 426 0   8.629 33.473 29.531 1.00 13.99
ATOM 3239 CG2 VAL A 426 0  10.390 34.874 28.536 1.00 12.37
ATOM 3240 N   VAL A 427 0   9.274 33.090 32.766 1.00 12.82
ATOM 3241 CA  VAL A 427 0   8.979 31.969 33.639 1.00 12.27
ATOM 3242 C   VAL A 427 0   7.495 31.589 33.651 1.00 14.14
ATOM 3243 O   VAL A 427 0   6.594 32.426 33.682 1.00 14.10
ATOM 3244 CB  VAL A 427 0   9.458 32.315 35.056 1.00 11.46
ATOM 3245 CG1 VAL A 427 0   8.732 33.549 35.594 1.00  9.39
ATOM 3246 CG2 VAL A 427 0   9.353 31.116 35.982 1.00 10.53
ATOM 3247 N   SER A 428 0   7.229 30.282 33.622 1.00 13.74
ATOM 3248 CA  SER A 428 0   5.889 29.766 33.721 1.00 15.16
ATOM 3249 C   SER A 428 0   5.445 29.878 35.171 1.00 15.48
ATOM 3250 O   SER A 428 0   6.186 29.505 36.087 1.00 15.38
ATOM 3251 CB  SER A 428 0   5.776 28.323 33.206 1.00 16.37
ATOM 3252 OG  SER A 428 0   4.464 27.821 33.484 1.00 17.00
ATOM 3253 N   LEU A 429 0   4.246 30.376 35.399 1.00 15.74
ATOM 3254 CA  LEU A 429 0   3.686 30.489 36.744 1.00 15.73
ATOM 3255 C   LEU A 429 0   3.035 29.184 37.198 1.00 16.41
ATOM 3256 O   LEU A 429 0   2.741 29.041 38.390 1.00 15.74
ATOM 3257 CB  LEU A 429 0   2.669 31.627 36.886 1.00 14.99
ATOM 3258 CG  LEU A 429 0   3.155 33.027 36.540 1.00 16.60
ATOM 3259 CD1 LEU A 429 0   2.043 34.042 36.862 1.00 17.78
```

5032-WO

116

```
   ATOM 3260 CD2 LEU A 429 0   4.438 33.386 37.281 1.00 16.26
   ATOM 3261 N   GLY A 430 0   2.913 28.218 36.295 1.00 17.70
   ATOM 3262 CA  GLY A 430 0   2.419 26.904 36.701 1.00 19.84
   ATOM 3263 C   GLY A 430 0   0.894 26.836 36.778 1.00 20.72
 5 ATOM 3264 O   GLY A 430 0   0.178 27.498 36.029 1.00 20.89
   ATOM 3265 N   VAL A 431 0   0.428 26.056 37.729 1.00 22.04
   ATOM 3266 CA  VAL A 431 0  -0.956 25.713 37.966 1.00 22.61
   ATOM 3267 C   VAL A 431 0  -1.337 26.028 39.409 1.00 23.06
   ATOM 3268 O   VAL A 431 0  -0.476 26.392 40.218 1.00 22.42
10 ATOM 3269 CB  VAL A 431 0  -1.245 24.193 37.768 1.00 23.03
   ATOM 3270 CG1 VAL A 431 0  -0.795 23.672 36.416 1.00 22.74
   ATOM 3271 CG2 VAL A 431 0  -0.574 23.315 38.820 1.00 22.77
   ATOM 3272 N   THR A 432 0  -2.615 25.835 39.704 1.00 23.88
   ATOM 3273 CA  THR A 432 0  -3.168 26.067 41.041 1.00 24.18
15 ATOM 3274 C   THR A 432 0  -2.324 25.401 42.092 1.00 23.94
   ATOM 3275 O   THR A 432 0  -1.915 24.249 41.909 1.00 24.69
   ATOM 3276 CB  THR A 432 0  -4.625 25.565 41.069 1.00 25.75
   ATOM 3277 OG1 THR A 432 0  -5.336 26.344 40.087 1.00 25.87
   ATOM 3278 CG2 THR A 432 0  -5.319 25.800 42.398 1.00 26.65
20 ATOM 3279 N   GLY A 433 0  -1.924 26.136 43.124 1.00 24.45
   ATOM 3280 CA  GLY A 433 0  -1.035 25.589 44.159 1.00 22.27
   ATOM 3281 C   GLY A 433 0   0.394 26.120 43.983 1.00 23.26
   ATOM 3282 O   GLY A 433 0   1.103 26.212 45.000 1.00 23.30
   ATOM 3283 N   ASP A 434 0   0.833 26.481 42.776 1.00 21.12
25 ATOM 3284 CA  ASP A 434 0   2.192 26.986 42.586 1.00 20.62
   ATOM 3285 C   ASP A 434 0   2.360 28.408 43.126 1.00 22.36
   ATOM 3286 O   ASP A 434 0   1.425 29.225 43.076 1.00 21.24
   ATOM 3287 CB  ASP A 434 0   2.548 27.024 41.087 1.00 18.78
   ATOM 3288 CG  ASP A 434 0   2.827 25.616 40.597 1.00 19.71
30 ATOM 3289 OD1 ASP A 434 0   3.304 24.828 41.409 1.00 20.43
   ATOM 3290 OD2 ASP A 434 0   2.596 25.242 39.432 1.00 21.58
   ATOM 3291 N   GLU A 435 0   3.585 28.721 43.562 1.00 22.08
   ATOM 3292 CA  GLU A 435 0   3.853 30.077 44.068 1.00 23.24
   ATOM 3293 C   GLU A 435 0   5.244 30.512 43.612 1.00 20.24
35 ATOM 3294 O   GLU A 435 0   6.201 30.611 44.372 1.00 19.50
   ATOM 3295 CB  GLU A 435 0   3.659 30.068 45.572 1.00 25.56
   ATOM 3296 CG  GLU A 435 0   3.739 31.409 46.258 1.00 30.52
   ATOM 3297 CD  GLU A 435 0   3.107 31.350 47.657 1.00 35.00
```

```
ATOM  3298 OE1 GLU A 435  0   2.093 30.603 47.760 1.00 35.71
ATOM  3299 OE2 GLU A 435  0   3.658 32.020 48.579 1.00 35.91
ATOM  3300 N   VAL A 436  0   5.344 30.690 42.297 1.00 17.80
ATOM  3301 CA  VAL A 436  0   6.564 31.083 41.640 1.00 15.30
ATOM  3302 C   VAL A 436  0   7.049 32.416 42.221 1.00 17.15
ATOM  3303 O   VAL A 436  0   6.326 33.402 42.275 1.00 17.48
ATOM  3304 CB  VAL A 436  0   6.360 31.219 40.129 1.00 14.63
ATOM  3305 CG1 VAL A 436  0   7.463 32.009 39.454 1.00 10.79
ATOM  3306 CG2 VAL A 436  0   6.238 29.806 39.536 1.00 14.13
ATOM  3307 N   THR A 437  0   8.290 32.391 42.691 1.00 16.51
ATOM  3308 CA  THR A 437  0   8.940 33.505 43.364 1.00 16.19
ATOM  3309 C   THR A 437  0  10.254 33.817 42.668 1.00 15.24
ATOM  3310 O   THR A 437  0  11.100 32.940 42.419 1.00 15.47
ATOM  3311 CB  THR A 437  0   9.190 33.067 44.827 1.00 14.95
ATOM  3312 OG1 THR A 437  0   7.969 32.499 45.308 1.00 13.50
ATOM  3313 CG2 THR A 437  0   9.599 34.232 45.697 1.00 13.41
ATOM  3314 N   ILE A 438  0  10.413 35.059 42.251 1.00 13.38
ATOM  3315 CA  ILE A 438  0  11.597 35.471 41.510 1.00 15.78
ATOM  3316 C   ILE A 438  0  12.292 36.590 42.264 1.00 15.86
ATOM  3317 O   ILE A 438  0  11.617 37.270 43.048 1.00 17.32
ATOM  3318 CB  ILE A 438  0  11.249 35.848 40.053 1.00 15.40
ATOM  3319 CG1 ILE A 438  0  10.340 37.055 39.985 1.00 15.85
ATOM  3320 CG2 ILE A 438  0  10.602 34.653 39.346 1.00 17.11
ATOM  3321 CD1 ILE A 438  0   9.971 37.607 38.632 1.00 17.49
ATOM  3322 N   ARG A 439  0  13.599 36.789 42.055 1.00 16.02
ATOM  3323 CA  ARG A 439  0  14.315 37.896 42.671 1.00 13.90
ATOM  3324 C   ARG A 439  0  15.181 38.645 41.676 1.00 13.52
ATOM  3325 O   ARG A 439  0  15.748 38.056 40.762 1.00 14.74
ATOM  3326 CB  ARG A 439  0  15.193 37.501 43.850 1.00 15.15
ATOM  3327 CG  ARG A 439  0  14.457 37.235 45.147 1.00 14.83
ATOM  3328 CD  ARG A 439  0  15.367 37.337 46.355 1.00 14.08
ATOM  3329 NE  ARG A 439  0  14.613 37.000 47.566 1.00 17.06
ATOM  3330 CZ  ARG A 439  0  15.192 36.922 48.767 1.00 18.01
ATOM  3331 NH1 ARG A 439  0  16.487 37.176 48.908 1.00 17.76
ATOM  3332 NH2 ARG A 439  0  14.459 36.604 49.818 1.00 18.55
ATOM  3333 N   PHE A 440  0  15.314 39.957 41.853 1.00 14.44
ATOM  3334 CA  PHE A 440  0  16.204 40.737 40.993 1.00 15.97
ATOM  3335 C   PHE A 440  0  16.645 41.986 41.761 1.00 15.86
```

```
ATOM 3336 O   PHE A 440 0  16.113 42.313 42.801 1.00 15.79
ATOM 3337 CB  PHE A 440 0  15.638 41.081 39.620 1.00 15.17
ATOM 3338 CG  PHE A 440 0  14.416 41.948 39.647 1.00 16.95
ATOM 3339 CD1 PHE A 440 0  14.525 43.333 39.528 1.00 17.23
ATOM 3340 CD2 PHE A 440 0  13.158 41.377 39.798 1.00 16.35
ATOM 3341 CE1 PHE A 440 0  13.397 44.152 39.566 1.00 17.07
ATOM 3342 CE2 PHE A 440 0  12.026 42.180 39.841 1.00 17.12
ATOM 3343 CZ  PHE A 440 0  12.144 43.575 39.719 1.00 18.30
ATOM 3344 N   VAL A 441 0  17.676 42.648 41.268 1.00 16.10
ATOM 3345 CA  VAL A 441 0  18.172 43.874 41.879 1.00 16.29
ATOM 3346 C   VAL A 441 0  17.776 45.035 40.972 1.00 14.00
ATOM 3347 O   VAL A 441 0  17.866 44.924 39.736 1.00 12.72
ATOM 3348 CB  VAL A 441 0  19.675 43.769 42.144 1.00 18.13
ATOM 3349 CG1 VAL A 441 0  20.195 45.040 42.794 1.00 18.53
ATOM 3350 CG2 VAL A 441 0  19.969 42.583 43.065 1.00 18.55
ATOM 3351 N   THR A 442 0  17.328 46.125 41.579 1.00 11.73
ATOM 3352 CA  THR A 442 0  16.905 47.291 40.800 1.00 13.02
ATOM 3353 C   THR A 442 0  18.055 48.208 40.432 1.00 14.83
ATOM 3354 O   THR A 442 0  18.218 49.323 40.947 1.00 15.17
ATOM 3355 CB  THR A 442 0  15.840 48.127 41.558 1.00 14.62
ATOM 3356 OG1 THR A 442 0  16.314 48.463 42.864 1.00 14.34
ATOM 3357 CG2 THR A 442 0  14.552 47.299 41.727 1.00 13.82
ATOM 3358 N   ASP A 443 0  18.818 47.764 39.437 1.00 15.48
ATOM 3359 CA  ASP A 443 0  20.004 48.449 38.964 1.00 16.57
ATOM 3360 C   ASP A 443 0  19.807 49.010 37.569 1.00 15.38
ATOM 3361 O   ASP A 443 0  20.788 49.208 36.858 1.00 15.57
ATOM 3362 CB  ASP A 443 0  21.133 47.391 38.962 1.00 19.75
ATOM 3363 CG  ASP A 443 0  20.877 46.264 37.990 1.00 22.78
ATOM 3364 OD1 ASP A 443 0  21.711 45.353 37.789 1.00 25.70
ATOM 3365 OD2 ASP A 443 0  19.836 46.161 37.313 1.00 23.88
ATOM 3366 N   ASN A 444 0  18.593 49.278 37.144 1.00 13.71
ATOM 3367 CA  ASN A 444 0  18.388 49.721 35.752 1.00 15.87
ATOM 3368 C   ASN A 444 0  17.245 50.728 35.702 1.00 17.00
ATOM 3369 O   ASN A 444 0  16.052 50.419 35.614 1.00 16.83
ATOM 3370 CB  ASN A 444 0  18.198 48.453 34.930 1.00 15.78
ATOM 3371 CG  ASN A 444 0  18.225 48.675 33.442 1.00 18.49
ATOM 3372 OD1 ASN A 444 0  18.505 49.809 33.047 1.00 19.42
ATOM 3373 ND2 ASN A 444 0  17.925 47.689 32.588 1.00 15.91
```

```
   ATOM 3374 N   PRO A 445 0   17.598 52.003 35.890 1.00 17.59
   ATOM 3375 CA  PRO A 445 0   16.683 53.137 35.938 1.00 16.56
   ATOM 3376 C   PRO A 445 0   15.788 53.217 34.721 1.00 16.99
   ATOM 3377 O   PRO A 445 0   16.293 53.246 33.594 1.00 17.02
 5 ATOM 3378 CB  PRO A 445 0   17.552 54.418 35.951 1.00 18.28
   ATOM 3379 CG  PRO A 445 0   18.870 53.871 36.474 1.00 18.09
   ATOM 3380 CD  PRO A 445 0   19.002 52.409 36.084 1.00 16.05
   ATOM 3381 N   GLY A 446 0   14.462 53.194 34.918 1.00 17.16
   ATOM 3382 CA  GLY A 446 0   13.560 53.281 33.743 1.00 15.84
10 ATOM 3383 C   GLY A 446 0   12.297 52.453 33.984 1.00 14.24
   ATOM 3384 O   GLY A 446 0   12.192 51.797 35.005 1.00 12.22
   ATOM 3385 N   PRO A 447 0   11.285 52.697 33.181 1.00 15.53
   ATOM 3386 CA  PRO A 447 0    9.999 52.048 33.195 1.00 15.24
   ATOM 3387 C   PRO A 447 0   10.101 50.737 32.401 1.00 13.82
15 ATOM 3388 O   PRO A 447 0   10.514 50.733 31.240 1.00 13.85
   ATOM 3389 CB  PRO A 447 0    9.013 52.976 32.473 1.00 16.21
   ATOM 3390 CG  PRO A 447 0    9.933 53.729 31.554 1.00 16.19
   ATOM 3391 CD  PRO A 447 0   11.347 53.707 32.096 1.00 17.15
   ATOM 3392 N   TRP A 448 0    9.787 49.623 33.021 1.00 11.83
20 ATOM 3393 CA  TRP A 448 0    9.898 48.317 32.371 1.00 14.30
   ATOM 3394 C   TRP A 448 0    8.610 47.493 32.427 1.00 13.12
   ATOM 3395 O   TRP A 448 0    8.013 47.355 33.502 1.00 11.63
   ATOM 3396 CB  TRP A 448 0   10.985 47.483 33.095 1.00 13.17
   ATOM 3397 CG  TRP A 448 0   12.321 48.160 33.124 1.00 14.54
25 ATOM 3398 CD1 TRP A 448 0   12.897 48.728 34.239 1.00 14.19
   ATOM 3399 CD2 TRP A 448 0   13.211 48.382 32.029 1.00 14.38
   ATOM 3400 NE1 TRP A 448 0   14.083 49.290 33.873 1.00 15.02
   ATOM 3401 CE2 TRP A 448 0   14.308 49.095 32.527 1.00 14.41
   ATOM 3402 CE3 TRP A 448 0   13.193 48.053 30.672 1.00 15.39
30 ATOM 3403 CZ2 TRP A 448 0   15.388 49.467 31.729 1.00 14.57
   ATOM 3404 CZ3 TRP A 448 0   14.250 48.446 29.867 1.00 14.92
   ATOM 3405 CH2 TRP A 448 0   15.355 49.135 30.399 1.00 14.93
   ATOM 3406 N   PHE A 449 0    8.231 46.884 31.315 1.00 14.03
   ATOM 3407 CA  PHE A 449 0    7.023 46.039 31.297 1.00 13.60
35 ATOM 3408 C   PHE A 449 0    7.231 44.712 32.016 1.00 15.32
   ATOM 3409 O   PHE A 449 0    8.312 44.093 31.993 1.00 13.66
   ATOM 3410 CB  PHE A 449 0    6.627 45.773 29.845 1.00 16.19
   ATOM 3411 CG  PHE A 449 0    5.221 46.033 29.380 1.00 18.26
```

120

```
ATOM  3412  CD1 PHE A 449 0   4.165 46.288 30.226 1.00 17.95
ATOM  3413  CD2 PHE A 449 0   4.962 46.027 28.011 1.00 20.73
ATOM  3414  CE1 PHE A 449 0   2.899 46.565 29.745 1.00 18.55
ATOM  3415  CE2 PHE A 449 0   3.701 46.293 27.503 1.00 20.13
ATOM  3416  CZ  PHE A 449 0   2.664 46.543 28.387 1.00 18.59
ATOM  3417  N   PHE A 450 0   6.195 44.245 32.715 1.00 12.79
ATOM  3418  CA  PHE A 450 0   6.119 42.963 33.359 1.00 14.38
ATOM  3419  C   PHE A 450 0   4.775 42.323 32.952 1.00 15.45
ATOM  3420  O   PHE A 450 0   3.743 42.812 33.423 1.00 15.30
ATOM  3421  CB  PHE A 450 0   6.186 43.041 34.879 1.00 15.06
ATOM  3422  CG  PHE A 450 0   6.210 41.693 35.555 1.00 15.95
ATOM  3423  CD1 PHE A 450 0   7.157 40.734 35.204 1.00 16.36
ATOM  3424  CD2 PHE A 450 0   5.325 41.398 36.570 1.00 15.45
ATOM  3425  CE1 PHE A 450 0   7.222 39.518 35.855 1.00 13.87
ATOM  3426  CE2 PHE A 450 0   5.386 40.187 37.224 1.00 16.10
ATOM  3427  CZ  PHE A 450 0   6.317 39.236 36.854 1.00 15.90
ATOM  3428  N   HIS A 451 0   4.737 41.301 32.122 1.00 15.54
ATOM  3429  CA  HIS A 451 0   3.443 40.841 31.610 1.00 16.24
ATOM  3430  C   HIS A 451 0   3.461 39.426 31.073 1.00 16.95
ATOM  3431  O   HIS A 451 0   4.526 38.860 30.812 1.00 17.42
ATOM  3432  CB  HIS A 451 0   2.996 41.743 30.435 1.00 14.01
ATOM  3433  CG  HIS A 451 0   3.921 41.696 29.281 1.00 16.98
ATOM  3434  ND1 HIS A 451 0   3.791 40.844 28.201 1.00 18.14
ATOM  3435  CD2 HIS A 451 0   5.058 42.435 29.046 1.00 17.88
ATOM  3436  CE1 HIS A 451 0   4.759 41.060 27.337 1.00 17.83
ATOM  3437  NE2 HIS A 451 0   5.554 42.011 27.842 1.00 18.98
ATOM  3438  N   CYS A 452 0   2.261 38.863 30.951 1.00 16.78
ATOM  3439  CA  CYS A 452 0   2.167 37.537 30.388 1.00 16.34
ATOM  3440  C   CYS A 452 0   2.604 37.623 28.924 1.00 14.77
ATOM  3441  O   CYS A 452 0   2.167 38.514 28.188 1.00 13.61
ATOM  3442  CB  CYS A 452 0   0.727 36.983 30.451 1.00 18.22
ATOM  3443  SG  CYS A 452 0   0.701 35.325 29.692 1.00 19.80
ATOM  3444  N   HIS A 453 0   3.388 36.640 28.474 1.00 13.29
ATOM  3445  CA  HIS A 453 0   3.867 36.716 27.100 1.00 13.19
ATOM  3446  C   HIS A 453 0   2.983 35.987 26.099 1.00 13.47
ATOM  3447  O   HIS A 453 0   3.296 35.974 24.906 1.00 11.93
ATOM  3448  CB  HIS A 453 0   5.314 36.251 27.033 1.00 13.98
ATOM  3449  CG  HIS A 453 0   6.124 36.860 25.945 1.00 11.89
```

5032-WO

121

```
   ATOM  3450 ND1 HIS A 453  0   5.835 36.763 24.612 1.00 10.68
   ATOM  3451 CD2 HIS A 453  0   7.270 37.594 26.072 1.00 12.71
   ATOM  3452 CE1 HIS A 453  0   6.776 37.418 23.923 1.00 12.37
   ATOM  3453 NE2 HIS A 453  0   7.663 37.930 24.793 1.00 13.20
 5 ATOM  3454 N   ILE A 454  0   1.860 35.429 26.549 1.00 15.35
   ATOM  3455 CA  ILE A 454  0   0.849 34.937 25.600 1.00 15.85
   ATOM  3456 C   ILE A 454  0   0.214 36.238 25.089 1.00 18.65
   ATOM  3457 O   ILE A 454  0  -0.452 36.997 25.824 1.00 17.92
   ATOM  3458 CB  ILE A 454  0  -0.156 34.001 26.280 1.00 16.46
10 ATOM  3459 CG1 ILE A 454  0   0.456 32.598 26.512 1.00 15.26
   ATOM  3460 CG2 ILE A 454  0  -1.402 33.898 25.419 1.00 14.21
   ATOM  3461 CD1 ILE A 454  0  -0.249 31.804 27.592 1.00 16.26
   ATOM  3462 N   GLU A 455  0   0.448 36.607 23.832 1.00 21.02
   ATOM  3463 CA  GLU A 455  0  -0.024 37.856 23.289 1.00 23.78
15 ATOM  3464 C   GLU A 455  0  -1.526 38.042 23.422 1.00 24.40
   ATOM  3465 O   GLU A 455  0  -1.953 39.161 23.700 1.00 24.30
   ATOM  3466 CB  GLU A 455  0   0.399 38.090 21.830 1.00 27.20
   ATOM  3467 CG  GLU A 455  0   0.602 39.599 21.595 1.00 33.86
   ATOM  3468 CD  GLU A 455  0   1.783 40.205 22.309 1.00 37.49
20 ATOM  3469 OE1 GLU A 455  0   2.311 39.657 23.320 1.00 41.51
   ATOM  3470 OE2 GLU A 455  0   2.303 41.284 21.907 1.00 41.22
   ATOM  3471 N   PHE A 456  0  -2.347 37.005 23.334 1.00 23.97
   ATOM  3472 CA  PHE A 456  0  -3.775 37.163 23.516 1.00 24.68
   ATOM  3473 C   PHE A 456  0  -4.084 37.533 24.959 1.00 25.11
25 ATOM  3474 O   PHE A 456  0  -5.181 38.092 25.170 1.00 27.37
   ATOM  3475 CB  PHE A 456  0  -4.552 35.919 23.023 1.00 24.76
   ATOM  3476 CG  PHE A 456  0  -4.098 35.614 21.606 1.00 24.98
   ATOM  3477 CD1 PHE A 456  0  -4.392 36.500 20.590 1.00 24.98
   ATOM  3478 CD2 PHE A 456  0  -3.331 34.506 21.320 1.00 24.42
30 ATOM  3479 CE1 PHE A 456  0  -3.988 36.292 19.291 1.00 25.44
   ATOM  3480 CE2 PHE A 456  0  -2.913 34.293 20.015 1.00 26.40
   ATOM  3481 CZ  PHE A 456  0  -3.226 35.171 18.997 1.00 25.10
   ATOM  3482 N   HIS A 457  0  -3.205 37.294 25.922 1.00 22.35
   ATOM  3483 CA  HIS A 457  0  -3.508 37.682 27.291 1.00 22.55
35 ATOM  3484 C   HIS A 457  0  -3.053 39.121 27.561 1.00 23.81
   ATOM  3485 O   HIS A 457  0  -3.756 39.832 28.262 1.00 21.33
   ATOM  3486 CB  HIS A 457  0  -2.912 36.766 28.336 1.00 20.96
   ATOM  3487 CG  HIS A 457  0  -3.345 35.346 28.201 1.00 22.51
```

```
   ATOM 3488 ND1 HIS A 457 0  -2.745 34.329 28.905 1.00 21.40
   ATOM 3489 CD2 HIS A 457 0  -4.291 34.771 27.404 1.00 22.50
   ATOM 3490 CE1 HIS A 457 0  -3.320 33.184 28.575 1.00 22.51
   ATOM 3491 NE2 HIS A 457 0  -4.237 33.428 27.666 1.00 23.19
 5 ATOM 3492 N   LEU A 458 0  -1.876 39.481 27.028 1.00 23.74
   ATOM 3493 CA  LEU A 458 0  -1.357 40.817 27.125 1.00 24.76
   ATOM 3494 C   LEU A 458 0  -2.411 41.828 26.616 1.00 26.52
   ATOM 3495 O   LEU A 458 0  -2.757 42.751 27.351 1.00 25.18
   ATOM 3496 CB  LEU A 458 0  -0.108 40.986 26.252 1.00 23.81
10 ATOM 3497 CG  LEU A 458 0   0.898 42.062 26.624 1.00 24.09
   ATOM 3498 CD1 LEU A 458 0   1.619 42.606 25.390 1.00 24.28
   ATOM 3499 CD2 LEU A 458 0   0.351 43.195 27.462 1.00 23.72
   ATOM 3500 N   MET A 459 0  -2.896 41.611 25.388 1.00 28.19
   ATOM 3501 CA  MET A 459 0  -3.914 42.458 24.785 1.00 31.98
15 ATOM 3502 C   MET A 459 0  -5.207 42.436 25.603 1.00 29.95
   ATOM 3503 O   MET A 459 0  -5.886 43.439 25.520 1.00 29.10
   ATOM 3504 CB  MET A 459 0  -4.148 42.226 23.284 1.00 35.99
   ATOM 3505 CG  MET A 459 0  -5.056 41.103 22.852 1.00 42.66
   ATOM 3506 SD  MET A 459 0  -5.296 40.817 21.069 1.00 49.28
20 ATOM 3507 CE  MET A 459 0  -6.238 39.291 21.119 1.00 47.39
   ATOM 3508 N   ASN A 460 0  -5.523 41.486 26.464 1.00 29.07
   ATOM 3509 CA  ASN A 460 0  -6.706 41.539 27.296 1.00 29.41
   ATOM 3510 C   ASN A 460 0  -6.407 41.908 28.746 1.00 28.46
   ATOM 3511 O   ASN A 460 0  -7.183 41.577 29.645 1.00 26.89
25 ATOM 3512 CB  ASN A 460 0  -7.537 40.253 27.210 1.00 31.34
   ATOM 3513 CG  ASN A 460 0  -8.325 40.243 25.900 1.00 33.82
   ATOM 3514 OD1 ASN A 460 0  -7.909 39.609 24.926 1.00 34.29
   ATOM 3515 ND2 ASN A 460 0  -9.437 40.971 25.861 1.00 34.55
   ATOM 3516 N   GLY A 461 0  -5.320 42.655 28.981 1.00 26.30
30 ATOM 3517 CA  GLY A 461 0  -5.020 43.198 30.268 1.00 24.99
   ATOM 3518 C   GLY A 461 0  -4.043 42.601 31.235 1.00 24.75
   ATOM 3519 O   GLY A 461 0  -3.879 43.228 32.304 1.00 22.69
   ATOM 3520 N   LEU A 462 0  -3.375 41.478 30.914 1.00 22.85
   ATOM 3521 CA  LEU A 462 0  -2.478 40.872 31.913 1.00 22.10
35 ATOM 3522 C   LEU A 462 0  -1.071 41.485 31.890 1.00 21.56
   ATOM 3523 O   LEU A 462 0  -0.116 40.876 31.415 1.00 20.28
   ATOM 3524 CB  LEU A 462 0  -2.477 39.376 31.669 1.00 20.03
   ATOM 3525 CG  LEU A 462 0  -2.010 38.393 32.720 1.00 20.40
```

```
   ATOM 3526 CD1 LEU A 462 0  -2.603 38.608 34.093 1.00 20.35
   ATOM 3527 CD2 LEU A 462 0  -2.385 36.983 32.229 1.00 21.01
   ATOM 3528 N   ALA A 463 0  -0.908 42.695 32.408 1.00 20.00
   ATOM 3529 CA  ALA A 463 0   0.350 43.432 32.381 1.00 20.74
 5 ATOM 3530 C   ALA A 463 0   0.398 44.511 33.481 1.00 21.85
   ATOM 3531 O   ALA A 463 0  -0.667 44.965 33.934 1.00 22.85
   ATOM 3532 CB  ALA A 463 0   0.559 44.179 31.060 1.00 15.13
   ATOM 3533 N   ILE A 464 0   1.605 44.810 33.950 1.00 19.91
   ATOM 3534 CA  ILE A 464 0   1.852 45.905 34.850 1.00 19.81
10 ATOM 3535 C   ILE A 464 0   3.180 46.579 34.434 1.00 19.41
   ATOM 3536 O   ILE A 464 0   3.938 46.003 33.660 1.00 18.24
   ATOM 3537 CB  ILE A 464 0   1.910 45.678 36.347 1.00 19.13
   ATOM 3538 CG1 ILE A 464 0   2.867 44.546 36.697 1.00 19.39
   ATOM 3539 CG2 ILE A 464 0   0.520 45.455 36.924 1.00 18.48
15 ATOM 3540 CD1 ILE A 464 0   3.205 44.549 38.179 1.00 21.00
   ATOM 3541 N   VAL A 465 0   3.380 47.791 34.924 1.00 18.95
   ATOM 3542 CA  VAL A 465 0   4.579 48.570 34.637 1.00 18.36
   ATOM 3543 C   VAL A 465 0   5.327 48.928 35.931 1.00 18.07
   ATOM 3544 O   VAL A 465 0   4.787 49.424 36.931 1.00 15.19
20 ATOM 3545 CB  VAL A 465 0   4.329 49.913 33.918 1.00 19.73
   ATOM 3546 CG1 VAL A 465 0   5.659 50.605 33.602 1.00 18.34
   ATOM 3547 CG2 VAL A 465 0   3.522 49.766 32.629 1.00 18.74
   ATOM 3548 N   PHE A 466 0   6.649 48.655 35.879 1.00 17.55
   ATOM 3549 CA  PHE A 466 0   7.499 49.051 37.013 1.00 14.72
25 ATOM 3550 C   PHE A 466 0   8.251 50.344 36.653 1.00 12.68
   ATOM 3551 O   PHE A 466 0   9.007 50.420 35.679 1.00 12.23
   ATOM 3552 CB  PHE A 466 0   8.484 47.978 37.381 1.00 15.19
   ATOM 3553 CG  PHE A 466 0   7.962 46.770 38.080 1.00 15.90
   ATOM 3554 CD1 PHE A 466 0   7.328 46.856 39.299 1.00 16.23
30 ATOM 3555 CD2 PHE A 466 0   8.153 45.533 37.492 1.00 16.23
   ATOM 3556 CE1 PHE A 466 0   6.861 45.720 39.936 1.00 15.97
   ATOM 3557 CE2 PHE A 466 0   7.665 44.389 38.133 1.00 18.27
   ATOM 3558 CZ  PHE A 466 0   7.018 44.480 39.352 1.00 16.74
   ATOM 3559 N   ALA A 467 0   8.045 51.361 37.443 1.00 10.60
35 ATOM 3560 CA  ALA A 467 0   8.788 52.648 37.194 1.00 12.27
   ATOM 3561 C   ALA A 467 0  10.007 52.526 38.111 1.00 12.02
   ATOM 3562 O   ALA A 467 0   9.905 52.728 39.325 1.00 12.43
   ATOM 3563 CB  ALA A 467 0   7.845 53.790 37.501 1.00 10.50
```

5032-WO

124

```
ATOM 3564 N   GLU A 468 0  11.126 51.989 37.625 1.00 12.62
ATOM 3565 CA  GLU A 468 0  12.263 51.683 38.515 1.00 14.63
ATOM 3566 C   GLU A 468 0  13.195 52.883 38.685 1.00 13.91
ATOM 3567 O   GLU A 468 0  13.631 53.369 37.651 1.00 13.05
ATOM 3568 CB  GLU A 468 0  13.049 50.546 37.843 1.00 14.51
ATOM 3569 CG  GLU A 468 0  14.256 50.035 38.629 1.00 16.84
ATOM 3570 CD  GLU A 468 0  14.805 48.779 37.975 1.00 17.96
ATOM 3571 OE1 GLU A 468 0  15.985 48.479 38.124 1.00 16.98
ATOM 3572 OE2 GLU A 468 0  14.086 48.043 37.260 1.00 18.42
ATOM 3573 N   ASP A 469 0  13.546 53.286 39.886 1.00 15.17
ATOM 3574 CA  ASP A 469 0  14.491 54.371 40.116 1.00 16.85
ATOM 3575 C   ASP A 469 0  14.134 55.630 39.333 1.00 16.33
ATOM 3576 O   ASP A 469 0  14.851 56.046 38.437 1.00 16.59
ATOM 3577 CB  ASP A 469 0  15.899 53.920 39.748 1.00 19.86
ATOM 3578 CG  ASP A 469 0  17.040 54.766 40.289 1.00 21.40
ATOM 3579 OD1 ASP A 469 0  16.811 55.793 40.943 1.00 22.21
ATOM 3580 OD2 ASP A 469 0  18.216 54.403 40.069 1.00 22.21
ATOM 3581 N   MET A 470 0  13.007 56.246 39.635 1.00 16.12
ATOM 3582 CA  MET A 470 0  12.522 57.373 38.853 1.00 18.77
ATOM 3583 C   MET A 470 0  13.451 58.576 38.950 1.00 16.31
ATOM 3584 O   MET A 470 0  13.591 59.208 37.925 1.00 13.55
ATOM 3585 CB  MET A 470 0  11.116 57.847 39.302 1.00 20.06
ATOM 3586 CG  MET A 470 0  10.041 56.941 38.684 1.00 23.99
ATOM 3587 SD  MET A 470 0   8.375 57.337 39.283 1.00 26.08
ATOM 3588 CE  MET A 470 0   8.030 58.581 38.020 1.00 24.40
ATOM 3589 N   ALA A 471 0  14.046 58.793 40.117 1.00 14.69
ATOM 3590 CA  ALA A 471 0  14.953 59.906 40.287 1.00 16.97
ATOM 3591 C   ALA A 471 0  16.141 59.864 39.335 1.00 18.79
ATOM 3592 O   ALA A 471 0  16.602 60.956 38.945 1.00 21.08
ATOM 3593 CB  ALA A 471 0  15.471 59.927 41.728 1.00 17.62
ATOM 3594 N   ASN A 472 0  16.623 58.695 38.912 1.00 17.28
ATOM 3595 CA  ASN A 472 0  17.788 58.675 38.015 1.00 16.56
ATOM 3596 C   ASN A 472 0  17.457 58.355 36.572 1.00 16.99
ATOM 3597 O   ASN A 472 0  18.407 58.143 35.795 1.00 18.74
ATOM 3598 CB  ASN A 472 0  18.811 57.645 38.548 1.00 14.60
ATOM 3599 CG  ASN A 472 0  19.417 58.132 39.887 1.00 14.00
ATOM 3600 OD1 ASN A 472 0  18.895 57.830 40.967 1.00 12.71
ATOM 3601 ND2 ASN A 472 0  20.468 58.916 39.775 1.00 10.80
```

```
ATOM 3602 N   THR A 473  0  16.174 58.284 36.239 1.00 14.26
ATOM 3603 CA  THR A 473  0  15.789 57.885 34.882 1.00 15.82
ATOM 3604 C   THR A 473  0  16.150 58.891 33.812 1.00 16.81
ATOM 3605 O   THR A 473  0  16.599 58.455 32.746 1.00 15.89
ATOM 3606 CB  THR A 473  0  14.267 57.576 34.826 1.00 16.10
ATOM 3607 OG1 THR A 473  0  14.001 56.416 35.609 1.00 15.41
ATOM 3608 CG2 THR A 473  0  13.750 57.337 33.427 1.00 15.24
ATOM 3609 N   VAL A 474  0  16.000 60.195 34.081 1.00 18.57
ATOM 3610 CA  VAL A 474  0  16.355 61.192 33.050 1.00 21.06
ATOM 3611 C   VAL A 474  0  17.859 61.209 32.817 1.00 19.12
ATOM 3612 O   VAL A 474  0  18.339 61.234 31.688 1.00 19.95
ATOM 3613 CB  VAL A 474  0  15.860 62.616 33.424 1.00 22.91
ATOM 3614 CG1 VAL A 474  0  16.467 63.702 32.538 1.00 23.06
ATOM 3615 CG2 VAL A 474  0  14.346 62.721 33.334 1.00 23.04
ATOM 3616 N   ASP A 475  0  18.647 61.175 33.886 1.00 19.20
ATOM 3617 CA  ASP A 475  0  20.109 61.168 33.741 1.00 18.98
ATOM 3618 C   ASP A 475  0  20.578 59.899 33.047 1.00 17.52
ATOM 3619 O   ASP A 475  0  21.386 60.028 32.130 1.00 18.31
ATOM 3620 CB  ASP A 475  0  20.780 61.273 35.119 1.00 20.27
ATOM 3621 CG  ASP A 475  0  22.283 61.075 35.107 1.00 20.18
ATOM 3622 OD1 ASP A 475  0  22.950 61.889 34.431 1.00 21.73
ATOM 3623 OD2 ASP A 475  0  22.798 60.139 35.750 1.00 18.03
ATOM 3624 N   ALA A 476  0  20.062 58.725 33.392 1.00 18.26
ATOM 3625 CA  ALA A 476  0  20.539 57.486 32.793 1.00 18.93
ATOM 3626 C   ALA A 476  0  20.165 57.269 31.343 1.00 20.62
ATOM 3627 O   ALA A 476  0  20.845 56.502 30.661 1.00 22.64
ATOM 3628 CB  ALA A 476  0  19.966 56.298 33.551 1.00 18.48
ATOM 3629 N   ASN A 477  0  19.047 57.787 30.858 1.00 22.66
ATOM 3630 CA  ASN A 477  0  18.605 57.512 29.491 1.00 25.22
ATOM 3631 C   ASN A 477  0  18.578 58.782 28.683 1.00 28.55
ATOM 3632 O   ASN A 477  0  17.969 59.755 29.143 1.00 30.20
ATOM 3633 CB  ASN A 477  0  17.172 56.948 29.560 1.00 24.22
ATOM 3634 CG  ASN A 477  0  17.114 55.666 30.380 1.00 23.73
ATOM 3635 OD1 ASN A 477  0  16.747 55.672 31.570 1.00 21.33
ATOM 3636 ND2 ASN A 477  0  17.512 54.575 29.736 1.00 20.87
ATOM 3637 N   ASN A 478  0  19.208 58.878 27.514 1.00 31.69
ATOM 3638 CA  ASN A 478  0  19.036 60.131 26.776 1.00 33.61
ATOM 3639 C   ASN A 478  0  18.758 59.770 25.331 1.00 32.22
```

5032-WO

126

```
ATOM 3640 O   ASN A 478 0  19.602 59.478 24.508 1.00 32.16
ATOM 3641 CB  ASN A 478 0  20.086 61.194 27.017 1.00 38.57
ATOM 3642 CG  ASN A 478 0  21.426 60.602 27.370 1.00 40.94
ATOM 3643 OD1 ASN A 478 0  21.928 59.903 26.484 1.00 44.60
ATOM 3644 ND2 ASN A 478 0  21.866 60.861 28.578 1.00 41.32
ATOM 3645 N   PRO A 479 0  17.461 59.733 25.075 1.00 32.37
ATOM 3646 CA  PRO A 479 0  16.890 59.381 23.790 1.00 31.84
ATOM 3647 C   PRO A 479 0  17.268 60.448 22.776 1.00 32.35
ATOM 3648 O   PRO A 479 0  17.422 61.609 23.136 1.00 32.66
ATOM 3649 CB  PRO A 479 0  15.364 59.385 23.931 1.00 31.68
ATOM 3650 CG  PRO A 479 0  15.126 59.724 25.373 1.00 31.69
ATOM 3651 CD  PRO A 479 0  16.416 60.071 26.064 1.00 32.23
ATOM 3652 N   PRO A 480 0  17.399 60.036 21.537 1.00 31.62
ATOM 3653 CA  PRO A 480 0  17.670 60.939 20.422 1.00 30.72
ATOM 3654 C   PRO A 480 0  16.452 61.827 20.225 1.00 30.37
ATOM 3655 O   PRO A 480 0  15.362 61.525 20.733 1.00 29.47
ATOM 3656 CB  PRO A 480 0  17.935 60.035 19.203 1.00 29.87
ATOM 3657 CG  PRO A 480 0  17.111 58.811 19.590 1.00 30.44
ATOM 3658 CD  PRO A 480 0  17.161 58.657 21.093 1.00 30.35
ATOM 3659 N   VAL A 481 0  16.559 62.906 19.458 1.00 31.72
ATOM 3660 CA  VAL A 481 0  15.398 63.788 19.268 1.00 30.68
ATOM 3661 C   VAL A 481 0  14.335 63.090 18.446 1.00 29.51
ATOM 3662 O   VAL A 481 0  13.134 63.284 18.648 1.00 27.97
ATOM 3663 CB  VAL A 481 0  15.818 65.132 18.648 1.00 33.04
ATOM 3664 CG1 VAL A 481 0  16.126 65.010 17.161 1.00 31.91
ATOM 3665 CG2 VAL A 481 0  14.717 66.171 18.907 1.00 33.32
ATOM 3666 N   GLU A 482 0  14.746 62.167 17.562 1.00 28.90
ATOM 3667 CA  GLU A 482 0  13.755 61.402 16.803 1.00 29.62
ATOM 3668 C   GLU A 482 0  12.839 60.565 17.691 1.00 28.33
ATOM 3669 O   GLU A 482 0  11.704 60.287 17.280 1.00 28.36
ATOM 3670 CB  GLU A 482 0  14.449 60.498 15.788 1.00 30.63
ATOM 3671 CG  GLU A 482 0  15.143 61.256 14.666 1.00 32.78
ATOM 3672 CD  GLU A 482 0  16.522 61.784 14.990 1.00 34.96
ATOM 3673 OE1 GLU A 482 0  17.021 61.746 16.141 1.00 34.62
ATOM 3674 OE2 GLU A 482 0  17.170 62.297 14.033 1.00 37.13
ATOM 3675 N   TRP A 483 0  13.311 60.124 18.857 1.00 25.91
ATOM 3676 CA  TRP A 483 0  12.496 59.280 19.711 1.00 25.49
ATOM 3677 C   TRP A 483 0  11.224 60.011 20.125 1.00 26.47
```

```
ATOM  3678 O   TRP A 483  0   10.155 59.405 20.116 1.00 26.95
ATOM  3679 CB  TRP A 483  0   13.216 58.807 20.974 1.00 21.98
ATOM  3680 CG  TRP A 483  0   12.376 58.144 22.013 1.00 21.49
ATOM  3681 CD1 TRP A 483  0   11.960 56.827 22.003 1.00 20.81
ATOM  3682 CD2 TRP A 483  0   11.818 58.730 23.194 1.00 20.14
ATOM  3683 NE1 TRP A 483  0   11.187 56.575 23.143 1.00 20.29
ATOM  3684 CE2 TRP A 483  0   11.097 57.736 23.868 1.00 20.29
ATOM  3685 CE3 TRP A 483  0   11.875 60.006 23.754 1.00 21.32
ATOM  3686 CZ2 TRP A 483  0   10.422 57.973 25.062 1.00 20.89
ATOM  3687 CZ3 TRP A 483  0   11.217 60.248 24.946 1.00 20.78
ATOM  3688 CH2 TRP A 483  0   10.495 59.227 25.596 1.00 21.44
ATOM  3689 N   ALA A 484  0   11.342 61.261 20.560 1.00 28.59
ATOM  3690 CA  ALA A 484  0   10.165 62.003 21.029 1.00 30.73
ATOM  3691 C   ALA A 484  0    9.226 62.350 19.869 1.00 30.42
ATOM  3692 O   ALA A 484  0    8.024 62.337 20.071 1.00 31.34
ATOM  3693 CB  ALA A 484  0   10.583 63.244 21.806 1.00 31.05
ATOM  3694 N   GLN A 485  0    9.702 62.488 18.653 1.00 30.79
ATOM  3695 CA  GLN A 485  0    8.927 62.742 17.466 1.00 33.16
ATOM  3696 C   GLN A 485  0    8.026 61.608 17.017 1.00 32.81
ATOM  3697 O   GLN A 485  0    7.044 61.847 16.302 1.00 32.74
ATOM  3698 CB  GLN A 485  0    9.859 63.113 16.290 1.00 34.56
ATOM  3699 CG  GLN A 485  0   10.631 64.361 16.686 1.00 39.67
ATOM  3700 CD  GLN A 485  0   11.559 64.919 15.640 1.00 42.86
ATOM  3701 OE1 GLN A 485  0   11.528 66.145 15.434 1.00 45.48
ATOM  3702 NE2 GLN A 485  0   12.375 64.103 14.982 1.00 44.07
ATOM  3703 N   LEU A 486  0    8.328 60.380 17.443 1.00 30.46
ATOM  3704 CA  LEU A 486  0    7.500 59.231 17.095 1.00 27.76
ATOM  3705 C   LEU A 486  0    6.051 59.510 17.509 1.00 28.23
ATOM  3706 O   LEU A 486  0    5.100 59.331 16.752 1.00 26.71
ATOM  3707 CB  LEU A 486  0    8.043 58.034 17.838 1.00 25.03
ATOM  3708 CG  LEU A 486  0    8.988 57.012 17.226 1.00 24.18
ATOM  3709 CD1 LEU A 486  0    9.780 57.416 16.011 1.00 21.41
ATOM  3710 CD2 LEU A 486  0    9.864 56.464 18.342 1.00 23.28
ATOM  3711 N   CYS A 487  0    5.870 59.974 18.739 1.00 28.05
ATOM  3712 CA  CYS A 487  0    4.560 60.263 19.279 1.00 30.77
ATOM  3713 C   CYS A 487  0    3.823 61.350 18.499 1.00 33.19
ATOM  3714 O   CYS A 487  0    2.627 61.170 18.263 1.00 33.69
ATOM  3715 CB  CYS A 487  0    4.643 60.637 20.752 1.00 27.94
```

5032-WO

```
ATOM   3716  SG  CYS A 487   0     5.214  59.280  21.781  1.00 27.23
ATOM   3717  N   GLU A 488   0     4.543  62.373  18.064  1.00 35.80
ATOM   3718  CA  GLU A 488   0     3.871  63.458  17.334  1.00 39.12
ATOM   3719  C   GLU A 488   0     3.384  62.928  15.995  1.00 37.78
ATOM   3720  O   GLU A 488   0     2.186  63.025  15.711  1.00 37.61
ATOM   3721  CB  GLU A 488   0     4.737  64.697  17.257  1.00 42.04
ATOM   3722  CG  GLU A 488   0     5.667  64.822  16.064  1.00 47.75
ATOM   3723  CD  GLU A 488   0     5.634  66.239  15.500  1.00 51.36
ATOM   3724  OE1 GLU A 488   0     5.501  66.422  14.266  1.00 52.66
ATOM   3725  OE2 GLU A 488   0     5.743  67.154  16.358  1.00 53.40
ATOM   3726  N   ILE A 489   0     4.263  62.253  15.267  1.00 36.63
ATOM   3727  CA  ILE A 489   0     3.906  61.647  14.004  1.00 36.74
ATOM   3728  C   ILE A 489   0     2.754  60.662  14.113  1.00 36.98
ATOM   3729  O   ILE A 489   0     1.847  60.664  13.276  1.00 38.60
ATOM   3730  CB  ILE A 489   0     5.089  60.903  13.361  1.00 36.57
ATOM   3731  CG1 ILE A 489   0     6.267  61.853  13.148  1.00 36.46
ATOM   3732  CG2 ILE A 489   0     4.651  60.305  12.030  1.00 36.90
ATOM   3733  CD1 ILE A 489   0     7.535  61.194  12.654  1.00 35.62
ATOM   3734  N   TYR A 490   0     2.758  59.808  15.105  1.00 36.22
ATOM   3735  CA  TYR A 490   0     1.771  58.765  15.298  1.00 35.95
ATOM   3736  C   TYR A 490   0     0.413  59.314  15.692  1.00 37.83
ATOM   3737  O   TYR A 490   0    -0.581  58.816  15.165  1.00 39.24
ATOM   3738  CB  TYR A 490   0     2.206  57.817  16.409  1.00 32.47
ATOM   3739  CG  TYR A 490   0     1.314  56.641  16.663  1.00 30.55
ATOM   3740  CD1 TYR A 490   0     1.176  55.623  15.726  1.00 29.96
ATOM   3741  CD2 TYR A 490   0     0.610  56.536  17.849  1.00 29.79
ATOM   3742  CE1 TYR A 490   0     0.378  54.528  15.975  1.00 29.51
ATOM   3743  CE2 TYR A 490   0    -0.192  55.441  18.114  1.00 29.64
ATOM   3744  CZ  TYR A 490   0    -0.288  54.445  17.171  1.00 29.51
ATOM   3745  OH  TYR A 490   0    -1.101  53.363  17.437  1.00 32.06
ATOM   3746  N   ASP A 491   0     0.369  60.302  16.564  1.00 40.86
ATOM   3747  CA  ASP A 491   0    -0.909  60.887  16.963  1.00 43.97
ATOM   3748  C   ASP A 491   0    -1.586  61.633  15.811  1.00 45.30
ATOM   3749  O   ASP A 491   0    -2.809  61.752  15.820  1.00 45.60
ATOM   3750  CB  ASP A 491   0    -0.764  61.800  18.170  1.00 44.67
ATOM   3751  CG  ASP A 491   0    -0.441  61.101  19.475  1.00 45.90
ATOM   3752  OD1 ASP A 491   0     0.149  61.761  20.364  1.00 46.32
ATOM   3753  OD2 ASP A 491   0    -0.763  59.911  19.669  1.00 46.04
```

5032-WO

129

```
ATOM 3754  N   ASP A 492 0  -0.871 62.107 14.817 1.00 46.75
ATOM 3755  CA  ASP A 492 0  -1.323 62.804 13.653 1.00 48.98
ATOM 3756  C   ASP A 492 0  -1.702 61.936 12.460 1.00 49.48
ATOM 3757  O   ASP A 492 0  -2.002 62.458 11.378 1.00 50.24
ATOM 3758  CB  ASP A 492 0  -0.155 63.649 13.107 1.00 51.54
ATOM 3759  CG  ASP A 492 0  -0.168 65.081 13.587 1.00 53.57
ATOM 3760  OD1 ASP A 492 0  -0.886 65.375 14.570 1.00 54.07
ATOM 3761  OD2 ASP A 492 0   0.576 65.857 12.939 1.00 55.04
ATOM 3762  N   LEU A 493 0  -1.554 60.630 12.584 1.00 49.01
ATOM 3763  CA  LEU A 493 0  -1.896 59.732 11.483 1.00 47.63
ATOM 3764  C   LEU A 493 0  -3.377 59.872 11.137 1.00 47.61
ATOM 3765  O   LEU A 493 0  -4.209 60.018 12.027 1.00 47.02
ATOM 3766  CB  LEU A 493 0  -1.661 58.296 11.940 1.00 46.08
ATOM 3767  CG  LEU A 493 0  -0.485 57.463 11.464 1.00 45.24
ATOM 3768  CD1 LEU A 493 0   0.616 58.224 10.756 1.00 43.57
ATOM 3769  CD2 LEU A 493 0   0.075 56.710 12.669 1.00 44.62
ATOM 3770  N   PRO A 494 0  -3.694 59.763  9.866 1.00 48.01
ATOM 3771  CA  PRO A 494 0  -5.049 59.734  9.353 1.00 49.11
ATOM 3772  C   PRO A 494 0  -5.617 58.339  9.570 1.00 51.21
ATOM 3773  O   PRO A 494 0  -4.919 57.325  9.495 1.00 50.61
ATOM 3774  CB  PRO A 494 0  -4.938 59.995  7.843 1.00 48.94
ATOM 3775  CG  PRO A 494 0  -3.559 59.463  7.544 1.00 48.47
ATOM 3776  CD  PRO A 494 0  -2.714 59.538  8.797 1.00 48.22
ATOM 3777  N   PRO A 495 0  -6.915 58.238  9.796 1.00 53.24
ATOM 3778  CA  PRO A 495 0  -7.630 57.006 10.055 1.00 53.93
ATOM 3779  C   PRO A 495 0  -7.404 55.890  9.058 1.00 54.84
ATOM 3780  O   PRO A 495 0  -7.348 54.705  9.423 1.00 55.08
ATOM 3781  CB  PRO A 495 0  -9.126 57.362 10.146 1.00 54.40
ATOM 3782  CG  PRO A 495 0  -9.090 58.848 10.391 1.00 54.17
ATOM 3783  CD  PRO A 495 0  -7.787 59.420  9.895 1.00 53.58
ATOM 3784  N   GLU A 496 0  -7.190 56.198  7.784 1.00 55.36
ATOM 3785  CA  GLU A 496 0  -6.936 55.187  6.763 1.00 55.83
ATOM 3786  C   GLU A 496 0  -5.582 54.521  6.971 1.00 54.09
ATOM 3787  O   GLU A 496 0  -5.345 53.406  6.505 1.00 53.29
ATOM 3788  CB  GLU A 496 0  -7.091 55.805  5.378 1.00 57.96
ATOM 3789  CG  GLU A 496 0  -6.030 55.604  4.339 1.00 61.30
ATOM 3790  CD  GLU A 496 0  -6.448 54.984  3.025 1.00 63.68
ATOM 3791  OE1 GLU A 496 0  -7.449 55.411  2.388 1.00 65.15
```

```
ATOM 3792 OE2 GLU A 496  0  -5.747 54.034  2.586 1.00 64.91
ATOM 3793 N   ALA A 497  0  -4.665 55.217  7.630 1.00 52.35
ATOM 3794 CA  ALA A 497  0  -3.326 54.738  7.886 1.00 50.83
ATOM 3795 C   ALA A 497  0  -3.245 53.626  8.924 1.00 49.08
ATOM 3796 O   ALA A 497  0  -2.361 52.773  8.794 1.00 47.61
ATOM 3797 CB  ALA A 497  0  -2.443 55.910  8.317 1.00 51.23
ATOM 3798 N   THR A 498  0  -4.113 53.630  9.926 1.00 48.01
ATOM 3799 CA  THR A 498  0  -4.086 52.617 10.964 1.00 48.73
ATOM 3800 C   THR A 498  0  -5.271 51.656 10.938 1.00 48.99
ATOM 3801 O   THR A 498  0  -5.425 50.852 11.862 1.00 47.81
ATOM 3802 CB  THR A 498  0  -4.055 53.223 12.388 1.00 49.04
ATOM 3803 OG1 THR A 498  0  -5.315 53.816 12.752 1.00 47.95
ATOM 3804 CG2 THR A 498  0  -2.919 54.223 12.514 1.00 48.94
ATOM 3805 N   SER A 499  0  -6.101 51.756  9.911 1.00 49.78
ATOM 3806 CA  SER A 499  0  -7.307 50.933  9.814 1.00 51.20
ATOM 3807 C   SER A 499  0  -7.048 49.470  9.494 1.00 49.98
ATOM 3808 O   SER A 499  0  -6.257 49.143  8.617 1.00 48.80
ATOM 3809 CB  SER A 499  0  -8.223 51.606  8.800 1.00 52.62
ATOM 3810 OG  SER A 499  0  -8.428 50.827  7.596 1.00 55.22
ATOM 3811 N   ILE A 500  0  -7.706 48.585 10.230 1.00 50.08
ATOM 3812 CA  ILE A 500  0  -7.563 47.151 10.077 1.00 51.25
ATOM 3813 C   ILE A 500  0  -8.642 46.518  9.207 1.00 53.08
ATOM 3814 O   ILE A 500  0  -9.785 46.351  9.639 1.00 54.00
ATOM 3815 CB  ILE A 500  0  -7.631 46.428 11.436 1.00 50.61
ATOM 3816 CG1 ILE A 500  0  -6.475 46.866 12.336 1.00 50.22
ATOM 3817 CG2 ILE A 500  0  -7.619 44.907 11.302 1.00 50.34
ATOM 3818 CD1 ILE A 500  0  -6.806 46.617 13.800 1.00 50.52
ATOM 3819 N   GLN A 501  0  -8.263 46.074  8.024 1.00 54.35
ATOM 3820 CA  GLN A 501  0  -9.177 45.360  7.129 1.00 55.14
ATOM 3821 C   GLN A 501  0  -9.298 43.904  7.564 1.00 55.85
ATOM 3822 O   GLN A 501  0  -8.335 43.130  7.556 1.00 55.59
ATOM 3823 CB  GLN A 501  0  -8.594 45.485  5.732 1.00 55.56
ATOM 3824 CG  GLN A 501  0  -9.262 44.736  4.604 1.00 56.32
ATOM 3825 CD  GLN A 501  0  -8.874 45.369  3.271 1.00 57.46
ATOM 3826 OE1 GLN A 501  0  -8.480 44.667  2.336 1.00 57.35
ATOM 3827 NE2 GLN A 501  0  -8.998 46.697  3.219 1.00 57.61
ATOM 3828 N   THR A 502  0 -10.493 43.506  7.968 1.00 57.08
ATOM 3829 CA  THR A 502  0 -10.788 42.146  8.401 1.00 58.28
```

```
     ATOM  3830  C   THR A 502  0  -10.966  41.205   7.216  1.00 58.80
     ATOM  3831  O   THR A 502  0  -11.199  41.604   6.074  1.00 58.71
     ATOM  3832  CB  THR A 502  0  -12.046  42.108   9.293  1.00 58.99
     ATOM  3833  OG1 THR A 502  0  -11.794  42.909  10.464  1.00 59.62
 5   ATOM  3834  CG2 THR A 502  0  -12.421  40.707   9.749  1.00 58.74
     ATOM  3835  N   VAL A 503  0  -10.746  39.922   7.471  1.00 59.20
     ATOM  3836  CA  VAL A 503  0  -10.904  38.877   6.468  1.00 60.27
     ATOM  3837  C   VAL A 503  0  -11.687  37.736   7.119  1.00 61.11
     ATOM  3838  O   VAL A 503  0  -11.606  37.563   8.341  1.00 61.03
10   ATOM  3839  CB  VAL A 503  0   -9.589  38.430   5.823  1.00 59.97
     ATOM  3840  CG1 VAL A 503  0   -8.337  38.964   6.507  1.00 59.65
     ATOM  3841  CG2 VAL A 503  0   -9.467  36.914   5.722  1.00 59.97
     ATOM  3842  N   VAL A 504  0  -12.478  37.002   6.341  1.00 61.77
     ATOM  3843  CA  VAL A 504  0  -13.203  35.863   6.911  1.00 62.40
15   ATOM  3844  C   VAL A 504  0  -12.673  34.579   6.259  1.00 62.99
     ATOM  3845  O   VAL A 504  0  -11.811  33.894   6.803  1.00 63.13
     ATOM  3846  CB  VAL A 504  0  -14.730  35.882   6.756  1.00 62.39
     ATOM  3847  CG1 VAL A 504  0  -15.392  36.931   7.635  1.00 61.89
     ATOM  3848  CG2 VAL A 504  0  -15.127  36.068   5.297  1.00 62.17
20   ATOM  3849  C1  NAG A 800  0   -2.401  42.835  45.802  1.00 30.44
     ATOM  3850  C2  NAG A 800  0   -1.327  43.232  46.780  1.00 31.80
     ATOM  3851  N2  NAG A 800  0   -0.119  43.561  45.983  1.00 31.37
     ATOM  3852  C7  NAG A 800  0    0.179  44.844  45.683  1.00 32.37
     ATOM  3853  O7  NAG A 800  0   -0.549  45.688  45.982  1.00 34.61
25   ATOM  3854  C8  NAG A 800  0    1.457  45.094  44.983  1.00 31.67
     ATOM  3855  C3  NAG A 800  0   -1.015  42.187  47.801  1.00 32.94
     ATOM  3856  O3  NAG A 800  0   -0.264  42.838  48.796  1.00 34.46
     ATOM  3857  C4  NAG A 800  0   -2.351  41.662  48.377  1.00 34.05
     ATOM  3858  O4  NAG A 800  0   -2.097  40.644  49.344  1.00 35.62
30   ATOM  3859  C5  NAG A 800  0   -3.128  41.025  47.202  1.00 35.11
     ATOM  3860  O5  NAG A 800  0   -3.466  42.046  46.295  1.00 33.06
     ATOM  3861  C6  NAG A 800  0   -4.444  40.420  47.673  1.00 36.66
     ATOM  3862  O6  NAG A 800  0   -5.199  41.411  48.288  1.00 39.73
     ATOM  3863  C1  GLC A 900  0   -8.957  50.280   6.333  1.00 58.53
35   ATOM  3864  C2  GLC A 900  0   -8.500  49.605   5.037  1.00 59.25
     ATOM  3865  C3  GLC A 900  0   -7.806  50.686   4.219  1.00 59.71
     ATOM  3866  C4  GLC A 900  0   -8.691  51.905   3.987  1.00 60.13
     ATOM  3867  C5  GLC A 900  0   -9.595  52.289   5.142  1.00 59.22
```

5032-WO

132

```
   ATOM   3868  O5   GLC A 900  0  -10.004 51.177  5.937 1.00 59.71
   ATOM   3869  CU   IUM B   1  0   -1.332 34.401 30.132 1.00 29.47
   ATOM   3870  CU   IUM B   2  0    7.297 42.245 26.618 1.00 27.01
   ATOM   3871  CU   IUM B   3  0    9.569 38.786 23.923 1.00 21.38
 5 ATOM   3872  O    IUM B   5  0    7.445 40.703 25.162 1.00 26.99
   ATOM   3873  OW0  WAT W   1  0   19.509 36.893 30.054 1.00 13.07
   ATOM   3874  OW0  WAT W   2  0   24.726 29.672 16.651 1.00  7.67
   ATOM   3875  OW0  WAT W   3  0   15.295 17.988 35.061 1.00  8.65
   ATOM   3876  OW0  WAT W   4  0    6.481 28.311 23.427 1.00  8.00
10 ATOM   3877  OW0  WAT W   5  0   14.921 45.178 24.306 1.00 17.04
   ATOM   3878  OW0  WAT W   6  0   14.413 44.401 28.162 1.00 10.12
   ATOM   3879  OW0  WAT W   7  0    9.967 21.576  9.620 1.00 11.43
   ATOM   3880  OW0  WAT W   8  0   10.088 28.675 13.038 1.00  9.27
   ATOM   3881  OW0  WAT W   9  0    9.808 47.902 28.959 1.00 12.71
15 ATOM   3882  OW0  WAT W  10  0   21.976 23.052 35.604 1.00 11.72
   ATOM   3883  OW0  WAT W  11  0   10.862 25.744 29.928 1.00 10.21
   ATOM   3884  OW0  WAT W  12  0   26.087 32.996 23.097 1.00 14.21
   ATOM   3885  OW0  WAT W  13  0   22.256 58.745 37.931 1.00 17.85
   ATOM   3886  OW0  WAT W  14  0   -0.104 29.831 35.249 1.00 16.36
20 ATOM   3887  OW0  WAT W  15  0   18.153 61.857 36.641 1.00 14.38
   ATOM   3888  OW0  WAT W  16  0    9.426 38.431  9.161 1.00 15.35
   ATOM   3889  OW0  WAT W  17  0    7.639 24.371  3.713 1.00 22.18
   ATOM   3890  OW0  WAT W  18  0   27.977 11.643  9.481 1.00 19.22
   ATOM   3891  OW0  WAT W  19  0    3.140 21.028 24.695 1.00 11.12
25 ATOM   3892  OW0  WAT W  20  0    9.847 20.701 30.902 1.00 16.16
   ATOM   3893  OW0  WAT W  21  0   -1.517 29.009 43.180 1.00 27.18
   ATOM   3894  OW0  WAT W  22  0    3.497 29.138 26.088 1.00 17.22
   ATOM   3895  OW0  WAT W  23  0   20.614 32.765 40.433 1.00 17.63
   ATOM   3896  OW0  WAT W  24  0   19.098 51.778 39.452 1.00 22.33
30 ATOM   3897  OW0  WAT W  25  0    0.977 21.396  5.064 1.00 18.54
   ATOM   3898  OW0  WAT W  26  0    8.546 16.150 21.761 1.00 16.40
   ATOM   3899  OW0  WAT W  27  0    6.102 19.858 10.350 1.00 17.79
   ATOM   3900  OW0  WAT W  28  0   11.702 55.189 41.955 1.00 18.92
   ATOM   3901  OW0  WAT W  29  0    3.360 42.251 18.209 1.00 16.26
35 ATOM   3902  OW0  WAT W  30  0    6.232 14.672 22.473 1.00 24.49
   ATOM   3903  OW0  WAT W  31  0   16.729 26.542 39.731 1.00 15.28
   ATOM   3904  OW0  WAT W  32  0    2.834 30.640 40.601 1.00 18.11
   ATOM   3905  OW0  WAT W  33  0   21.893 42.837 27.884 1.00 15.08
```

```
ATOM 3906 OW0 WAT W 34 0   1.581 28.193 27.914 1.00 17.77
ATOM 3907 OW0 WAT W 35 0  -3.503 21.749 11.578 1.00 15.32
ATOM 3908 OW0 WAT W 36 0   7.131 33.344 11.786 1.00 18.18
ATOM 3909 OW0 WAT W 37 0  17.312 38.603 29.961 1.00 14.75
ATOM 3910 OW0 WAT W 38 0  -6.705 40.723 39.909 1.00 23.49
ATOM 3911 OW0 WAT W 39 0   9.010 31.121 11.736 1.00 19.99
ATOM 3912 OW0 WAT W 40 0   9.376 28.353 33.076 1.00 16.22
ATOM 3913 OW0 WAT W 41 0  30.104 29.895 20.857 1.00 25.77
ATOM 3914 OW0 WAT W 42 0  -6.950 33.663 21.335 1.00 26.62
ATOM 3915 OW0 WAT W 43 0   8.541 27.867 36.827 1.00 12.80
ATOM 3916 OW0 WAT W 44 0   3.590 21.651 11.893 1.00 14.46
ATOM 3917 OW0 WAT W 45 0  23.290 21.665 37.787 1.00 28.75
ATOM 3918 OW0 WAT W 46 0  22.724 11.873 22.270 1.00 23.07
ATOM 3919 OW0 WAT W 47 0  -1.090 42.001 12.877 1.00 19.33
ATOM 3920 OW0 WAT W 48 0  14.091 27.298 40.583 1.00 18.51
ATOM 3921 OW0 WAT W 49 0   2.336 52.026 29.983 1.00 25.66
ATOM 3922 OW0 WAT W 50 0  15.475 14.450 22.853 1.00 20.37
ATOM 3923 OW0 WAT W 51 0  25.945 26.568 40.287 1.00 24.49
ATOM 3924 OW0 WAT W 52 0  19.545 41.598 35.087 1.00 20.70
ATOM 3925 OW0 WAT W 53 0  -3.802 47.942  9.638 1.00 29.98
ATOM 3926 OW0 WAT W 54 0  -7.478 41.160  9.585 1.00 24.26
ATOM 3927 OW0 WAT W 55 0  -2.938 29.733 36.048 1.00 22.93
ATOM 3928 OW0 WAT W 56 0  29.051 32.114 22.680 1.00 22.50
ATOM 3929 OW0 WAT W 57 0   0.360 29.505  5.595 1.00 17.78
ATOM 3930 OW0 WAT W 58 0   8.583 57.422 21.440 1.00 21.90
ATOM 3931 OW0 WAT W 59 0  25.151 31.947 34.812 1.00 22.13
ATOM 3932 OW0 WAT W 60 0  25.133 62.204 32.968 1.00 25.75
ATOM 3933 OW0 WAT W 61 0  14.909 40.770 30.294 1.00 17.25
ATOM 3934 OW0 WAT W 62 0  20.825 30.520 34.676 1.00 16.18
ATOM 3935 OW0 WAT W 63 0   5.509 26.744 43.167 1.00 30.12
ATOM 3936 OW0 WAT W 64 0   5.280 57.279 14.627 1.00 22.66
ATOM 3937 OW0 WAT W 65 0   2.944 53.436 32.359 1.00 22.97
ATOM 3938 OW0 WAT W 66 0  11.266 43.508  3.407 1.00 20.01
ATOM 3939 OW0 WAT W 67 0  21.535 45.549 26.563 1.00 24.47
ATOM 3940 OW0 WAT W 68 0   0.412 33.358 11.837 1.00 19.89
ATOM 3941 OW0 WAT W 69 0  26.466 32.305 25.785 1.00 20.19
ATOM 3942 OW0 WAT W 70 0   0.910 45.068  7.829 1.00 22.05
ATOM 3943 OW0 WAT W 71 0  -2.060 46.506 39.381 1.00 23.49
```

```
ATOM 3944 OW0 WAT W  72 0  20.236 56.718 25.851 1.00 23.74
ATOM 3945 OW0 WAT W  73 0   3.253 23.017 38.254 1.00 24.83
ATOM 3946 OW0 WAT W  74 0   9.653 22.835 35.143 1.00 25.79
ATOM 3947 OW0 WAT W  75 0  16.877 52.904 47.331 1.00 24.42
ATOM 3948 OW0 WAT W  76 0  14.293 22.021  3.993 1.00 32.28
ATOM 3949 OW0 WAT W  77 0  -5.287 19.835 18.528 1.00 24.65
ATOM 3950 OW0 WAT W  78 0   8.414 38.317 49.069 1.00 28.77
ATOM 3951 OW0 WAT W  79 0   7.070 32.466 47.926 1.00 21.83
ATOM 3952 OW0 WAT W  80 0  -0.452 28.307 25.779 1.00 16.58
ATOM 3953 OW0 WAT W  81 0  14.774 15.006 34.455 1.00 25.63
ATOM 3954 OW0 WAT W  82 0  11.515 54.942 35.962 1.00 14.20
ATOM 3955 OW0 WAT W  83 0  25.643 33.451 32.105 1.00 30.31
ATOM 3956 OW0 WAT W  84 0  11.869 12.221 20.394 1.00 31.37
ATOM 3957 OW0 WAT W  85 0  11.653 51.587 22.411 1.00 16.48
ATOM 3958 OW0 WAT W  86 0  17.334 40.837 51.079 1.00 30.26
ATOM 3959 OW0 WAT W  87 0   4.355 25.208 34.030 1.00 32.26
ATOM 3960 OW0 WAT W  88 0  18.816 52.360 32.512 1.00 21.19
ATOM 3961 OW0 WAT W  89 0  -2.704 46.518 35.364 1.00 21.99
ATOM 3962 OW0 WAT W  90 0  18.793 27.893 49.481 1.00 24.52
ATOM 3963 OW0 WAT W  91 0  22.459 46.584 28.898 1.00 18.99
ATOM 3964 OW0 WAT W  92 0   7.958 34.422 49.370 1.00 26.14
ATOM 3965 OW0 WAT W  93 0  23.972 16.246  6.806 1.00 24.35
ATOM 3966 OW0 WAT W  94 0   1.340 49.185 26.307 1.00 31.64
ATOM 3967 OW0 WAT W  95 0  -1.830 35.291 12.266 1.00 27.28
ATOM 3968 OW0 WAT W  96 0  20.460 17.486  3.589 1.00 33.51
ATOM 3969 OW0 WAT W  97 0  15.177  6.964  9.868 1.00 24.40
ATOM 3970 OW0 WAT W  98 0  18.616 57.927 43.922 1.00 30.76
ATOM 3971 OW0 WAT W  99 0  10.562 32.112  9.972 1.00 28.90
ATOM 3972 OW0 WAT W 100 0   1.630 61.363 10.878 1.00 33.92
ATOM 3973 OW0 WAT W 101 0  -4.939 49.989 33.211 1.00 29.73
ATOM 3974 OW0 WAT W 102 0  19.385 44.813 34.546 1.00 23.52
ATOM 3975 OW0 WAT W 103 0  19.055 43.063 37.581 1.00 30.59
ATOM 3976 OW0 WAT W 105 0  28.703 33.555 27.406 1.00 32.92
ATOM 3977 OW0 WAT W 106 0  28.835 19.646 10.759 1.00 40.44
ATOM 3978 OW0 WAT W 107 0  22.047 22.465  9.758 1.00 29.98
ATOM 3979 OW0 WAT W 108 0  14.689 61.032 36.346 1.00 30.63
ATOM 3980 OW0 WAT W 109 0  16.998 24.042  9.318 1.00 23.90
ATOM 3981 OW0 WAT W 110 0  13.472 30.533 11.848 1.00 34.83
```

```
ATOM 3982 OW0 WAT W 111  0   -2.175 35.601 41.496 1.00 28.55
ATOM 3983 OW0 WAT W 112  0    1.528 17.373 -1.396 1.00 38.21
ATOM 3984 OW0 WAT W 113  0   -2.856 29.748 19.681 1.00 30.55
ATOM 3985 OW0 WAT W 114  0    2.377 42.810 47.971 1.00 26.87
ATOM 3986 OW0 WAT W 115  0   10.947 12.820 33.745 1.00 31.60
ATOM 3987 OW0 WAT W 116  0    9.807 58.194 12.442 1.00 29.63
ATOM 3988 OW0 WAT W 117  0   18.488 62.559 29.470 1.00 45.83
ATOM 3989 OW0 WAT W 118  0   11.708 61.566 40.940 1.00 37.19
ATOM 3990 OW0 WAT W 119  0  -10.101 22.257 15.091 1.00 30.48
ATOM 3991 OW0 WAT W 120  0   -1.930 15.913  7.386 1.00 36.63
ATOM 3992 OW0 WAT W 121  0   23.988 43.686 29.319 1.00 32.15
ATOM 3993 OW0 WAT W 122  0    7.354 57.153 12.809 1.00 28.10
ATOM 3994 OW0 WAT W 123  0   24.207 22.101 11.958 1.00 32.83
ATOM 3995 OW0 WAT W 124  0   -1.268 15.083  9.738 1.00 32.53
ATOM 3996 OW0 WAT W 125  0   19.363  5.047 13.812 1.00 34.57
ATOM 3997 OW0 WAT W 126  0    4.799 41.145 23.688 1.00 28.33
ATOM 3998 OW0 WAT W 127  0   15.975 23.287  5.889 1.00 30.95
ATOM 3999 OW0 WAT W 128  0    3.698 38.582 -2.369 1.00 36.84
ATOM 4000 OW0 WAT W 129  0   -2.601 49.124 11.710 1.00 28.91
ATOM 4001 OW0 WAT W 130  0   15.779 56.598 43.285 1.00 27.76
ATOM 4002 OW0 WAT W 131  0   26.306 32.724 13.233 1.00 37.94
ATOM 4003 OW0 WAT W 132  0    3.610 46.947 23.991 1.00 35.49
ATOM 4004 OW0 WAT W 133  0   18.354 11.929 29.348 1.00 33.88
ATOM 4005 OW0 WAT W 134  0   13.966 41.517 27.765 1.00 18.02
ATOM 4006 OW0 WAT W 135  0   23.545 49.080 27.785 1.00 25.21
ATOM 4007 OW0 WAT W 136  0   16.876 25.082 41.791 1.00 28.71
ATOM 4008 OW0 WAT W 137  0   15.439 54.809 45.527 1.00 35.30
ATOM 4009 OW0 WAT W 138  0   11.733 25.676 43.264 1.00 38.24
ATOM 4010 OW0 WAT W 139  0    9.795 34.460 11.898 1.00 31.61
ATOM 4011 OW0 WAT W 140  0   13.328 57.569 42.356 1.00 30.66
ATOM 4012 OW0 WAT W 141  0   14.146  7.869 20.604 1.00 35.72
ATOM 4013 OW0 WAT W 142  0   23.330 12.948  3.922 1.00 29.83
ATOM 4014 OW0 WAT W 143  0   16.607 10.575 24.347 1.00 36.47
ATOM 4015 OW0 WAT W 144  0    8.509 25.546 35.012 1.00 35.43
ATOM 4016 OW0 WAT W 145  0   12.597 44.457  1.450 1.00 39.54
ATOM 4017 OW0 WAT W 146  0   21.680 51.509 39.154 1.00 40.08
ATOM 4018 OW0 WAT W 147  0   -0.702 52.593 39.700 1.00 29.62
ATOM 4019 OW0 WAT W 148  0   23.269 14.719 22.589 1.00 30.24
```

5032-WO

```
ATOM 4020 OW0 WAT W 149 0   27.149 22.972 41.846 1.00 35.00
ATOM 4021 OW0 WAT W 150 0    2.854  9.792  8.923 1.00 46.35
ATOM 4022 OW0 WAT W 151 0   24.831 15.672 24.889 1.00 29.22
ATOM 4023 OW0 WAT W 152 0   24.965 51.606 19.113 1.00 32.19
ATOM 4024 OW0 WAT W 153 0   -4.611 25.034 37.817 1.00 46.51
ATOM 4025 OW0 WAT W 154 0   12.225 39.382 28.864 1.00 25.42
ATOM 4026 OW0 WAT W 155 0   18.332 22.341 43.180 1.00 36.18
ATOM 4027 OW0 WAT W 156 0   36.467 20.701 17.144 1.00 44.13
ATOM 4028 OW0 WAT W 157 0   -4.903 47.901 40.886 1.00 33.97
ATOM 4029 OW0 WAT W 158 0   12.979 13.955  3.208 1.00 33.60
ATOM 4030 OW0 WAT W 159 0   32.383 12.693 24.743 1.00 30.25
ATOM 4031 OW0 WAT W 160 0   30.796 26.296 14.368 1.00 44.37
ATOM 4032 OW0 WAT W 161 0   19.332 37.280 40.057 1.00 31.54
ATOM 4033 OW0 WAT W 162 0   17.625 20.028 41.642 1.00 45.88
ATOM 4034 OW0 WAT W 163 0   19.917 56.115 46.103 1.00 40.37
ATOM 4035 OW0 WAT W 164 0   -4.743 14.204 16.748 1.00 40.86
ATOM 4036 OW0 WAT W 165 0    0.738 46.912 21.790 1.00 38.56
ATOM 4037 OW0 WAT W 166 0   22.648 62.277 30.976 1.00 24.37
ATOM 4038 OW0 WAT W 167 0   -4.322 45.754 26.894 1.00 48.97
ATOM 4039 OW0 WAT W 168 0   -2.386 24.601  0.665 1.00 32.57
ATOM 4040 OW0 WAT W 169 0   -0.459 41.618 35.838 1.00 35.25
ATOM 4041 OW0 WAT W 170 0   26.659  4.722 11.434 1.00 41.25
ATOM 4042 OW0 WAT W 171 0   13.720 11.379 22.121 1.00 39.59
ATOM 4043 OW0 WAT W 172 0   15.266  7.451  6.576 1.00 41.71
ATOM 4044 OW0 WAT W 173 0    0.134 17.450  6.165 1.00 42.12
ATOM 4045 OW0 WAT W 174 0   38.646 32.884 25.247 1.00 41.80
ATOM 4046 OW0 WAT W 175 0   10.591 17.398  3.251 1.00 29.37
ATOM 4047 OW0 WAT W 176 0   22.444 49.424 25.264 1.00 19.51
ATOM 4048 OW0 WAT W 177 0    0.429 23.224 28.598 1.00 33.54
ATOM 4049 OW0 WAT W 178 0   -2.302 27.278 34.780 1.00 44.76
ATOM 4050 OW0 WAT W 179 0    2.054 25.866 16.462 1.00 34.29
ATOM 4051 OW0 WAT W 180 0   30.277 18.006 25.789 1.00 42.28
ATOM 4052 OW0 WAT W 181 0    2.316 18.424 27.884 1.00 47.39
ATOM 4053 OW0 WAT W 182 0   19.401 41.164 39.560 1.00 39.68
ATOM 4054 OW0 WAT W 183 0   23.742 10.982 24.879 1.00 43.32
ATOM 4055 OW0 WAT W 184 0    3.926 24.450 44.251 1.00 48.95
ATOM 4056 OW0 WAT W 185 0   25.186 21.211 40.951 1.00 39.05
ATOM 4057 OW0 WAT W 186 0   20.353 34.816 48.799 1.00 34.08
```

5032-WO

137

```
ATOM  4058  OW0 WAT W 187  0   35.782  22.476  21.693  1.00 40.04
ATOM  4059  OW0 WAT W 188  0   27.256  23.617  12.235  1.00 40.85
ATOM  4060  OW0 WAT W 189  0    6.777  12.502  12.641  1.00 53.37
ATOM  4061  OW0 WAT W 190  0   -4.663  38.998   4.159  1.00 39.85
ATOM  4062  OW0 WAT W 191  0   24.398  52.064  24.607  1.00 45.51
ATOM  4063  OW0 WAT W 192  0    1.808  15.541   4.832  1.00 41.06
ATOM  4064  OW0 WAT W 193  0    5.341  36.359   7.569  1.00 39.36
ATOM  4065  OW0 WAT W 194  0   32.192  38.650  21.799  1.00 37.18
ATOM  4066  OW0 WAT W 195  0  -10.782  36.616  38.705  1.00 50.35
ATOM  4067  OW0 WAT W 196  0    4.119  64.116  32.946  1.00 34.51
ATOM  4068  OW0 WAT W 197  0   19.427  22.772   5.898  1.00 37.94
ATOM  4069  OW0 WAT W 198  0   -4.671  33.476   1.652  1.00 43.38
ATOM  4070  OW0 WAT W 199  0   -8.983  23.757  17.693  1.00 57.10
ATOM  4071  OW0 WAT W 200  0   -6.735  22.473  20.432  1.00 38.49
ATOM  4072  OW0 WAT W 201  0   -6.954  26.746  37.309  1.00 55.48
ATOM  4073  OW0 WAT W 202  0   23.418  38.662  33.700  1.00 42.20
ATOM  4074  OW0 WAT W 203  0    9.004  24.070  36.971  1.00 40.06
ATOM  4075  OW0 WAT W 204  0   18.890  42.920  51.502  1.00 46.29
ATOM  4076  OW0 WAT W 205  0   13.301  18.514   3.624  1.00 42.17
ATOM  4077  OW0 WAT W 206  0   31.189  12.995  19.645  1.00 51.92
ATOM  4078  OW0 WAT W 207  0   15.589  57.456  13.738  1.00 38.96
ATOM  4079  OW0 WAT W 208  0   -3.389  12.961  12.738  1.00 46.99
ATOM  4080  OW0 WAT W 209  0    9.321  30.475   6.320  1.00 49.75
ATOM  4081  OW0 WAT W 210  0    1.680  61.379  33.738  1.00 37.48
ATOM  4082  OW0 WAT W 211  0   -3.811  36.417   3.807  1.00 46.01
ATOM  4083  OW0 WAT W 212  0   17.087  46.902   3.830  1.00 45.12
ATOM  4084  OW0 WAT W 213  0   23.702  22.325  43.022  1.00 36.14
ATOM  4085  OW0 WAT W 214  0   10.849  60.003  14.389  1.00 32.05
ATOM  4086  OW0 WAT W 215  0   34.001  25.493  20.855  1.00 40.75
ATOM  4087  OW0 WAT W 216  0   27.422  37.093  28.951  1.00 42.33
ATOM  4088  OW0 WAT W 217  0    2.471  63.256  35.173  1.00 48.36
ATOM  4089  OW0 WAT W 218  0   -0.973  59.086  28.720  1.00 53.14
ATOM  4090  OW0 WAT W 219  0   28.841   9.287   6.463  1.00 39.02
ATOM  4091  OW0 WAT W 220  0   -5.593  21.802   9.619  1.00 44.21
ATOM  4092  OW0 WAT W 221  0   22.109  15.521   1.696  1.00 38.33
ATOM  4093  OW0 WAT W 222  0   13.029  32.860  12.233  1.00 37.63
ATOM  4094  OW0 WAT W 223  0   11.840  33.823   3.800  1.00 42.20
ATOM  4095  OW0 WAT W 224  0    8.476  42.976  -0.104  1.00 40.23
```

```
    ATOM 4096 OW0 WAT W 225  0   6.607  9.754 13.906 1.00 41.30
    ATOM 4097 OW0 WAT W 226  0  22.513 32.613 49.067 1.00 47.26
    ATOM 4098 OW0 WAT W 227  0  13.790  4.924 16.718 1.00 38.05
    ATOM 4099 OW0 WAT W 228  0   4.578 46.381  2.146 1.00 38.90
  5 ATOM 4100 OW0 WAT W 229  0  -0.178 18.054 23.533 1.00 43.42
    ATOM 4101 OW0 WAT W 230  0  -5.146 34.010  4.766 1.00 38.90
    ATOM 4102 OW0 WAT W 231  0  20.232 28.890 51.507 1.00 44.95
    ATOM 4103 OW0 WAT W 232  0  16.083 32.879 10.309 1.00 45.29
    ATOM 4104 OW0 WAT W 233  0  22.111 51.333 10.599 1.00 34.03
 10 ATOM 4105 OW0 WAT W 234  0   3.247 15.790 28.046 1.00 50.25
    ATOM 4106 OW0 WAT W 235  0   5.547 11.598  9.674 1.00 56.39
    ATOM 4107 OW0 WAT W 236  0  -1.085 18.297 -2.265 1.00 45.26
    ATOM 4108 OW0 WAT W 237  0  30.994 12.013 22.690 1.00 50.37
    ATOM 4109 OW0 WAT W 238  0  24.691 33.260 27.819 1.00 37.65
 15 ATOM 4110 OW0 WAT W 239  0  18.911 40.770  5.815 1.00 44.15
    ATOM 4111 OW0 WAT W 240  0  21.532 53.033 33.280 1.00 31.23
    ATOM 4112 OW0 WAT W 241  0  19.745 46.029  4.364 1.00 46.38
    ATOM 4113 OW0 WAT W 242  0  27.516 16.526 25.474 1.00 51.75
    ATOM 4114 OW0 WAT W 243  0  34.171 19.604  8.423 1.00 55.79
 20 ATOM 4115 OW0 WAT W 244  0  23.870 53.512 11.474 1.00 42.01
    ATOM 4116 OW0 WAT W 245  0  14.492 23.842 44.882 1.00 52.25
    ATOM 4117 OW0 WAT W 246  0  -3.070 63.260 33.189 1.00 40.77
    ATOM 4118 OW0 WAT W 247  0  22.185 55.701 37.353 1.00 39.52
    ATOM 4119 OW0 WAT W 248  0  14.144 26.239 42.825 1.00 42.50
 25 ATOM 4120 OW0 WAT W 249  0  25.026 36.545 35.213 1.00 58.19
    ATOM 4121 OW0 WAT W 250  0  27.072 34.293 43.895 1.00 46.58
    ATOM 4122 OW0 WAT W 251  0  11.742  7.192  4.856 1.00 42.78
    ATOM 4123 OW0 WAT W 252  0   0.730 46.405 24.947 1.00 39.31
    ATOM 4124 OW0 WAT W 253  0  28.346 34.036 30.808 1.00 43.10
 30 ATOM 4125 OW0 WAT W 254  0  -3.838 40.281  1.903 1.00 38.67
    ATOM 4126 OW0 WAT W 255  0   6.837 35.163 51.935 1.00 58.57
    ATOM 4127 OW0 WAT W 256  0  19.740 62.853 17.880 1.00 52.39
    ATOM 4128 OW0 WAT W 258  0  -0.994 41.755 22.088 0.00 69.57
    ATOM 4129 OW0 WAT W 259  0   1.221 10.473 15.458 1.00 54.80
 35 ATOM 4130 OW0 WAT W 260  0  23.445 55.367 31.430 1.00 48.90
    ATOM 4131 OW0 WAT W 261  0  23.757 57.854 34.657 1.00 37.69
    ATOM 4132 OW0 WAT W 262  0   8.508 19.111 34.572 1.00 55.52
    ATOM 4133 OW0 WAT W 263  0  22.806 22.381  3.611 1.00 64.20
```

```
   ATOM  4134  OW0 WAT W 264  0    0.398 22.602 42.625 1.00 58.86
   ATOM  4135  OW0 WAT W 265  0    4.195 52.287 43.465 1.00 36.84
   ATOM  4136  OW0 WAT W 266  0   20.211  6.536  4.911 1.00 39.34
   ATOM  4137  OW0 WAT W 267  0   14.680 16.117  2.803 1.00 45.76
 5 ATOM  4138  OW0 WAT W 268  0   14.938 25.582  6.850 1.00 41.01
   ATOM  4139  OW0 WAT W 269  0    7.763  7.940 31.891 0.00 71.30
   ATOM  4140  OW0 WAT W 270  0   -3.459 33.491 39.400 1.00 40.80
   ATOM  4141  OW0 WAT W 271  0   23.154 22.897  6.985 1.00 48.25
   ATOM  4142  OW0 WAT W 272  0   34.916 25.555 28.092 1.00 52.63
10 ATOM  4143  OW0 WAT W 273  0    8.332 45.481 50.776 1.00 47.23
   ATOM  4144  OW0 WAT W 274  0   -3.441 57.643 28.775 1.00 49.70
   ATOM  4145  OW0 WAT W 275  0   23.213 40.573 47.561 1.00 56.02
   ATOM  4146  OW0 WAT W 276  0    5.421 55.179 45.172 1.00 52.70
   ATOM  4147  OW0 WAT W 277  0   -3.012 21.908 40.933 1.00 41.69
15 ATOM  4148  OW0 WAT W 278  0   26.328 53.637 17.905 1.00 37.80
   ATOM  4149  OW0 WAT W 279  0    9.740 58.922 43.485 1.00 52.06
   ATOM  4150  OW0 WAT W 280  0   23.545 15.660  4.258 1.00 41.55
   ATOM  4151  OW0 WAT W 281  0   22.652 31.154 51.246 1.00 58.65
   ATOM  4152  OW0 WAT W 282  0   22.192 51.135  8.251 1.00 44.76
20 ATOM  4153  OW0 WAT W 283  0   -6.046 22.886 24.288 1.00 52.40
   ATOM  4154  OW0 WAT W 284  0   19.949 45.276 49.516 1.00 54.58
   ATOM  4155  OW0 WAT W 285  0    7.388 22.308 32.108 1.00 43.62
   ATOM  4156  OW0 WAT W 286  0   15.080 50.452  2.795 1.00 52.20
   ATOM  4157  OW0 WAT W 287  0    1.016 62.235 30.878 1.00 56.81
25 ATOM  4158  OW0 WAT W 288  0   23.803 52.570 27.699 1.00 56.22
   ATOM  4159  OW0 WAT W 289  0  -10.525 31.623 13.870 1.00 47.21
   ATOM  4160  OW0 WAT W 290  0    1.599 55.502 24.567 1.00 44.50
   ATOM  4161  OW0 WAT W 291  0  -15.671 37.251 14.660 1.00 83.62
   ATOM  4162  OW0 WAT W 292  0    7.231  7.950 17.754 1.00 50.61
30 ATOM  4163  OW0 WAT W 293  0   -4.009 34.057 42.492 1.00 78.48
   ATOM  4164  OW0 WAT W 294  0   21.004 58.371 18.690 1.00 61.15
   ATOM  4165  OW0 WAT W 295  0   16.405 48.869 52.211 1.00 53.17
   ATOM  4166  OW0 WAT W 296  0    7.329 31.202  1.964 1.00 38.86
   ATOM  4167  OW0 WAT W 297  0    9.518 53.886  5.467 1.00 41.62
35 ATOM  4168  OW0 WAT W 298  0   10.398 48.995  0.335 1.00 49.64
   ATOM  4169  OW0 WAT W 299  0    9.889 15.077  3.774 1.00 42.28
   ATOM  4170  OW0 WAT W 300  0   15.854 56.731 10.934 1.00 44.02
```

What is claimed is:

1. A variant of a parent *Polyporus pinsitus* (I) laccase, which comprises a mutation in a position corresponding to at least one of the following positions in SEQ ID No. 2:
W107,
Y116,
Y108,
Y152,
M57, and/or
M328.

2. A variant of a parent *Polyporus pinsitus* (II) laccase, which comprises a mutation in a position corresponding to at least one of the following positions in SEQ ID No. 3:
W107,
Y116,
Y108,
Y152; and/or
M57.

3. A variant of a parent *Phlebia radiata* laccase, which comprises a mutation in a position corresponding to at least one of the following positions in SEQ ID No. 4:
W128,
Y137,
Y129,
Y137, and/or
M78.

4. A variant of a parent *Rhizoctonia solani* (I) laccase, which comprises a mutation in a position corresponding to at least one of the following positions in SEQ ID No. 5:
W126,
Y135,
Y127,
Y171, and/or
M76.

5. A variant of a parent *Rhizoctonia solani* (II) laccase, which comprises a mutation in a position corresponding to at least one of the following positions in SEQ ID No. 6:
W439,
W125,
Y134,
Y126,
Y170, and/or
M75.

6. A variant of a parent *Rhizoctonia solani* (III) laccase, which comprises a mutation in a position corresponding to at least one of the following positions in SEQ ID No. 7:
W411,
W125,
Y134,
Y126,
Y170, and/or
M75.

7. A variant of a parent *Rhizoctonia solani* (IV) laccase, which comprises a mutation in a position corresponding to at least one of the following positions in SEQ ID No. 8:
W411,
W125,
Y134,
Y126,
Y170, and/or
M75.

8. A variant of a parent *Scytalidiur thermophilum* laccase, which comprises a mutation in a position corresponding to at least one of the following positions in SEQ ID No. 9:
M483,
W422,
W181,
Y190,
M530,
Y182,
Y221,
M300, and/or
M313.

9. A variant of a parent *Myceliophthora thermophila* laccase, which comprises a mutation in a position corresponding to at least one of the following positions in SEQ ID No. 10:
W507,
M433,
W373,
W136,
Y145,
M480,
Y137,
Y176, and/or
M254.

* * * * *